US012540132B2

(12) United States Patent
Bao et al.

(10) Patent No.: US 12,540,132 B2
(45) Date of Patent: Feb. 3, 2026

(54) PREPARATION OF TETRAHYDROINDAZOLE DERIVATIVES AS NOVEL DIACYLGLYCERIDE O-ACYLTRANSFERASE 2 INHIBITORS

(71) Applicant: Merck Sharp & Dohme LLC, Rahway, NJ (US)

(72) Inventors: Jianming Bao, Princeton, NJ (US); Chen Cheng, Millbrae, CA (US); Faben A. Cruz, Burlingame, CA (US); Yeon-Hee Lim, South San Francisco, CA (US); Cedric L. Hugelshofer, Oakland, CA (US); Jinlong Jiang, Scotch Plains, NJ (US); Victor W. Mak, South San Francisco, CA (US); Emma Helen Southgate, Mountain View, CA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 350 days.

(21) Appl. No.: 18/257,133

(22) PCT Filed: Dec. 17, 2021

(86) PCT No.: PCT/US2021/063948

§ 371 (c)(1),
(2) Date: Jun. 13, 2023

(87) PCT Pub. No.: WO2022/140169

PCT Pub. Date: Jun. 30, 2022

(65) Prior Publication Data

US 2024/0140938 A1 May 2, 2024

Related U.S. Application Data

(60) Provisional application No. 63/128,915, filed on Dec. 22, 2020.

(51) Int. Cl.
*C07D 409/12* (2006.01)
*C07D 409/14* (2006.01)

(52) U.S. Cl.
CPC ......... *C07D 409/14* (2013.01); *C07D 409/12* (2013.01)

(58) Field of Classification Search
None
See application file for complete search history.

(56) References Cited

U.S. PATENT DOCUMENTS

| | | | |
|---|---|---|---|
| 10,029,988 | B2 | 7/2018 | Jacques et al. |
| 2015/0259323 | A1 | 9/2015 | Cabral et al. |
| 2018/0001628 | A1 | 1/2018 | Maxfield |
| 2019/0330239 | A1 | 10/2019 | Shen et al. |

FOREIGN PATENT DOCUMENTS

| | | | |
|---|---|---|---|
| CN | 101316844 | A | 12/2008 |
| JP | 2018117503 | A | 11/2019 |
| JP | 2019117556 | A | 12/2020 |
| RU | 2665554 | C2 | 8/2018 |
| WO | 2003053363 | A2 | 7/2003 |
| WO | 2013150416 | A1 | 10/2013 |
| WO | 2015077299 | A1 | 5/2015 |
| WO | 2016036633 | A1 | 3/2016 |
| WO | 2016036636 | A1 | 3/2016 |
| WO | 2016036638 | A1 | 3/2016 |
| WO | 2017011276 | A1 | 1/2017 |
| WO | 2017075182 | A1 | 5/2017 |
| WO | 2018033832 | A1 | 2/2018 |
| WO | 2018093696 | A1 | 5/2018 |
| WO | 2018093698 | A1 | 5/2018 |
| WO | 2021064590 | A1 | 4/2021 |

OTHER PUBLICATIONS

Belikov, V.G., Pharmaceutical Chemistry, Moscow MEDpress-inform, 4th Edition, 27-29, 2007.
Kummerer, K., Pharmaceuticals in the environment, Annual Review of Environment and Resources, 35, 57-75, 2010.
Choi et al., Suppression of Diacylglycerol Acyltransferase-2 (DGAT2), but Not DGAT1, with Antisense Oligonucleotides Reverses Diet-induced Hepatic Steatosis and Insulin Resistance, Journal of Biological Chemistry, 2007, 22678-22688, 282(31).
Li, Chen et al., Roles of Acyl-CoA:Diacylglycerol Acyltransferases 1 and 2 in Triacylglycerol Synthesis and Secretion in Primary Hepatocytes, Arterioscler. Thromb. Vasc. Biol., 2015, 1080-1091, 35.

(Continued)

*Primary Examiner* — Samantha L Shterengarts
(74) *Attorney, Agent, or Firm* — Kristi K. Harman; Catherine D. Fitch

(57) ABSTRACT

Invented are compounds of formula I and the pharmaceutically acceptable salts, esters, and prodrugs thereof, which are DGAT2 inhibitors. Also provided are methods of making compounds of Formula I, pharmaceutical compositions comprising compounds of Formula I, and methods of using these compounds to treat hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions, comprising administering a compound of Formula I to a patient in need thereof.

I

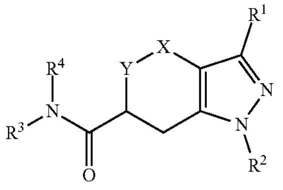

33 Claims, No Drawings

(56) References Cited

OTHER PUBLICATIONS

Liu et al., Knockdown of Acyl-CoA:diacylglycerol acyltransferase 2 with antisense oligonucleotide reduces VLDL TG and ApoB secretion in mice, Biochimica et Biophysica Acta, Molecular and Cell Biology of Lipids, 2008, 97-104, 1781 (3).
Pubchem, Substance Record for SID 227907042, Available Date: Feb. 12, 2015 [retrieved 1 on Feb. 8, 2022]. Retrieved from the Internet: URL:https://pubchem.ncbi.nlm.nih.gov/substance/227907042. entire document (8 pages).
Pubchem, Substance Record for SID 355304193, Available Date: Apr. 8, 2018 [retrieved on 1 Mar. 30, 2022]. Retrieved from the Internet: URL:https://pubchem.ncbi.nlm.nih.gov/substance/355304193. entire document (6 pages).
Yen, Chi-Liang Eric et al., DGAT enzymes and triacylglycerol biosynthesis, Journal of Lipid Research, 2008, 2283-2301, 49.
Yu, Xing Xian et al., Antisense Oligonucleotide Reduction of DGAT2 Expression Improves Hepatic Steatosis and Hyperlipidemia in Obese Mice, Hepatology, 2005, 362-371, 42.

PREPARATION OF TETRAHYDROINDAZOLE DERIVATIVES AS NOVEL DIACYLGLYCERIDE O-ACYLTRANSFERASE 2 INHIBITORS

CROSS-REFERENCE TO RELATED APPLICATIONS

This is a U.S. National Phase entry under 35 U.S.C. § 371 of PCT/US2021/063948, filed Dec. 17, 2021, which published as WO2022/140169 on Jun. 30, 2022; which claims priority to U.S. Provisional Application No. 63/128,915, filed Dec. 22, 2020; the content of each of which is hereby incorporated by reference in its entirety.

FIELD OF THE INVENTION

The present invention is directed to novel pharmaceutical compounds which inhibit diacylglyceride O-acyltransferase 2 ("DGAT2"), and may be useful for preventing, treating or acting as a reversing agent for hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure, and related diseases and conditions, as well as methods of making such compounds and pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DAG") to form TG. The reaction is catalyzed by acyl-CoA:diacylglycerol acyltransferase ("DGAT") enzymes. There have been identified two DGAT enzymes, DGAT1 and DGAT2. Although DGAT1 and DGAT2 catalyze the same reaction, they differ significantly at the level of DNA and protein sequences. DGAT2 can utilize endogenous fatty acid to synthesize TG in in vitro assays, whereas DGAT1 appears to be more dependent on exogenous fatty acid (Yen et al., *J. Lipid Research,* 2008, 49, 2283). Inactivation of DGAT2 impaired cytosolic lipid droplet growth, whereas inactivation of DGAT1 exerts opposite effect. (Li et al., *Arterioscler. Thromb. Vasc. Biol.* 2015, 35, 1080).

DGAT2 is an integral membrane protein of the endoplasmic reticulum and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable (Yen et al., *J. Lipid Research,* 2008, 49, 2283).

Despite this perinatal lethal phenotype, the metabolic role of DGAT2 has been mostly comprehended from effort exploiting anti-sense oligonucleotides (ASO) in rodents. In this setting, DGAT2 knockdown in ob/ob mice with a DGAT2 gene-specific ASO resulted in a dose dependent decrease in very low density lipoprotein ("VLDL") and a reduction in plasma TG, total cholesterol, and ApoB (Liu, et al., *Biochim. Biophys Acta* 2008, 1781, 97). In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia (Yu, et al., *Hepatology,* 2005, 42, 362). Another study showed that diet-induced hepatic steatosis and insulin resistance was improved by knocking down DGAT2 in rats. These effects seem to be unique to inhibition of DGAT2, as ASO against DGAT1 did not lead to similar beneficial effects. Although the molecular mechanism behind these observations remains uncertain, the collective data suggest that suppression of DGAT2 is associated with reduced expression of lipogenic genes (SREBP1c, ACC1, SCD1, and mtGPAT) and increased expression of oxidative/thermogenic genes (CPT1, UCP2) (Choi et al., *J. Bio. Chem.,* 2007, 282, 22678).

In light of the above description, inhibitors of DGAT2 are useful for treating disease related to the spectrum of metabolic syndrome such as hepatic steatosis, non-alcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases and heart failure and related diseases and conditions.

DGAT2 inhibitor compounds are described in WO2021064590, WO2016036633, WO2016036636, WO2016036638, WO2018093696, WO2018093698, WO2013150416, US20150259323, WO2015077299, WO2017011276, WO2018033832, US201801628, WO2003053363.

SUMMARY OF THE INVENTION

The present disclosure is directed to compounds having structural Formula I.

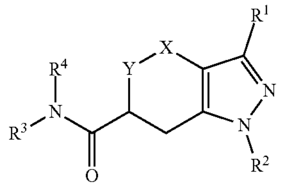

I or pharmaceutically acceptable salts thereof wherein:

X and Y are independently selected from O or $C(R^5)_2$, wherein both X and Y are both not O; and $R^1$ is (1) phenyl unsubstituted or substituted with 1, 2, or 3 $R^6$, (2) 5- or 6-membered heteroaryl containing 1, 2, 3 or 4 heteroatoms independently selected from N, O, and S, wherein the heteroaryl is unsubstituted or substituted with 1, 2, or 3 $R^6$, or (3) 8- to 10-membered fused heteroaryl containing 1, 2, 3 heteroatoms independently selected from N, O, and S, wherein the heteroaryl is unsubstituted or substituted with 1, 2, or 3 $R^6$;

$R^2$ is (1) phenyl unsubstituted or substituted with 1, 2, or 3 $R^7$, (2) 5- or 6-membered heteroaryl containing 1, 2 or 3 heteroatoms independently selected from N, O, and S, wherein the heteroaryl is unsubstituted or substituted with 1, 2, or 3 $R^7$, (3) $C_{1-6}$alkyl unsubstituted or optionally mono-substituted, disubstituted or trisubstituted with halogen, OH, $CF_3$, —CN, or $(C_{3-6})$cycloalkyl, (4) $(C_{3-6})$cycloalkyl unsubstituted or optionally mono-substituted, disubstituted or trisubstituted with $C_{1-6}$alkyl, halogen, OH, $CF_3$, or —CN, (5) —$(C_{3-6})$alkyl-C(O)$NH_2$, (6) 4- to 6-membered heterocyclyl containing 1 or 2 heteroatoms independently selected from N, O and S wherein the heterocyclyl is unsubstituted or substituted by 1, 2, or 3 $R^7$, (7) —$CH_2$-heteroaryl unsubstituted or substituted by 1, 2, or 3 $R^7$, (8) —$CH_2$-aryl unsubstituted or substituted by 1, 2, or 3 $R^7$, (9) —$CH_2$-heterocyclyl unsubstituted or substituted by 1, 2, or 3 $R^7$,

(10) —C(═O) $(C_{1-6})$alkyl unsubstituted or substituted with 1, 2, or 3 $R^7$,

(11) —C(═O) $(C_{3-6})$cycloalkyl unsubstituted or substituted with 1, 2, or 3 $R^7$,

(12) —C(═O) $(C_{1-6})$heterocyclyl unsubstituted or substituted with 1, 2, or 3 $R^7$,

(13) —C(═O) aryl unsubstituted or substituted with 1, 2, or 3 $R^7$,

(14) —$SO_2(C_{1-6})$alkyl unsubstituted or substituted with 1, 2, or 3 $R^7$,

(15) —$SO_2(C_{3-6})$cycloalkyl unsubstituted or substituted with 1, 2, or 3 $R^7$,

(16) —$SO_2$-aryl unsubstituted or substituted with 1, 2, or 3 $R^7$, $R^3$ is (1) 4- to 7-membered heterocyclyl containing 1 or 2 heteroatoms independently selected from N, O and S, (2) 5- or 6-membered heteroaryl containing 1, 2 or 3 heteroatoms independently selected from N, O, and S, (3) —$(C_{1-6})$alkyl-heteroaryl, wherein the heteroaryl is a 5- or 6-membered heteroaryl containing 1, 2 or 3 heteroatoms independently selected from N, O and S, (4) —$(C_{1-6})$alkyl-aryl, (5) —$(C_{1-6})$alkyl-heterocyclyl, wherein the heterocyclyl is a 3- to 6-membered ring containing 1 or 2 heteroatoms independently selected from N, O and S, (6) —$(C_{1-6})$alkyl, (7) —$(C_{3-6})$cycloalkyl, (8) —$(C_{3-6})$cycloalkyl-heterocyclyl wherein the heterocyclyl is a 3- to 6-membered ring containing 1 or 2 heteroatoms independently selected from N, O and S, (9) —$(C_{1-6})$hydroxyalkyl,

(10) —$(C_{1-6})$alkyl-$S(O)_2$—$NR^{8a}R^{8b}$,

(11) —$(C_{1-6})$alkyl-$S(O)_2$—$(C_{1-3})$alkyl,

(12) —$(C_{1-3})$alkyl-heteroaryl, wherein the heteroaryl is an 8- to 10-membered fused ring, and wherein the heteroaryl contains 1, 2, 3, or 4 heteroatoms independently selected from N, O, and S,

(13) —$(C_{1-6})$alkyl-SONH—$(C_{1-3})$alkyl,

(14) —$(C_{1-6})$alkyl-$(C_{3-6})$cycloalkyl,

(15) fused aryl,

(16) —$C(_{1-6})$alkyl-$N(R^{11})_2$,

(17) —$C(_{1-6}$alkyl)-O—$C_{1-3}$alkyl, or

(18) —$C(_{1-6})$alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$;

$R^4$ is (1) hydrogen, (2) $(C_{1-3})$alkyl, or $R^3$ and $R^4$, together with the nitrogen atom to which they are attached, combine to form a mono- or bicyclic heterocyclyl ring containing 1 N and optionally containing 1 additional heteroatoms independently selected from N, O and S, wherein the heterocyclyl ring is unsubstituted or substituted by 1, 2, or 3 $R^{11}$;

when present, each $R^5$ is selected from (1) hydrogen, (2) halogen, or (3) cyano;

when present, each $R^6$ is independently selected from (1) cyano, (2) halogen, (3) $(C_{1-6})$alkyl or $OC_{1-6}$alkyl wherein the alkyl moiety is optionally substituted with cyano, (4) $(C_{3-6})$cycloalkyl, optionally substituted with halogen, $C_{1-6}$alkyl, $C_{1-6}$haloalkyl, cyano, OH or $OC_{1-6}$ alkyl, (5) —$C(O)N(R^1)_2$, (6) $(C_{3-6})$cycloalkyloxy wherein the cycloalkyl is optionally substituted with halogen, $C_{1-6}$alkyl, $C_{1-6}$haloalkyl, cyano, OH, or $OC_{1-6}$alkyl, (7) hydroxy, (8) —$NR^{11}R^{11}$, (9) $(C_{1-6})$haloalkyl-,

(10) $(C_{1-6})$haloalkoxy-,

(11) —$SO_2(C_{1-6})$alkyl,

(12) —$SONH(C_{1-6})$alkyl,

(13) $C_{1-6}$alkyl-$NR^{11}R^{11}$, or

(14) 5 membered heteroaryl comprising 2 nitrogen atoms;

when present, each $R^7$ is independently selected from (1) $(C_{1-6})$alkyl, (2) halo, (3) $(C_{1-6})$alkoxy-, (4) $(C_{1-6})$haloalkyl-, (5) $(C_{3-6})$cycloalkyl, (6) C(O)H or —C(O)—OH, (7) $C(O)(C_{1-6})$alkyl or —C(O)O—$(C_{1-6})$alkyl, (8) hydroxy, (9) CN,

(10) deuterium,

(11) $OC_{1-3}$haloalkyl, or

(12) oxo;

when present, $R^{8a}$ and $R^{8b}$ are independently selected from (1) hydrogen, (2) $(C_{1-3})$alkyl, (3) —$(C_{1-3})$alkyl-phenyl, (4) 5- or 6-membered heteroaryl containing 1, 2, or 3 heteroatoms independently selected from N, O, and S, or (5) phenyl;

when present, each $R^9$ is independently selected from (1) $(C_{1-3})$alkyl, (2) $(C_{1-3})$haloalkyl-, (3) oxo, (4) $(C_{3-6})$cycloalkyl, (5) —C(O)O—$(C_{1-4})$alkyl, (6) —$NR^{11}R^{11}$, (7) hydroxy, (8) phenyl unsubstituted or substituted with halo, (9) hydroxy$(C_{1-3})$alkyl-,

(10) cyano,

(11) halo,

(12) $C(O)C_{1-6}$alkyl or $C(O)C_{3-6}$cycloalkyl,

(13) $C(O)NHC_{1-3}$alkyl, or

(14) 6 membered heterocycle containing one Oxygen and one Nitrogen;

when present, $R^{10}$ is (1) $(C_{1-3})$alkyl, (2) $(C_{1-3})$ hydroxy alkyl-, (3) $(C_{1-3})$alkoxy-, (4) hydroxy, (5) halogen, (6) $(C_{1-3})$haloalkyl-, (7) $N(R^1)_2$, (8) $(C_{1-3})$alkyl-S—, or (9) phenyl;

when present, each $R^{11}$ is independently (1) hydrogen, or (2) $(C_{1-6})$alkyl;

when present, $R^{12}$, $R^{12a}$ and $R^{12b}$ are independently (1) hydrogen, (2) $(C_{1-6})$alkyl, (3) $(C_{3-6})$cycloalkyl, or (4) $(C_{1-6})$haloalkyl.

In Embodiment 1 of this disclosure are compounds of Formula I, or a pharmaceutically acceptable salt of any of the foregoing, wherein $R^1$ is a) phenyl substituted with one to three substituents independently selected from hydroxy, halogen, hydroxy, CN, $C_{1-3}$alkyl, $C_{1-3}$alkyl-CN, $OC_{1-3}$alkyl-CN, $C_{1-3}$haloalkyl, $C_{3-6}$cycloalkyl —$OC_{1-3}$alkyl, —$OC_{1-3}$haloalkyl, —$OC_{3-6}$cycloalkyl, 5 membered heteroaryl containing 2 nitrogen atoms, $(C_{3-6})$cycloalkyloxy, $S(O)_2C_{1-6}$alkyl, $S(O)_2NHC_{1-3}$alkyl, or $C_{1-3}$alkyl$NH_2$, and wherein the alkyl moiety is optionally further substituted with cyano, wherein the cycloalkyl moiety is optionally further substituted with 1 or two of the following: halogen, $C_{1-6}$alkyl, $C_{1-6}$haloalkyl, cyano, OH, or $OC_{1-6}$alkyl;

b) a 6 membered heteroaryl containing one or two nitrogen atoms substituted with one to two substituents selected from: halogen, hydroxy, $C_{1-3}$alkyl, $C_{1-3}$haloalkyl, $C_{3-6}$cycloalkyl, —$OC_{1-3}$alkyl, —$OC_{1-3}$haloalkyl, —O—$C_{3-6}$cycloalkyl, $C(O)NC_{1-6}$alkyl, or CN, and wherein the cycloalkyl moiety is optionally further substituted with 1 or 2 fluoro atoms or $C_{1-3}$alkyl;

c) a 5 membered heteroaryl containing one to three heteroatoms optionally substituted with one to two substituents independently selected from with halogen, $(C_{1-3})$alkyl, $(C_{3-6})$cycloalkyl, $(C_{1-3})$haloalkyl-, OH or $OC_{1-3}$alkyl; or d) 8- to 10-membered fused heteroaryl containing at least one nitrogen and optionally containing one oxygen optionally substituted with 1 or 2 substituents independently selected from halogen, $C_{1-3}$alkyl, $C_{1-3}$haloalkyl, $OC_{1-3}$alkyl, or $OC_{1-3}$haloalkyl.

In Embodiment 2 of this disclosure are compounds of Formula I, or any one of Embodiments 1, or a pharmaceutically acceptable salt of any of the foregoing, wherein $R^1$ is a) phenyl substituted with one or two substituents selected from: hydroxy, halogen, CN, $C_{1-3}$alkyl, $C_{1-3}$alkyl-CN, $OC_{1-3}$alkyl-CN, $C_{1-3}$haloalkyl, $C_{3-6}$cycloalkyl, —$OC_{1-3}$ alkyl, —$OC_{1-3}$haloalkyl, —O-cyclopropyl, 5 membered heteroaryl containing 2 nitrogen atoms, $S(O)_2C_{1-3}$alkyl, $S(O)_2NHC_{1-3}$alkyl, or $C_{1-3}$alkyl$NH_2$—, and wherein the alkyl moiety is optionally further substituted with cyano, and wherein the cycloalkyl moiety is optionally further substituted with F, $CH_3$, $CF_3$, CN, or OH;

b) a 6 membered heteroaryl containing one or two nitrogen atoms substituted with one or two substituents selected from: halogen, hydroxy, $C_{1-3}$alkyl, $C_{1-3}$haloalkyl, —$OC_{1-3}$alkyl, —$OC_{1-3}$haloalkyl, —O-cyclopropyl, or $C(O)NHC_{1-6}$alkyl, and wherein the cycloalkyl moiety is optionally further substituted with 1 or 2 fluoro atoms or $CH_3$;

c) 5 membered heteroaryl containing one to three heteroatoms optionally substituted with one to two substituents independently selected from with halogen, or $(C_{1-3})$alkyl; or d) 9 or 10-membered fused heteroaryl containing at least one nitrogen and optionally containing one oxygen atom optionally substituted with 1 or 2 methyl substituents.

In Embodiment 3 of this disclosure are compounds of Formula I, or any one of Embodiments 1-2, or a pharmaceutically acceptable salt of any of the foregoing, wherein $R^1$ is

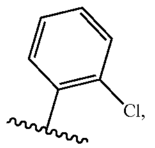
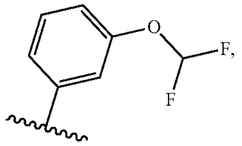
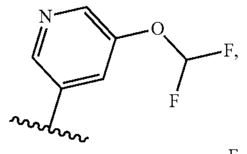
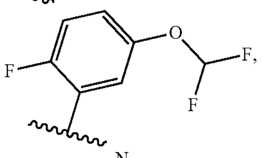
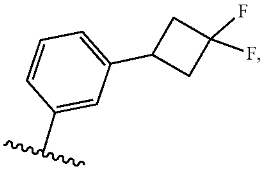
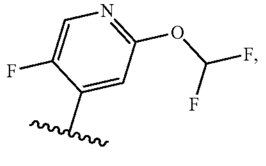
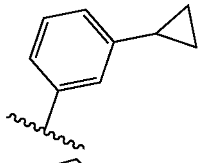
,
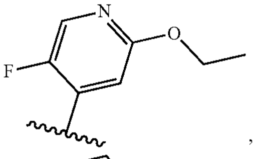
,
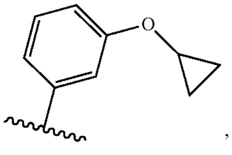
,
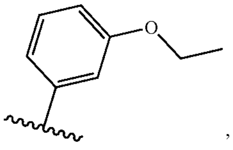
, -continued
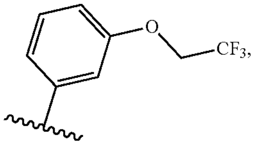
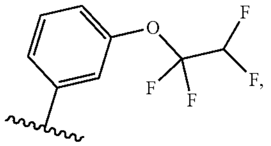
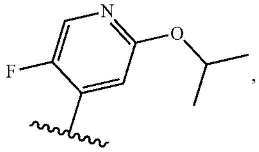
,
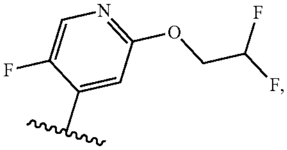
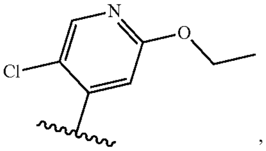
,
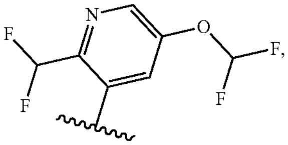
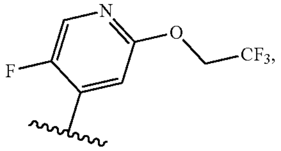
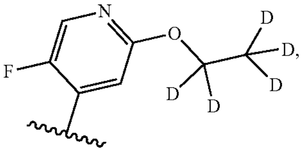
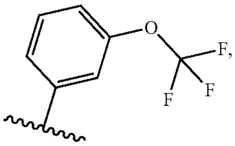
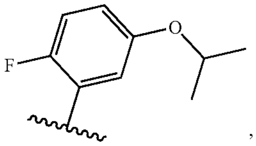
,
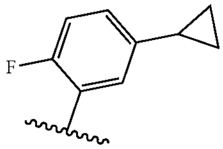
,
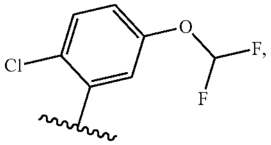
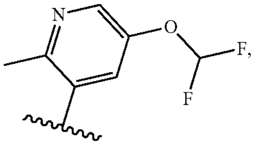
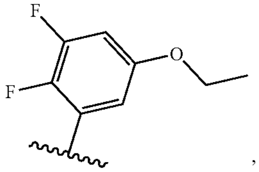
,
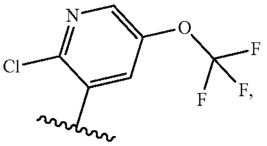
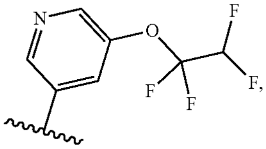
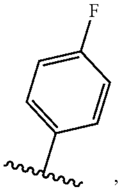
,
-continued
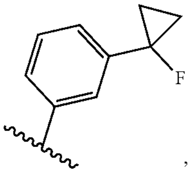
,
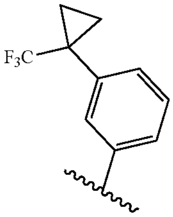
,
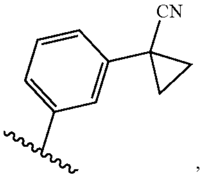
,
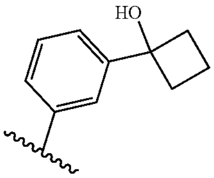
,
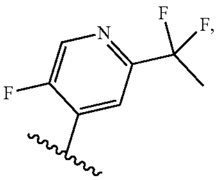
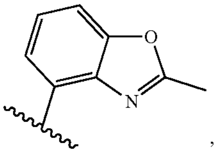
,
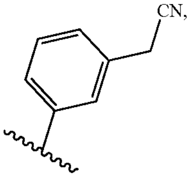
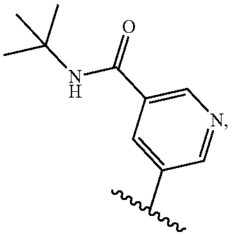
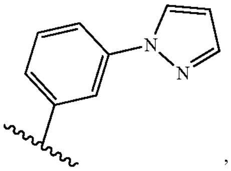
,
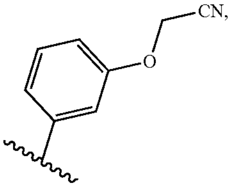
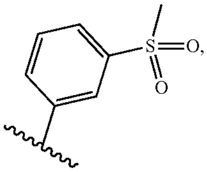
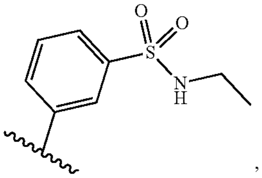
, -continued

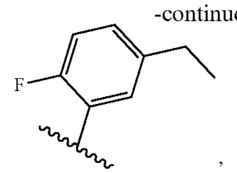

,

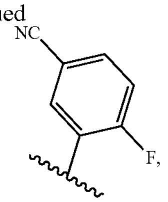

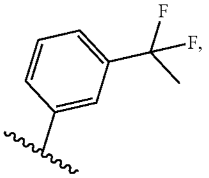

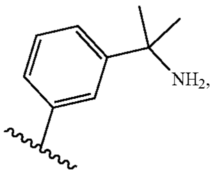

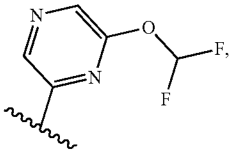

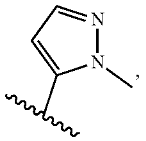

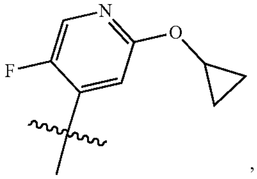

,

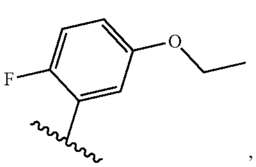

,

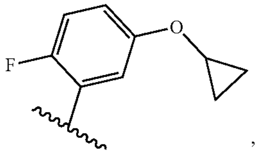

, or

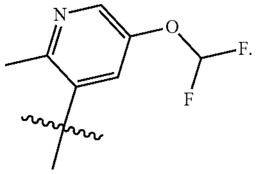

In Embodiment 4 of this disclosure are compounds of Formula I, or any one of Embodiments 1-3 or a pharmaceutically acceptable salt of any of the foregoing, wherein $R^1$ is phenyl substituted with a substituent selected from: hydroxy, halogen CN, $C_{1-3}$alkyl, $C_{1-3}$alkyl-CN, $OC_{1-3}$alkyl-CN, $C_{1-3}$haloalkyl, $C_{3-6}$cycloalkyl, —$OC_{1-3}$alkyl, —$OC_{1-3}$ haloalkyl, —O-cyclopropyl, 5 membered heteroaryl containing 2 nitrogen atoms, $S(O)_2C_{1-3}$alkyl, $S(O)_2NHC_{1-3}$ alkyl, or $C_{1-3}$alkyl$NH_2$, and wherein the cycloalkyl moiety is optionally further substituted with F, $CH_3$, $CF_3$, CN, or OH.

In Embodiment 5 of this disclosure are compounds of Formula I, or any one of Embodiments 1-3 or a pharmaceutically acceptable salt of any of the foregoing, wherein $R^1$ is a 6 membered heteroaryl containing one or two nitrogen atoms substituted with one or two substituents selected from: halogen, $C_{1-3}$alkyl, $C_{1-3}$haloalkyl, —$OC_{1-3}$ alkyl, —$OC_{1-3}$haloalkyl, —O-cyclopropyl, C(O)NHC-6alkyl, and wherein the cycloalkyl moiety is optionally further substituted with 1 or 2 fluoro atoms or $CH_3$.

In Embodiment 6 of this disclosure are compounds of Formula I, or any one of Embodiments 1-3 or a pharmaceutically acceptable salt of any of the foregoing, wherein $R^1$ is 5 membered heteroaryl containing one to three heteroatoms optionally substituted with one to two substituents independently selected from with halogen, or $(C_{1-3})$alkyl.

In Embodiment 7 of this disclosure are compounds of Formula I, or any one of Embodiments 1-3 or a pharmaceutically acceptable salt of any of the foregoing, wherein $R^1$ is 9 or 10-membered fused heteroaryl containing one or two heteroatoms independently selected from nitrogen or oxygen optionally substituted with 1 or 2 methyl substituents.

In Embodiment 8 of this disclosure are compounds of Formula I, or any one of Embodiments 1-7 or a pharmaceutically acceptable salt of any of the foregoing, wherein $R^1$

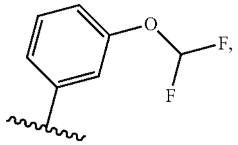

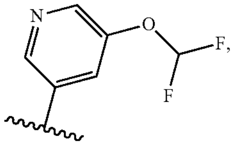

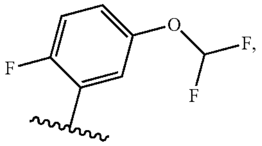

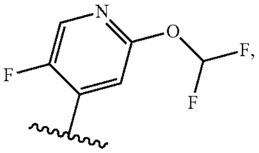

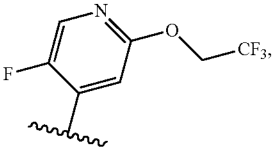

or

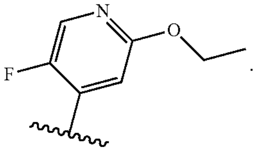

In Embodiment 9 of this disclosure are compounds of Formula I, or any one of Embodiments 1-8 or a pharmaceutically acceptable salt of any of the foregoing, wherein $R^2$ is (1) phenyl unsubstituted or substituted with 1, 2, or 3 $R^7$, (2) 5- or 6-membered heteroaryl containing 1, 2 or 3 heteroatoms independently selected from N, O, and S, wherein the heteroaryl is unsubstituted or substituted with 1, 2, or 3 $R^7$, (3) $C_{1-6}$alkyl unsubstituted or mono-substituted, disubstituted, or trisubstituted with halogen, OH, $CF_3$, —CN, deuterium, or $(C_{3-6})$cycloalkyl, (4) $(C_{3-6})$cycloalkyl unsubstituted or optionally mono-substituted, disubstituted or trisubstituted with $C_{1-6}$alkyl, halogen, OH, $CF_3$, or —CN, (5) —$(C_{3-6})$alkylC(O)$NH_2$, (6) 4- to 6-membered heterocyclyl containing 1 or 2 heteroatoms independently selected from N, O and S wherein the heterocyclyl is unsubstituted or substituted by 1, 2, or 3 $R^7$, (7) —$CH_2$-heteroaryl unsubstituted or substituted by 1, 2, or 3 $R^7$, (8) —$CH_2$-aryl unsubstituted or substituted by 1, 2, or 3 $R^7$, (9) —$CH_2$-heterocyclyl unsubstituted or substituted by 1, 2, or 3 $R^7$,

(10) —C(═O) $(C_{1-6})$alkyl unsubstituted or substituted with 1, 2, or 3 $R^7$,

(11) —C(═O) $(C_{3-6})$cycloalkyl unsubstituted or substituted with 1, 2, or 3 $R^7$,

(12) —C(═O) $(C_{1-6})$heterocyclyl unsubstituted or substituted with 1, 2, or 3 $R^7$,

(13) —C(═O) aryl unsubstituted or substituted with 1, 2, or 3 $R^7$,

(14) —$SO_2(C_{1-6})$alkyl unsubstituted or substituted with 1, 2, or 3 $R^7$

(15) —$SO_2(C_{3-6})$cycloalkyl unsubstituted or substituted with 1, 2, or 3 $R^7$,

(16) —$SO_2$-aryl unsubstituted or substituted with 1, 2, or 3 $R^7$,

In Embodiment 10 of this disclosure are compounds of Formula I, or Embodiments 1-9, or a class thereof, or a pharmaceutically acceptable salt of any of the foregoing, wherein $R^2$ is (1) phenyl unsubstituted or substituted with 1, 2, or 3 $R^7$,
(2) 5- or 6-membered heteroaryl containing 1, 2 or 3 heteroatoms independently selected from N and S, wherein the heteroaryl is unsubstituted or substituted with 1 or 2 halogen, $C_{1-3}$alkyl, or cyclopropyl,
(3) $C_{1-6}$alkyl unsubstituted or mono-substituted, disubstituted, or trisubstituted with halogen, OH, $CF_3$, —CN, deuterium, or $(C_{3-6})$cycloalkyl,
(4) $(C_{3-6})$cycloalkyl unsubstituted or optionally mono-substituted, disubstituted or trisubstituted with halogen, $C_{1-6}$alkyl, $OC_{1-3}$haloalkyl, OH, $CF_3$, or —CN,
(5) —$(C_{3-6})$alkylC(O)$NH_2$,
(6) 4- to 6-membered heterocyclyl containing 1 or 2 heteroatoms independently selected from N, O and S wherein the heterocyclyl is unsubstituted or substituted with 1 or 2 substituents selected from $CH_3$ or oxo,
(7) —$CH_2$-heteroaryl unsubstituted or substituted with 1 or 2 methyl substituents,
(8) —$CH_2$-aryl,
(9) —$CH_2$-heterocyclyl,
(10) —C(=O) $(C_{1-6})$alkyl,
(11) —C(=O) $(C_{3-6})$cycloalkyl,
(12) —C(=O) $(C_{1-6})$heterocyclyl,
(13) —C(=O) aryl,
(14) —$SO_2(C_{1-6})$alkyl, or
(15) —$SO_2(C_{3-6})$cycloalkyl.

In Embodiment 11 of this disclosure are compounds of Formula I, or Embodiments 1-10, or a class thereof, or a pharmaceutically acceptable salt of any of the foregoing, wherein $R^2$ is (1) phenyl unsubstituted or substituted with halogen or $OCHF_2$,
(2) 5- or 6-membered heteroaryl containing 1, 2 or 3 heteroatoms independently selected from N and S, wherein the heteroaryl is unsubstituted or substituted with 1 or 2 halogen, $C_{1-3}$alkyl, or cyclopropyl,
(3) $C_{1-6}$alkyl unsubstituted or mono-substituted, disubstituted, or trisubstituted with halogen, OH, $CF_3$, —CN, deuterium, or $(C_{3-6})$cycloalkyl,
(4) $(C_{3-6})$cycloalkyl unsubstituted or optionally mono-substituted, disubstituted or trisubstituted with halogen, $C_{1-6}$alkyl, $OC_{1-3}$haloalkyl, OH, $CF_3$, or —CN,
(5) —$(C_{3-6})$alkylC(O)$NH_2$,
(6) 4- to 6-membered heterocyclyl containing 1 or 2 heteroatoms independently selected from N, O and S wherein the heterocyclyl is unsubstituted or substituted with 1 or 2 substituents selected from $CH_3$ or oxo,
(7) —$CH_2$-heteroaryl unsubstituted or substituted with 1 or 2 methyl substituents,
(8) —$CH_2$-aryl,
(9) —$CH_2$-heterocyclyl,
(10) —C(=O) $(C_{1-6})$alkyl,
(11) —C(=O) $(C_{3-6})$cycloalkyl,
(12) —C(=O) $(C_{1-6})$heterocyclyl,
(13) —C(=O) aryl,
(14) —$SO_2(C_{1-6})$alkyl, or
(15) —$SO_2(C_{3-6})$cycloalkyl.

In Embodiment 12 of this disclosure are compounds of Formula I, or Embodiments 1-11, or a class thereof, or a pharmaceutically acceptable salt of any of the foregoing, wherein $R^2$ is phenyl unsubstituted or substituted with halogen or $OCHF_2$.

In Embodiment 13 of this disclosure are compounds of Formula I, or Embodiments 1-11, or a class thereof, or a pharmaceutically acceptable salt of any of the foregoing, wherein $R^2$ is 5- or 6-membered heteroaryl containing 1, 2 or 3 heteroatoms independently selected from N and S, wherein the heteroaryl is unsubstituted or substituted with 1 or 2 halogen, $C_{1-3}$alkyl, or cyclopropyl.

In Embodiment 14 of this disclosure are compounds of Formula I, or Embodiments 1-11, or a class thereof, or a pharmaceutically acceptable salt of any of the foregoing, wherein $R^2$ is $C_{1-6}$alkyl unsubstituted or optionally mono-substituted, disubstituted, or trisubstituted with halogen, OH, $CF_3$, —CN, deuterium, or $(C_{3-6})$cycloalkyl.

In Embodiment 15 of this disclosure are compounds of Formula I, or Embodiments 1-11, or a class thereof, or a pharmaceutically acceptable salt of any of the foregoing, wherein $R^2$ is $(C_{3-6})$cycloalkyl unsubstituted or optionally mono-substituted, disubstituted or trisubstituted with halogen, $C_{1-6}$alkyl, $OC_{1-3}$haloalkyl, OH, $CF_3$, or —CN.

In Embodiment 16 of this disclosure are compounds of Formula I, or Embodiments 1-11, or a class thereof, or a pharmaceutically acceptable salt of any of the foregoing, wherein $R^2$ is —$(C_{3-6})$alkylC(O)$NH_2$.

In Embodiment 17 of this disclosure are compounds of Formula I, or Embodiments 1-11, or a class thereof, or a pharmaceutically acceptable salt of any of the foregoing, wherein $R^2$ is 4- to 6-membered heterocyclyl containing 1 or 2 heteroatoms independently selected from N, O and S wherein the heterocyclyl is unsubstituted or substituted with 1 or 2 substituents selected from $CH_3$ or oxo.

In Embodiment 18 of this disclosure are compounds of Formula I, or Embodiments 1-11, or a class thereof, or a pharmaceutically acceptable salt of any of the foregoing, wherein $R^2$ is —$CH_2$-heteroaryl unsubstituted or substituted with 1 or 2 methyl substituents.

In Embodiment 19 of this disclosure are compounds of Formula I, or Embodiments 1-11, or a class thereof, or a pharmaceutically acceptable salt of any of the foregoing, wherein $R^2$ is —$CH_2$-aryl.

In Embodiment 20 of this disclosure are compounds of Formula I, or Embodiments 1-11, or a class thereof, or a pharmaceutically acceptable salt of any of the foregoing, wherein $R^2$ is —$CH_2$-heterocyclyl.

In Embodiment 21 of this disclosure are compounds of Formula I, or Embodiments 1-11, or a class thereof, or a pharmaceutically acceptable salt of any of the foregoing, wherein $R^2$ is —C(=O) $(C_{1-6})$alkyl.

In Embodiment 22 of this disclosure are compounds of Formula I, or Embodiments 1-11, or a class thereof, or a pharmaceutically acceptable salt of any of the foregoing, wherein $R^2$ is —C(=O) $(C_{3-6})$cycloalkyl.

In Embodiment 23 of this disclosure are compounds of Formula I, or Embodiments 1-11, or a class thereof, or a pharmaceutically acceptable salt of any of the foregoing, wherein $R^2$ is —C(=O) $(C_{1-6})$heterocyclyl.

In Embodiment 24 of this disclosure are compounds of Formula I, or Embodiments 1-11, or a class thereof, or a pharmaceutically acceptable salt of any of the foregoing, wherein $R^2$ is —C(=O) aryl.

In Embodiment 25 of this disclosure are compounds of Formula I, or Embodiments 1-11, or a class thereof, or a pharmaceutically acceptable salt of any of the foregoing, wherein $R^2$ is —$SO_2(C_{1-6})$alkyl.

In Embodiment 26 of this disclosure are compounds of Formula I, or Embodiments 1-11, or a class thereof, or a pharmaceutically acceptable salt of any of the foregoing, wherein $R^2$ is $-SO_2(C_{3-6})$cycloalkyl.

In Embodiment 27 of this disclosure are compounds of Formula I, or Embodiments 1-26, or a class thereof, or a pharmaceutically acceptable salt of any of the foregoing, wherein $R^2$ is

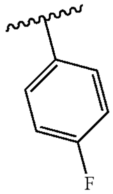 , 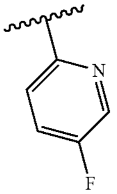 , 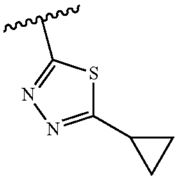 ,

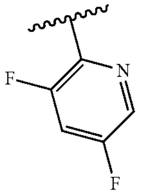 , 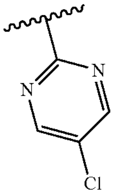 , 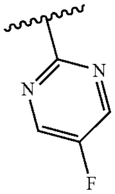 ,

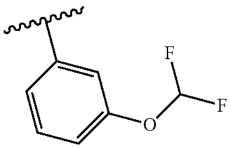 , 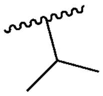 , 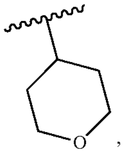 ,

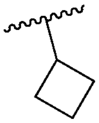 , 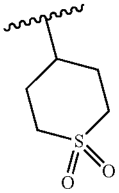 , 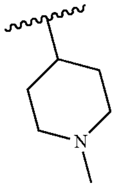 ,

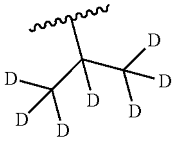 , 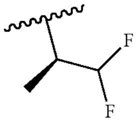 , 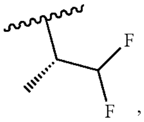 ,

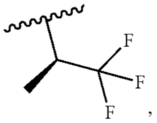 , 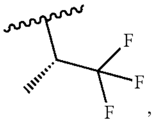 , 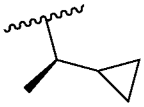 ,

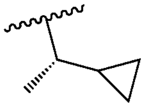 , 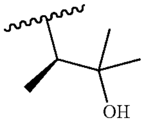 , 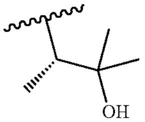 ,

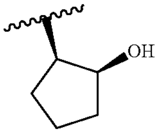 , 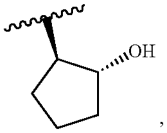 , 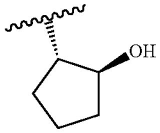 ,

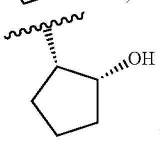 , 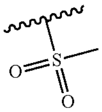 , 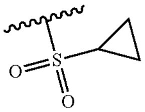 ,

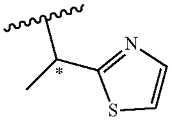 , 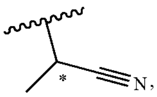 , 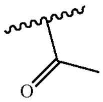 ,

-continued

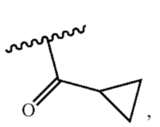 , 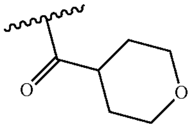 ,

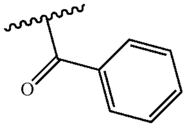 , 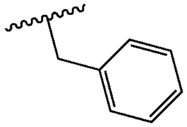 , or

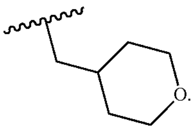

In Embodiment 28 of this disclosure are compounds of Formula I, or Embodiments 1-12, or 27, or a class thereof, or a pharmaceutically acceptable salt of any of the foregoing, wherein $R^2$ is

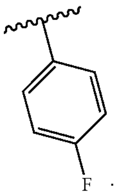

In Embodiment 29 of this disclosure are compounds of Formula I, or Embodiments 1-11, 13, or 27, or a class thereof, or a pharmaceutically acceptable salt of any of the foregoing, wherein $R^2$ is

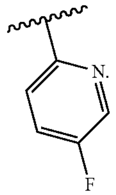 [SMILES: *c1ccc(F)cn1]

In Embodiment 30 of this disclosure are compounds of Formula I, or Embodiments 1-11, 14, or 27, or a class thereof, or a pharmaceutically acceptable salt of any of the foregoing, wherein $R^2$ is

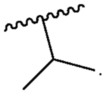

In Embodiment 31 of this disclosure are compounds of Formula I, or Embodiments 1-11, 14, or 27, or a class thereof, or a pharmaceutically acceptable salt of any of the foregoing, wherein $R^2$ is

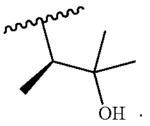 [SMILES: *[C@H](C)C(C)(C)O]

In Embodiment 32 of this disclosure are compounds of Formula I, or Embodiments 1-11, 14, or 27, or a class thereof, or a pharmaceutically acceptable salt of any of the foregoing, wherein $R^2$ is

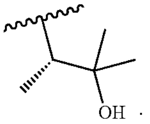 [SMILES: *[C@@H](C)C(C)(C)O]

In Embodiment 33 of this disclosure are compounds of Formula I, or Embodiments 1-11, 14, or 27, or a class thereof, or a pharmaceutically acceptable salt of any of the foregoing, wherein $R^2$ is

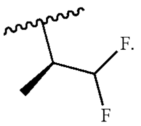 [SMILES: *[C@H](C)C(F)F]

In Embodiment 34 of this disclosure are compounds of Formula I, or Embodiments 1-11, 14, or 27, or a class thereof, or a pharmaceutically acceptable salt of any of the foregoing, wherein $R^2$ is

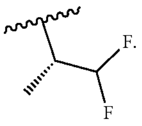 [SMILES: *[C@@H](C)C(F)F]

In Embodiment 35 of this disclosure are compounds of Formula I, or any one of Embodiments 1-34, or a pharmaceutically acceptable salt of any of the foregoing, wherein $R^3$ is (1) 4- to 7-membered heterocyclyl containing 1 or 2 heteroatoms independently selected from N, O and S,
(2) 5- or 6-membered heteroaryl containing 1, 2 or 3 heteroatoms independently selected from N, O, and S,
(3) —($C_{1-6}$)alkyl-heteroaryl, wherein the heteroaryl is a 5- or 6-membered heteroaryl containing 1, 2, or 3 heteroatoms independently selected from N, O and S,
(4) —($C_{1-6}$)alkyl-aryl,
(5) —($C_{1-6}$)alkyl-heterocyclyl, wherein the heterocyclyl is a 3- to 6-membered ring containing 1 or 2 heteroatoms independently selected from N, O and S,
(6) —($C_{1-6}$)alkyl,
(7) —($C_{3-6}$)cycloalkyl,
(8) —($C_{3-6}$)cycloalkyl-heterocyclyl wherein the heterocyclyl is a 3- to 6-membered ring containing 1 or 2 heteroatoms independently selected from N, O and S,
(9) —($C_{1-6}$)hydroxyalkyl,
(10) —($C_{1-6}$)alkyl-S(O)$_2$—$NR^{8a}R^{8b}$,
(11) —($C_{1-6}$)alkyl-S(O)$_2$—($C_{1-3}$)alkyl,
(12) —($C_{1-3}$)alkyl-heteroaryl, wherein the heteroaryl is an 8- to 10-membered fused ring, and wherein the heteroaryl contains 1, 2, 3, or 4 heteroatoms independently selected from N, O, and S,
(13) —($C_{1-6}$)alkyl-SONH—($C_{1-3}$)alkyl,
(14) —($C_{1-6}$)alkyl-($C_{3-6}$)cycloalkyl,
(15) fused aryl,
(16) —C($_{1-6}$)alkyl-N($R^1$)$_2$,
(17) —C($_{1-6}$)alkyl-O—$C_{1-3}$alkyl, or
(18) —C($_{1-6}$)alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 36 of this disclosure are compounds of Formula I, or any one of Embodiments 1-35, or a pharmaceutically acceptable salt of any of the foregoing, wherein $R^3$ is (1) 4- to 7-membered heterocyclyl containing 1 or 2 heteroatoms independently selected from N, O and S,
(2) 5- or 6-membered heteroaryl containing 1, 2 or 3 heteroatoms independently selected from N, O, and S,
(3) —($C_{1-6}$)alkyl-heteroaryl, wherein the heteroaryl is a 5- or 6-membered heteroaryl containing 1, 2, or 3 heteroatoms independently selected from N, O and S,
(4) —($C_{1-6}$)alkyl-aryl,
(5) —($C_{1-6}$)alkyl-heterocyclyl, wherein the heterocyclyl is a 3- to 6-membered ring containing 1 or 2 heteroatoms independently selected from N, O and S,
(6) —($C_{1-6}$)alkyl,
(7) —($C_{3-6}$)cycloalkyl,
(8) —($C_{3-6}$)cycloalkyl-heterocyclyl wherein the heterocyclyl is a 3- to 6-membered ring containing 1 or 2 heteroatoms independently selected from N, O and S,
(9) —($C_{1-6}$)alkyl-S(O)$_2$—$NR^{8a}R^{8b}$,
(10) —C($_{1-6}$)alkyl-O—$C_{1-3}$alkyl, or
(11) —C($_{1-6}$)alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 37 of this disclosure are compounds of Formula I, or any one of Embodiments 1-36, or a pharmaceutically acceptable salt of any of the foregoing, wherein $R^3$ is 4- to 7-membered heterocyclyl containing 1 or 2 heteroatoms independently selected from N, O and S, wherein the heterocyclyl is unsubstituted or substituted with 1, 2, or 3 $R^9$.

In Embodiment 38 of this disclosure are compounds of Formula I, or any one of Embodiments 1-36, or a pharmaceutically acceptable salt of any of the foregoing, wherein $R^3$ is a 5- or 6-membered heteroaryl containing 1, 2 or 3 heteroatoms independently selected from N, O, and S, wherein the heteroaryl is unsubstituted or substituted with 1, 2, or 3 $R^9$.

In Embodiment 39 of this disclosure are compounds of Formula I, or any one of Embodiments 1-36, or a pharmaceutically acceptable salt of any of the foregoing, wherein $R^3$ is —($C_{1-6}$)alkyl-heteroaryl, wherein the heteroaryl is a 5- or 6-membered heteroaryl containing 1, 2, or 3 heteroatoms independently selected from N, O and S, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 40 of this disclosure are compounds of Formula I, or any one of Embodiments 1-36, or a pharmaceutically acceptable salt of any of the foregoing, wherein $R^3$ is —$(C_{1-6})$alkyl-aryl, wherein each aryl, fused aryl, or cycloalkyl, is unsubstituted or substituted with 1, 2, or 3 $R^9$, and wherein each alkyl is unsubstituted or substituted with 1, 2, or 3 $R^{10}$.

In Embodiment 41 of this disclosure are compounds of Formula I, or any one of Embodiments 1-36, or a pharmaceutically acceptable salt of any of the foregoing, wherein $R^3$ is —$(C_{1-6})$alkyl-heterocyclyl, wherein the heterocyclyl is a 3- to 6-membered ring containing 1 or 2 heteroatoms independently selected from N, O and S, wherein each cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 42 of this disclosure are compounds of Formula I, or any one of Embodiments 1-36, or a pharmaceutically acceptable salt of any of the foregoing, wherein $R^3$ is —$(C_{1-6})$alkyl, wherein each alkyl is unsubstituted or substituted with 1, 2, or 3 $R^{10}$.

In Embodiment 43 of this disclosure are compounds of Formula I, or any one of Embodiments 1-36, or a pharmaceutically acceptable salt of any of the foregoing, wherein $R^3$ is —$(C_{3-6})$cycloalkyl, wherein each cycloalkyl, is unsubstituted or substituted with 1, 2, or 3 $R^9$.

In Embodiment 44 of this disclosure are compounds of Formula I, or any one of Embodiments 1-36, or a pharmaceutically acceptable salt of any of the foregoing, wherein $R^3$ is —$(C_{3-6})$cycloalkyl-heterocyclyl wherein the heterocyclyl is a 3- to 6-membered ring containing 1 or 2 heteroatoms independently selected from N, O and S, wherein each cycloalkyl, or heterocyclyl is unsubstituted or substituted with 1, 2, or 3 $R^9$, and wherein each alkyl is unsubstituted or substituted with 1, 2, or 3 $R^{10}$.

In Embodiment 45 of this disclosure are compounds of Formula I, or any one of Embodiments 1-36, or a pharmaceutically acceptable salt of any of the foregoing, wherein $R^3$ is —$(C_{1-6})$alkyl-$S(O)_2$—$NR^{8a}R^{8b}$, wherein each alkyl is unsubstituted or substituted with 1, 2, or 3 $R^{10}$.

In Embodiment 46 of this disclosure are compounds of Formula I, or any one of Embodiments 1-36, or a pharmaceutically acceptable salt of any of the foregoing, wherein $R^3$ is —$C_{(1-6)}$alkyl-O—$C_{1-3}$alkyl or —$C_{(1-6)}$alkyl-O—$C_{3-6}$ cycloalkyl, and wherein each alkyl is unsubstituted or substituted with 1, 2, or 3 $R^{10}$, and wherein the cycloalkyl is unsubstituted or substituted with 1, 2, or 3 $R^9$.

In Embodiment 47 of this disclosure are compounds of Formula I, or any one of Embodiments 1-36, or a pharmaceutically acceptable salt of any of the foregoing, wherein $R^3$ is

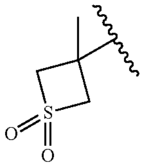
,
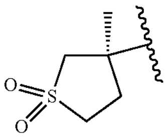
,
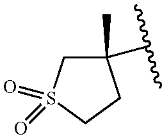
,
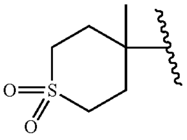
,
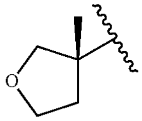
,
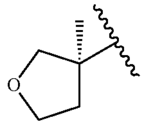
, -continued

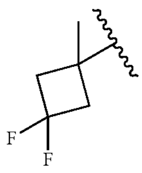
,
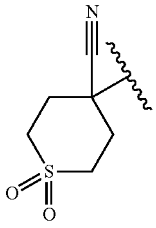
,
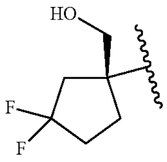
,
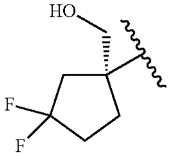
,
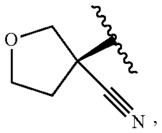
,
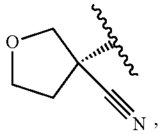
,
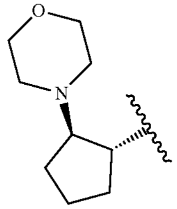
,
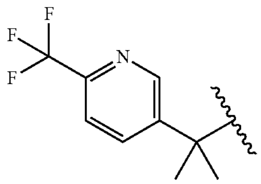
,
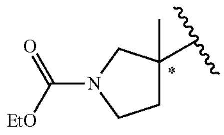
,
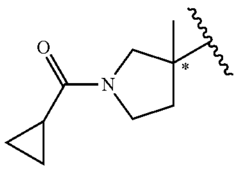
,
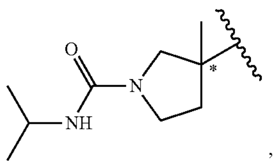
,
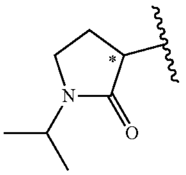
,
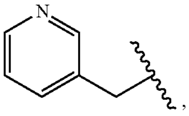
,
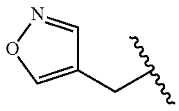
,
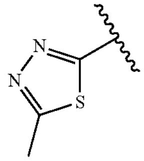
,
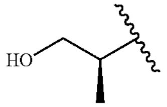
,
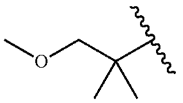
,
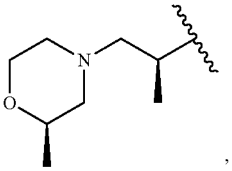
,
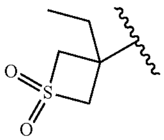
,
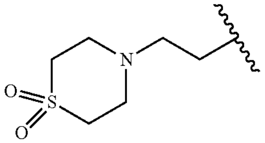
, or
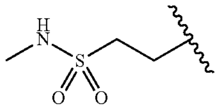
.

In Embodiment 48 of this disclosure are compounds of Formula I, or any one of Embodiments 1-38 or 47, or a pharmaceutically acceptable salt of any of the foregoing, wherein $R^3$ is

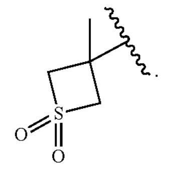 [SMILES: *C1(C)CS(=O)(=O)C1]

In Embodiment 49 of this disclosure are compounds of Formula I, or any one of Embodiments 1-38 or 47, or a pharmaceutically acceptable salt of any of the foregoing, wherein $R^3$ is

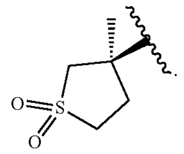 [SMILES: *[C@@]1(C)CCS(=O)(=O)C1]

In Embodiment 50 of this disclosure are compounds of Formula I, I-a, or I-b, or any one of Embodiments 1-38 or 47, or a pharmaceutically acceptable salt of any of the foregoing, wherein $R^3$ is

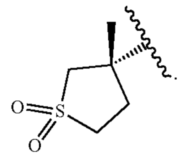 [SMILES: *[C@]1(C)CCS(=O)(=O)C1]

In Embodiment 51 of this disclosure are compounds of Formula I, I-a, or I-b, or any one of Embodiments 1-38 or 47, or a pharmaceutically acceptable salt of any of the foregoing, wherein $R^3$ is

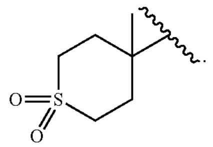 [SMILES: *C1(C)CCS(=O)(=O)CC1]

In Embodiment 52 of this disclosure are compounds of Formula I, I-a, or I-b, or Embodiments 1-51, or a class thereof, or a pharmaceutically acceptable salt of any of the foregoing, wherein $R^4$ is H.

In Embodiment 53 of this disclosure are compounds of Formula I, I-a, or I-b, or Embodiments 1-52, or a class thereof, or a pharmaceutically acceptable salt of any of the foregoing, wherein $R^5$ is H, halogen, or CN.

In Embodiment 54 of this disclosure are compounds of Formula I, I-a, or I-b, or Embodiments 1-53, or a class thereof, or a pharmaceutically acceptable salt of any of the foregoing, wherein $R^5$ is H, F, Cl, or CN.

In Embodiment 55 of this disclosure are compounds of Formula I, or Embodiments 1-54, or a class thereof, or a pharmaceutically acceptable salt of any of the foregoing, wherein $R^6$ is halogen, hydroxy, CN, $C_{1-3}$alkyl, $C_{1-3}$haloalkyl, $C_{3-6}$cycloalkyl, $OC_{1-3}$alkyl, $OC_{1-3}$haloalkyl, $OC_{3-6}$cycloalkyl, $S(O)_2C_{1-3}$alkyl, $S(O)_2NHC_{1-3}$alkyl, $C(O)NHC_{1-3}$alkyl, $C_{1-6}$alkyl-$NR^{11}R^{11}$, or 5 membered heteroaryl with 2 N atoms, and wherein the cycloalkyl is optionally substituted with halogen.

In Embodiment 56 of this disclosure are compounds of Formula I, I-a, or I-b, or Embodiments 1-55, or a class thereof, or a pharmaceutically acceptable salt of any of the foregoing, wherein $R^6$ is $C_{1-3}$alkyl, O—$C_{3-6}$cycloalkyl, $OC_{1-3}$alkyl, $S(O)_2C_{1-3}$alkyl, $S(O)_2NHC_{1-3}$alkyl, $C(O)NHC_{1-3}$alkyl, $C_{1-6}$alkyl-$NR^{11}R^{11}$, or 5 membered heteroaryl with 2 N atoms, and wherein the cycloalkyl is additionally optionally substituted with 1-3 F.

In Embodiment 57 of this disclosure are compounds of Formula I, I-a, or I-b, or Embodiments 1-56, or a class thereof, or a pharmaceutically acceptable salt of any of the foregoing, wherein $R^6$ is F, Cl, $CHF_2$, $CH_3$, $OCHF_2$, $OCF_3$, $OCH_2CH_3$, $OCH(CH_3)_2$, $OCF_2CHF_2$, $OCH_2CHF_2$, $C(CH_3)F_2$, $CH_2CN$, $C(O)NHC(CH_3)_3$, $OCH_3CN$, $CH_2CH_3$, CN, $C(CH_3)_2NH_2$, $S(O_2)CH_3$, $S(O_2)NHCH_2CH_3$, $OCD_2CD_3$, pyrazolidine, cyclopropyl, cyclobutyl, or O-cyclopropyl, and wherein the cyclopropyl or cyclobutyl is additionally optionally substituted with one to three halogen atoms. CN, $CF_3$, or OH.

In Embodiment 58 of this disclosure are compounds of Formula I, I-a, or I-b, or Embodiments 1-57, or a class thereof, or a pharmaceutically acceptable salt of any of the foregoing, wherein $R^6$ is $CH_3$, $OCH_2CH_3$, $C(O)NHC(CH_3)_3$, $C(CH_3)_2NH_2$, $S(O_2)CH_3$, $S(O_2)NHCH_2CH_3$, $OCD_2CD_3$, pyrazolidine, or O-cyclopropyl, and wherein the cyclopropyl is additionally optionally substituted with one to three halogen atoms. CN, $CF_3$, or OH.

In Embodiment 59 of this disclosure are compounds of Formula I, I-a, or I-b, or Embodiments 1-58, or a class thereof, or a pharmaceutically acceptable salt of any of the foregoing, wherein $R^7$ is halogen, oxo, $C_{1-6}$alkyl, $OC_{1-6}$haloalkyl, CN, deuterium, or $C_{3-6}$cycloalkyl.

In Embodiment 60 of this disclosure are compounds of Formula I, I-a, or I-b, or Embodiments 1-59, or a class thereof, or a pharmaceutically acceptable salt of any of the foregoing, wherein $R^7$ is F, Cl, oxo, $OCHF_2$, $CH_3$, CN, deuterium, or cyclopropyl.

In Embodiment 61 of this disclosure are compounds of Formula I, I-a, or I-b, or Embodiments 1-60, or a class thereof, or a pharmaceutically acceptable salt of any of the foregoing, wherein $R^{8a}$ and $R^{8b}$ are independently selected from hydrogen or $(C_{1-3})$alkyl.

In Embodiment 62 of this disclosure are compounds of Formula I, I-a, or I-b, or Embodiments 1-61, or a class thereof, or a pharmaceutically acceptable salt of any of the foregoing, wherein $R^{8a}$ is H.

In Embodiment 63 of this disclosure are compounds of Formula I, I-a, or I-b, or Embodiments 1-62, or a class thereof, or a pharmaceutically acceptable salt of any of the foregoing, wherein $R^{8b}$ is H.

I In Embodiment 64 of this disclosure are compounds of Formula I, I-a, or I-b, or Embodiments 1-61, or a class thereof, or a pharmaceutically acceptable salt of any of the foregoing, wherein $R^{8a}$ is $CH_3$.

In Embodiment 65 of this disclosure are compounds of Formula I, I-a, or I-b, or Embodiments 1-61, or a class thereof, or a pharmaceutically acceptable salt of any of the foregoing, wherein $R^{8b}$ is $CH_3$.

In Embodiment 66 of this disclosure are compounds of Formula I, I-a, or I-b, or Embodiments 1-65, or a class thereof, or a pharmaceutically acceptable salt of any of the foregoing, wherein $R^9$ is =O, halogen, OH, $C_{1-6}$alkyl, $C_{1-6}$haloalkyl, $C_{1-3}$alkyl-CN, $C(O)C_{1-6}$alkyl, $C(O)C_{3-6}$cycloalkyl, $C(O)C_{1-3}alkylOH$, $C(O)NHC_{1-3}alkyl$, $C_{1-6}alkylOH$, or a 6 membered heterocycle containing one Oxygen and one Nitrogen atom.

In Embodiment 67 of this disclosure are compounds of Formula I, I-a, or I-b, or Embodiments 1-66, or a class thereof, or a pharmaceutically acceptable salt of any of the foregoing, wherein $R^9$ is ═O, $CH_3$, $CH_2CH_3$, F, $CF_3$, $CH_3CN$, C(O)cyclopropyl, C(O)EtO, $CH(CH_3)_2$, or $C(O)NHCH(CH_3)_2$, or a 6 membered heterocycle containing one Oxygen and one Nitrogen atom.

In Embodiment 68 of this disclosure are compounds of Formula I, I-a, or I-b, or Embodiments 1-67, or a class thereof, or a pharmaceutically acceptable salt of any of the foregoing, wherein $R^{10}$ is ═O, halogen, OH, $C_{1-6}alkyl$, $C_{1-6}haloalkyl$, or $C_{1-6}alkylOH$.

In Embodiment 69 of this disclosure are compounds of Formula I, I-a, or I-b, or Embodiments 1-68, or a class thereof, or a pharmaceutically acceptable salt of any of the foregoing, wherein $R^{10}$ is OH, $CH_3$, or $OCH_3$.

In Embodiment 70 of this disclosure are compounds of Formula or any one of Embodiments 1-69, or a pharmaceutically acceptable salt of any of the foregoing, wherein X and Y are $C(R^5)$.

In Embodiment 71 of this disclosure are compounds of Formula or any one of Embodiments 1-69, or a pharmaceutically acceptable salt of any of the foregoing, wherein X is O, and Y is $C(R^5)$ In Embodiment 72 of this disclosure are compounds of Formula or any one of Embodiments 1-69, or a pharmaceutically acceptable salt of any of the foregoing, wherein X is $C(R^5)$, and Y is O.

In Embodiment 73, the present invention provides a compound as described in any one of Examples 1-128 as set forth below, or a pharmaceutically acceptable salt thereof.

In Embodiment 74 of the invention, the compound of formula I, or a pharmaceutically acceptable salt thereof, is:

3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (S)-3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N-(3-methyl-1,1-dioxidothietan-3-yl)-4,5,6,7-tetrahydro-1H-indazole-6-carboxamide, 1-(5-cyclopropyl-1,3,4-thiadiazol-2-yl)-3-(5-(difluoromethoxy)pyridin-3-yl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N—((R)-3-methyltetrahydrofuran-3-yl)-4,5,6,7-tetrahydro-1H-indazole-6-carboxamide, (R)-3-(3-(difluoromethoxy)phenyl)-1-(5-fluoropyridin-2-yl)-N—((S)-3-methyltetrahydrofuran-3-yl)-4,5,6,7-tetrahydro-1H-indazole-6-carboxamide, (R)—N-(3,3-difluoro-1-methylcyclobutyl)-3-(3-(difluoromethoxy)phenyl)-1-(5-fluoropyridin-2-yl)-4,5,6,7-tetrahydro-1H-indazole-6-carboxamide, (R)—N—((R)-3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide, (R)—N—((S)-3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide, (R)-3-(3-(difluoromethoxy)phenyl)-1-(3,5-difluoropyridin-2-yl)-N-(3-methyl-1,1-dioxidothietan-3-yl)-4,5,6,7-tetrahydro-1H-indazole-6-carboxamide, 1-(5-chloropyrimidin-2-yl)-3-(3-(difluoromethoxy)phenyl)-N—((S)-3-methyl-1,1-dioxidotetrahydrothiophen-3-yl)-4,5,6,7-tetrahydro-1H-indazole-6-carboxamide, ((R)-3-(5-(difluoromethoxy)-2-fluorophenyl)-1-(3,5-difluoropyridin-2-yl)-N-(3-methyl-1,1-dioxidothietan-3-yl)-4,5,6,7-tetrahydro-1H-indazole-6-carboxamide, (R)-3-(5-(difluoromethoxy)pyridin-3-yl)-1-(5-fluoropyridin-2-yl)-N-(3-methyl-1,1-dioxidothietan-3-yl)-4,5,6,7-tetrahydro-1H-indazole-6-carboxamide, (R)-3-(3-(3,3-difluorocyclobutyl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(5-(difluoromethoxy)pyridin-3-yl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)—N—((S)-3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide, (R)—N—((R)-3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide, 3-(3-(difluoromethoxy)phenyl)-1-(5-fluoropyridin-2-yl)-N-((1R,2R)-2-morpholinocyclopentyl)-4,5,6,7-tetrahydro-1H-indazole-6-carboxamide, (R)-3-(2-(difluoromethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(3-(difluoromethoxy)phenyl)-N-(3-methyl-1,1-dioxidothietan-3-yl)-1-(tetrahydro-2H-pyran-4-yl)-4,5,6,7-tetrahydro-1H-indazole-6-carboxamide, (R)-3-(3-(difluoromethoxy)phenyl)-1-(1,1-dioxidotetrahydro-2H-thiopyran-4-yl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-isopropyl-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-isopropyl-N-(3-methyl-1,1-dioxidothietan-3-yl)-4,5,6,7-tetrahydro-1H-indazole-6-carboxamide, (R)-3-(3-(difluoromethoxy)phenyl)-1-(tetrahydro-2H-pyran-4-yl)-N-(2-(6-(trifluoromethyl)pyridin-3-yl)propan-2-yl)-4,5,6,7-tetrahydro-1H-indazole-6-carboxamide, (R)-3-(5-(difluoromethoxy)-2-fluorophenyl)-1-isopropyl-N—((S)-3-methyl-1,1-dioxidotetrahydrothiophen-3-yl)-4,5,6,7-tetrahydro-1H-indazole-6-carboxamide, (R)-3-(5-(difluoromethoxy)-2-fluorophenyl)-1-isopropyl-N—((R)-3-methyl-1,1-dioxidotetrahydrothiophen-3-yl)-4,5,6,7-tetrahydro-1H-indazole-6-carboxamide, (R)-3-(5-(difluoromethoxy)-2-fluorophenyl)-1-isopropyl-N-(4-methyl-1,1-dioxidotetrahydro-2H-thiopyran-4-yl)-4,5,6,7-tetrahydro-1H-indazole-6-carboxamide, (R)-3-(3-(difluoromethoxy)phenyl)-1-isopropyl-N-(4-methyl-1,1-dioxidotetrahydro-2H-thiopyran-4-yl)-4,5,6,7-tetrahydro-1H-indazole-6-carboxamide, (R)-3-(3-cyclopropoxyphenyl)-1-isopropyl-N-(4-methyl-1,1-dioxidotetrahydro-2H-thiopyran-4-yl)-4,5,6,7-tetrahydro-1H-indazole-6-carboxamide, (R)-3-(3-ethoxyphenyl)-1-isopropyl-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-isopropyl-N-(3-methyl-1,1-dioxidothietan-3-yl)-4,5,6,7-tetrahydro-1H-indazole-6-carboxamide, (R)-1-isopropyl-N—((S)-3-methyl-1,1-dioxidotetrahydrothiophen-3-yl)-3-(3-(2,2,2-trifluoroethoxy)phenyl)-4,5,6,7-tetrahydro-1H-indazole-6-carboxamide, (R)-1-isopropyl-N-(4-methyl-1,1-dioxidotetrahydro-2H-thiopyran-4-yl)-3-(3-(1,1,2,2-tetrafluoroethoxy)phenyl)-4,5,6,7-tetrahydro-1H-indazole-6-carboxamide, (R)-3-(2-cyclopropoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(5-fluoro-2-isopropoxypyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(5-chloro-2-ethoxypyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(2-(2,2-difluoroethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(2-(difluoromethoxy)-5-fluoropyridin-4-yl)-1-isopropyl-N—((S)-3-methyl-1,1-dioxidotetrahydrothiophen-3-yl)-4,5,6,7-tetrahydro-1H-indazole-6-carboxamide, (R)-3-(5-(difluoromethoxy)-2-(difluoromethyl)pyridin-3-yl)-1-isopropyl-N-(4-methyl-1,1-dioxidotetrahydro-2H-thiopyran-4-yl)-4,5,6,7-tetrahydro-1H-indazole-6-carboxamide, (R)-3-(5-fluoro-2-(2,2,2-trifluoroethoxy)pyridin-4-yl)-1-isopropyl-N-(3-methyl-1,1-dioxidothietan-3-yl)-4,5,6,7-tetrahydro-1H-indazole-6-carboxamide, (R)-3-(5-fluoro-2-(2,2,2-trifluoroethoxy)pyridin-4-yl)-1-isopropyl-N—((S)-3-methyl-1,1-dioxidotetrahydrothiophen-3-yl)-4,5,6,7-tetrahydro-1H-indazole-6-carboxamide, (R)-3-(5-fluoro-2-(2,2,2-trifluoroethoxy)pyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-3-(5-(difluoromethoxy)-2-fluorophenyl)-N-(4-methyl-1,1-dioxidotetrahydro-2H-thiopyran-4-yl)-1-(propan-2-yl-$d_7$)-4,5,6,7-tetrahydro-1H-indazole-6-carboxamide, (R)-3-(2-ethoxy-5-fluoropyridin-4-yl)-N-(4-methyl-1,1-dioxidotetrahydro-2H-thiopyran-4-yl)-1-(propan-2-yl-$d_7$)-4,5,6,7-tetrahydro-1H-indazole-6-carboxamide, (R)-3-(5-(difluoromethoxy)-2-fluorophenyl)-1-((R)-1,1-difluoropropan-2-yl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((S)-1,1-difluoropropan-2-yl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((R)-1,1-difluoropropan-2-yl)-N-(4-methyl-1,1-dioxidotetrahydro-2H-thiopyran-4-yl)-4,5,6,7-tetrahydro-1H-indazole-6-carboxamide, (R)-3-(5-(difluoromethoxy)-2-fluorophenyl)-1-((S)-1,1-difluoropropan-2-yl)-N-(4-methyl-1,1-dioxidotetrahydro-2H-thiopyran-4-yl)-4,5,6,7-tetrahydro-1H-indazole-6-carboxamide, (R)-3-(2-(ethoxy-$d_5$)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)—N-(4-cyano-1,1-dioxidotetrahydro-2H-thiopyran-4-yl)-3-(5-(difluoromethoxy)-2-fluorophenyl)-1-(propan-2-yl-$d_7$)-4,5,6,7-tetrahydro-1H-indazole-6-carboxamide, (R)—N-(4-cyano-1,1-dioxidotetrahydro-2H-thiopyran-4-yl)-3-(5-(difluoromethoxy)-2-fluorophenyl)-1-isopropyl-4,5,6,7-tetrahydro-1H-indazole-6-carboxamide, (R)-3-(2-ethoxy-5-fluoropyridin-4-yl)-N-(4-methyl-1,1-dioxidotetrahydro-2H-thiopyran-4-yl)-1-((R)-1,1,1-trifluoropropan-2-yl)-4,5,6,7-tetrahydro-1H-indazole-6-carboxamide, (R)-3-(2-ethoxy-5-fluoropyridin-4-yl)-N-(4-methyl-1,1-dioxidotetrahydro-2H-thiopyran-4-yl)-1-((S)-1,1,1-trifluoropropan-2-yl)-4,5,6,7-tetrahydro-1H-indazole-6-carboxamide, (R)-3-(5-ethoxy-2-fluorophenyl)-1-isopropyl-N-(4-methyl-1,1-dioxidotetrahydro-2H-thiopyran-4-yl)-4,5,6,7-tetrahydro-1H-indazole-6-carboxamide, (R)-1-isopropyl-N-(4-methyl-1,1-dioxidotetrahydro-2H-thiopyran-4-yl)-3-(3-(trifluoromethoxy)phenyl)-4,5,6,7-tetrahydro-1H-indazole-6-carboxamide, (R)-3-(5-(difluoromethoxy)pyridin-3-yl)-1-isopropyl-N-(4-methyl-1,1-dioxidotetrahydro-2H-thiopyran-4-yl)-4,5,6,7-tetrahydro-1H-indazole-6-carboxamide, (R)-1-cyclobutyl-3-(5-(difluoromethoxy)-2-fluorophenyl)-N-(3-methyl-1,1-dioxidothietan-3-yl)-4,5,6,7-tetrahydro-1H-indazole-6-carboxamide, (R)-1-((R)-1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide, (R)-1-((S)-1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide, ethyl 3-((R)-3-(5-(difluoromethoxy)-2-fluorophenyl)-1-isopropyl-4,5,6,7-tetrahydro-1H-indazole-6-carboxamido)-3-methylpyrrolidine-1-carboxylate, (6R)-3-(5-(difluoromethoxy)-2-fluorophenyl)-1-isopropyl-N-(1-(isopropylcarbamoyl)-3-methylpyrrolidin-3-yl)-4,5,6,7-tetrahydro-1H-indazole-6-carboxamide, (6R)—N-(1-(cyclopropanecarbonyl)-3-methylpyrrolidin-3-yl)-3-(5-(difluoromethoxy)-2-fluorophenyl)-1-isopropyl-4,5,6,7-tetrahydro-1H-indazole-6-carboxamide, (R)-3-(2-fluoro-5-isopropoxyphenyl)-1-isopropyl-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-isopropyl-N-(3-methyl-1,1-dioxidothietan-3-yl)-4,5,6,7-tetrahydro-1H-indazole-6-carboxamide, (R)-3-(5-cyclopropyl-2-fluorophenyl)-1-isopropyl-N-(3-methyl-1,1-dioxidothietan-3-yl)-4,5,6,7-tetrahydro-1H-indazole-6-carboxamide, (R)-3-(2-chloro-5-(difluoromethoxy)phenyl)-1-isopropyl-N-(3-methyl-1,1-dioxidothietan-3-yl)-4,5,6,7-tetrahydro-1H-indazole-6-carboxamide, (R)-3-(5-cyclopropoxy-2-fluorophenyl)-1-isopropyl-N-(3-methyl-1,1-dioxidothietan-3-yl)-4,5,6,7-tetrahydro-1H-indazole-6-carboxamide, (R)-3-(5-(difluoromethoxy)-2-methylpyridin-3-yl)-1-isopropyl-N-(3-methyl-1,1-dioxidothietan-3-yl)-4,5,6,7-tetrahydro-1H-indazole-6-carboxamide, (R)-3-(5-ethoxy-2,3-difluorophenyl)-1-isopropyl-N-(3-methyl-1,1-dioxidothietan-3-yl)-4,5,6,7-tetrahydro-1H-indazole-6-carboxamide, (R)-3-(2-chloro-5-(trifluoromethoxy)pyridin-3-yl)-1-isopropyl-N-(3-methyl-1,1-dioxidothietan-3-yl)-4,5,6,7-tetrahydro-1H-indazole-6-carboxamide, (R)—N-(3,3-difluoro-1-methylcyclobutyl)-3-(5-(difluoromethoxy)-2-methylpyridin-3-yl)-1-isopropyl-4,5,6,7-tetrahydro-1H-indazole-6-carboxamide, (R)-1-isopropyl-N-(3-methyl-1,1-dioxidothietan-3-yl)-3-(5-(1,1,2,2-tetrafluoroethoxy)pyridin-3-yl)-4,5,6,7-tetrahydro-1H-indazole-6-carboxamide, (R)-1-isopropyl-N—((S)-3-methyl-1,1-dioxidotetrahydrothiophen-3-yl)-3-(5-(1,1,2,2-tetrafluoroethoxy)pyridin-3-yl)-4,5,6,7-tetrahydro-1H-indazole-6-carboxamide, (R)-1-isopropyl-N-(4-methyl-1,1-dioxidotetrahydro-2H-thiopyran-4-yl)-3-(5-(1,1,2,2-tetrafluoroethoxy)pyridin-3-yl)-4,5,6,7-tetrahydro-1H-indazole-6-carboxamide, (R)-3-(5-fluoro-2-(2,2,2-trifluoroethoxy)pyridin-4-yl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-fluoro-2-(2,2,2-trifluoroethoxy)pyridin-4-yl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-((R)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(2-ethoxy-5-fluoropyridin-4-yl)-1-((S)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(2-ethoxy-5-fluoropyridin-4-yl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-(difluoromethoxy)-2-fluorophenyl)-1-((R)-3-hydroxy-3-methylbutan-2-yl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((S)-3-hydroxy-3-methylbutan-2-yl)-N-(3-methyl-1,1-dioxidothietan-3-yl)-4,5,6,7-tetrahydro-1H-indazole-6-carboxamide, (R)-3-(3-(difluoromethoxy)phenyl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(3-(difluoromethoxy)phenyl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-fluoro-2-(2,2,2-trifluoroethoxy)pyridin-4-yl)-1-((R)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(5-fluoro-2-(2,2,2-trifluoroethoxy)pyridin-4-yl)-1-((S)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)—N-(4-cyano-1,1-dioxidotetrahydro-2H-thiopyran-4-yl)-3-(5-fluoro-2-(2,2,2-trifluoroethoxy)pyridin-4-yl)-1-((R)-3-hydroxy-3-methylbutan-2-yl)-4,5,6,7-tetrahydro-1H-indazole-6-carboxamide, (R)—N-(4-cyano-1,1-dioxidotetrahydro-2H-thiopyran-4-yl)-3-(5-fluoro-2-(2,2,2-trifluoroethoxy)pyridin-4-yl)-1-((S)-3-hydroxy-3-methylbutan-2-yl)-4,5,6,7-tetrahydro-1H-indazole-6-carboxamide, (R)-3-(5-(difluoromethoxy)-2-fluorophenyl)-1-((1R,2S)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1R,2R)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1S,2S)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1S,2R)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-N-(3-methyl-1,1-dioxidothietan-3-yl)-1-(methylsulfonyl)-4,5,6,7-tetrahydro-1H-indazole-6-carboxamide, (R)-1-(cyclopropylsulfonyl)-3-(5-(difluoromethoxy)-2-fluorophenyl)-N-(3-methyl-1,1-dioxidothietan-3-yl)-4,5,6,7-tetrahydro-1H-indazole-6-carboxamide, 3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, (R)-3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, (S)-3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, 3-(3-(difluoromethoxy)phenyl)-1-(5-fluoropyridin-2-yl)-N—((S)-3-methyl-1,1-dioxidotetrahydrothiophen-3-yl)-1,5,6,7-tetrahydropyrano[3,2-c]pyrazole-6-carboxamide, 3-(3-(difluoromethoxy)phenyl)-1-(5-fluoropyridin-2-yl)-N-(3-methyl-1,1-dioxidothietan-3-yl)-1,5,6,7-tetrahydropyrano[3,2-c]pyrazole-6-carboxamide, 3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, (S)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, (R)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, 3-(5-(difluoromethoxy)-2-fluorophenyl)-1-isopropyl-N-(3-methyl-1,1-dioxidothietan-3-yl)-1,5,6,7-tetrahydropyrano[3,2-c]pyrazole-6-carboxamide, 3-(5-(difluoromethoxy)-2-fluorophenyl)-1-isopropyl-N—((S)-3-methyl-1,1-dioxidotetrahydrothiophen-3-yl)-1,5,6,7-tetrahydropyrano[3,2-c]pyrazole-6-carboxamide, 3-(5-(difluoromethoxy)-2-fluorophenyl)-1-isopropyl-N—((R)-3-methyl-1,1-dioxidotetrahydrothiophen-3-yl)-1,5,6,7-tetrahydropyrano[3,2-c]pyrazole-6-carboxamide, N-(3,3-difluoro-1-methylcyclobutyl)-3-(3-(difluoromethoxy)phenyl)-1-isopropyl-1,5,6,7-tetrahydropyrano[3,2-c]pyrazole-6-carboxamide, (S)-3-(3-cyclopropylphenyl)-1-isopropyl-N-(3-methyl-1,1-dioxidothietan-3-yl)-1,5,6,7-tetrahydropyrano[3,2-c]pyrazole-6-carboxamide, (R)-3-(3-(1-fluorocyclopropyl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(2-aminopropan-2-yl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(6-(difluoromethoxy)pyrazin-2-yl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)-1-(5-fluoropyridin-2-yl)-N—((S)-3-methyl-1,1-dioxidotetrahydrothiophen-3-yl)-3-(1-methyl-1H-pyrazol-5-yl)-4,5,6,7-tetrahydro-1H-indazole-6-carboxamide, (R)-3-(3-(difluoromethoxy)phenyl)-1-isopropyl-N-(pyridin-3-ylmethyl)-4,5,6,7-tetrahydro-1H-indazole-6-carboxamide, (R)-3-(3-(difluoromethoxy)phenyl)-1-isopropyl-N-(isoxazol-4-ylmethyl)-4,5,6,7-tetrahydro-1H-indazole-6-carboxamide, (6R)-3-(5-(difluoromethoxy)-2-fluorophenyl)-1-isopropyl-N-(1-isopropyl-2-oxopyrrolidin-3-yl)-4,5,6,7-tetrahydro-1H-indazole-6-carboxamide, (R)-3-(3-(difluoromethoxy)phenyl)-N—((S)-1-hydroxypropan-2-yl)-1-isopropyl-4,5,6,7-tetrahydro-1H-indazole-6-carboxamide, (R)-3-(3-(difluoromethoxy)phenyl)-1-isopropyl-N-(1-methoxy-2-methylpropan-2-yl)-4,5,6,7-tetrahydro-1H-indazole-6-carboxamide, (R)-3-(3-(difluoromethoxy)phenyl)-N-(5-methyl-1,3,4-thiadiazol-2-yl)-1-(tetrahydro-2H-pyran-4-yl)-4,5,6,7-tetrahydro-1H-indazole-6-carboxamide, (R)-3-(5-(difluoromethoxy)pyridin-3-yl)-1-isopropyl-N—((S)-1-((R)-2-methylmorpholino)propan-2-yl)-4,5,6,7-tetrahydro-1H-indazole-6-carboxamide, (R)-3-(3-(difluoromethoxy)phenyl)-N-(3-ethyl-1,1-dioxidothietan-3-yl)-1-isopropyl-4,5,6,7-tetrahydro-1H-indazole-6-carboxamide, (R)-3-(3-(difluoromethoxy)phenyl)-N-(2-(1,1-dioxidothiomorpholino)ethyl)-1-isopropyl-4,5,6,7-tetrahydro-1H-indazole-6-carboxamide, (R)-3-(3-(difluoromethoxy)phenyl)-1-isopropyl-N-(2-(N-methylsulfamoyl)ethyl)-4,5,6,7-tetrahydro-1H-indazole-6-carboxamide, (R)-3-(3-(difluoromethoxy)phenyl)-N—((R)-3-methyl-1,1-dioxidotetrahydrothiophen-3-yl)-1-(1-methylpiperidin-4-yl)-4,5,6,7-tetrahydro-1H-indazole-6-carboxamide, (R)-1-acetyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-1-(cyclopropanecarbonyl)-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-N—((S)-3-methyl-1,1-dioxidotetrahydrothiophen-3-yl)-1-(tetrahydro-2H-pyran-4-carbonyl)-4,5,6,7-tetrahydro-1H-indazole-6-carboxamide, (R)-1-benzoyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-1-benzyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-N—((S)-3-methyl-1,1-dioxidotetrahydrothiophen-3-yl)-1-((tetrahydro-2H-pyran-4-yl)methyl)-4,5,6,7-tetrahydro-1H-indazole-6-carboxamide, (6R)-1-(1-cyanoethyl)-3-(5-(difluoromethoxy)-2-fluorophenyl)-N-(3-methyl-1,1-dioxidothietan-3-yl)-4,5,6,7-tetrahydro-1H-indazole-6-carboxamide, (6R)-3-(5-(difluoromethoxy)-2-fluorophenyl)-N-(3-methyl-1,1-dioxidothietan-3-yl)-1-(1-(thiazol-2-yl)ethyl)-4,5,6,7-tetrahydro-1H-indazole-6-carboxamide, (R)-1-isopropyl-N-(3-methyl-1,1-dioxidothietan-3-yl)-3-(3-(1-(trifluoromethyl)cyclopropyl)phenyl)-4,5,6,7-tetrahydro-1H-indazole-6-carboxamide, (R)-3-(3-(1-cyanocyclopropyl)phenyl)-1-isopropyl-N-(3-methyl-1,1-dioxidothietan-3-yl)-4,5,6,7-tetrahydro-1H-indazole-6-carboxamide, (R)-3-(2-(1,1-difluoroethyl)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide, (R)-1-isopropyl-N-(3-methyl-1,1-dioxidothietan-3-yl)-3-(2-methylbenzo[d]oxazol-4-yl)-4,5,6,7-tetrahydro-1H-indazole-6-carboxamide, (R)-3-(3-(cyanomethyl)phenyl)-1-isopropyl-N-(3-methyl-1,1-dioxidothietan-3-yl)-4,5,6,7-tetrahydro-1H-indazole-6-carboxamide, (R)-3-(5-(tert-butylcarbamoyl)pyridin-3-yl)-1-isopropyl-N-(3-methyl-1,1-dioxidothietan-3-yl)-4,5,6,7-tetrahydro-1H-indazole-6-carboxamide, (R)-3-(3-(cyanomethoxy)phenyl)-1-isopropyl-N-(3-methyl-1,1-dioxidothietan-3-yl)-4,5,6,7-tetrahydro-1H-indazole-6-carboxamide, (R)-3-(3-(1H-pyrazol-1-yl)phenyl)-1-isopropyl-N-(3-methyl-1,1-dioxidothietan-3-yl)-4,5,6,7-tetrahydro-1H-indazole-6-carboxamide, (R)-1-isopropyl-N-(3-methyl-1,1-dioxidothietan-3-yl)-3-(3-(methylsulfonyl)phenyl)-4,5,6,7-tetrahydro-1H-indazole-6-carboxamide, (R)-3-(3-(N-ethylsulfamoyl)phenyl)-1-isopropyl-N-(3-methyl-1,1-dioxidothietan-3-yl)-4,5,6,7-tetrahydro-1H-indazole-6-carboxamide, (R)-3-(5-ethyl-2-fluorophenyl)-1-isopropyl-N-(3-methyl-1,1-dioxidothietan-3-yl)-4,5,6,7-tetrahydro-1H-indazole-6-carboxamide, (R)-3-(5-cyano-2-fluorophenyl)-1-isopropyl-N-(3-methyl-1,1-dioxidothietan-3-yl)-4,5,6,7-tetrahydro-1H-indazole-6-carboxamide, (R)-3-(3-(1,1-difluoroethyl)phenyl)-1-isopropyl-N-(3-methyl-1,1-dioxidothietan-3-yl)-4,5,6,7-tetrahydro-1H-indazole-6-carboxamide, (R)—N-(3,3-difluoro-1-methylcyclobutyl)-3-(3-(1-hydroxycyclobutyl)phenyl)-1-isopropyl-4,5,6,7-tetrahydro-1H-indazole-6-carboxamide, (R)-3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide, (S)-3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide, (R)-3-(5-(difluoromethoxy)-2-fluorophenyl)-1-isopropyl-N-(3-methyl-1,1-dioxidothietan-3-yl)-1,4,6,7-tetrahydropyrano[4,3-c]pyrazole-6-carboxamide, or (R)-3-(5-cyclopropyl-2-fluorophenyl)-1-isopropyl-N-(3-methyl-1,1-dioxidothietan-3-yl)-1,4,6,7-tetrahydropyrano[4,3-c]pyrazole-6-carboxamide.

In Embodiment 75 of the invention, the compound of formula I, or a pharmaceutically acceptable salt thereof, is:

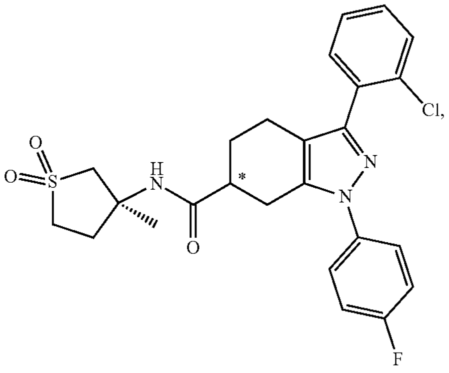
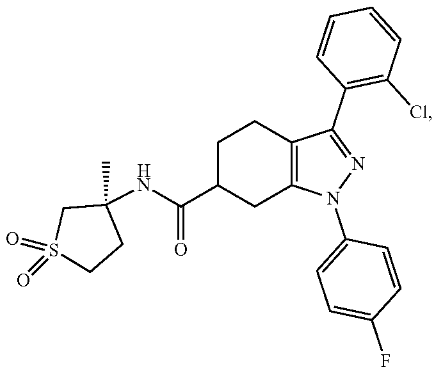
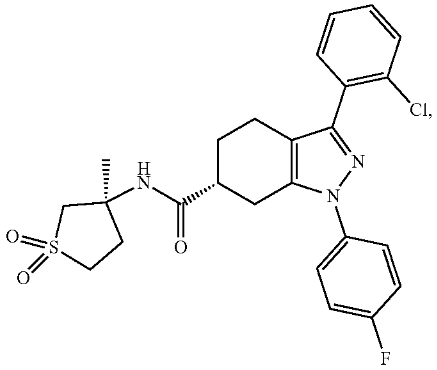
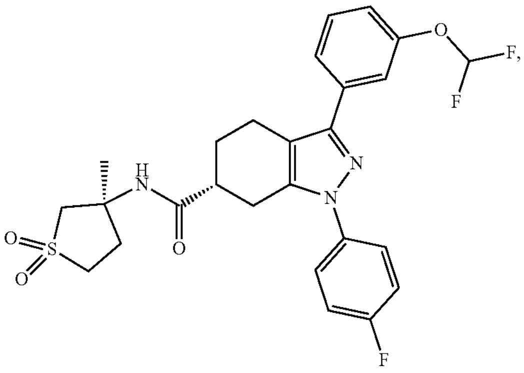
-continued
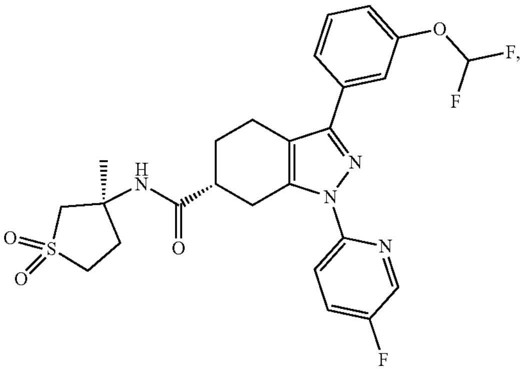
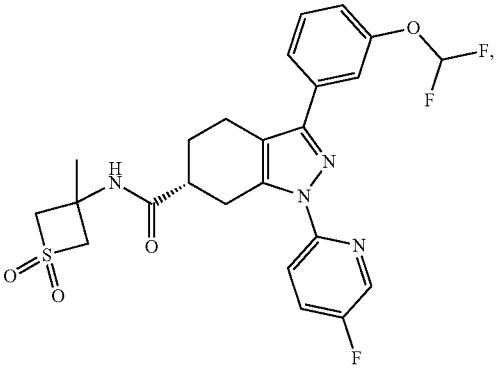
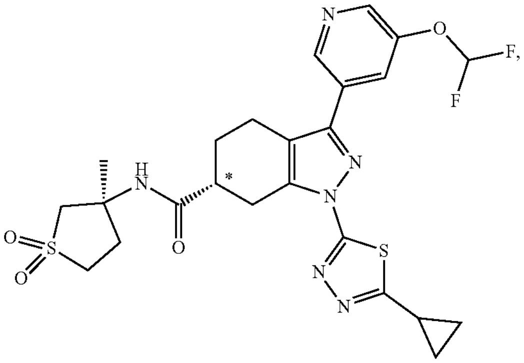
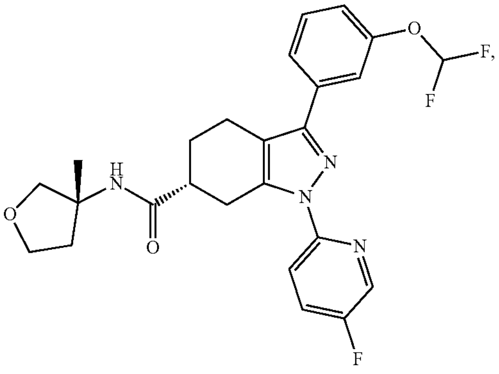

-continued
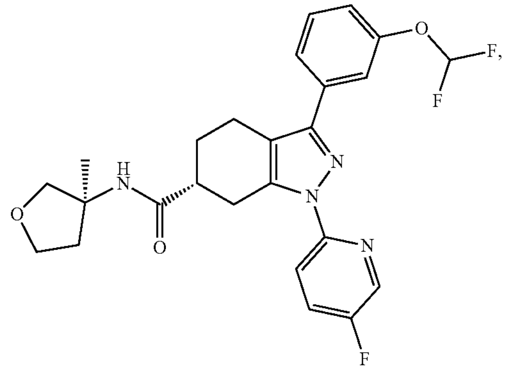
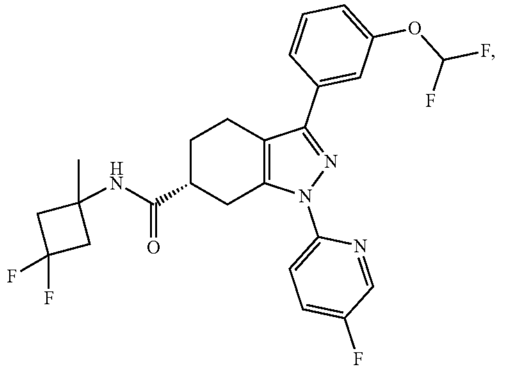
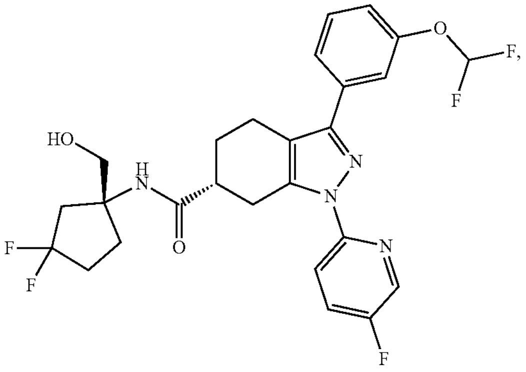
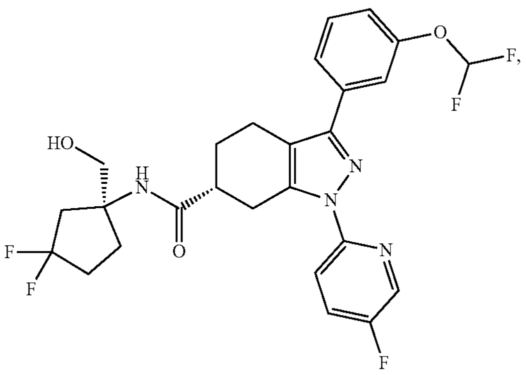
-continued
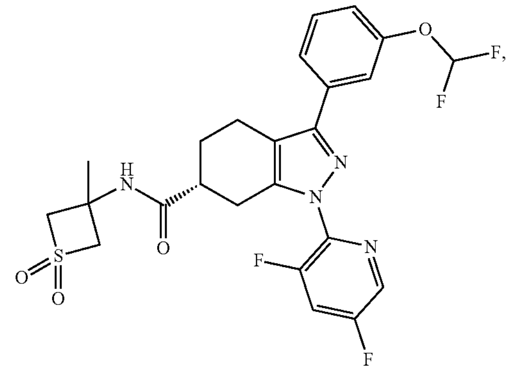
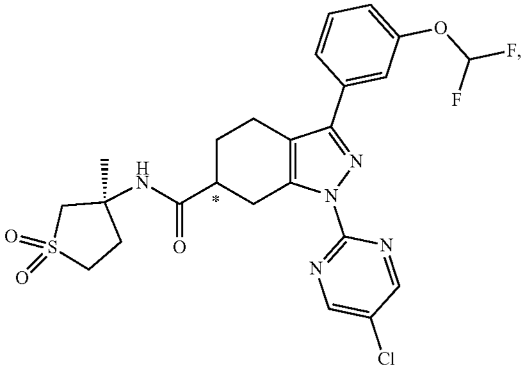
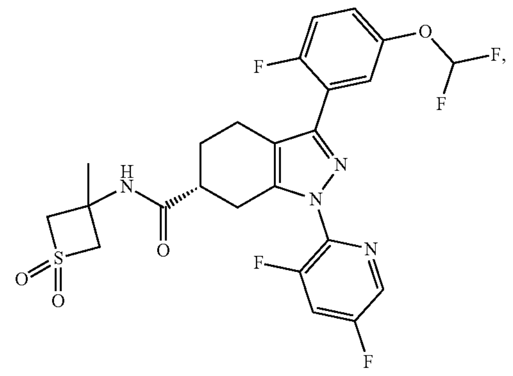
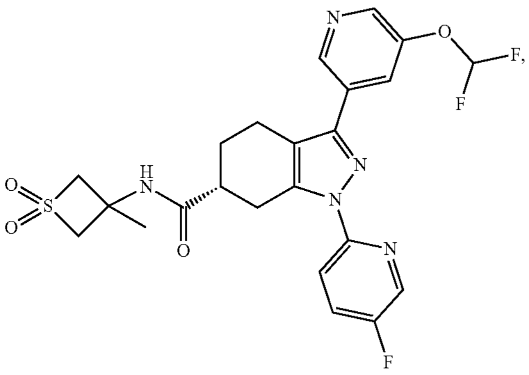

-continued
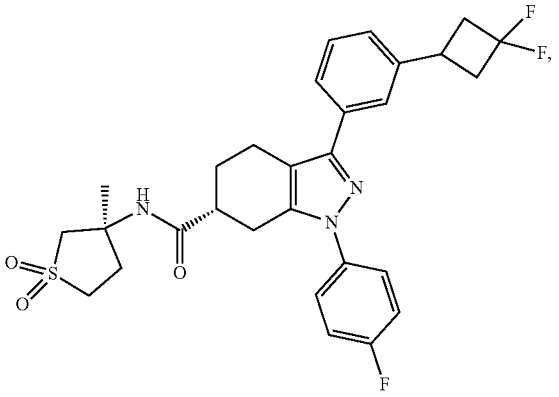
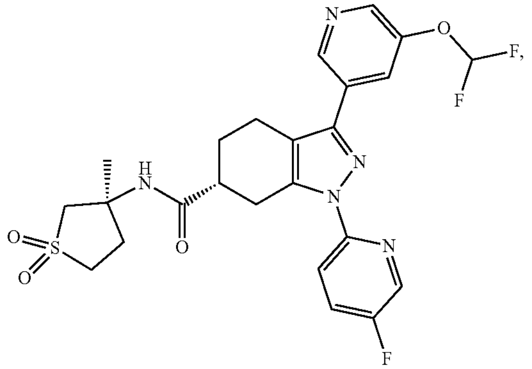
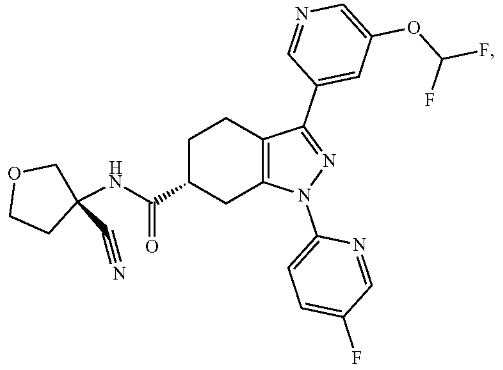
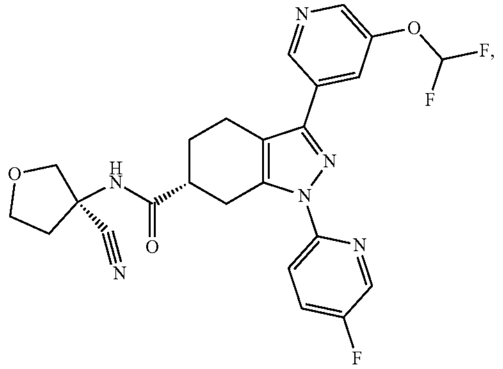
-continued
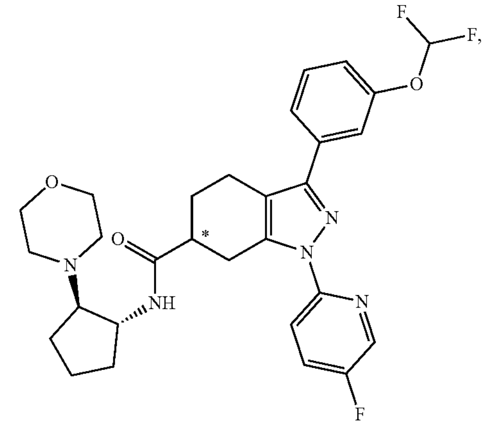
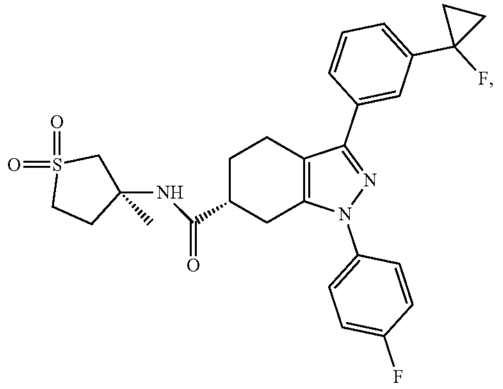
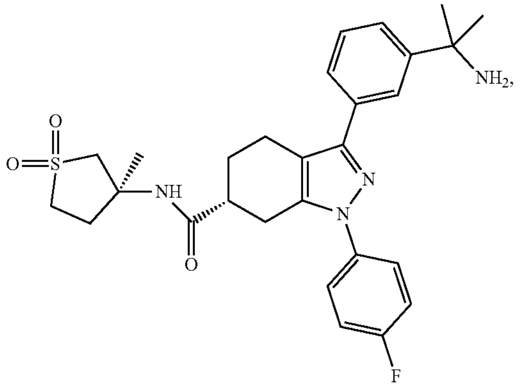
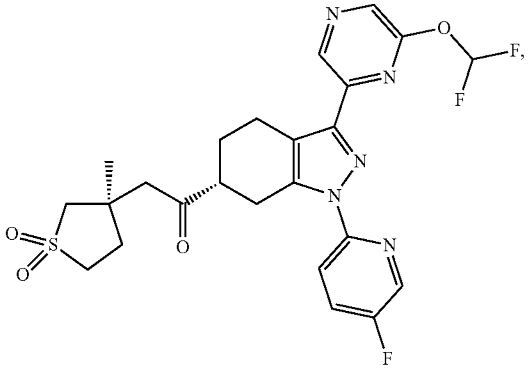

-continued
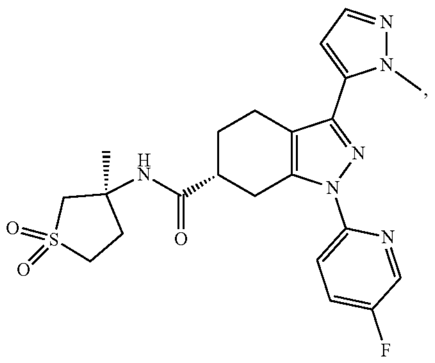
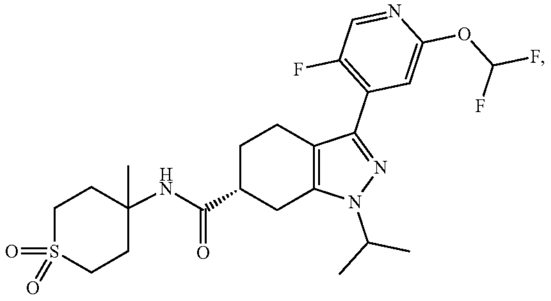
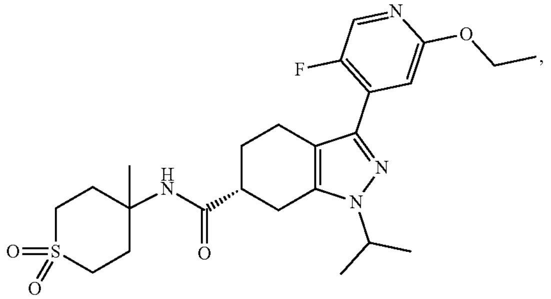
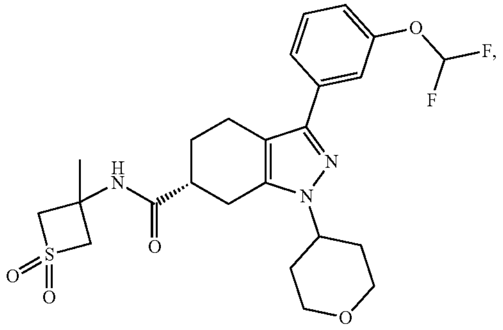
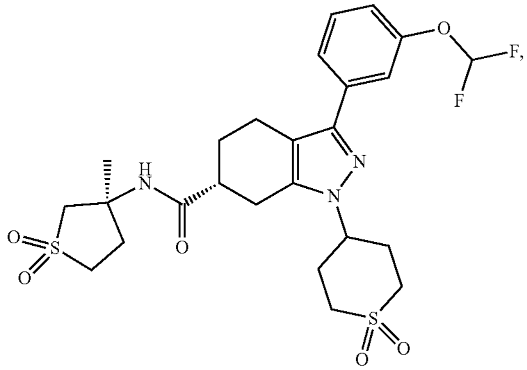
-continued
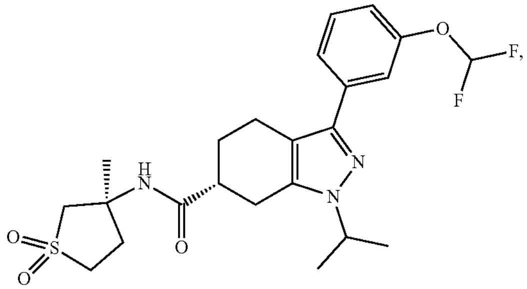
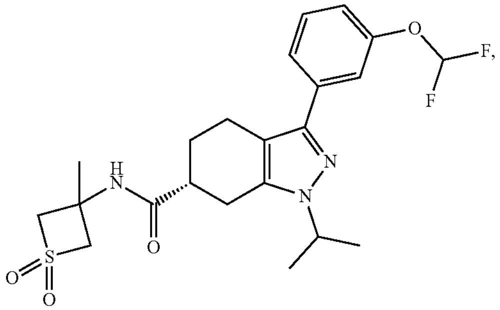
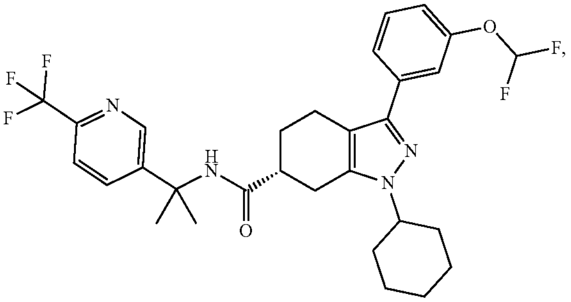
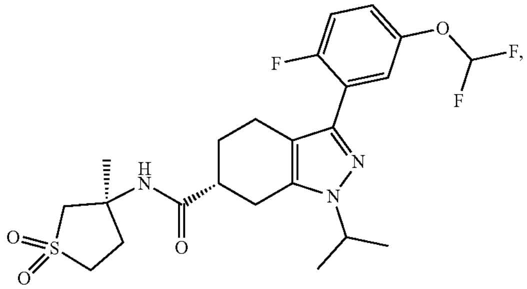
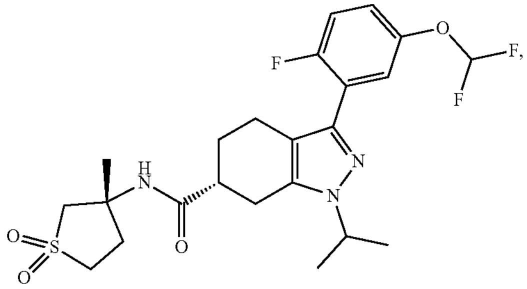

-continued
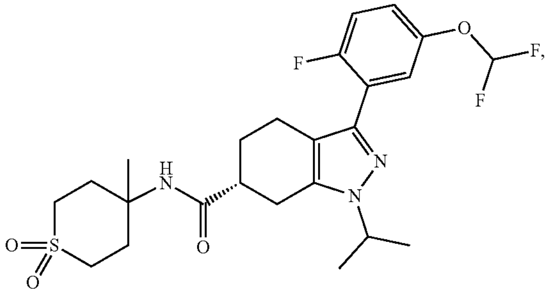
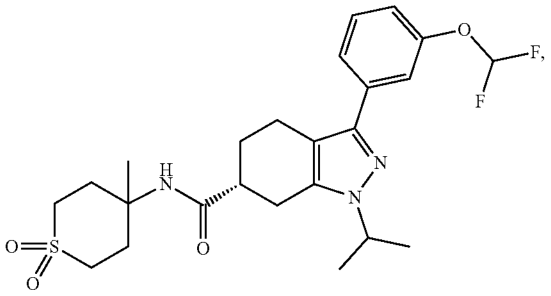
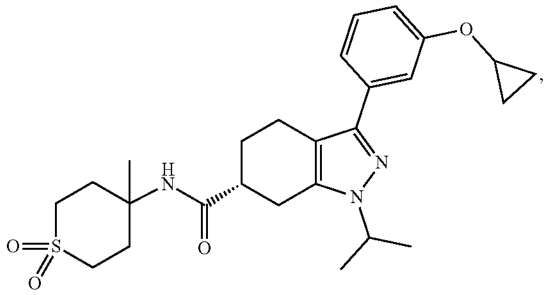
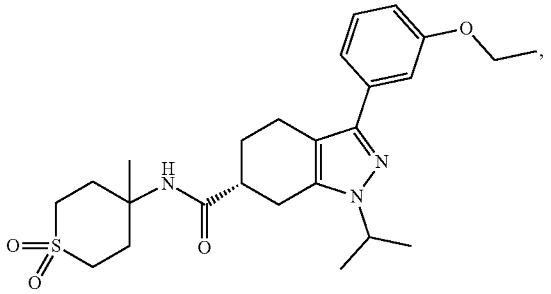
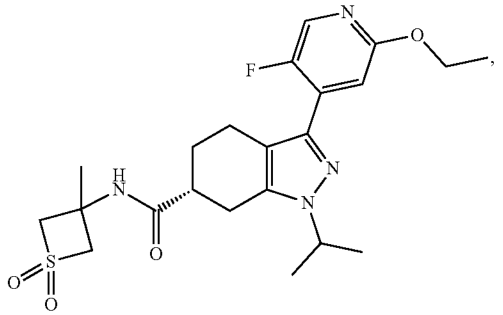
-continued
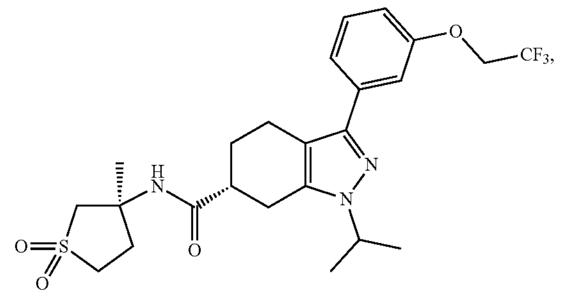
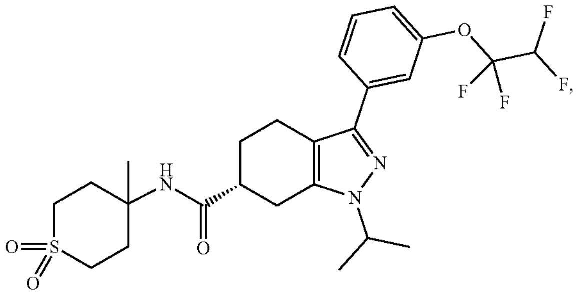
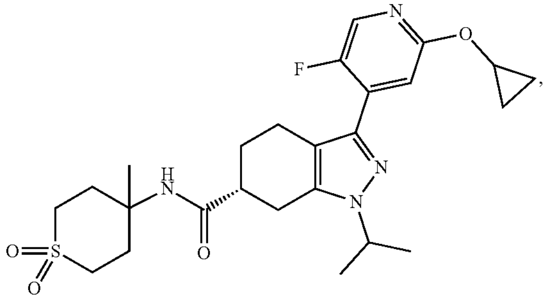
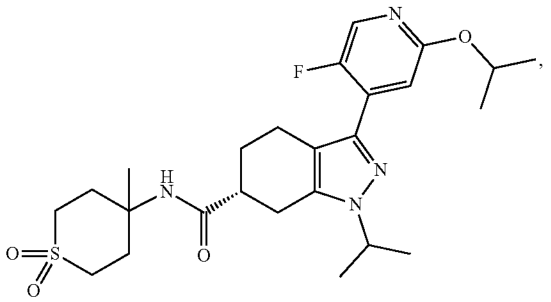
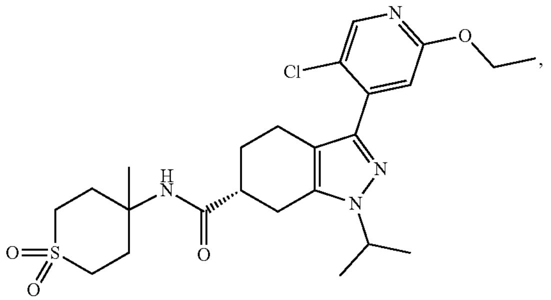

-continued
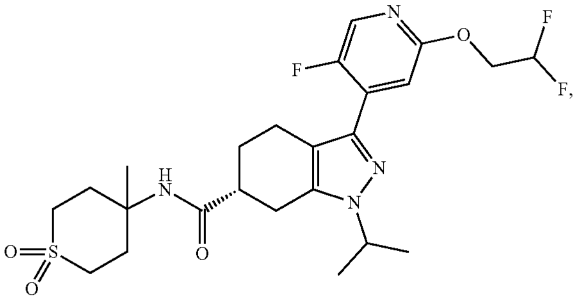
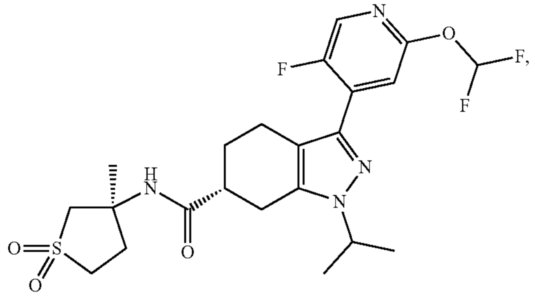
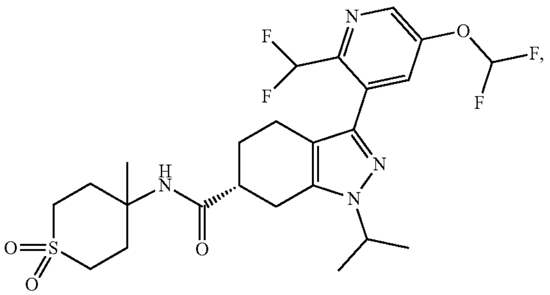
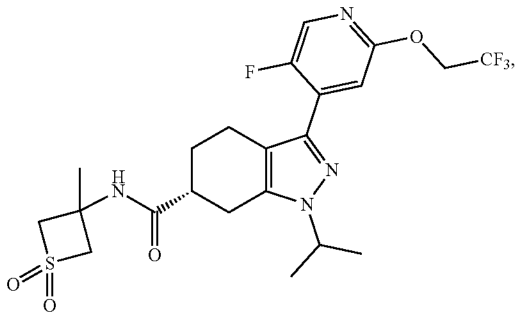
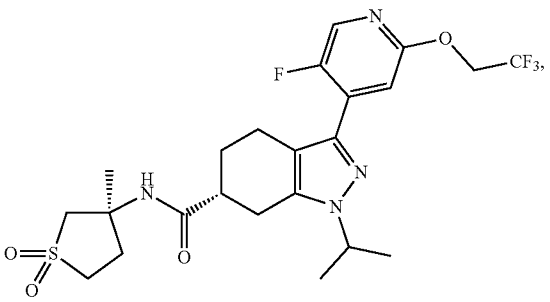
-continued
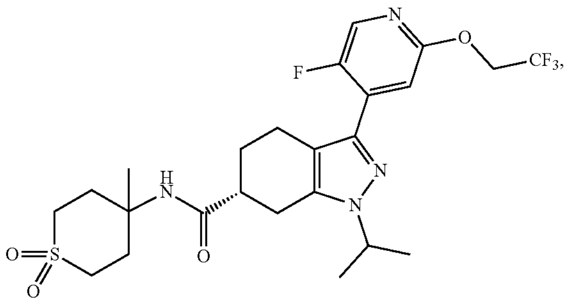
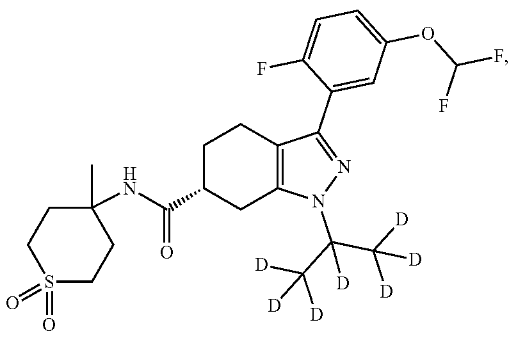
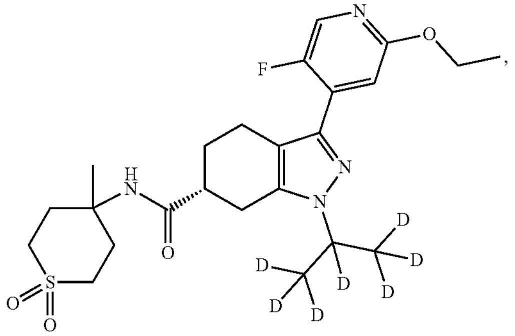
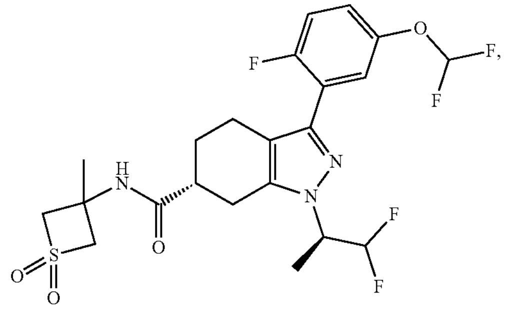
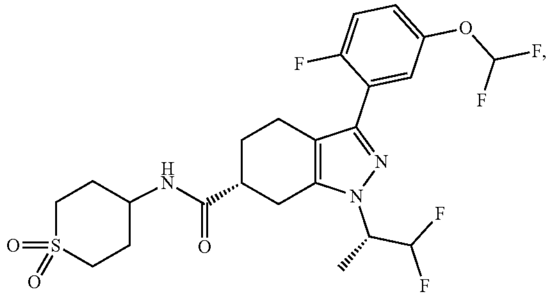

-continued
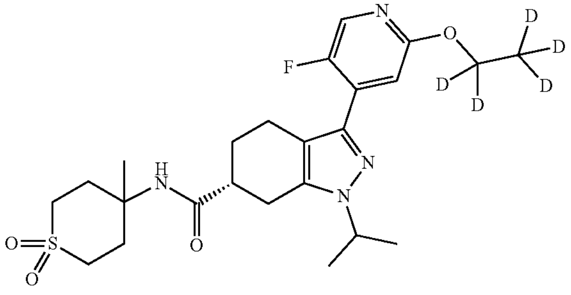
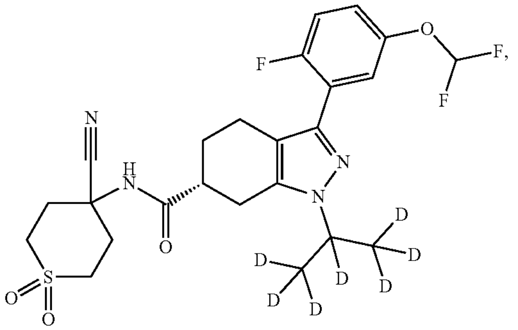
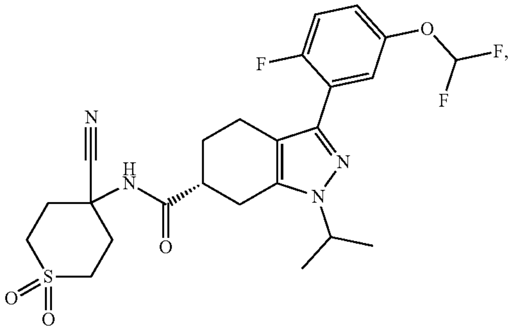
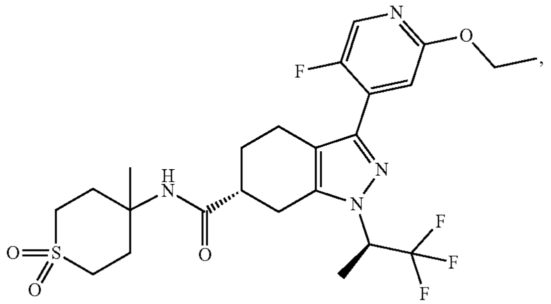
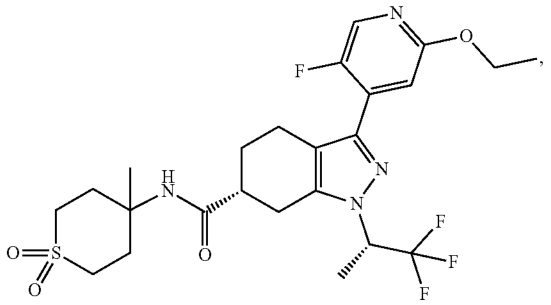
-continued
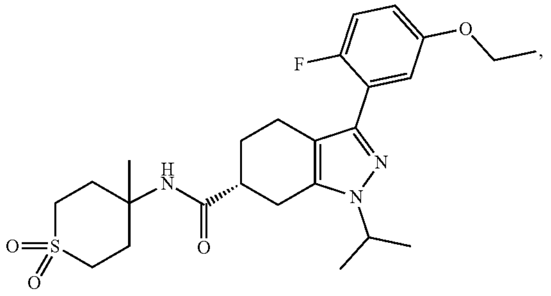
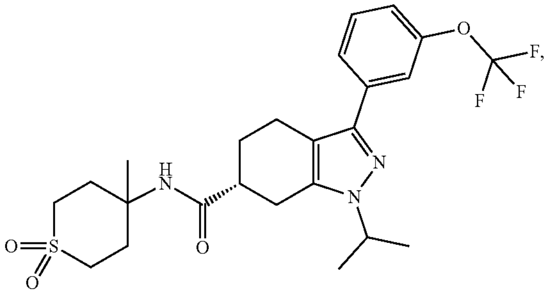
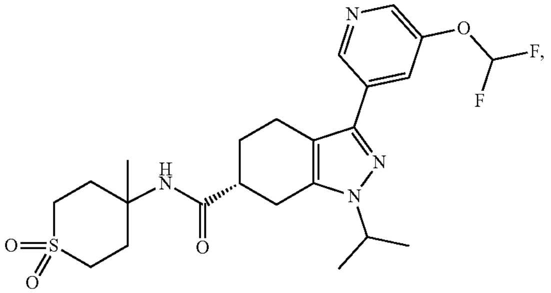
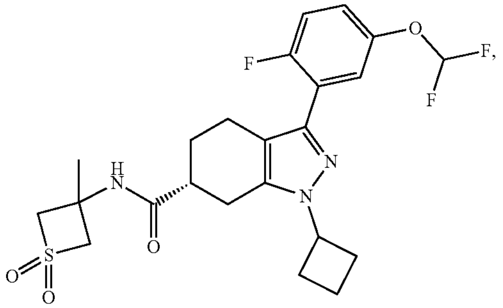
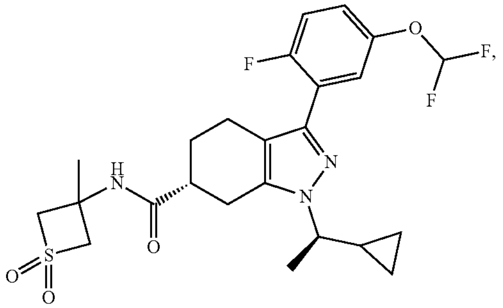

-continued
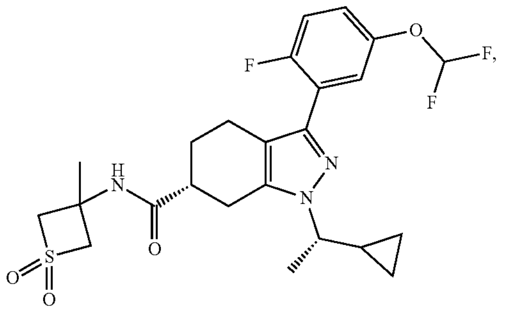
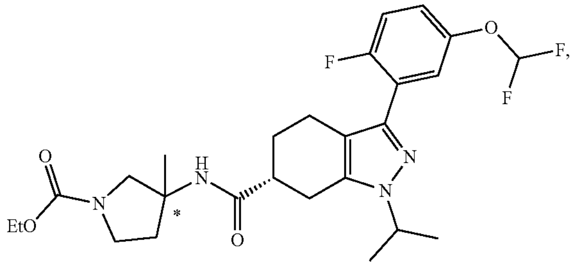
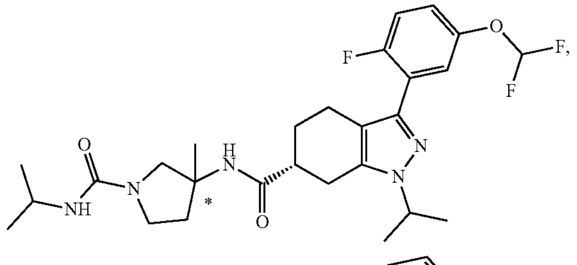
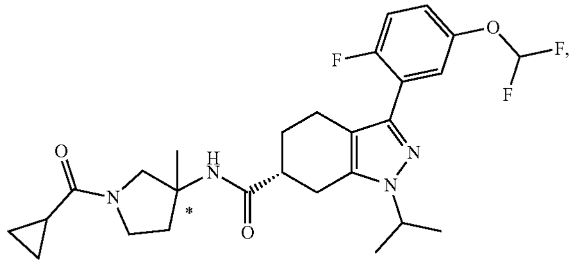
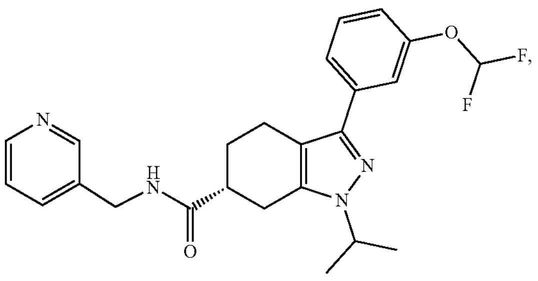
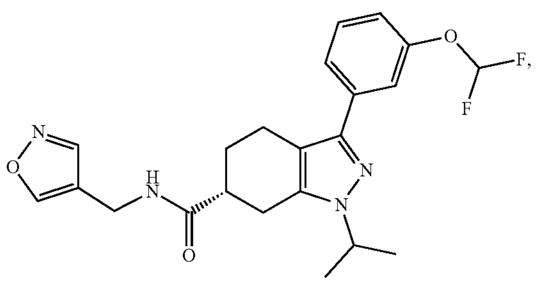
-continued
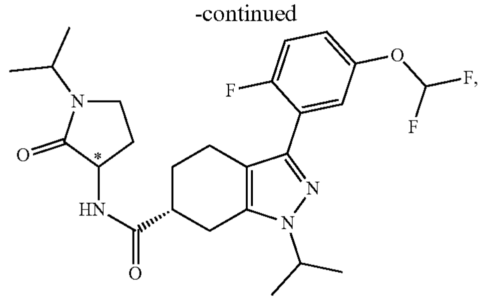
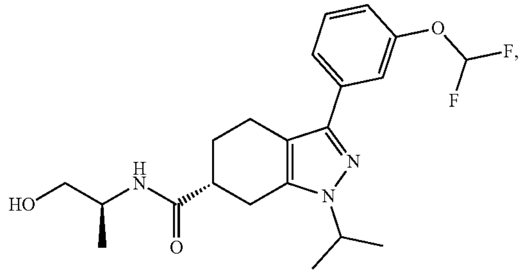
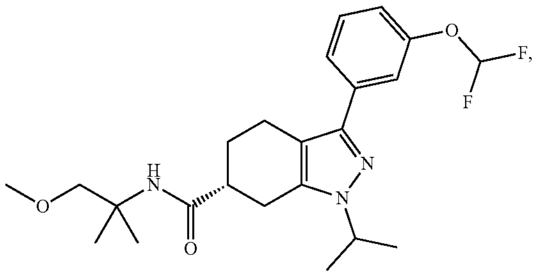
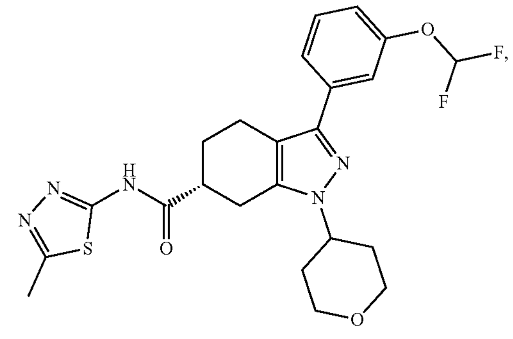
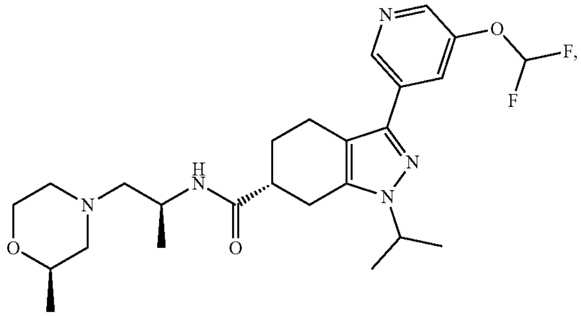

-continued
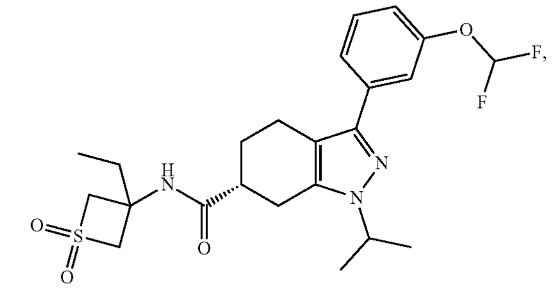
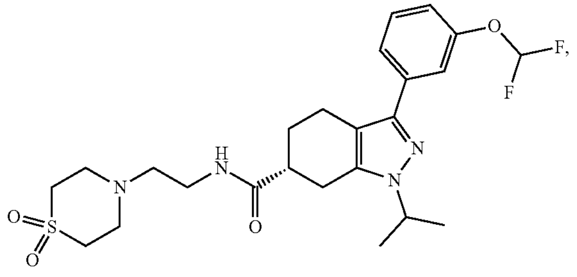
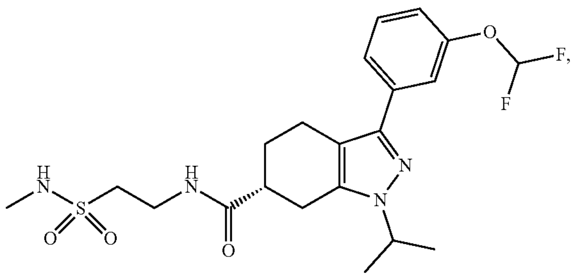
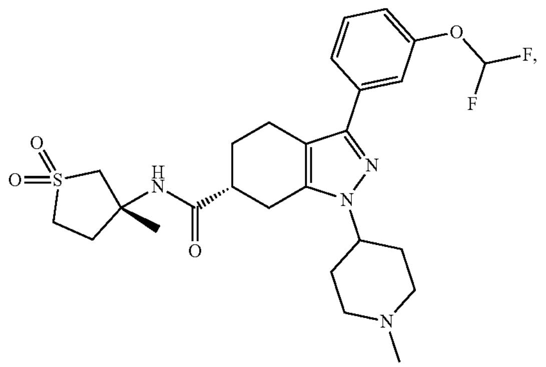
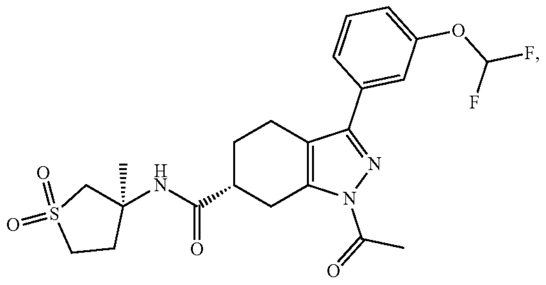
-continued
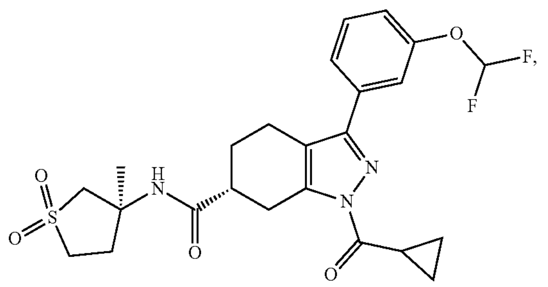
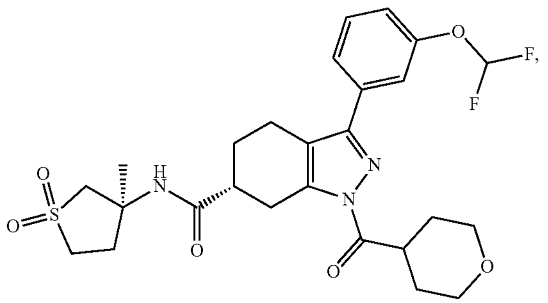
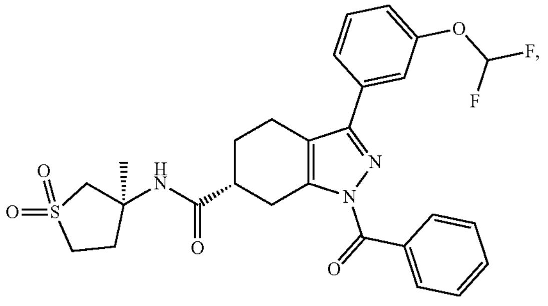
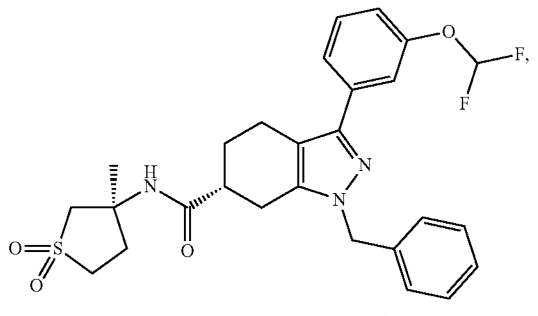
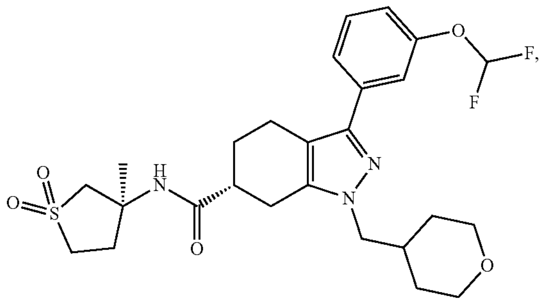

-continued
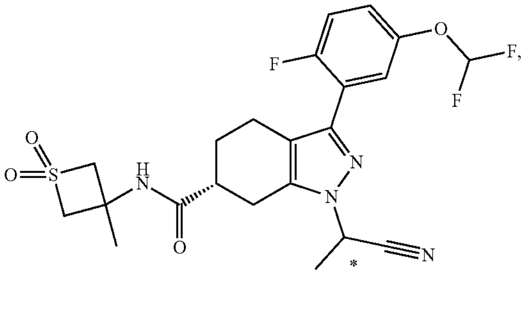
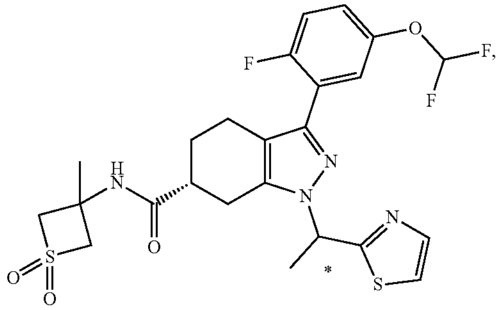
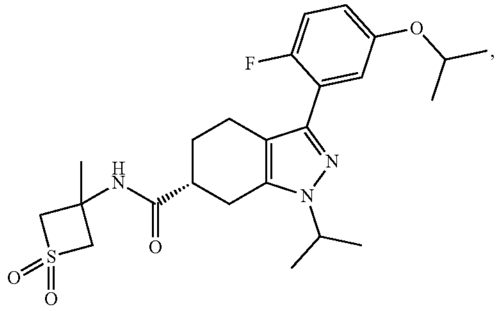
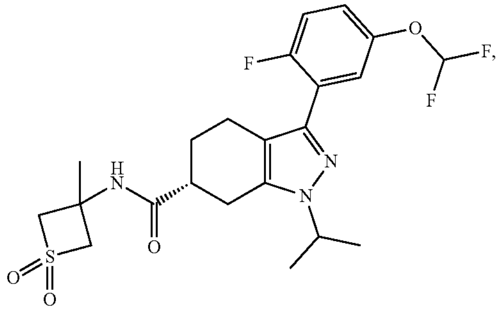
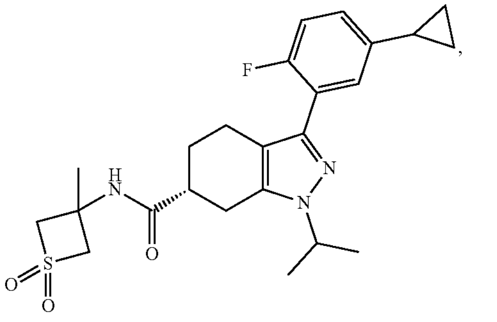
-continued
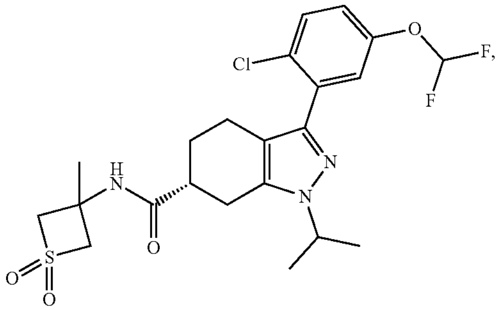
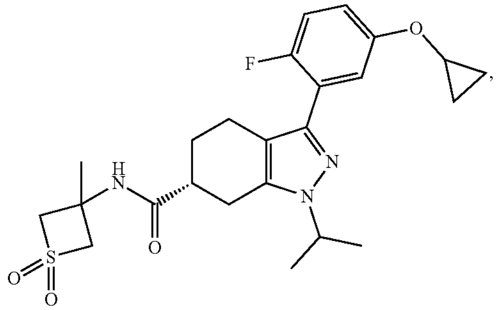
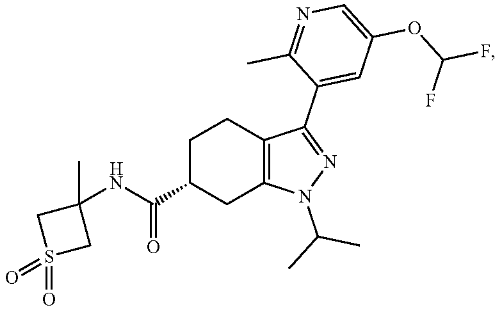
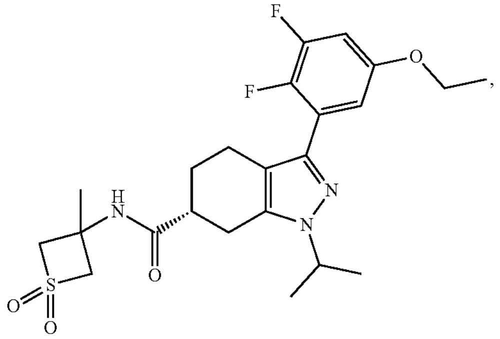
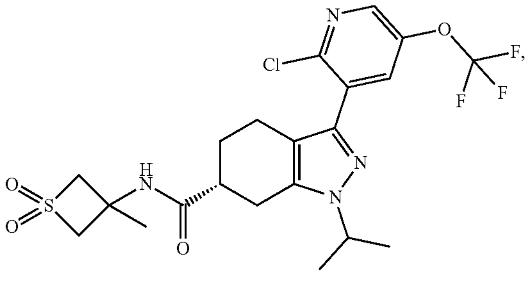

-continued
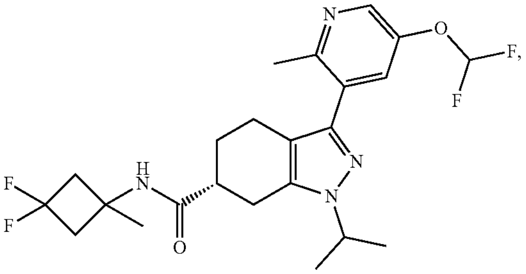
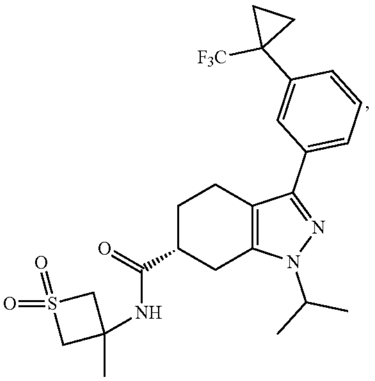
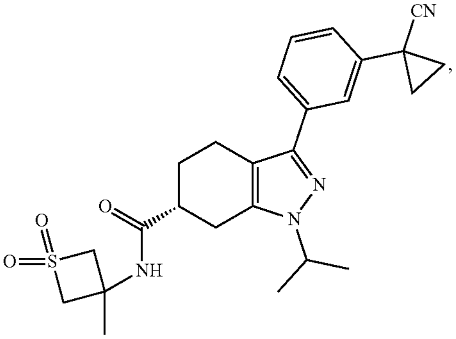
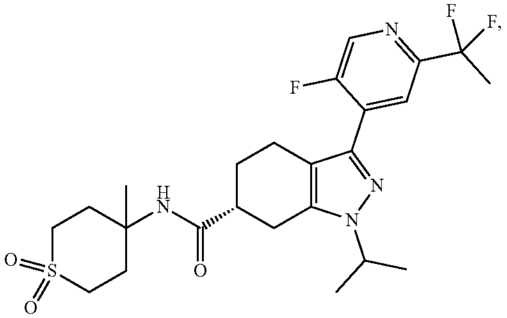
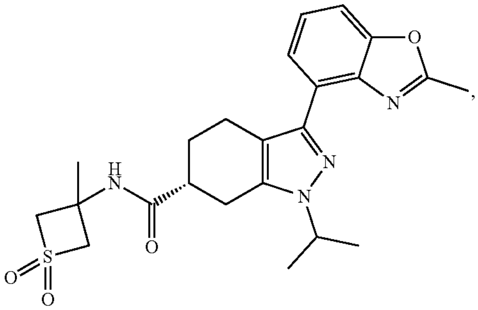
-continued
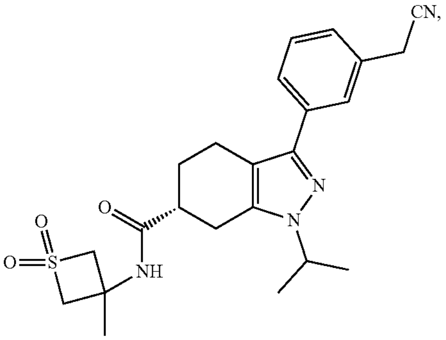
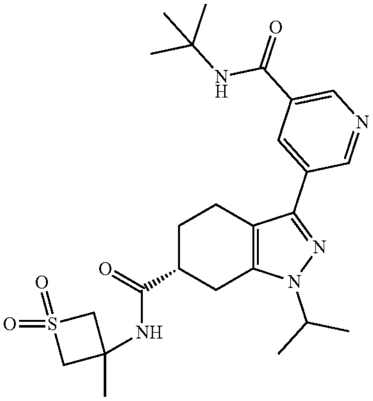
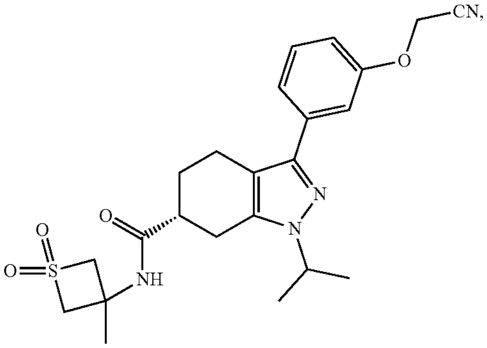
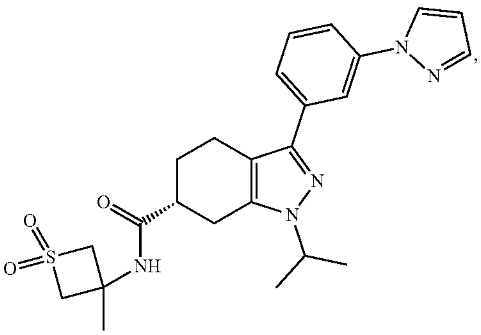

-continued
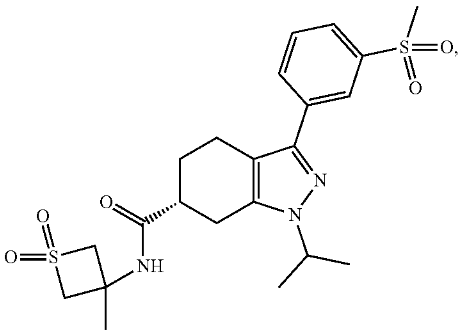
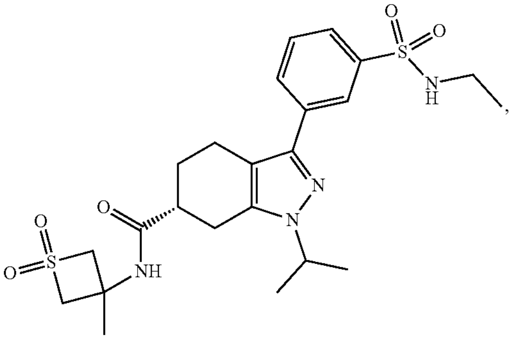
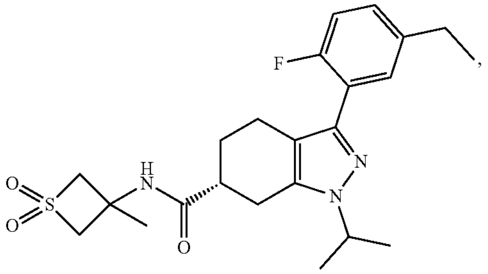
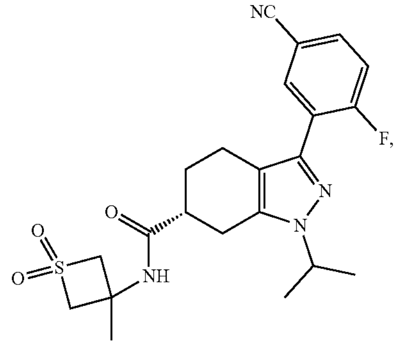
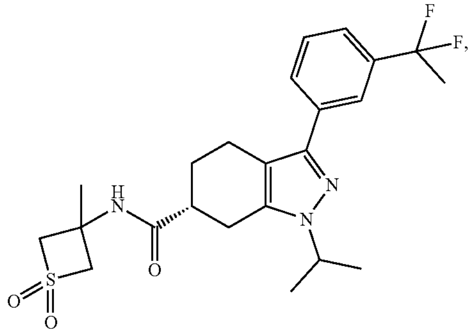
-continued
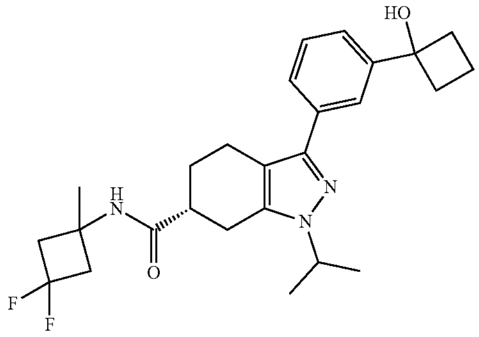
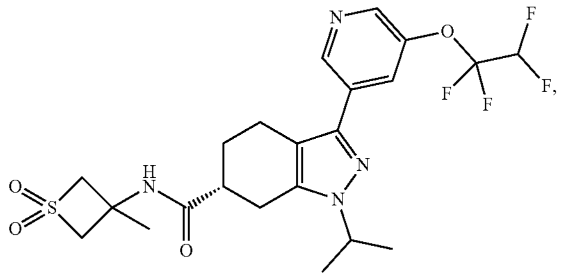
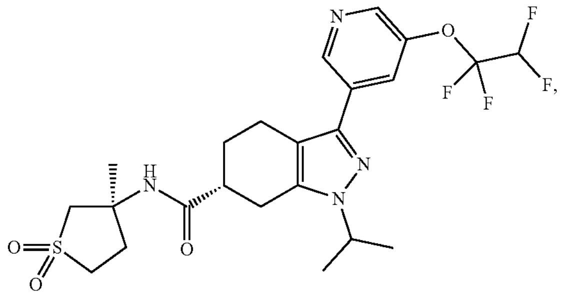
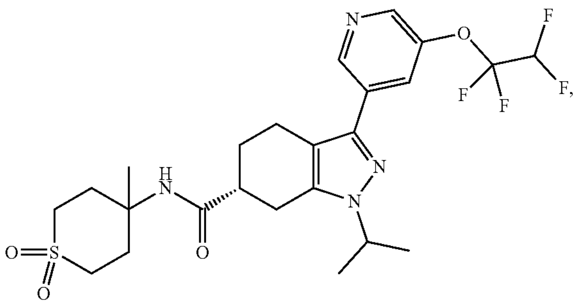
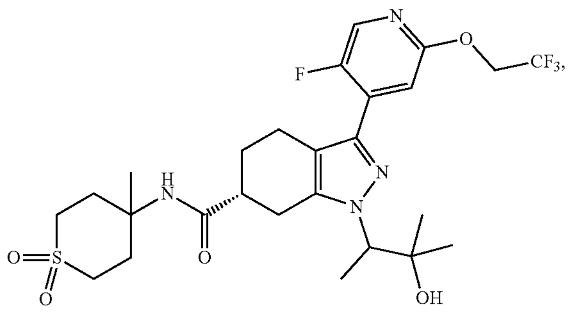

-continued
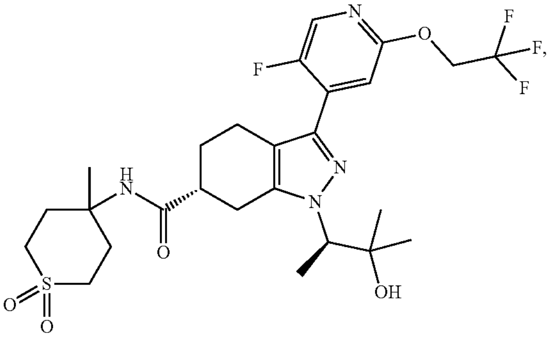
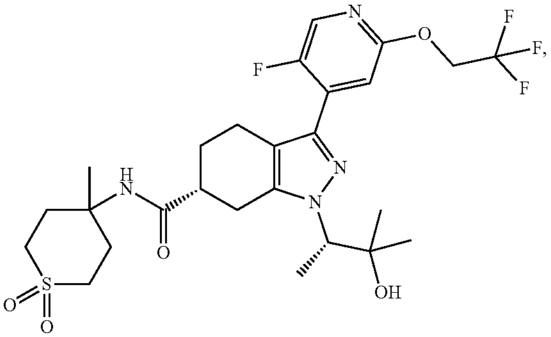
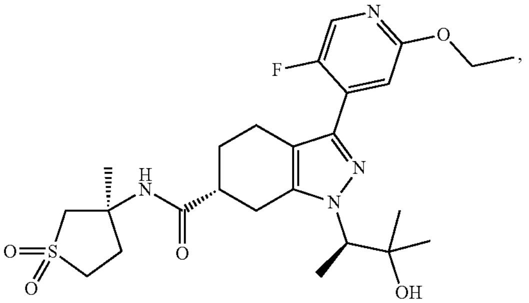
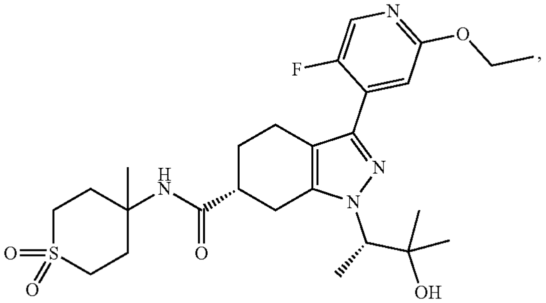
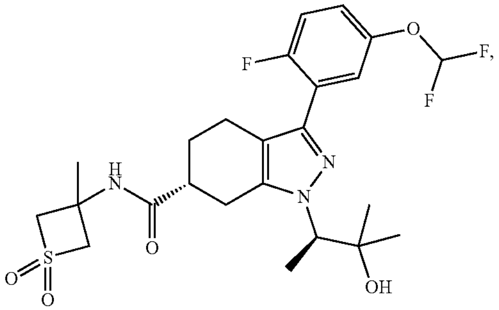
-continued
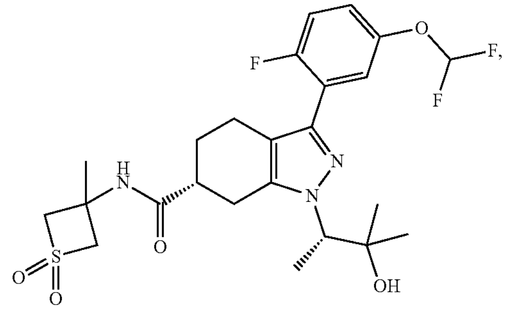
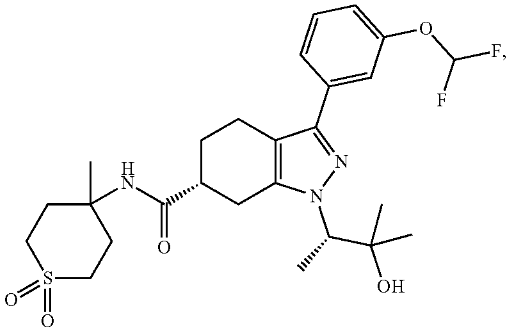
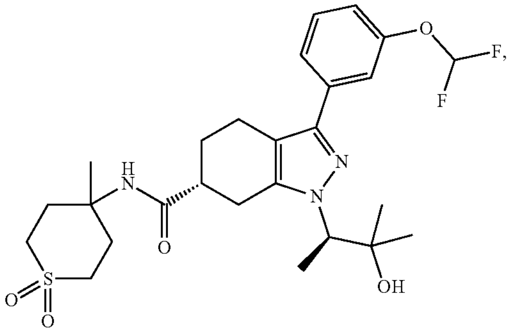
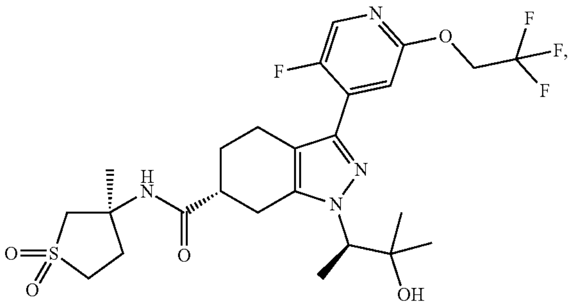
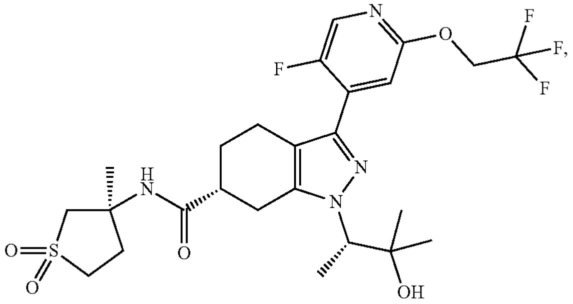

-continued
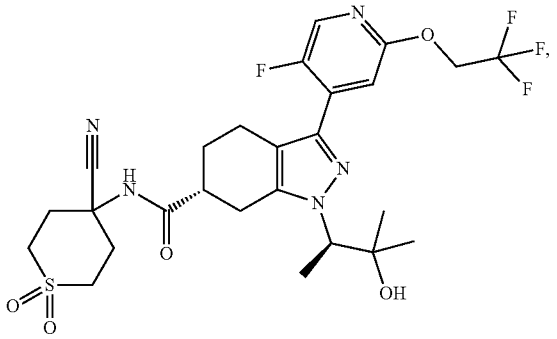
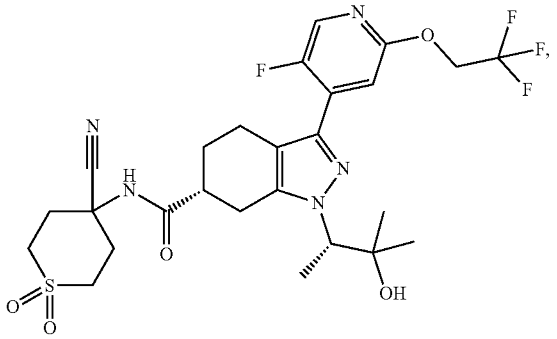
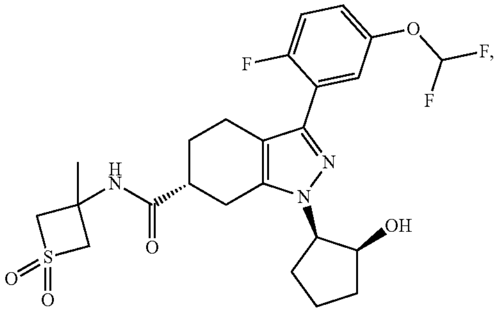
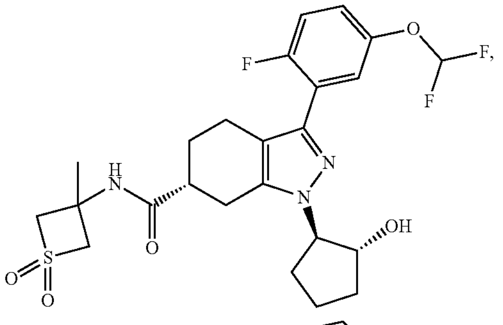
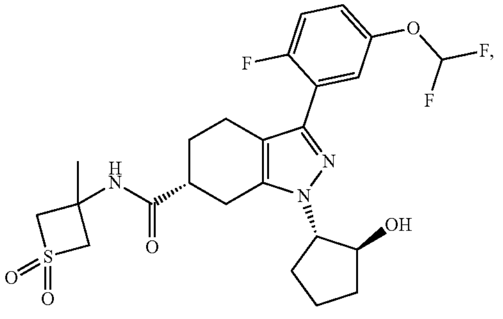
-continued
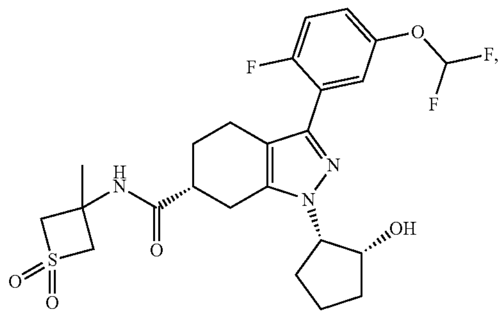
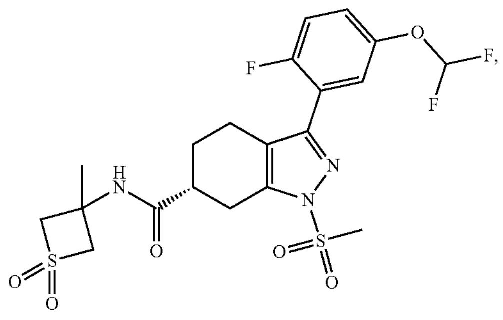
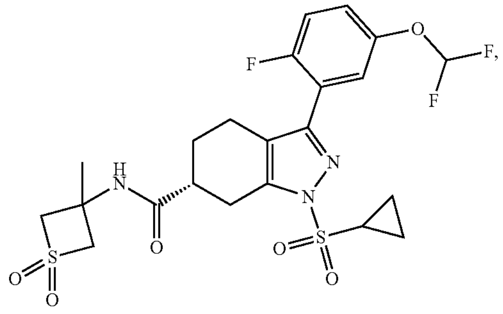
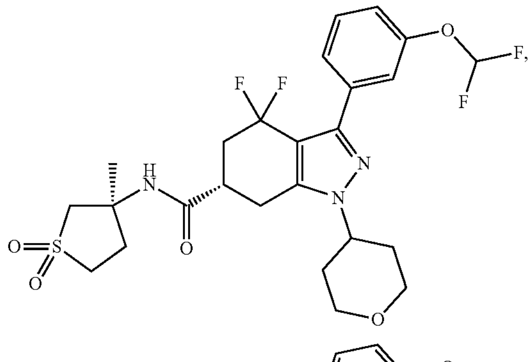
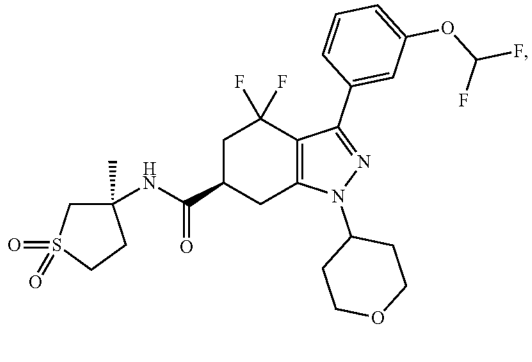

-continued
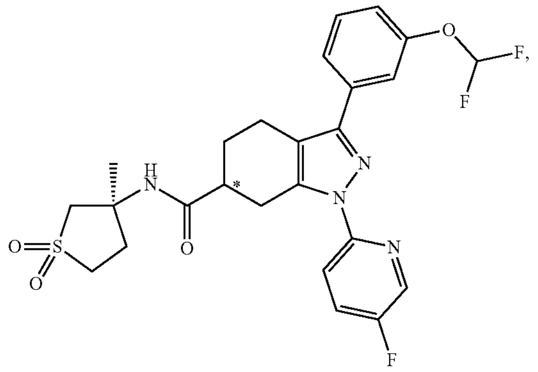
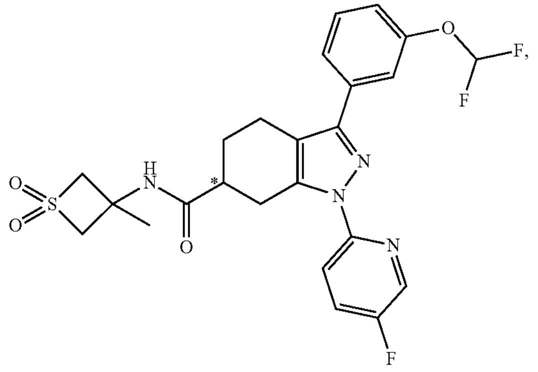
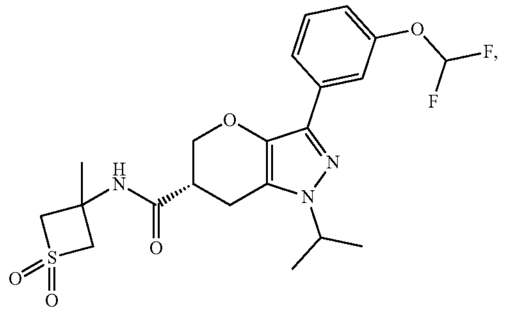
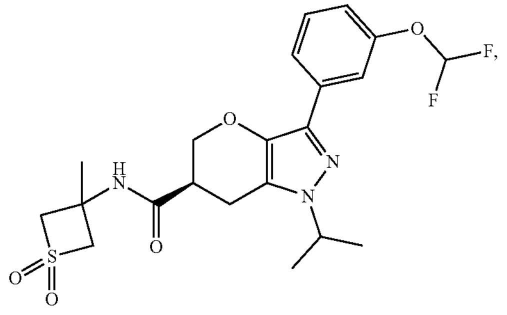
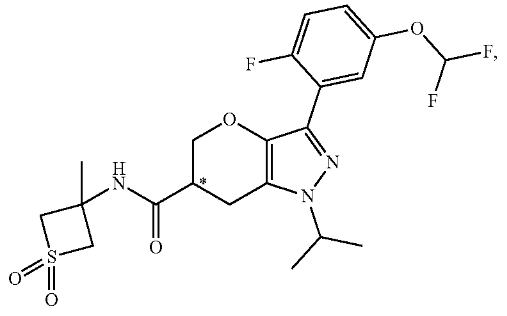
-continued
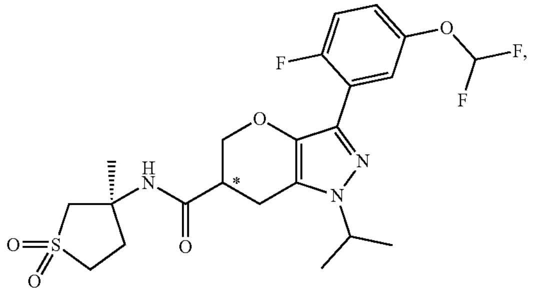
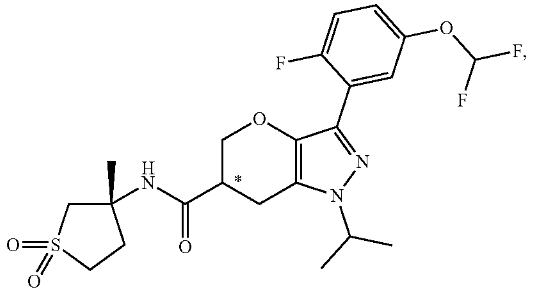
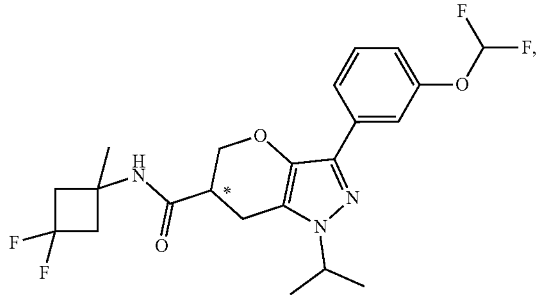
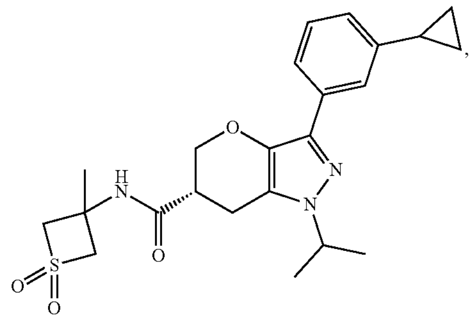
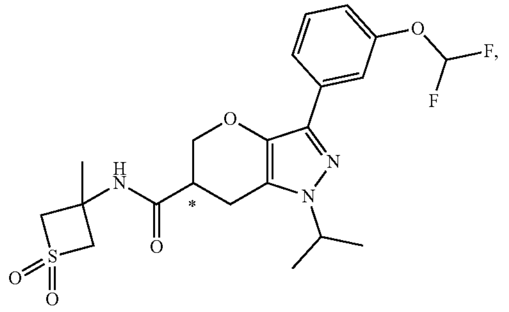

-continued

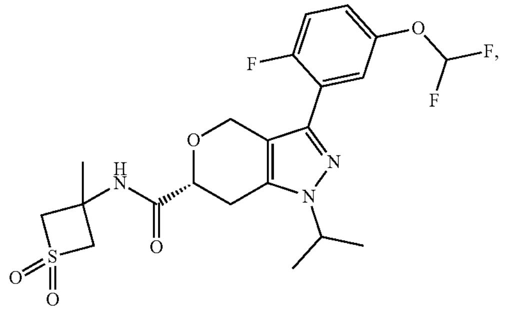

or

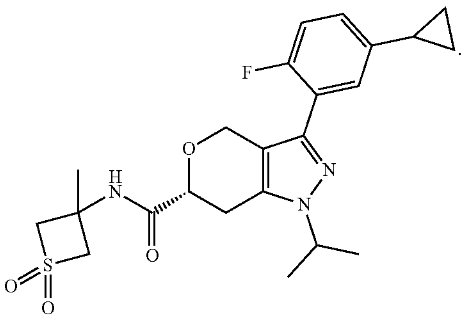

In Embodiment 76 of the invention, the compound of formula I, or a pharmaceutically acceptable salt thereof, is:

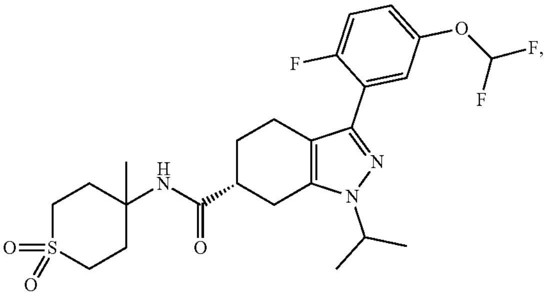

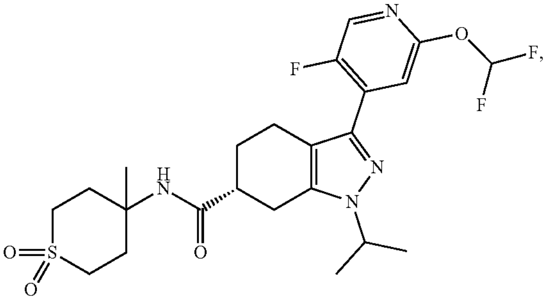

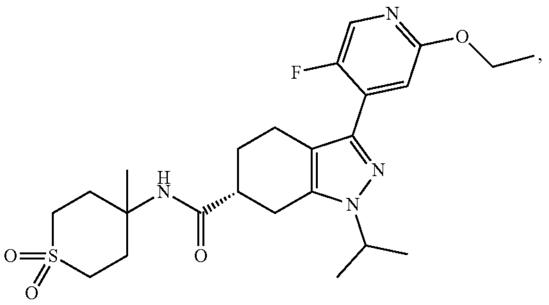

-continued

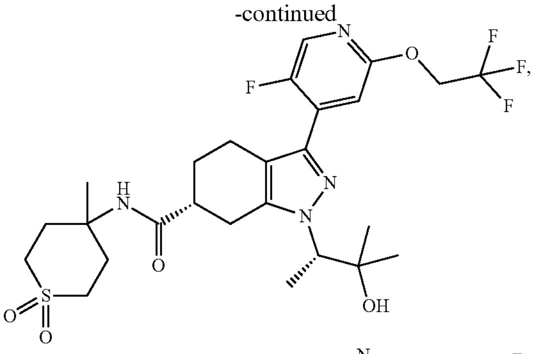

or

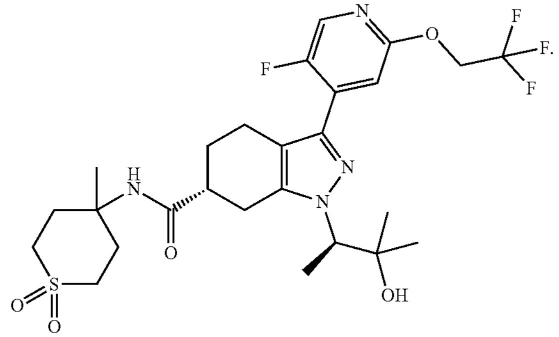

The present invention includes the pharmaceutically acceptable salts of the compounds defined therein.

In one embodiment, the present invention is a composition comprising an effective amount of at least one compound of Formula I, or a pharmaceutically acceptable salt thereof.

The invention also provides a pharmaceutical composition comprising an effective amount of at least one compound of Formula I, or a pharmaceutically acceptable salt thereof, and a pharmaceutically acceptable carrier.

The invention also provides a pharmaceutical composition comprising an effective amount of at least one compound of Formula I, or a pharmaceutically acceptable salt thereof, and an effective amount of at least one other pharmaceutically active ingredient (such as, for example, a chemotherapeutic agent).

The invention also provides a pharmaceutical composition comprising an effective amount of at least one compound of Formula I, or a pharmaceutically acceptable salt thereof, and an effective amount of at least one other pharmaceutically active ingredient (such as, for example, a chemotherapeutic agent), and a pharmaceutically acceptable carrier.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure comprising an acceptable carrier and a compound of Formula I, or a pharmaceutically acceptable salt thereof.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of Formula I, or a pharmaceutically acceptable salt thereof.

In one embodiment, the present invention provides a composition for treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure, comprising a compound of Formula I, or a pharmaceutically acceptable salt thereof, and a pharmaceutically acceptable carrier.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a subject in need of such treatment, comprising administering to said subject a therapeutically effective amount of at least one compound of Formula I, or a pharmaceutically acceptable salt thereof.

In one embodiment, the present invention provides a method of treating hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases such as chronic kidney diseases or heart failure in a patient in need thereof, comprising administering to said patient a therapeutically effective amount of at least one compound of Formula I, or a pharmaceutically acceptable salt thereof, and a pharmaceutically acceptable carrier.

The methods of the invention include the administration of a pharmaceutical composition comprising at least one compound of the invention, or a pharmaceutically acceptable salt thereof, and a pharmaceutically acceptable carrier.

In another embodiment, the present invention includes a method of treating NASH and/or fibrosis, comprising administering to a patient in need thereof a compound of Formula I, or a pharmaceutically acceptable salt thereof.

In another embodiment, the present invention includes a method of treating NASH and/or fibrosis, comprising administering to a patient in need thereof a compound of Formula I, or a pharmaceutically acceptable salt thereof, and a pharmaceutically acceptable carrier.

In another embodiment, the present invention includes a method of treating NASH and/or fibrosis, comprising administering to a patient in need thereof a composition comprising a compound of Formula I, or a pharmaceutically acceptable salt thereof.

In another embodiment, the present invention includes a method of treating NASH and/or fibrosis, comprising administering to a patient in need thereof a composition comprising a compound of Formula I, or a pharmaceutically acceptable salt thereof, and a pharmaceutically acceptable carrier.

In another embodiment, the present invention provides for the use of a compound of Formula I, or a pharmaceutically acceptable salt thereof, in the manufacture of a medicament for treating NASH and/or fibrosis, In another embodiment, the present invention includes the use of a compound of Formula I, or a pharmaceutically acceptable salt thereof, for the preparation of a medicament for the treatment of NASH and/or fibrosis, "Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, cyclopropyl, butyl, sec- and tert-butyl, pentyl, hexyl, octyl, nonyl, and the like. For example, the term "$C_{1-6}$alkyl" includes all of "$C_{1-4}$alkyl" defined as follows, plus the linear or branched chain alkyl groups, including all possible isomers, having 5 or 6 carbon atoms. "$C_{1-6}$alkyl" means linear or branched chain alkyl groups, including all possible isomers, having 1, 2, 3, 4, 5 or 6 carbon atoms, and includes each of the alkyl groups within $C_{1-6}$alkyl including each of the hexyl and pentyl isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). Commonly used abbreviations for alkyl groups are used throughout the specification, e.g. methyl may be represented by conventional abbreviations including "Me" or $CH_3$ or a symbol that is an extended bond as the terminal group, e.g.

"  ", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. For example, the structures

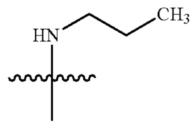 and 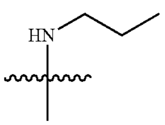

have equivalent meanings. $C_{1-6}$ alkyl includes n-, iso, sec- and t-butyl, n- and isopropyl, ethyl and methyl. If no number is specified, 1-6 carbon atoms are intended for linear or branched alkyl groups.

"Cyclic amine" refers to a cyclic ring comprising one nitrogen atom.

"Alkoxy" refers to an alkyl group linked to oxygen. Examples of alkoxy groups include methoxy, ethoxy, propoxy and the like.

"Aryl" refers to an aromatic monocyclic or multicyclic ring moiety comprising 6 to 14 ring carbon atoms. In one embodiment, an aryl group contains from about 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Fused Aryl" refers to an aryl ring fused with heterocyclyl or cycloalkyl.

"Halogen" or "Halo" includes fluorine, chlorine, bromine and iodine.

"Cycloalkyl" refers to a non-aromatic mono- or multicyclic ring system comprising about 3 to 10 ring carbon atoms. If no number of atoms is specified, 3-10 carbon atoms are intended. Cycloalkyl may also be fused, forming 1-3 carbocyclic rings. Non-limiting examples of monocyclic cycloalkyl include cyclopropyl, cyclobutyl, cyclopentyl, cyclohexyl, cycloheptyl, and cyclooctyl. The term $C_{1-6}$cycloalkyl" refers to a cycloalkyl group having 1 to 6 ring carbon atoms. The term $C_{3-6}$cycloalkyl" refers to a cycloalkyl group having 3 to 6 ring carbon atoms. Thus, for example, "$C_{3-6}$ cycloalkyl" includes each of cyclopropyl, cyclobutyl, cyclopentyl, and cyclohexyl. A cycloalkyl group is unsubstituted or substituted with one or more ring system substituents which may be the same or different, and are as defined within. When cycloalkyl is a substituent on an alkyl group, the cycloalkyl substituent can be bonded to any available carbon in the alkyl group. The following are illustrations of —$C_{3-6}$cycloalkyl substituents on an alkyl group wherein the substituent is cyclopropyl in bold:

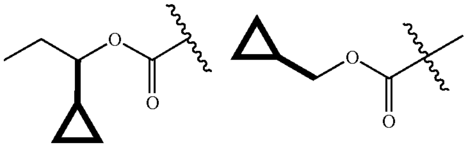

"Haloalkyl" refers to an alkyl group as defined within, wherein one or more of the alkyl group's hydrogen atoms has been replaced with a halogen. In one embodiment, a haloalkyl group has from 1 to 6 carbon atoms. Non-limiting examples of haloalkyl groups include $CH_2F$, $CHF_2$, $CF_3$, $CH_2CF_3$, $CH_2CHF_2$, $CF_2CF_3$, $CF_2CHF_2$, $CH_2Cl$ and $CCl_3$. The term "$C_{1-6}$haloalkyl" or "halo$C_{1-6}$alkyl" refers to a haloalkyl group having from 1 to 6 carbons.

"Haloalkoxy," "haloalkyl-O" and derivatives such as "halo($C_{1-6}$)alkoxy" are used interchangeably and refer to halo substituted alkyl groups linked through the oxygen atom. Haloalkoxy include mono-substituted as well as multiple halo substituted alkoxy groups. For example, trifluoromethoxy, chloromethoxy, and bromomethoxy are included as well as $OCH_2CF_3$, $OCH_2CHF_2$, $OCF_2CF_3$, and $OCF_2CHF_2$.

"Heterocyclyl," "heterocycle" or "heterocyclic" refers to monocyclic ring structures in which one or more atoms in the ring, the heteroatom(s), is an element other than carbon. Heteroatoms are typically O, S or N atoms. A heterocycle containing more than one heteroatom may contain different heteroatoms. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or unsaturated. The heterocycle may be attached to the rest of the molecule via a ring carbon atom, a ring oxygen atom or a ring nitrogen atom. Examples of heterocyclyl groups include: piperidine, piperazine, morpholine, pyrrolidine, tetrahydrofuran, azetidine, oxirane, or aziridine, and the like.

"Bicyclic heterocyclyl," "bicyclic heterocycle" or "bicyclic heterocyclic" refers to a heterocyclic ring fused to another ring system. The fusion may be bridged or unbridged.

Except where noted, the term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline.

"Fused heteroaryl" is heteroaryl fused with an aryl or heteroaryl.

"Oxo" means an oxygen linked to an atom by a double bond. An example of an oxo group is a doubly bonded oxygen in a ketone, sulfoxide, sulfone and sulfate.

"Hydroxyalkyl" or "-hydroxy($C_{1-3}$)alkyl" means an alkyl group having one or more hydrogen atoms replaced by hydroxyl (—OH) groups "Cyanoalkyl" means an alkyl group having one or more hydrogen atoms replaced by cyano (—CN) groups.

"Hydroxyhaloalkyl" means an alkyl group having one or more hydrogen atoms replaced by hydroxyl (—OH) groups, and one or more hydrogen atoms replaced by a halogen.

"Hydroxycycloalkyl" means a cyclic alkyl group having one or more hydrogen atoms replaced by hydroxyl (—OH) groups.

The term "composition" is intended to encompass a product comprising the specified ingredients in the specified amounts, as well as any product which results, directly or indirectly, from combination of the specified ingredients in the specified amounts.

The term "at least one" means one or more than one. The meaning of "at least one" with reference to the number of compounds of the invention is independent of the meaning with reference to the number of chemotherapeutic agents.

The term "chemotherapeutic agent" means a drug (medicament or pharmaceutically active ingredient) for treating cancer (i.e., an antineoplastic agent).

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Except where noted herein, the term "carbocycle" (and variations thereof such as "carbocyclic" or "carbocyclyl") as used herein, unless otherwise indicated, refers to a $C_3$ to $C_6$ monocyclic ring, e.g., $C_{3-6}$ monocyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

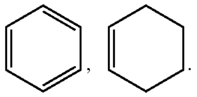

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The compounds of the present disclosure are limited to stable compounds embraced by Formula I and its embodiments. For example, certain moieties as defined in Formula I, may be unsubstituted or substituted, and the latter is intended to encompass substitution patterns (i.e., number and kind of substituents) that are chemically possible for the moiety and that result in a stable compound.

The term "substituted" means that one or more hydrogens on the designated atom is replaced with a selected from the indicated group, provided that the designated atom's normal valency under the existing circumstances is not exceeded, and that the substitution results in a stable compound. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. Combinations of substituents and/or variables are permissible only if such combinations result in stable compounds. If a substituent is itself substituted with more than one group, it is understood that these multiple groups may be on the same carbon or on different carbons, so long as a stable structure result. By optionally substituted, it is meant that compounds containing the specified optional substituent(s) as well as compounds that do not contain the optional substituent(s).

The wavy line , as used herein, indicates a point of attachment to the rest of the compound.

Where ring atoms are represented by variables such as "X", e.g.,

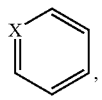

the variables are defined by indicating the atom located at the variable ring position without depicting the ring bonds associated with the atom. For example, when X in the above ring is nitrogen, the definition will show "N" and will not depict the bonds associated with it, e.g., will not show "═N—". Likewise, when X is a carbon atom that is substituted with bromide, the definition will show "C—Br" and will not depict the bonds associated with it, e.g., will not show

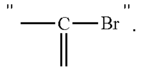

The invention also includes derivatives of the compound of Formula I, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of Formula I. Such prodrugs include those that demonstrate enhanced bioavailability, tissue specificity, and/or cellular delivery, to improve drug absorption of the compound of I. The effect of such prodrugs may result from modification of physicochemical properties such as lipophilicity, molecular weight, charge, and other physicochemical properties that determine the permeation properties of the drug.

For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Included are those esters and acyl groups known in the art for modifying the solubility or hydrolysis characteristics for use as sustained-release or prodrug formulations. Examples of pharmaceutically acceptable pro-drug modifications include, but are not limited to, —$C_{1-6}$alkyl esters and —$C_{1-6}$alkyl substituted with phenyl esters.

"Celite®" (Fluka) diatomite is diatomaceous earth, and can be referred to as "celite".

When any variable (e.g., $R^1$ etc.) occurs more than one time in any constituent or in Formula I or other generic Formula herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^1$ etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound.

It should be noted that, if a discrepancy between the chemical name and structure exists, the structure is understood to dominate.

Compounds of structural Formula I may contain one or more asymmetric centers and can thus occur as racemates and racemic mixtures, single enantiomers, diastereoisomeric mixtures and individual diastereoisomers. Centers of asymmetry that are present in the compounds of Formula I can all independently of one another have S configuration or R configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formulas. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formula I.

Compounds of structural Formula I may be separated into their individual diastereoisomers by, for example, fractional crystallization from a suitable solvent, for example MeOH or EtOAc or a mixture thereof, or via chiral chromatography using an optically active stationary phase. Optionally a derivatization can be carried out before a separation of stereoisomers. The separation of a mixture of stereoisomers can be carried out at an intermediate step during the synthesis of a compound of Formula I, or it can be done on a final racemic product. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formula I may be obtained by stereospecific synthesis using optically pure starting materials or reagents of known absolute configuration. The present invention includes all such isomers, as well as salts, solvates (including hydrates) and solvated salts of such racemates, enantiomers, diastereomers and tautomers and mixtures thereof.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formula I described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formula I of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formula I, and embodiments thereof. For example, different isotopic forms of hydrogen (H) include protium ($^1$H) and deuterium ($^2$H, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

It will be understood that the compounds of structural Formula I, may be prepared as pharmaceutically acceptable salts or as salts that are not pharmaceutically acceptable when they are used as precursors to the free compounds or their pharmaceutically acceptable salts or in other synthetic manipulations. The compounds of the present invention, including the compounds of the Examples, may also include all salts of the compounds of Formula I, which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids.

Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In one embodiment, the salts of acidic compounds are as follows, the ammonium, calcium, magnesium, potassium, and sodium salts.

With basic reagents such as hydroxides, carbonates, hydrogencarbonates, alkoxides and ammonia, organic bases or alternatively basic amino acids the compounds of the Formula I, form stable alkali metal, alkaline earth metal or optionally substituted ammonium salts.

Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the Formula I, capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, simultaneously contain acidic and basic groups in the molecule the invention also includes, in addition to the salt forms mentioned, inner salts or betaines (zwitterions). Salts can be obtained from the compounds of Formula I, by customary methods which are known to the person skilled in the art, for example by combination with an organic or inorganic acid or base in a solvent or dispersant, or by anion exchange or cation exchange from other salts.

The present invention includes compounds of structural Formula I, as well as salts thereof, particularly pharmaceutically acceptable salts, solvates of such compounds and solvated salt forms thereof, where such forms are possible unless specified otherwise.

Furthermore, compounds of the present invention may exist in amorphous form and/or one or more crystalline forms, and as such all amorphous and crystalline forms and mixtures thereof of the compounds of Formula I, including the Examples, are intended to be included within the scope of the present invention. In addition, some of the compounds of the instant invention may form solvates with water (i.e., a hydrate) or common organic solvents such as but not limited to EtOAc. Such solvates and hydrates, particularly the pharmaceutically acceptable solvates and hydrates, of the instant compounds are likewise encompassed within the scope of this invention, along with un-solvated and anhydrous forms.

Accordingly, the compounds within the generic structural formulas, embodiments and specific compounds described in the Examples and claimed herein encompass salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise, The invention also relates to medicaments containing at least one compound of the Formula I, and/or of a pharmaceutically acceptable salt of the compound of the Formula I and/or an optionally stereoisomeric form of the compound of the Formula I, or a pharmaceutically acceptable salt of the stereoisomeric form of the compound of Formula I, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula I and other surfaces which come into contact with blood in the body is possible.

The invention also relates to a process for the production of a medicament, which comprises bringing at least one compound of the Formula I into a suitable administration form using a pharmaceutically acceptable carrier and optionally further suitable active substances, additives or auxiliaries.

The present invention also relates to processes for the preparation of the compounds of Formula I which are described in the following and by which the compounds of the invention are obtainable.

The terms "therapeutically effective (or efficacious) amount" and similar descriptions such as "an amount efficacious for treatment" are intended to mean that amount of a pharmaceutical drug that will alleviate the symptoms of the disorder, condition or disease being treated (i.e., disorder, condition or disease associated with DGAT2 activity) in an animal or human. The terms "prophylactically effective (or efficacious) amount" and similar descriptions such as "an amount efficacious for prevention" are intended to mean that amount of a pharmaceutical drug that will prevent or reduce the symptoms or occurrence of the disorder, condition or disease being treated (i.e., disorder, condition or disease associated with DGAT2 activity) in an animal or human. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for treatment of NASH.

Disorders, conditions and diseases which can be treated or prevented by inhibiting DGAT2 by using the compounds of Formula I are, for example, diseases such as non-alcoholic steatohepatitis (NASH), fibrosis, hyperlipidemia, type I diabetes, type II diabetes mellitus, cognitive decline, dementia, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, hypertriglyceridemia, insulin resistance, impaired glucose tolerance, erectile dysfunction, skin and connective tissue disorders, hyper-apo B lipoproteinemia, non-alcoholic fatty liver disease, cardiorenal diseases such as chronic kidney diseases and heart failure, and related diseases and conditions.

The compounds of Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may need, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Furthermore, a subject of the present invention are pharmaceutical preparations (or pharmaceutical compositions) which comprise as active component a therapeutically effective dose of at least one compound of Formula I and/or a pharmaceutically acceptable salt thereof and a customary pharmaceutically acceptable carrier, i.e., one or more pharmaceutically acceptable carrier substances and/or additives.

Thus, a subject of the invention is, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder, condition or disease to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I.

Combination Agents

The compounds of the present invention can be administered alone or in combination with one or more additional therapeutic agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound of Formula (I) and any of the agents described above can be formulated together in the same dosage form and administered simultaneously. Alternatively, a compound of Formula (I) and any of the agents described above can be simultaneously administered, wherein both the agents are present in separate formulations. In another alternative, a compound of Formula (I) can be administered just followed by and any of the agents described above, or vice versa. In some embodiments of the separate administration protocol, a compound of Formula (I) and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of Formula (I), and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral, parenteral; IV, transdermal and subcutaneous), are administered at different dosage intervals, or when titration of the individual components of the combination is desired by the prescribing health care professional.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I and also includes free-acid, free-base and pharmaceutically acceptable salts of said additional active agents. Generally, any suitable additional active agent or agents, including but not limited to anti-hypertensive agents, anti-obetic, anti-inflammatory, anti-fibrotic, and anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides, amino acids and derivatives, amino acid chains linked by non-peptidic bonds, di- and tri-peptide derivatives, peptidyl amino diols and peptidyl beta-aminoacyl aminodiol carbamates; also, and small molecule renin inhibitors including diol sulfonamides and, N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), cerivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and/or with an HMG-CoA reductase inhibitor; niacin receptor agonists such as acipimox and acifran, as well as niacin receptor partial agonists; anti-cholesterol agents such as PCSK9 inhibitors (alirocumab, evolocumab), Nexletol™ (bempedoic acid, ACL inhibitor), and Vascepa® (Icosapent ethyl); metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) β-klotho/FGFR1 activating monoclonal antibody (e.g. MK-3655), pan FGFR1-4/KLB modulators, FGF19 analogue (e.g. Aldafermin) (ii) PPARγ agonists, such as the glitazones (e.g. pioglitazone, AMG 131, CHS 131, MBX2044, mitoglitazone, lobeglitazone, IDR-105, rosiglitazone, and balaglitazone), and other PPAR ligands, including (1) PPARα/γ dual agonists (e.g.ZYH2, ZYH1, GFT505, chiglitazar, muraglitazar, aleglitazar, sodelglitazar, and naveglitazar); (2) PPARU agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); (4) PPARγ partial agonists, (5) PPAR α/δ dual agonists (e.g. Elafibranor); (iii) biguanides, such as metformin and its pharmaceutically acceptable salts, in particular, metformin hydrochloride, and extended-release formulations thereof, such as Glumetza™, Fortamet™, and GlucophageXR™; and (iv) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof), bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib): inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators (e.g. Aramchol); GPR-105 antagonists (e.g., such as those disclosed in WO 2009/000087); SGLT inhibitors (e.g., ASP1941, SGLT-3, SGLT-2 such as empagliflozin, dapagliflozin, canagliflozin, and ertugliflozin, BI-10773, remogloflozin, TS-071, tofogliflozin, ipragliflozin, and LX-4211); inhibitors of acyl coenzyme A carboxylase (ACC, MK-4074); inhibitors of diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; bile acid modulators; PACAP, PACAP mimetics, and PACAP receptor 3 agonists; IL-1b antibodies, (e.g., XOMA052 and canakinumab), anti-fibrotic and/or anti-inflammatory agents (CCR2/CCR5 dual receptor antagonist (e.g. cenicriviroc); galectin 3 inhibitor (e.g. belapectin, GB-1107, GB-1211), siRNA against HSP 47 (e.g. BMS-986263); NSAID derived from pirfenidone (e.g. hydronidone), A3AR agonist (e.g. namodenoson, FM101); TGFTX4 (e.g. nitazoxanide); 5-lipoxygenase inhibitor (e.g. tipelukast), Bifunctional urate inhibitor (e.g. ACQT1127), adiponectin receptor agonist (e.g. ALY688), TNF receptor antagonist (e.g. atrosimab), Autotaxin inhibitor (e.g. BLD-0409, TJC 0265, TJC 0316), CCL24 blocking monoclonal antibody (e.g. CM101), IL-11 inhibitor (e.g. ENx 108A), LPA1 receptor antagonist (e.g. EPGN 696), Dual JAK1/2 inhibitor (e.g. EX 76545), GPR antagonist (e.g. GPR91 antagonist), Integrin αvβ1, αvβ3 and αvβ6 inhibitor (e.g. IDL 2965), NLRP3 antagonist (e.g. IFM-514), inflammasome inhibitors (e.g. JT194, JT349), Cell membrane permeability inhibitor (e.g. Larazotide), CCR5 antagonist (e.g. Ieronlimab), TNF inhibitor (e.g. LIVNate), integrin αvβ6 inhibitor (e.g. MORF beta6), NLRP inflammasome antagonists, siRNA (e.g. OLX 701), dual TFGP/Hedgehog inhibitor (e.g. Oxy 200), GPR40 agonist/GPR84 antagonist (e.g. PBI-4547), neutrophil elastase inhibitor (e.g. PHP-303), integrin inhibitor (e.g. PLN-1474), TGF1 modulator (e.g.PRM-151), CCK receptor antagonist (e.g. proglumide), LOXL2 inhibitor (e.g. PXS-5338K, PXS-5382A), IL-11 inhibitors, MPYS protein inhibitor (e.g. cGAS/STING antagonists), kinase inhibiting RNase, membrane protein mAbs, tumor necrosis factor inhibitor, NRF2 activator (e.g. SCO 116), SSAO inhibitor (e.g. TERN 201), TRAIL2 agonist (e.g. TLY012), IL-6 receptor antagonist (e.g. TZLS 501), AOC3 inhibitor (e.g. UD-014), SSAO/VAP-1 inhibitor, TREM2); anti-oxidant (e.g. vitamin E); anti-inflammatory agents (e.g. norfloxacin, ciprofloxacin, ceftriaxone); coagulation modifiers (e.g. anti-coagulants, anti-platelet agents, pentoxifylline, vitamin K, DDAVP); dual GIP and GLP-1 receptor agonist (e.g. tirzepetide); dual GLP-1/GRA (e.g. cotadutide, ALT-801, DD 01, G49, PB-718); dual GLP-1 (e.g. CT 868); GLP-1/GRA/GIP triple agonist (e.g. HM15211); GRP120 stimulant/inflammasome modulator/PPARγ dual agonist (e.g. KDT501); GLP-1/FGF21 (e.g. YH25724); GLP-1 agonist (e.g. Ozempic (semaglutide sc), XW 003); selective thyroid hormone receptor-(1 agonist (e.g. resmetirom); apoptosis modulators (JNK-1 inhibitor (e.g. CC-90001), Peroxidase inhibitor (e.g. AZM198), ASK-1 inhibitor (e.g. CS-17919, SRT 015)); erythropoietin-stimulating agents (erythropoietin receptor agonist (e.g. cibinetide)); glucose pathway modulators (SGLT-2 inhibitor (e.g. Forxiga, Farxiga (dapagliflozin)); dual SGLT-1/2 inhibitor (e.g. licogliflozin), Glucose-6-P dehydrogenase inhibitor (e.g. fluasterone) LAPS glucagon combo (e.g. HM14320), SGLT-1 inhibitor (e.g. SGL5213)); immune modulators (TLR4 inhibitor (e.g. GBK-233), immunomodulatory polyclonal antibody (e.g. IMM-124E), TLR4 antagonist (e.g. JKB-122), CD3 monoclonal antibody (e.g. foralumab), TLR4 antagonist (e.g. JKB 133), TLR4 inhibitor (e.g. mosedipimod), Macrophage inhibitor via CD206 targeting (e.g. MT2002), TLR2/4 antagonist (e.g. VB-201, VB-703), immunomodulatory polyclonal antibody (e.g. IMM-124E)); incretin-based therapies (GLP-1 agonist (e.g. Ozempic (semaglutide sc), XW 003), GLP-1/glucagon dual receptor agonist (e.g. HM112525A), prandial insulin (e.g. ORMD 0801)); lipid modulators (AMPK Activator/Glutathione transferase (e.g. oltipraz), THR-beta agonist (e.g. resmetirom, VK2809, MGL-3745, ALG-009, ASC41, CNPT-101101, TERN 501), IBAT inhibitor (e.g. elobixibat, CJ 14199), omega-6-fatty acid (e.g. epeleuton), FASN inhibitor (e.g. TVB2640, FT 4101, FT 8225), ANGPTL3 inhibitor (e.g. vupanorsen), PNPLA3 inhibitor (e.g. AZD2693), RAS domain kinase inhibitor (e.g. BioE1115), NTCP inhibitor (e.g. bulevirtide), P2Y13 receptor agonist (e.g. CER-209), omega-3 fatty acid, HSD1713 inhibitor; metabolism modulators (FXR agonist (e.g. Ocaliva (obeticholic acid), IOT022), recombinant variant of FGF19 (e.g. aldafermin), bi-specific FGFR1/KLB antibody (e.g. BFKB8488A), mTOT modulator (e.g. MSDC-0602K), pegylated analog of FGF21 (e.g. pegbelfermin, BMS-986171), non-bile FXR agonist (e.g. cilofexor, EDP-305, EYP 001, tropifexor, MET409, AGN-242256, AGN-242266, EDP 297, HPG 1860, MET642, RDX023, TERN 101), ACC inhibitor (e.g. firsocostat, PF-05221304), ketohexokinase inhibitor (e.g. PF-06835919), AMPK activator (e.g. PXL770, MSTM 101, 0304), bile acid modulator (e.g. Albiero), FGF21 analog (e.g. BI089-100), MOTSc analog (e.g. CB4211), cyclophilin inhibitor (e.g. CRV 431), FGF19 (e.g. DEL 30), mitochondrial uncoupler (e.g. GEN 3026), FXR/GPCR dual agonist (e.g. INT-767), Cysteamine derivative (e.g. KB-GE-001), dual amylin and calcitonin receptor agonist (e.g. KBP-089), transient FXR agonist (e.g. M 1217), anti-beta-klotho (KLB)-FGFR1c receptor complex mAb (e.g. MK3655), GDF15 analog (e.g. NGM395), cyclophilin inhibitor (e.g. NV556), LXR modulator (e.g. PX 329, PX 655, PX 788), LXR inverse agonist (e.g. PX016), deuterated obeticholic acid (e.g. ZG 5216)); PPAR modulators (dual PPARα/γ agonist (e.g. elafibranor), PPAR pan agonist (e.g. lanifibranor), PPARα agonists (e.g. Parmodia), PPARγ agonist (e.g. CHS 131), MPC inhibitor (e.g. PXL065), PPAR δ/γ agonist (e.g. T3D 959)); RAAS mIM-Modulators (mineralocorticoid receptor antagonist (e.g. apararenone, eplerenone, spironolactone), angiotensin receptor blocker (e.g. losartan potassium)); neurotransmitter modulators (cannabinoid receptor modulator, CB1 receptor antagonist (e.g. CRB-4001, IM-102, nimacimab), TPH1 inhibitor (e.g. CU 02), GPR120 agonist (e.g. KBR2001), combination of cannabinoid and botanical anti-inflammatory compound (e.g. SCN 002)); PDE Modulator (PDE4 inhibitor (e.g. ART 648)); CYP2E1 inhibitor (e.g. SNP-610); cell therapies (e.g. HepaStem) and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The present invention includes the pharmaceutically acceptable salts of the compounds defined herein, including the pharmaceutically acceptable salts of all structural formulas, embodiments and classes defined herein. Reference to the compounds of structural Formula (I) includes the compounds of other generic structural Formulas, such as Formulas and embodiments that fall within the scope of Formula (I).

Dosages of the Compounds of Formula (I)

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician considers such factors as the patient's age, condition and size, as well as the severity of the condition being treated and the response of the patient to the treatment.

The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of an oncological condition, and a prophylactically effective amount, e.g., for prevention of an oncological condition.

While individual needs vary, determination of optimal ranges of effective amounts of the compound of the invention is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 500 mg/day, about 5 mg/day to about 250 mg/day, about 10 mg/day to about 100 mg/day, about 3 mg/day to about 10 mg/day, or about 100 mg/day to about 250 mg/day. Such doses may be administered in a single dose or may be divided into multiple doses.

Pharmaceutical Compositions

The compounds of Formula I and their pharmaceutically acceptable salts can be administered to animals, preferably to mammals, and in particular to humans, as pharmaceuticals by themselves, in mixtures with one another or in the form of pharmaceutical compositions. The term "subject" or "patient" includes animals, preferably mammals and especially humans, who use the instant active agents for the prevention or treatment of a medical condition.

Administering of the compound of Formula I to the subject includes both self-administration and administration to the patient by another person. The subject may need, or desire, treatment for an existing disease or medical condition, or may be in need of or desire prophylactic treatment to prevent or reduce the risk of occurrence of said disease or medical condition. As used herein, a subject "in need" of treatment of an existing condition or of prophylactic treatment encompasses both a determination of need by a medical professional as well as the desire of a patient for such treatment.

Methods for the safe and effective administration of most of these agents are known to those skilled in the art. In addition, their administration is described in the standard literature.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the condition being treated and the response of the patient to the treatment.

The amount and frequency of administration of the compound of Formula I, and any additional agents will be regulated according to the judgment of the attending clinician (physician) considering such factors as age, condition and size of the patient as well as severity of the condition being treated.

The compounds of the invention are also useful in preparing a medicament that is useful in treating NASH and fibrosis.

The instant compounds are also useful in combination with therapeutic, chemotherapeutic and anti-cancer agents for the treatment of hepatic cellular carcinoma. Combinations of the presently disclosed compounds with therapeutic, chemotherapeutic and anti-cancer agents are within the scope of the invention. Examples of such agents can be found in Cancer Principles and Practice of Oncology by V. T. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents. The particular choice of chemotherapeutic agent will depend upon the diagnosis of the attending physicians and their judgment of the condition of the patient and the appropriate treatment protocol.

The initial administration can be made according to established protocols known in the art, and then, based upon the observed effects, the dosage, modes of administration and times of administration can be modified by the skilled clinician.

The determination of the order of administration, and the number of repetitions of administration of the chemotherapeutic agent during a treatment protocol, is well within the knowledge of the skilled physician after evaluation of the condition being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The agent can be administered according to therapeutic protocols well known in the art. It will be apparent to those skilled in the art that the administration of the anti-cancer agent can be varied depending on the cancer being treated and the known effects of the anti-cancer agent on that disease.

The initial administration can be made according to established protocols known in the art, and then, based upon the observed effects, the dosage, modes of administration and times of administration can be modified by the skilled clinician.

The particular choice of agent will depend upon the diagnosis of the attending physicians and their judgment of the condition of the patient and the appropriate treatment protocol.

The determination of the order of administration, and the number of repetitions of administration of the agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: Liver: hepatoma (hepatocellular carcinoma), cholangiocarcinoma, hepatoblastoma, angiosarcoma, hepatocellular adenoma, hemangioma.

PD-1 inhibitors include pembrolizumab (lambrolizumab), nivolumab and MPDL3280A. PDL-inhibitors include atezolizumab, avelumab, and durvalumab.

The invention further relates to a method of treating hepatic cellular carcinoma in a human patient comprising administration of a compound of the invention (i.e., a compound of Formula I) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

A compound of the instant invention, or a pharmaceutically acceptable salt thereof, may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

Methods for Making the Compounds of Present Invention

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases, the order of carrying out the steps of reaction schemes may be varied to facilitate the reaction or to avoid unwanted reaction products. For stereoisomers, enantiomer A refers to the faster/earlier eluting enantiomer and enantiomer B refers to the slower/later eluting enantiomer at the point of separation and this nomenclature is maintained through the remainder of a synthetic sequence for a given enantiomeric series regardless of the possibility that subsequent intermediates and final compounds may have the same or opposite orders of elution.

List of Abbreviations

ACN=acetonitrile
aq.=aqueous
° C.=degrees Celcius
$Cu(OAc)_2$=copper acetate
DCM=dichloromethane
DEA=diethylamine
DIPEA=N,N-Diisopropylethylamine
DMAP=4-(dimethylamino)pyridine
DMF=dimethylformamide
DPPA=Diphenylphosphoryl azide
dppf=1,1'-bis(diphenylphosphino)ferrocene
EtOAc=ethyl acetate
EtOH=ethanol
$Et_3N$=triethylamine
FA=formic acid
$Fe(acac)_3$=ferric acetylacetonate
HATU=1-[Bis(dimnethylamino)methylene]-1H-1,2,3-triazolo[4,5-b]pyridinium 3-oxid-hexafluorophosphate, Hexafluorophosphate Azabenzotriazole Tetramethyl Uronium
h=hour(s)
Hex=hexanes
iPrOH=isopropanol
KOAc=potassium acetate
Me=methyl
MeCN=acetonitrile
MeOH=methanol
MsCl=methanesulfonyl chloride
min=minutes
NIS=N-Iodosuccinimide
$Pd(OAc)_2$=palladium acetate
$Pd_2(dba)_3$=tris(dibenylideneacetone)dipalladium (0)
rt or RT=room temperature
SFC=supercritical fluid chromatography
TFA=trifluoroacetic acid
THF=tetrahydrofuran
TsCl=4-methylbenzenesulfonyl chloride
TLC=thin layer chromatography
UV=ultraviolet
wt. %=percentage by weight
% w/v=percentage in weight of the former agent relative to the volume of the latter agent
Xantphos=4,5-bis(diphenylphosphino)-9,9-dimethylxanthene
$Zn(OAc)_2$=zinc acetate
LCMS conditions: column: ACQUITY UPLC-QDa BEH C18, 1.7 mm, 2.1×50 mm. Solvent system: A: Water 0.1% FA, B: ACN 0.1% FA
Gradient condition: 10-90% B, in 1.7 min, total run time 2.4 min General Synthetic Schemes While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention.

[General Scheme]

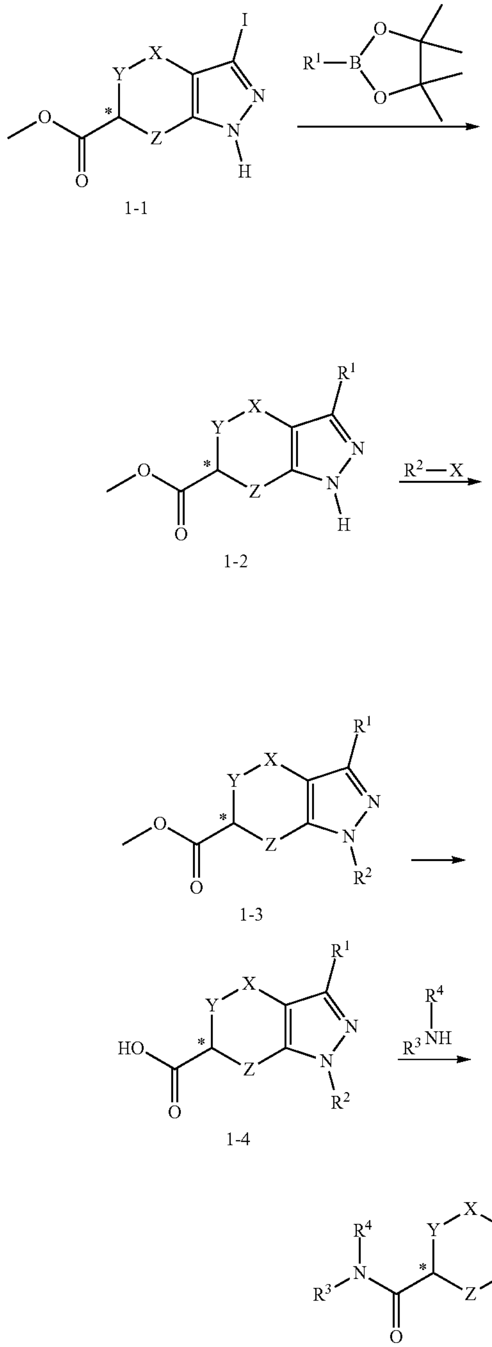

1-1

1-2

1-3

1-4

1

Compounds of formula I were prepared from 1-1 by C—C coupling with $R^1$-boronic acid or ester to provide 1-2. N-substituted compounds (1-3) were prepared with $R^2$—X via $SN_2$ for alkyl substituents or copper-mediated C—N coupling (Chan-Lam or Buchwald N-arylation) for aromatic substituents. Saponification of 1-3 provided the corresponding carboxylic acid (1-4) and subsequent amide coupling with the appropriate amines provided compounds of formula I as described by the general scheme. The order of steps for some examples may be varied to facilitate the syntheses.

INTERMEDIATES

Intermediate 1

2-(5-(difluoromethoxy)-2-fluorophenyl)-4,4,5,5-tetramethyl-1,3,2-dioxaborolane

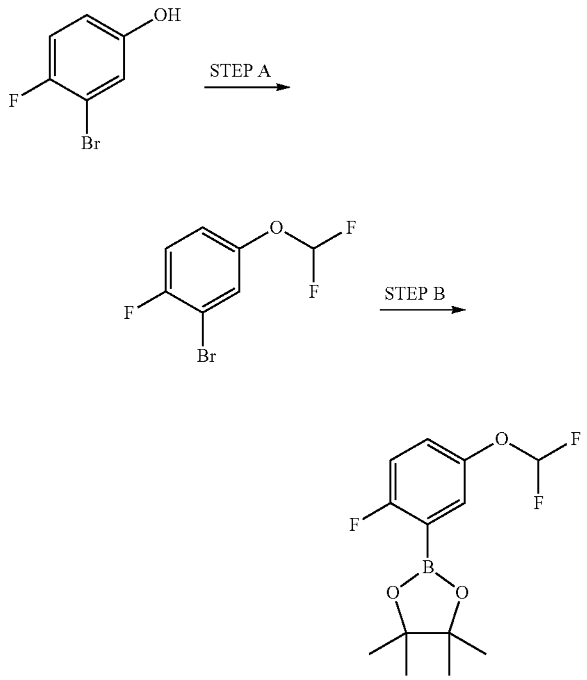

INT-1

Step A: 2-bromo-4-(difluoromethoxy)-1-fluorobenzene

At 0° C., to a stirred solution of 3-bromo-4-fluorophenol (10 g, 52.4 mmol), KOH (8.81 g, 157 mmol), MeCN (52.4 ml), and water (52.4 ml) was added diethyl (bromodifluoromethyl)phosphonate (28.0 g, 105 mmol). The mixture was stirred at rt for 1 h then extracted three times with EtOAc. The combined organic layers were washed with water and brine. The organic layer was then dried over $MgSO_4$ (s), filtered, and concentrated in vacuo. The crude product was purified by flash silica gel column chromatography (5% EtOAc in hexanes) to afford the title compound. LC/MS=241 [M+1].

Step B: 2-(5-(difluoromethoxy)-2-fluorophenyl)-4,4,5,5-tetramethyl-1,3,2-dioxaborolane To a stirred solution of 2-bromo-4-(difluoromethoxy)-1-fluorobenzene (2 g, 8.30 mmol), bis(pinacolato)diboron (2.53 g, 9.96 mmol), $PdCl_2$(dppf) (1.36 g, 1.66 mmol), and dioxane (16.6 ml) was added KOAc (2.44 g, 24.9 mmol). The mixture was stirred at 100° C. for 16 h. After cooling to rt, water was added and the aqueous layer was extracted three time with EtOAc. The combined organic layers were washed with water and brine. The organic layer was then dried over $MgSO_4$ (s), filtered, and concentrated in vacuo. The crude product was purified by flash silica gel column chromatography (5% EtOAc in hexanes) to afford the title compound. LC/MS=289 [M+1].

By using procedures similar to those described in Intermediate 1 with appropriate reagents, the following compounds were synthesized. These compounds were characterized by LC/MS.

| Intermediate | Structure | Name | LCMS [M + 1] |
|---|---|---|---|
| 2 | 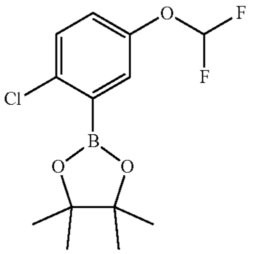 [SMILES: CC1(C)OB(c2cc(OC(F)F)ccc2Cl)OC1(C)C] | 2-(2-chloro-5-(difluoromethoxy)phenyl)-4,4,5,5-tetramethyl-1,3,2-dioxaborolane | 305 |
| 3 | 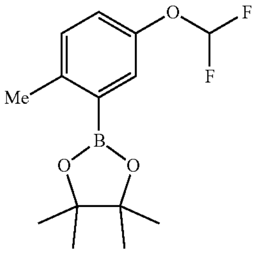 [SMILES: Cc1ccc(OC(F)F)cc1B1OC(C)(C)C(C)(C)O1] | 2-(5-(difluoromethoxy)-2-methylphenyl)-4,4,5,5-tetramethyl-1,3,2-dioxaborolane | 285 |

-continued

| Intermediate | Structure | Name | LCMS [M + 1] |
|---|---|---|---|
| 4 | 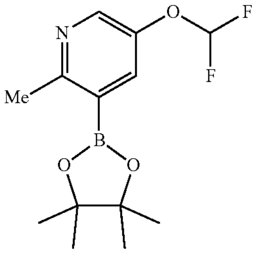 [SMILES: Cc1ncc(OC(F)F)cc1B1OC(C)(C)C(C)(C)O1] | 5-(difluoromethoxy)-2-methyl-3-(4,4,5,5-tetramethyl-1,3,2-dioxaborolan-2-yl)pyridine | 286 |
| 5 | 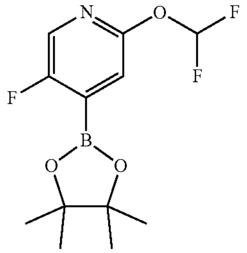 [SMILES: CC1(C)OB(c2cc(OC(F)F)ncc2F)OC1(C)C] | 2-(difluoromethoxy)-5-fluoro-4-(4,4,5,5-tetramethyl-1,3,2-dioxaborolan-2-yl)pyridine | 290 |

Intermediate 6

5-fluoro-4-(4,4,5,5-tetramethyl-1,3,2-dioxaborolan-2-yl)-2-(2,2,2-trifluoroethoxy)pyridine

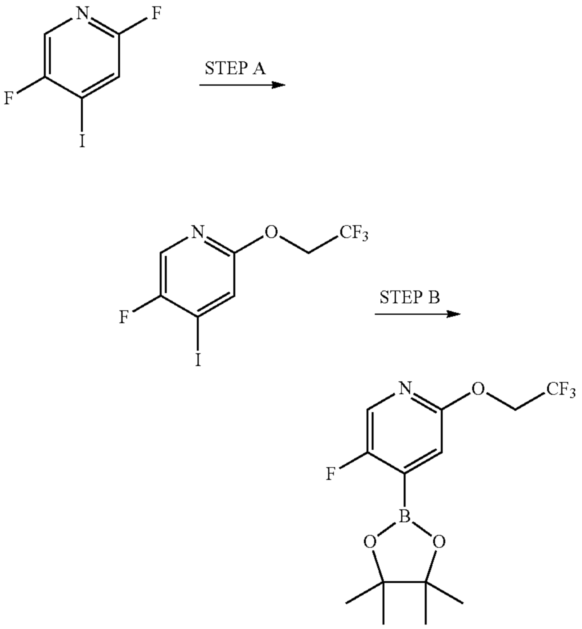

INT-6

Step A: 5-fluoro-4-iodo-2-(2,2,2-trifluoroethoxy)pyridine

To a stirred solution of NaH (480 mg, 12 mmol) and DMSO (20 mL) was added 2,2,2-trifluoroethan-1-ol (1.0 g, 10 mmol). The mixture was stirred at rt for 15 minutes then 2,5-difluoro-4-iodopyridine (4.1 g, 17 mmol) was added. The mixture was stirred for 2 h and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (10% EtOAc in hexanes) to afford the title compound. LC/MS=322 [M+1].

Step B: 5-fluoro-4-(4,4,5,5-tetramethyl-1,3,2-dioxaborolan-2-yl)-2-(2,2,2-trifluoroethoxy)pyridine To a stirred solution of 5-fluoro-4-iodo-2-(2,2,2-trifluoroethoxy)pyridine (1.06 g, 3.3 mmol), bis(pinacolato)diboron (1.67 g, 6.6 mmol), $PdCl_2$(dppf) (242 mg, 0.33 mmol), and dioxane (11 ml) was added KOAc (0.97 g, 9.9 mmol). The mixture was stirred at 100° C. for 16 h. After cooling to rt, water was added, and the aqueous layer was extracted three time with EtOAc. The combined organic layers were washed with water and brine. The organic layer was then dried over $MgSO_4$ (s), filtered, and concentrated in vacuo. The crude product was purified by flash silica gel column chromatography (30% EtOAc in hexanes) to afford the title compound. LC/MS=322 [M+1].

By using procedures similar to those described in Intermediate 6 with appropriate reagents, the following compounds were synthesized. These compounds were characterized by LC/MS.

| Intermediate | Structure | Name | LCMS [M + 1] |
|---|---|---|---|
| 7 | 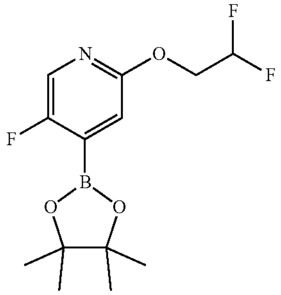 [SMILES: CC1(C)OB(c2cc(OCC(F)F)ncc2F)OC1(C)C] | 2-(2,2-difluoroethoxy)-5-fluoro-4-(4,4,5,5-tetramethyl-1,3,2-dioxaborolan-2-yl)pyridine | 304 |
| 8 | 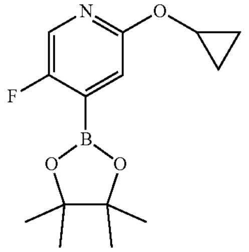 [SMILES: CC1(C)OB(c2cc(OC3CC3)ncc2F)OC1(C)C] | 2-cyclopropoxy-5-fluoro-4-(4,4,5,5-tetramethyl-1,3,2-dioxaborolan-2-yl)pyridine | 280 |

Intermediate 9

5-(difluoromethoxy)-2-(difluoromethyl)-3-(4,4,5,5-tetramethyl-1,3,2-dioxaborolan-2-yl)pyridine

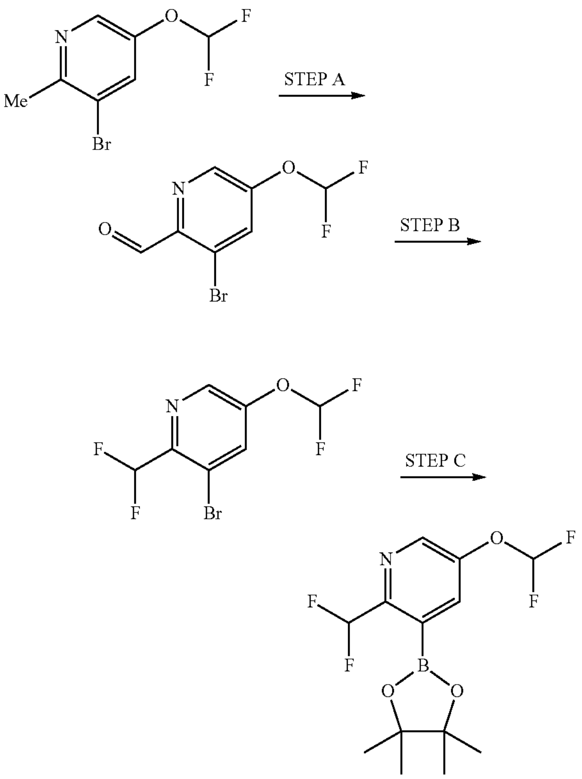

INT-9

Step A: 3-bromo-5-(difluoromethoxy)picolinaldehyde

To a stirred solution of 3-bromo-5-(difluoromethoxy)-2-methylpyridine (1.27 g, 5.3 mmol) and dioxane (11 mL) was added $SeO_2$ (5.9 g, 53 mmol). The mixture was stirred at 140° C. for 16 h. After cooling to rt the mixture was filtered and concentrated in vacuo. The crude product was purified by flash silica gel column chromatography (20% EtOAc in hexanes) to afford the title compound. LC/MS=252 [M+1].

Step B: 3-bromo-5-(difluoromethoxy)-2-(difluoromethyl)pyridine

At 0° C., to a stirred solution of 3-bromo-5-(difluoromethoxy)picolinaldehyde (1.14 g, 4.5 mmol) and DCM (9 mL) was added (diethylamino)sulfur trifluoride (2.4 mL, 18.1 mmol). The mixture was stirred at rt for 1 h. Sat. aq. $NaHCO_3$ was added and the aqueous layer was extracted three time with DCM. The combined organic layers were washed with water and brine. The organic layer was then dried over $MgSO_4$ (s), filtered, and concentrated in vacuo. The crude product was purified by flash silica gel column chromatography (10% EtOAc in hexanes) to afford the title compound. LC/MS=274 [M+1].

Step C: 5-(difluoromethoxy)-2-(difluoromethyl)-3-(4,4,5,5-tetramethyl-1,3,2-dioxaborolan-2-yl)pyridine To a stirred solution of 3-bromo-5-(difluoromethoxy)-2-(difluoromethyl)pyridine (0.98 g, 3.6 mmol), bis(pinacolato) diboron (1.82 g, 7.2 mmol), $PdCl_2(dppf)$ (263 mg, 0.36 mmol), and dioxane (12 ml) was added KOAc (1.06 g, 10.8 mmol). The mixture was stirred at 100° C. for 16 h. After cooling to rt, water was added and the aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (20% EtOAc in hexanes) to afford the title compound. LC/MS=322 [M+1].

Intermediate 10

5-fluoro-2-isopropoxy-4-(4,4,5,5-tetramethyl-1,3,2-dioxaborolan-2-yl)pyridine

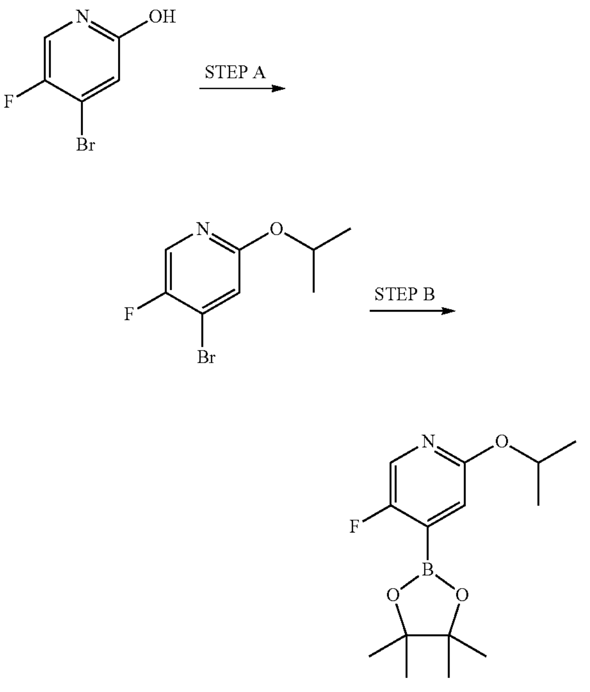

INT-10

Step A: 4-bromo-5-fluoro-2-isopropoxypyridine

To a stirred solution of 4-bromo-5-fluoropyridin-2-ol (512 mg, 2.7 mmol) 2-iodopropane (400 μL, 4 mmol) and DCE (5.3 mL) was added $Ag_2CO_3$ (1.5 g, 5.3 mmol). The mixture was stirred at rt for 16 h then filtered over Celite. The crude mixture was concentrated in vacuo and the crude product was used without further purification. LC/MS=234 [M+1].

Step B: 5-fluoro-2-isopropoxy-4-(4,4,5,5-tetramethyl-1,3,2-dioxaborolan-2-yl)pyridine To a stirred solution of 4-bromo-5-fluoro-2-isopropoxypyridine (600 g, 2.6 mmol), bis(pinacolato)diboron (1.3 g, 5.1 mmol), $PdCl_2$(dppf) (188 mg, 0.26 mmol), and dioxane (8.5 ml) was added KOAc (755 mg, 7.7 mmol). The mixture was stirred at 100° C. for 16 h. After cooling to rt, water was added and the aqueous layer was extracted three time with EtOAc. The combined organic layers were washed with water and brine. The organic layer was then dried over $MgSO_4$ (s), filtered, and concentrated in vacuo. The crude product was purified by flash silica gel column chromatography (20% EtOAc in hexanes) to afford the title compound. LC/MS=282 [M+1].

Intermediate 11

2-(3-(2,2-difluoroethoxy)phenyl)-4,4,5,5-tetramethyl-1,3,2-dioxaborolane

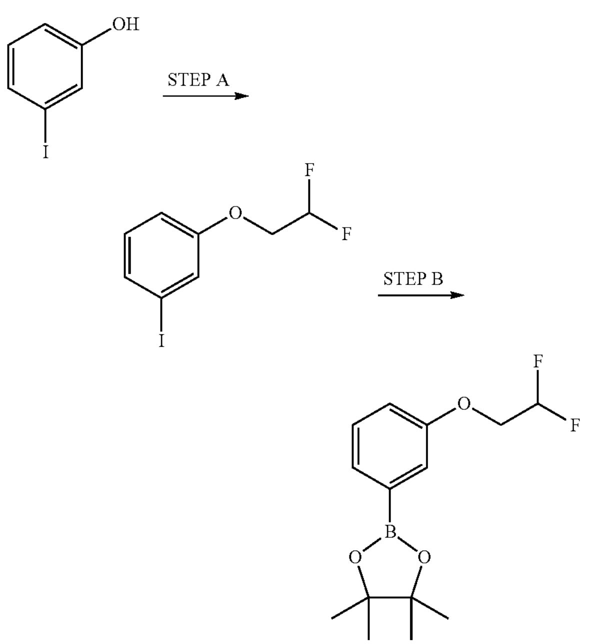

INT-11

Step A: 1-(2,2-difluoroethoxy)-3-iodobenzene

To a stirred solution of 3-iodophenol (1.0 g, 4.6 mmol), 2,2-difluoroethyl trifluoromethanesulfonate (1.95 g, 9.1 mmol), and DMF (9 mL) was added $Cs_2CO_3$ (5.9 g, 18.2 mmol). The reaction mixture was heated to 60° C. for 18 h. The reaction mixture was cooled to rt and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (10% EtOAc in hexanes) to afford the title compound. LC/MS=285 [M+1].

Step B: 2-(3-(2,2-difluoroethoxy)phenyl)-4,4,5,5-tetramethyl-1,3,2-dioxaborolane To a stirred solution of 1-(2,2-difluoroethoxy)-3-iodobenzene (500 mg, 1.76 mmol), bis(pinacolato)diboron (671 mg, 2.64 mmol), Pd(dppf)$Cl_2$ (258 mg, 0.35 mmol), and dioxane (5.8 mL) was added KOAc (691 mg, 7.04 mmol). The reaction mixture was heated to 100° C. for 21 h. The reaction mixture was cooled to rt and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (10% EtOAc in hexanes) to afford the title compound. LC/MS=285 [M+1].

By using procedures similar to those described in Intermediate 11 with appropriate reagents, the following compounds were synthesized. These compounds were characterized by LC/MS.

| Intermediate | Structure | Name | LCMS [M + 1] |
|---|---|---|---|
| 12 | 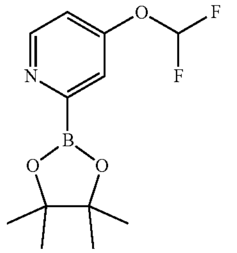 [SMILES: CC1(C)OB(c2cc(OC(F)F)ccn2)OC1(C)C] | 4-(difluoromethoxy)-2-(4,4,5,5-tetramethyl-1,3,2-dioxaborolan-2-yl)pyridine | 272 |
| 13 | 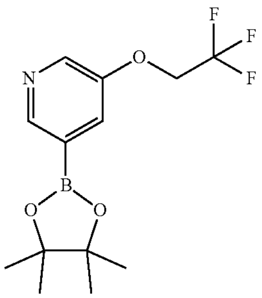 [SMILES: CC1(C)OB(c2cncc(OCC(F)(F)F)c2)OC1(C)C] | 3-(4,4,5,5-tetramethyl-1,3,2-dioxaborolan-2-yl)-5-(2,2,2-trifluoroethoxy)pyridine | 304 |
| 14 | 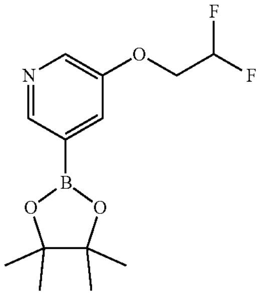 [SMILES: CC1(C)OB(c2cncc(OCC(F)F)c2)OC1(C)C] | 3-(2,2-difluoroethoxy)-5-(4,4,5,5-tetramethyl-1,3,2-dioxaborolan-2-yl)pyridine | 286 |

Intermediate 15

5-(difluoromethoxy)-2-methyl-3-(4,4,5,5-tetramethyl-1,3,2-dioxaborolan-2-yl)pyridine

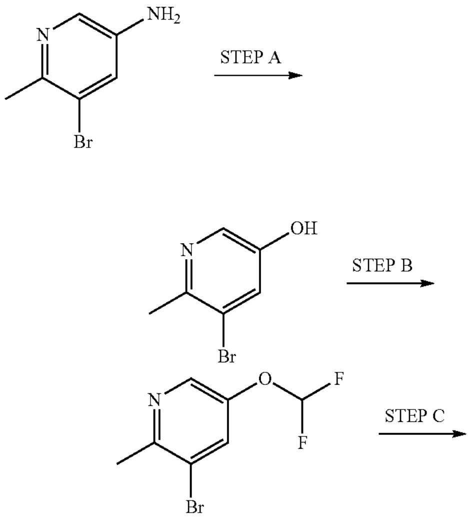

-continued

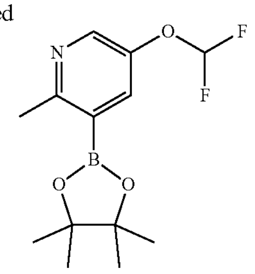

INT-15

Step A: 5-bromo-6-methylpyridin-3-ol

To a mixture of 5-bromo-6-methylpyridin-3-amine (2 g, 10.69 mmol), $HBF_4$ (10 ml, 10.69 mmol) and water (10 mL) was added sodium nitrite (0.812 g, 11.76 mmol) at 0° C. The resulting yellowish heterogeneous reaction mixture was stirred for 30 min at 0° C. After addition of water (5 mL), the mixture was heated to 100° C. and stirred for 12 h. LCMS showed that desired target was formed. The mixture was poured into $H_2O$, then the mixture was extracted with EtOAc (×3), the combined organic layers were washed with brine, dried over $Na_2SO_4$, then filtered and concentrated under reduced pressure. The residue was purified by column chromatography on silica (0-100% EtOAc/hexanes) to afford the title compound (1.3 g). LC/MS=188 and 190 [M+1].

Step B: 3-bromo-5-(difluoromethoxy)-2-methylpyridine

A 8 mL of tube was charged with 5-bromo-6-methylpyridin-3-ol (600 mg, 3.19 mmol), $Cs_2CO_3$ (3119 mg, 9.57 mmol) and DMF (4 mL) at 25° C. Then the mixture was bubble with chlorodifluoromethane (2759 mg, 31.9 mmol), and the reaction was stirred at 60° C. for 15 h. LCMS showed that desired target was formed. The mixture was poured into $H_2O$, then the mixture was extracted with EtOAc (×3), the combined organic layers were washed with brine, dried over $Na_2SO_4$, then filtered and concentrated under reduced pressure. The residue was purified by column chromatography on silica (0-100% EtOAc/hexanes) to afford the title compound. LC/MS=238 and 240 [M+1].

Step C: 5-(difluoromethoxy)-2-methyl-3-(4,4,5,5-tetramethyl-1,3,2-dioxaborolan-2-yl)pyridine A 8 mL of tube was charged with 3-bromo-5-(difluoromethoxy)-2-methylpyridine (330 mg, 1.386 mmol), 4,4,4',4',5,5,5',5'-octamethyl-2,2'-bi(1,3,2-dioxaborolane) (528 mg, 2.080 mmol), potassium acetate (408 mg, 4.16 mmol), $PdCl_2$(dppf) (101 mg, 0.139 mmol) and 1,4-Dioxane (3 mL) at 25° C. The mixture was bubbled with a stream of $N_2$ for 2 min. The tube was sealed and heated to 80° C. for 2 h. LCMS showed that desired target was formed. The mixture was poured into $H_2O$, then the mixture was extracted with EtOAc (×3). The combined organic layers were washed with brine, dried over $Na_2SO_4$, then filtered and concentrated under reduced pressure. The residue was purified by mass triggered reverse phase HPLC (ACN/water with 0.1% TFA modifier) to afford the title compound. LC/MS=204 [M+1] ((5-(difluoromethoxy)-2-methylpyridin-3-yl)boronic acid).

Intermediate 16

1,1-difluoropropan-2-yl 1,1,2,2,3,3,4,4,4-nonafluorobutane-1-sulfonate

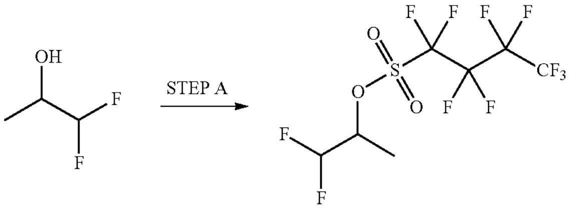

INT-16

Step A: 1,1-difluoropropan-2-yl 1,1,2,2,3,3,4,4,4-nonafluorobutane-1-sulfonate

At −78° C., to a stirred solution of 1,1-difluoropropan-2-ol (1.8 mL, 20.8 mmol) and DCM (10.4 mL) was added $Et_3N$ (2.9 mL, 20.8 mmol) and nonfluorobutanesulfonyl fluoride (4.9 mL, 27.1 mmol). The mixture was stirred at rt for 16 h then sat. aq. $NaHCO_3$ was added. The aqueous layer was extracted three times with DCM. The organic layer was then dried over $MgSO_4$ (s), filtered, and concentrated in vacuo. The crude product was used without purification. LC/MS=379 [M+1].

EXAMPLES

The following experimental procedures detail the preparation of specific examples of the instant disclosure. The examples are for illustrative purposes only and are not intended to limit the scope of the instant disclosure in any way.

Example 1

3-(2-chlorophenyl)-1-(4-fluorophenyl)-N-(3-methyl-1,1-dioxidotetrahydrothiophen-3-yl)-4,5,6,7-tetrahydro-1H-indazole-6-carboxamide

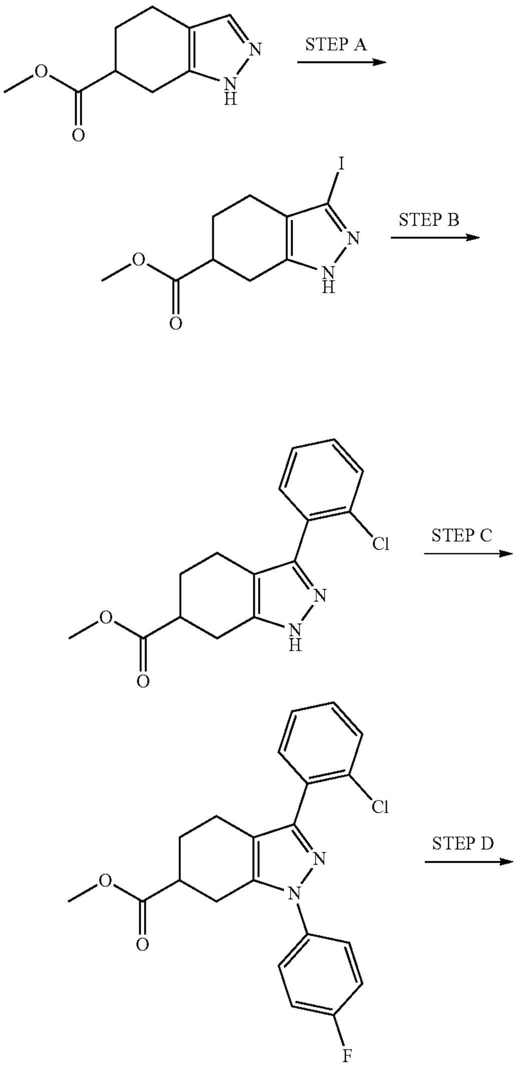

-continued

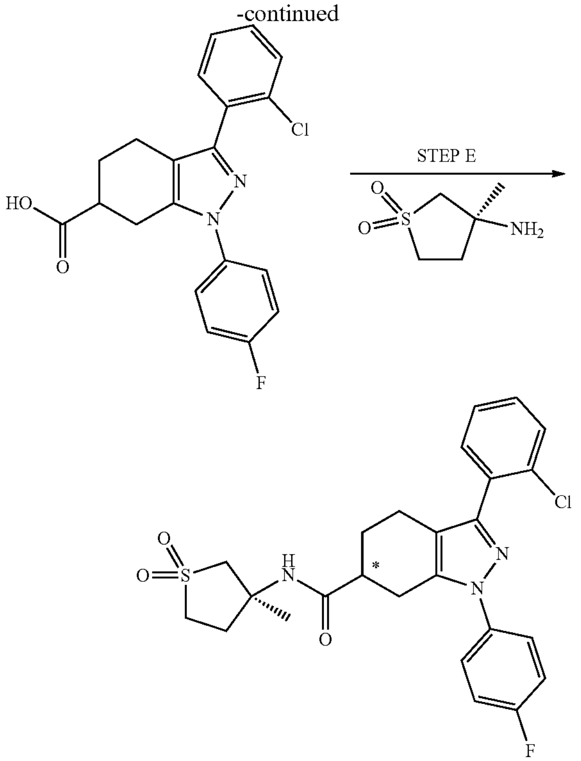

Ex-1

Step A: Methyl 3-iodo-4,5,6,7-tetrahydro-1H-indazole-6-carboxylate

To a round bottom flask was added methyl 4,5,6,7-tetrahydro-1H-indazole-6-carboxylate (3.0 g, 16.7 mmol), NIS (5.6 g, 25.0 mmol), and DMF (33 mL). The reaction mixture was stirred at 80° C. for 30 min. The reaction mixture was then cooled to rt and sat. $NaHCO_3$ (aq) was added. The aqueous layer was extracted three times with EtOAc. The combined organic layers were washed with sat. $NaHCO_3$ (aq), water, and brine. The organic layer was then dried over $MgSO_4$ (s), filtered, and concentrated in vacuo. The crude product was purified by flash silica gel column chromatography (30% EtOAc in hexanes) to afford the title compound. LC/MS=307 [M+1].

Step B: Methyl 3-(2-chlorophenyl)-4,5,6,7-tetrahydro-1H-indazole-6-carboxylate

To a stirred solution of methyl 3-iodo-4,5,6,7-tetrahydro-1H-indazole-6-carboxylate (1.50 g, 4.90 mmol), (2-chlorophenyl)boronic acid (0.92 g, 5.88 mmol), Pd(dppf)$Cl_2$ (0.36 g, 0.49 mmol), $Na_2CO_3$ (1.04 g, 9.80 mmol), and dioxane (12 mL) was added water (12 mL). The reaction mixture was sparged with $N_2$ for 5 min at rt then heated to 100° C. for 45 min. After cooling to rt water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (40% EtOAc in hexanes) to afford the title compound. LC/MS=291 [M+1].

Step C: Methyl 3-(2-chlorophenyl)-1-(4-fluorophenyl)-4,5,6,7-tetrahydro-1H-indazole-6-carboxylate To a stirred solution of methyl 3-(2-chlorophenyl)-4,5,6,7-tetrahydro-1H-indazole-6-carboxylate (600 mg, 2.06 mmol), $Cu(OAc)_2$ (562 mg, 3.10 mmol), and (4-fluorophenyl)boronic acid (577 mg, 4.13 mmol) in DCM (3.4 mL) was added pyridine (334 uL, 4.13 mmol). The reaction mixture was stirred open to air for 24 h. Water was added to the reaction mixture and extracted with DCM three times. The organic layer was then dried over $MgSO_4$ (s), filtered, and concentrated in vacuo. The crude product was purified by flash silica gel column chromatography (10% EtOAc in hexanes) to afford the title compound. LC/MS=385 [M+1].

Step D: 3-(2-chlorophenyl)-1-(4-fluorophenyl)-4,5,6,7-tetrahydro-1H-indazole-6-carboxylic acid To a stirred solution of methyl 3-(2-chlorophenyl)-1-(4-fluorophenyl)-4,5,6,7-tetrahydro-1H-indazole-6-carboxylate (467 mg, 1.21 mmol) in THF (2.6 mL) and MeOH (0.9 mL) was added a solution of NaOH (971 mg, 24.3 mmol) and water (2.6 mL). The reaction mixture was heated to 60° C. for 2 h. After cooling to rt the reaction mixture was acidified with concentrated HCl to pH 1. The reaction mixture was then extracted with EtOAc three times. The combined organic layers with washed with brine, dried with $MgSO_4$ (s), filtered, and concentrated in vacuo. The crude product was used without purification. LC/MS=371 [M+1].

Step E: 3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide To a stirred solution of 3-(2-chlorophenyl)-1-(4-fluorophenyl)-4,5,6,7-tetrahydro-1H-indazole-6-carboxylic acid (225 mg, 0.61 mmol) in DMF (3.0 mL) was added DIPEA (0.31 mL, 1.82 mmol), HATU (254 mg, 0.67 mmol), and (S)-3-amino-3-methyltetrahydrothiophene 1,1-dioxide (100 mg, 0.67 mmol). The reaction mixture was stirred at rt for 16 h. The mixture was filtered and purified by mass triggered reverse phase HPLC (ACN/water with 0.1% FA modifier) to afford the title compound (Ex-1). LC/MS=502 [M+1]. DGAT2 $IC_{50}$ (nm)=37.9. The mixture of two stereoisomers was purified by chiral preparative SFC (IC column, 20% MeOH/$CO_2$) to afford Ex-1a (faster eluting) and Ex-1b (slower eluting). Ex-1b: $^1$H NMR (600 MHz, Chloroform-d) δ 7.56-7.49 (m, 2H), 7.46 (td, J=5.7, 4.8, 2.9 Hz, 2H), 7.35-7.28 (m, 2H), 7.15 (t, J=8.5 Hz, 2H), 5.90 (d, J=7.3 Hz, 1H), 3.60 (dd, J=50.2, 13.8 Hz, 1H), 3.31 (dtd, J=12.5, 8.3, 4.1 Hz, 1H), 3.20 (ddt, J=12.3, 7.7, 3.6 Hz, 1H), 3.08 (dd, J=16.0, 10.6 Hz, 1H), 3.03 (dd, J=13.8, 8.2 Hz, 1H), 2.88-2.74 (m, 2H), 2.65-2.57 (m, 2H), 2.52-2.41 (m, 1H), 2.20-2.11 (m, 1H), 2.08 (dd, J=24.8, 10.2 Hz, 1H), 1.87 (ddd, J=21.8, 12.4, 8.6 Hz, 1H), 1.60 (d, J=2.8 Hz, 5H). LC/MS=502 [M+1].

By using procedures similar to those described in Example 1 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 1a | 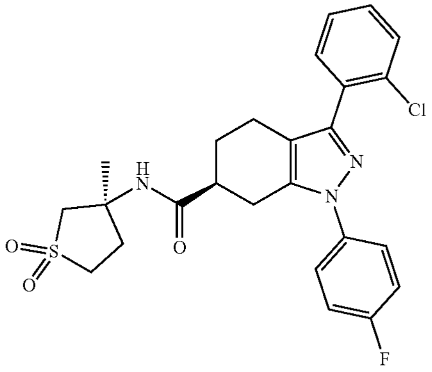 [SMILES: C[C@]1(NC(=O)[C@H]2CCc3c(-c4ccccc4Cl)nn(-c4ccc(F)cc4)c3C2)CCS(=O)(=O)C1] | (S)-3-(2-chlorophenyl)-1-(4-fluorophenyl)-N-((S)-3-methyl-1,1-dioxidotetrahydrothiophen-3-yl)-4,5,6,7-tetrahydro-1H-indazole-6-carboxamide (IC column, 20% MeOH/$CO_2$, faster eluting) | 502 | 3898 |
| 1b | 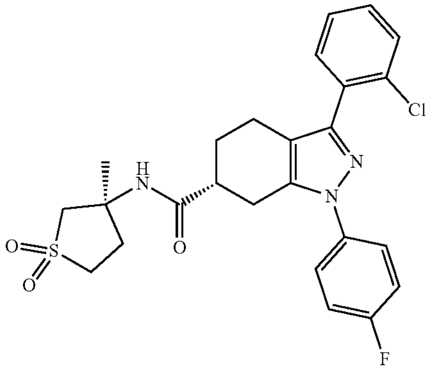 [SMILES: C[C@]1(NC(=O)[C@@H]2CCc3c(-c4ccccc4Cl)nn(-c4ccc(F)cc4)c3C2)CCS(=O)(=O)C1] | (R)-3-(2-chlorophenyl)-1-(4-fluorophenyl)-N-((S)-3-methyl-1,1-dioxidotetrahydrothiophen-3-yl)-4,5,6,7-tetrahydro-1H-indazole-6-carboxamide (IC column, 20% MeOH/$CO_2$, faster eluting) | 502 | 33.7 |
| 2 | 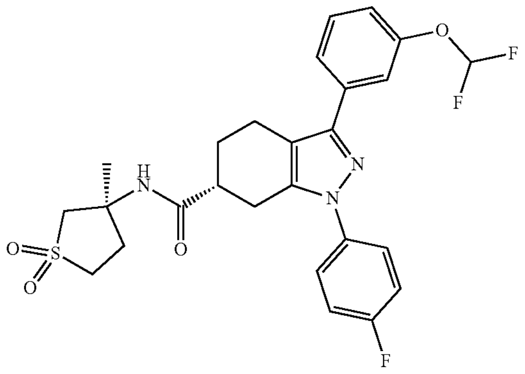 [SMILES: C[C@]1(NC(=O)[C@@H]2CCc3c(-c4cccc(OC(F)F)c4)nn(-c4ccc(F)cc4)c3C2)CCS(=O)(=O)C1] | (R)-3-(3-(difluoromethoxy)phenyl)-1-(4-fluorophenyl)-N-((S)-3-methyl-1,1-dioxidotetrahydrothiophen-3-yl)-4,5,6,7-tetrahydro-1H-indazole-6-carboxamide | 534 | 0.63 |
| 3 | 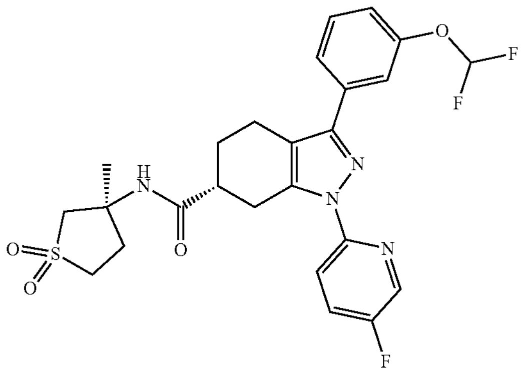 [SMILES: C[C@]1(NC(=O)[C@@H]2CCc3c(-c4cccc(OC(F)F)c4)nn(-c4ccc(F)cn4)c3C2)CCS(=O)(=O)C1] | (R)-3-(3-(difluoromethoxy)phenyl)-1-(5-fluoropyridin-2-yl)-N-((S)-3-methyl-1,1-dioxidotetrahydrothiophen-3-yl)-4,5,6,7-tetrahydro-1H-indazole-6-carboxamide | 535 | 4.9 |

-continued

| Example | Structure | Name | LCMS [M + 1] | DGAT2 $IC_{50}$ (nM) |
|---|---|---|---|---|
| 4 | 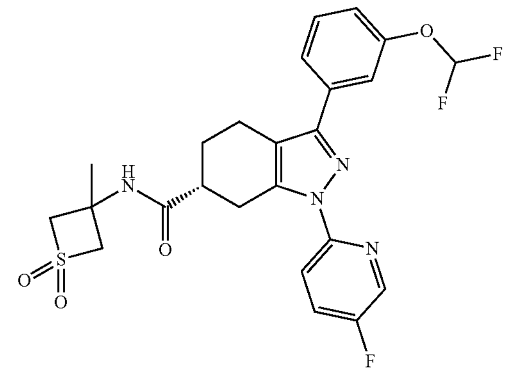 [SMILES: CC1(NC(=O)[C@@H]2CCc3c(-c4cccc(OC(F)F)c4)nn(-c4ccc(F)cn4)c3C2)CS(=O)(=O)C1] | (R)-3-(3-(difluoromethoxy)phenyl)-1-(5-fluoropyridin-2-yl)-N-(3-methyl-1,1-dioxidothietan-3-yl)-4,5,6,7-tetrahydro-1H-indazole-6-carboxamide | 521 | 5.1 |
| 5 | 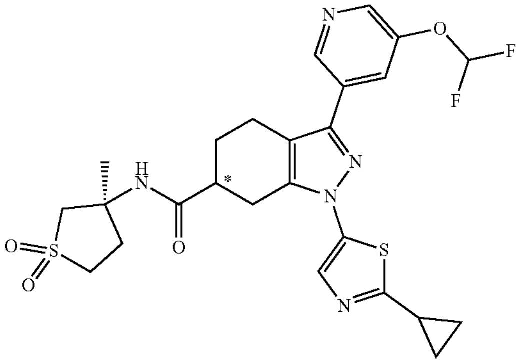 [SMILES: C[C@]1(NC(=O)C2CCc3c(-c4cncc(OC(F)F)c4)nn(-c4cnc(C5CC5)s4)c3C2)CCS(=O)(=O)C1] | 1-(5-cyclopropyl-1,3,4-thiadiazol-2-yl)-3-(5-(difluoromethoxy)pyridin-3-yl)-N-((S)-3-methyl-1,1-dioxidotetrahydrothiophen-3-yl)-4,5,6,7-tetrahydro-1H-indazole-6-carboxamide (mixture of diastereomers) | 565 | 542.2 |
| 6a | 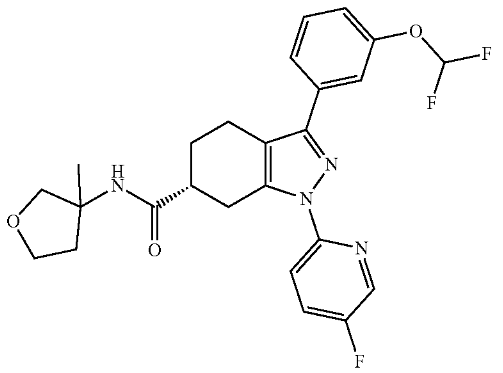 [SMILES: CC1(NC(=O)[C@@H]2CCc3c(-c4cccc(OC(F)F)c4)nn(-c4ccc(F)cn4)c3C2)CCOC1] | (6R)-3-(3-(difluoromethoxy)phenyl)-1-(5-fluoropyridin-2-yl)-N-(3-methyltetrahydrofuran-3-yl)-4,5,6,7-tetrahydro-1H-indazole-6-carboxamide (faster eluting with OD-H column, 30% iPrOH (0.1% DEA)/$CO_2$) | 487 | 37.4 |
| 6b | 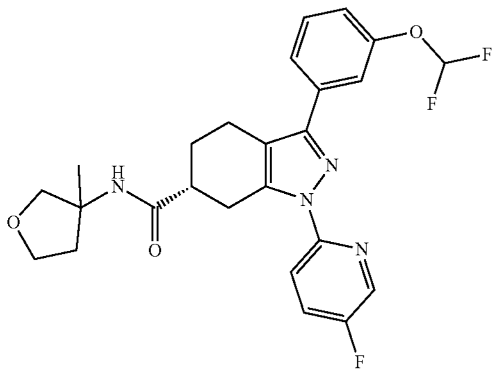 [SMILES: CC1(NC(=O)[C@@H]2CCc3c(-c4cccc(OC(F)F)c4)nn(-c4ccc(F)cn4)c3C2)CCOC1] | (6R)-3-(3-(difluoromethoxy)phenyl)-1-(5-fluoropyridin-2-yl)-N-(3-methyltetrahydrofuran-3-yl)-4,5,6,7-tetrahydro-1H-indazole-6-carboxamide (slower eluting with OD-H column, 30% iPrOH (0.1% DEA)/$CO_2$) | 487 | 2.0 |

-continued

| Example | Structure | Name | LCMS [M + 1] | DGAT2 $IC_{50}$ (nM) |
|---|---|---|---|---|
| 7 | 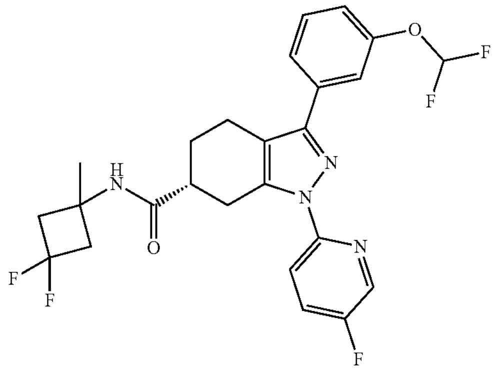 [SMILES: CC1(NC(=O)[C@@H]2CCc3c(-c4cccc(OC(F)F)c4)nn(-c4ccc(F)cn4)c3C2)CC(F)(F)C1] | (R)-N-(3,3-difluoro-1-methylcyclobutyl)-3-(3-(difluoromethoxy)phenyl)-1 -(5-fluoropyridin-2-yl)-4,5,6,7-tetrahydro-1H-indazole-6-carboxamide | 507 | 12.0 |
| 8a | 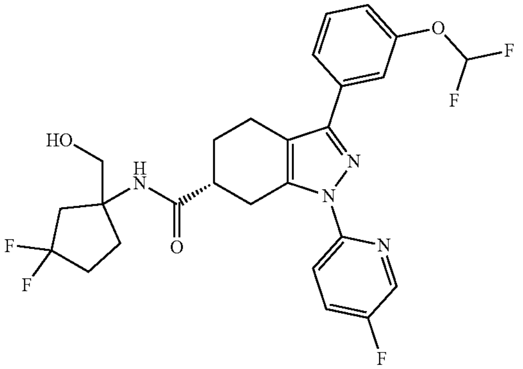 [SMILES: O=C(NC1(CO)CCC(F)(F)C1)[C@@H]1CCc2c(-c3cccc(OC(F)F)c3)nn(-c3ccc(F)cn3)c2C1] | (6R)-N-(3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide (3rd eluting with AD-H column, 35% $EtOH/CO_2$) | 537 | 5.0 |
| 8b | 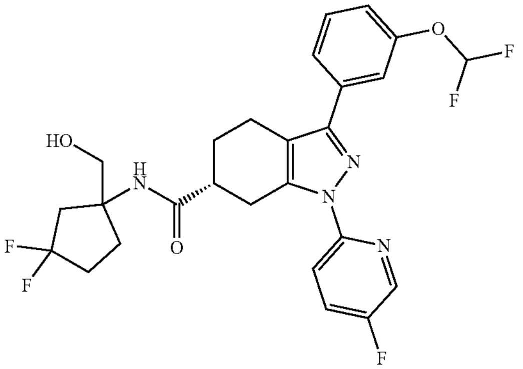 [SMILES: O=C(NC1(CO)CCC(F)(F)C1)[C@@H]1CCc2c(-c3cccc(OC(F)F)c3)nn(-c3ccc(F)cn3)c2C1] | (6R)-N-(3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide (4th eluting with AD-H column, 35% $EtOH/CO_2$) | 537 | 35 |
| 9 | 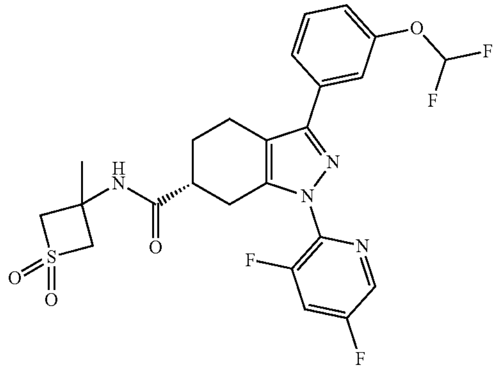 [SMILES: CC1(NC(=O)[C@@H]2CCc3c(-c4cccc(OC(F)F)c4)nn(-c4ncc(F)cc4F)c3C2)CS(=O)(=O)C1] | (R)-3-(3-(difluoromethoxy)phenyl)-1-(3,5-difluoropyridin-2-yl)-N-(3-methyl-1,1-dioxidothietan-3-yl)-4,5,6,7-tetrahydro-1H-indazole-6-carboxamide | 539 | 10.2 |

-continued

| Example | Structure | Name | LCMS [M + 1] | DGAT2 $IC_{50}$ (nM) |
|---|---|---|---|---|
| 10 | 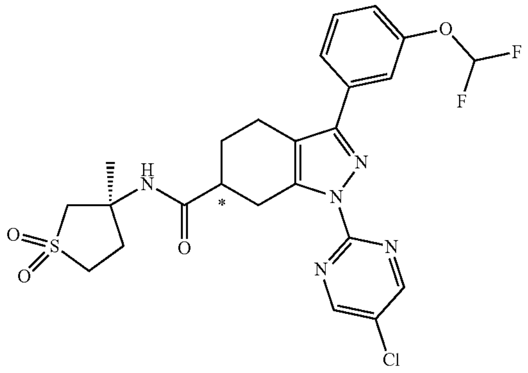 [SMILES: C[C@]1(NC(=O)C2CCc3c(-c4cccc(OC(F)F)c4)nn(-c4ncc(Cl)cn4)c3C2)CCS(=O)(=O)C1] | 1-(5-chloropyrimidin-2-yl)-3-(3-(difluoromethoxy)phenyl)-N-((S)-3-methyl-1,1-dioxidotetrahydrothiophen-3-yl)-4,5,6,7-tetrahydro-1H-indazole-6-carboxamide (mixture of diastereomers) | 552 | 37.02 |
| 11 | 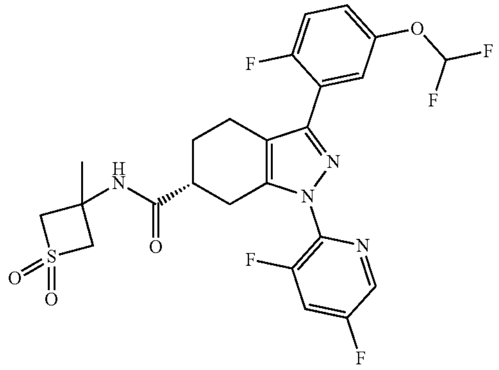 [SMILES: CC1(NC(=O)[C@@H]2CCc3c(-c4cc(OC(F)F)ccc4F)nn(-c4ncc(F)cc4F)c3C2)CS(=O)(=O)C1] | ((R)-3-(5-(difluoromethoxy)-2-fluorophenyl)-1-(3,5-difluoropyridin-2-yl)-N-(3-methyl-1,1-dioxidothietan-3-yl)-4,5,6,7-tetrahydro-1H-indazole-6-carboxamide | 557 | 0.33 |
| 12 | 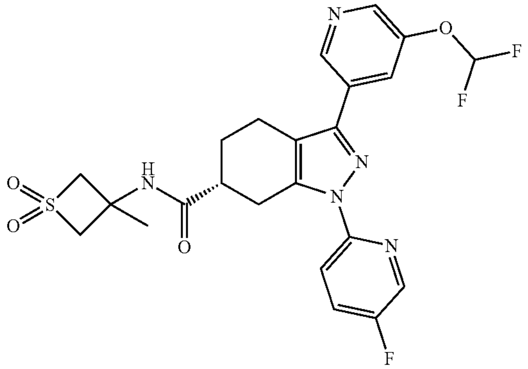 [SMILES: CC1(NC(=O)[C@@H]2CCc3c(-c4cncc(OC(F)F)c4)nn(-c4ccc(F)cn4)c3C2)CS(=O)(=O)C1] | (R)-3-(5-(difluoromethoxy)pyridin-3-yl)-1-(5-fluoropyridin-2-yl)-N-(3-methyl-1,1-dioxidothietan-3-yl)-4,5,6,7-tetrahydro-1H-indazole-6-carboxamide | 522 | 65.8 |
| 13 | 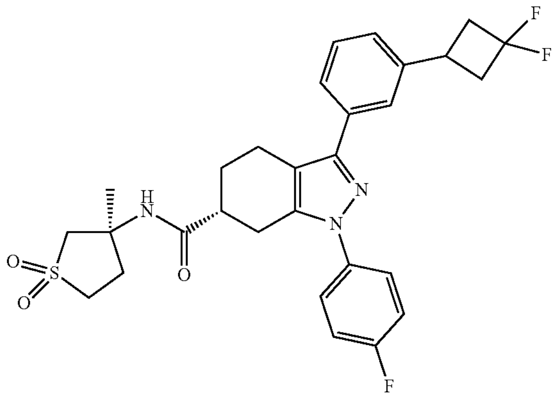 [SMILES: C[C@]1(NC(=O)[C@@H]2CCc3c(-c4cccc(C5CC(F)(F)C5)c4)nn(-c4ccc(F)cc4)c3C2)CCS(=O)(=O)C1] | (R)-3-(3-(3,3-difluorocyclobutyl)phenyl)-1-(4-fluorophenyl)-N-((S)-3-methyl-1,1-dioxidotetrahydrothiophen-3-yl)-4,5,6,7-tetrahydro-1H-indazole-6-carboxamide | 558 | 20.0 |

-continued

| Example | Structure | Name | LCMS [M + 1] | DGAT2 $IC_{50}$ (nM) |
|---|---|---|---|---|
| 14 | 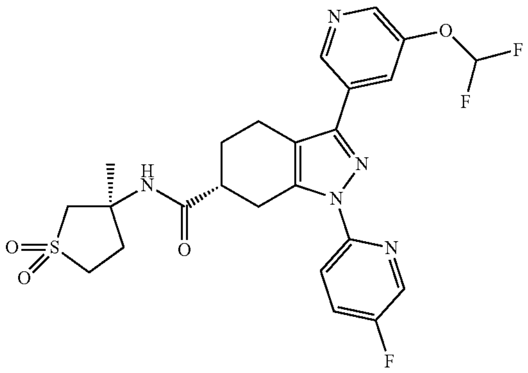 [SMILES: C[C@]1(NC(=O)[C@@H]2CCc3c(-c4cncc(OC(F)F)c4)nn(-c4ccc(F)cn4)c3C2)CCS(=O)(=O)C1] | (R)-3-(5-(difluoromethoxy)pyridin-3-yl)-1-(5-fluoropyridin-2-yl)-N-((S)-3-methyl-1,1-dioxidotetrahydrothiophen-3-yl)-4,5,6,7-tetrahydro-1H-indazole-6-carboxamide | 536 | 13.9 |
| 15a | 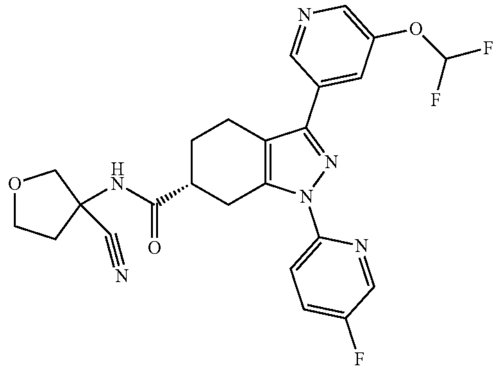 [SMILES: N#CC1(NC(=O)[C@@H]2CCc3c(-c4cncc(OC(F)F)c4)nn(-c4ccc(F)cn4)c3C2)CCOC1] | (6R)-N-(3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide (faster eluting with OD-H column, 30% iPrOH (0.1% DEA)/$CO_2$) | 499 | 17.4 |
| 15b | 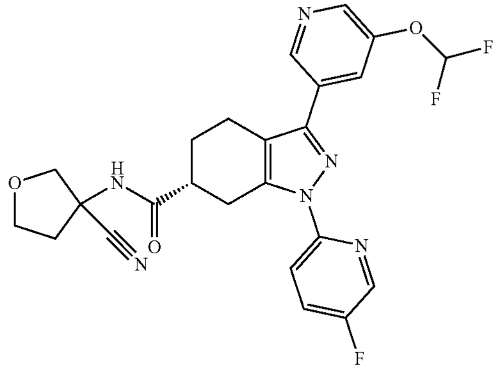 [SMILES: N#CC1(NC(=O)[C@@H]2CCc3c(-c4cncc(OC(F)F)c4)nn(-c4ccc(F)cn4)c3C2)CCOC1] | (6R)-N-(3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide (slower eluting with OD-H column, 30% iPrOH (0.1% DEA)/$CO_2$) | 499 | 236.4 |
| 16 | 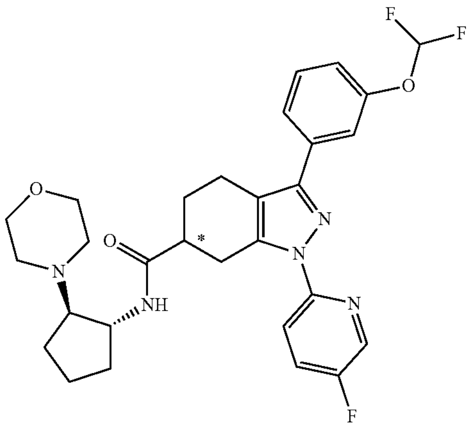 [SMILES: O=C(N[C@@H]1CCC[C@H]1N1CCOCC1)C1CCc2c(-c3cccc(OC(F)F)c3)nn(-c3ccc(F)cn3)c2C1] | 3-(3-(difluoromethoxy)phenyl)-1-(5-fluoropyridin-2-yl)-N-((1R,2R)-2-morpholinocyclopentyl)-4,5,6,7-tetrahydro-1H-indazole-6-carboxamide (mixture of diastereomers) | 556 | 66.9 |

-continued

| Example | Structure | Name | LCMS [M + 1] | DGAT2 $IC_{50}$ (nM) |
|---|---|---|---|---|
| 17 | 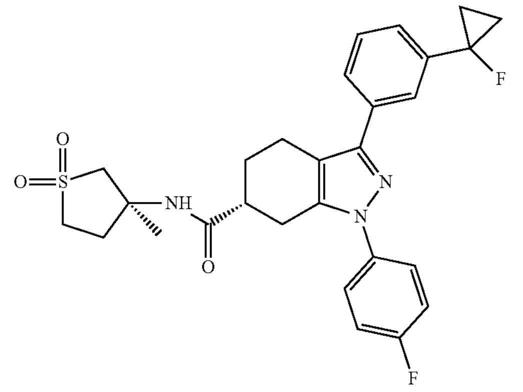 [SMILES: C[C@]1(NC(=O)[C@@H]2CCc3c(-c4cccc(C5(F)CC5)c4)nn(-c4ccc(F)cc4)c3C2)CCS(=O)(=O)C1] | (R)-3-(3-(1-fluorocyclopropyl)phenyl)-1-(4-fluorophenyl)-N-((S)-3-methyl-1,1-dioxidotetrahydrothiophen-3-yl)-4,5,6,7-tetrahydro-1H-indazole-6-carboxamide | 526 | 70.7 |
| 18 | 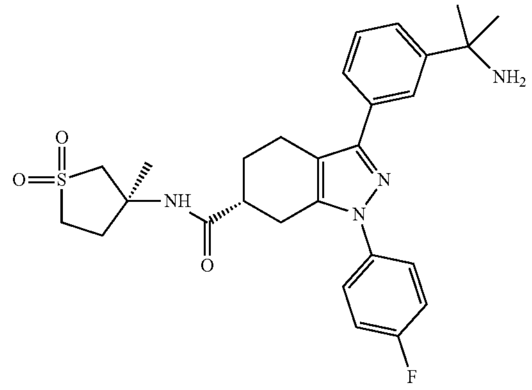 [SMILES: CC(C)(N)c1cccc(-c2nn(-c3ccc(F)cc3)c3c2CC[C@@H](C(=O)N[C@@]2(C)CCS(=O)(=O)C2)C3)c1] | (R)-3-(3-(2-aminopropan-2-yl)phenyl)-1-(4-fluorophenyl)-N-((S)-3-methyl-1,1-dioxidotetrahydrothiophen-3-yl)-4,5,6,7-tetrahydro-1H-indazole-6-carboxamide | 525 | >10000 |
| 19 | 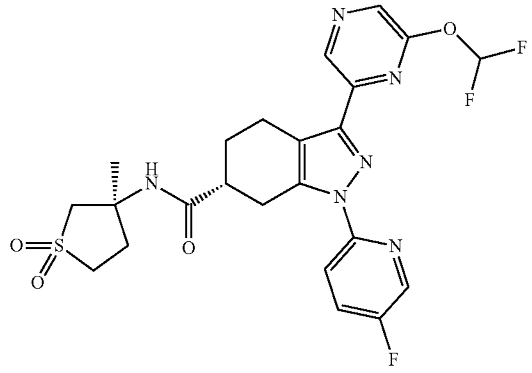 [SMILES: C[C@]1(NC(=O)[C@@H]2CCc3c(-c4cncc(OC(F)F)n4)nn(-c4ccc(F)cn4)c3C2)CCS(=O)(=O)C1] | (R)-3-(6-(difluoromethoxy)pyrazin-2-yl)-1-(5-fluoropyridin-2-yl)-N-((S)-3-methyl-1,1-dioxidotetrahydrothiophen-3-yl)-4,5,6,7-tetrahydro-1H-indazole-6-carboxamide | 537 | >10000 |
| 20 | 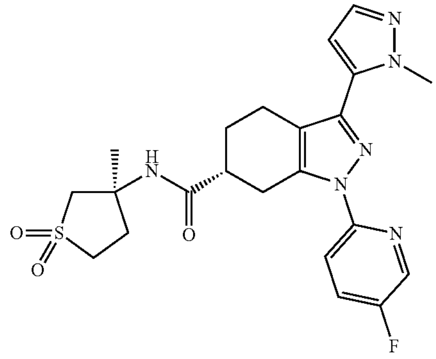 [SMILES: Cn1nccc1-c1nn(-c2ccc(F)cn2)c2c1CC[C@@H](C(=O)N[C@@]1(C)CCS(=O)(=O)C1)C2] | (R)-1-(5-fluoropyridin-2-yl)-N-((S)-3-methyl-1,1-dioxidotetrahydrothiophen-3-yl)-3-(1-methyl-1H-pyrazol-5-yl)-4,5,6,7-tetrahydro-1H-indazole-6-carboxamide | 473 | 8434 |

Example 21

(R)-3-(2-(difluoromethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide

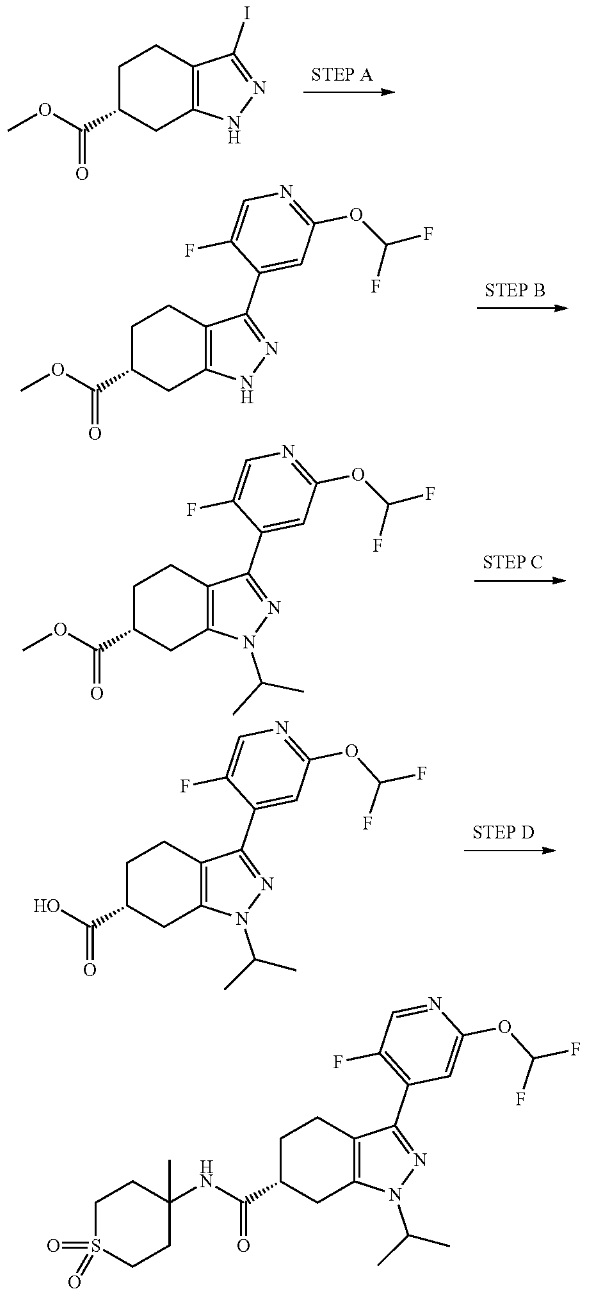

EX-21

Step A: (R)-3-(2-difluoromethoxy)-5-fluoropyridin-4-yl)4,5,6,7-tetrahydro-1H-indazole-6-carboxylate To a stirred solution of (R)-methyl 3-iodo-4,5,6,7-tetrahydro-1H-indazole-6-carboxylate (600 mg, 1.96 mmol), 2-(difluoromethoxy)-5-fluoro-4-(4,4,5,5-tetramethyl-1,3,2-dioxaborolan-2-yl)pyridine (567 mg, 1.96 mmol), Pd(dppf)$Cl_2$ (287 mg, 0.39 mmol), $Na_2CO_3$ (623 mg, 5.88 mmol), and dioxane (3.2 mL) was added water (3.2 mL). The reaction mixture was bubbled with $N_2$ for 5 minutes at rt then heated to 100° C. for 15 minutes. After cooling to rt water was added. The aqueous layer was extracted three times with EtOAc. The combined organic layers were washed with water and brine. The organic layer was then dried over $MgSO_4$, filtered, and concentrated in vacuo. The crude product was purified by flash silica gel column chromatography (40% EtOAc in hexanes) to afford the title compound. LC/MS=342 [M+1].

Step B: Methyl (R)-3-(2-(difluoromethoxy)-5-fluoropyridin-4-yl)-1-isopropyl-4,5,6,7-tetrahydro-1H-indazole-6-carboxylate To a stirred solution of methyl (R)-3-(2-(difluoromethoxy)-5-fluoropyridin-4-yl)-4,5,6,7-tetrahydro-1H-indazole-6-carboxylate (419 mg, 1.23 mmol), 2-iodopropane (417 mg, 2.46 mmol), and DMF (4.1 mL) was added cesium carbonate (1600 mg, 4.91 mmol). The reaction mixture was stirred at 100° C. for 15 minutes. Water was added after cooling to room temperature. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (20% EtOAc in hexanes) to afford the title compound. LC/MS=384 [M+1].

Step C: (R)-3-(2-(difluoromethoxy)-5-fluoropyridin-4-yl)-1-isopropyl-4,5,6,7-tetrahydro-1H-indazole-6-carboxylic acid To a stirred solution of methyl (R)-3-(2-(difluoromethoxy)-5-fluoropyridin-4-yl)-1-isopropyl-4,5,6,7-tetrahydro-1H-indazole-6-carboxylate (306 mg, 0.80 mmol), LiOH (76 mg, 3.2 mmol), THF (0.9 mL), and MeOH (0.9 mL) was added $H_2O$ (0.9 mL). After stirring at rt for 10 min, the reaction mixture was acidified with concentrated HCl to pH 1. The reaction mixture was then extracted with EtOAc three times. The combined organic layers with washed with brine, dried with $MgSO_4$ (s), filtered, and concentrated in vacuo. The crude product was used without purification. LC/MS=370 [M+1].

Step D: (R)-3-(2-(difluoromethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide To a stirred solution of (R)-3-(2-(difluoromethoxy)-5-fluoropyridin-4-yl)-1-isopropyl-4,5,6,7-tetrahydro-1H-indazole-6-carboxylic acid (140 mg, 0.38 mmol) in DMF (3.8 mL) was added DIPEA (0.3 mL, 1.9 mmol), HATU (173 mg, 0.46 mmol), and 4-amino-4-methyltetrahydro-2H-thiopyran 1,1-dioxide hydrochloride (76 mg, 0.38 mmol). The reaction mixture was stirred at rt for 25 min. The reaction mixture was filtered and purified by mass triggered reverse phase HPLC (ACN/water with 0.1% FA modifier) to afford the title compound. LC/MS=515 [M+1]. $^1H$ NMR (500 MHz, Chloroform-d) δ 8.04 (d, J=1.6 Hz, 1H), 7.53-7.21 (t, J=73.2 Hz, 1H), 7.22 (s, 1H), 5.36 (s, 1H), 4.41 (p, J=6.6 Hz, 1H), 3.14-3.04 (m, 2H), 3.03-2.93 (m, 3H), 2.93-2.80 (m, 2H), 2.76-2.51 (m, 5H), 2.26 (t, J=12.3 Hz, 2H), 2.07 (d, J=12.9 Hz, 1H), 1.83 (td, J=11.6, 5.8 Hz, 1H), 1.54-1.50 (m, 6H), 1.50 (s, 3H). DGAT2 $IC_{50}$ (nM)=43.8.

By using procedures similar to those described in Example 21 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 22 | 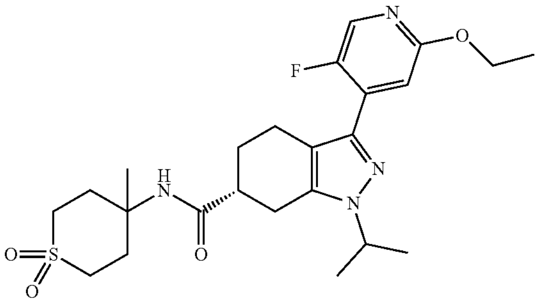 | (R)-3-(2-ethoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide | 493 | 144.0 |
| 23 | 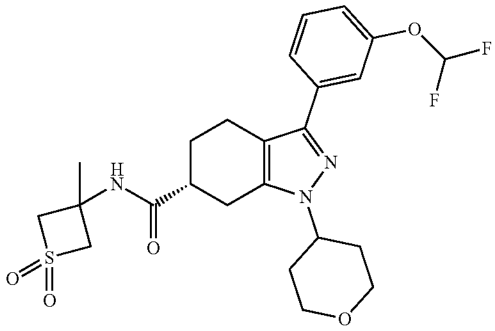 [SMILES: CC1(NC(=O)[C@@H]2CCc3c(-c4cccc(OC(F)F)c4)nn(C4CCOCC4)c3C2)CS(=O)(=O)C1] | (R)-3-(3-(difluoromethoxy)phenyl)-N-(3-methyl-1,1-dioxidothietan-3-yl)-1-(tetrahydro-2H-pyran-4-yl)-4,5,6,7-tetrahydro-1H-indazole-6-carboxamide | 510 | 168.8 |
| 24 | 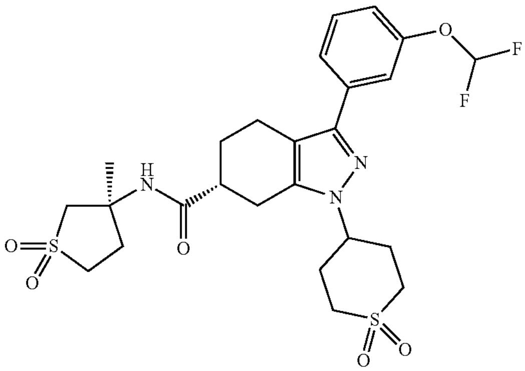 [SMILES: C[C@]1(NC(=O)[C@@H]2CCc3c(-c4cccc(OC(F)F)c4)nn(C4CCS(=O)(=O)CC4)c3C2)CCS(=O)(=O)C1] | (R)-3-(3-(difluoromethoxy)phenyl)-1-(1,1-dioxidotetrahydro-2H-thiopyran-4-yl)-N-((S)-3-methyl-1,1-dioxidotetrahydrothiophen-3-yl)-4,5,6,7-tetrahydro-1H-indazole-6-carboxamide | 572 | 144.5 |
| 25 | 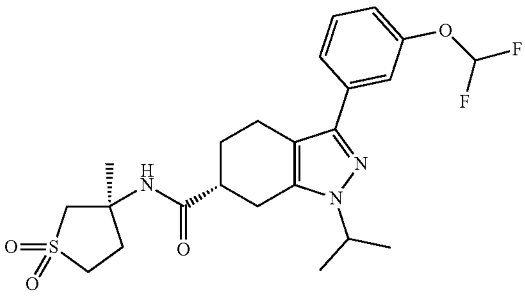 [SMILES: CC(C)n1nc(-c2cccc(OC(F)F)c2)c2c1C[C@H](C(=O)N[C@@]1(C)CCS(=O)(=O)C1)CC2] | (R)-3-(3-(difluoromethoxy)phenyl)-1-isopropyl-N-((S)-3-methyl-1,1-dioxidotetrahydrothiophen-3-yl)-4,5,6,7-tetrahydro-1H-indazole-6-carboxamide | 482 | 59.8 |

-continued

| Example | Structure | Name | LCMS [M + 1] | DGAT2 $IC_{50}$ (nM) |
|---|---|---|---|---|
| 26 | 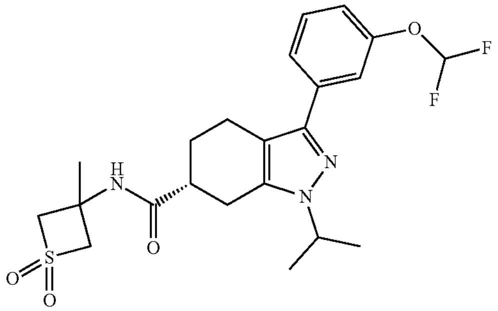 [SMILES: CC(C)n1nc(-c2cccc(OC(F)F)c2)c2c1C[C@H](C(=O)NC1(C)CS(=O)(=O)C1)CC2] | (R)-3-(3-(difluoromethoxy)phenyl)-1-isopropyl-N-(3-methyl-1,1-dioxidothietan-3-yl)-4,5,6,7-tetrahydro-1H-indazole-6-carboxamide | 468 | 318.9 |
| 27 | 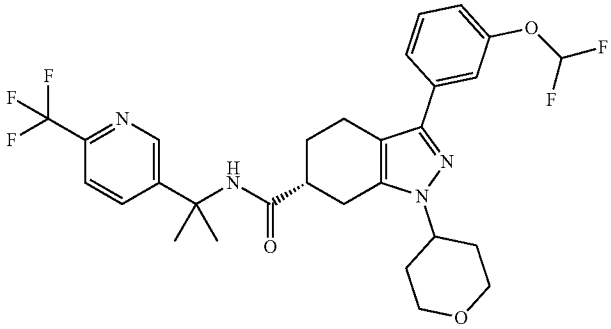 [SMILES: CC(C)(NC(=O)[C@@H]1CCc2c(-c3cccc(OC(F)F)c3)nn(C3CCOCC3)c2C1)c1ccc(C(F)(F)F)nc1] | (R)-3-(3-(difluoromethoxy)phenyl)-1-(tetrahydro-2H-pyran-4-yl)-N-(2-(6-(trifluoromethyl)pyridin-3-yl)propan-2-yl)-4,5,6,7-tetrahydro-1H-indazole-6-carboxamide | 579 | 128.0 |
| 28 | 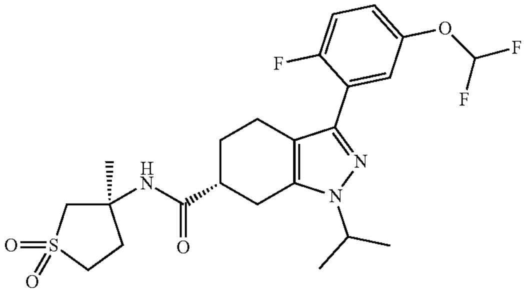 [SMILES: CC(C)n1nc(-c2cc(OC(F)F)ccc2F)c2c1C[C@H](C(=O)N[C@@]1(C)CCS(=O)(=O)C1)CC2] | (R)-3-(5-(difluoromethoxy)-2-fluorophenyl)-1-isopropyl-N-((S)-3-methyl-1,1-dioxidotetrahydrothiophen-3-yl)-4,5,6,7-tetrahydro-1H-indazole-6-carboxamide | 500 | 30.1 |
| 29 | 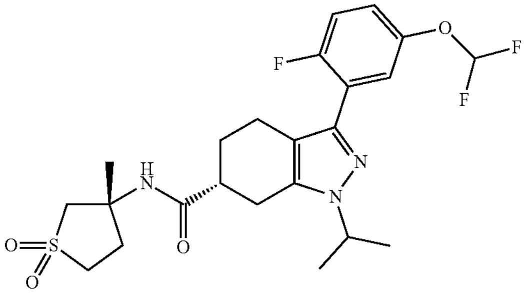 [SMILES: CC(C)n1nc(-c2cc(OC(F)F)ccc2F)c2c1C[C@H](C(=O)N[C@]1(C)CCS(=O)(=O)C1)CC2] | (R)-3-(5-(difluoromethoxy)-2-fluorophenyl)-1-isopropyl-N-((R)-3-methyl-1,1-dioxidotetrahydrothiophen-3-yl)-4,5,6,7-tetrahydro-1H-indazole-6-carboxamide | 500 | 60.1 |
| 30 | 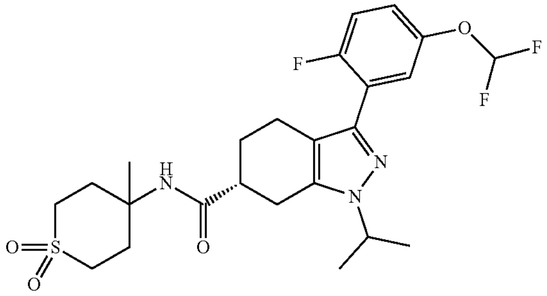 [SMILES: CC(C)n1nc(-c2cc(OC(F)F)ccc2F)c2c1C[C@H](C(=O)NC1(C)CCS(=O)(=O)CC1)CC2] | (R)-3-(5-(difluoromethoxy)-2-fluorophenyl)-1-isopropyl-N-(4-methyl-1,1-dioxidotetrahydro-2H-thiopyran-4-yl)-4,5,6,7-tetrahydro-1H-indazole-6-carboxamide | 514 | 5.5 |

-continued

| Example | Structure | Name | LCMS [M + 1] | DGAT2 $IC_{50}$ (nM) |
|---|---|---|---|---|
| 31 | 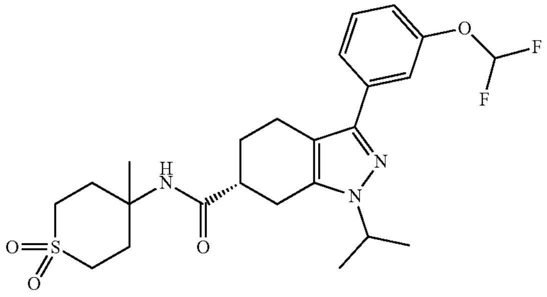 [SMILES: CC(C)n1nc(-c2cccc(OC(F)F)c2)c2c1C[C@H](C(=O)NC1(C)CCS(=O)(=O)CC1)CC2] | (R)-3-(3-(difluoromethoxy)phenyl)-1-isopropyl-N-(4-methyl-1,1-dioxidotetrahydro-2H-thiopyran-4-yl)-4,5,6,7-tetrahydro-1H-indazole-6-carboxamide | 496 | 24.7 |
| 32 | 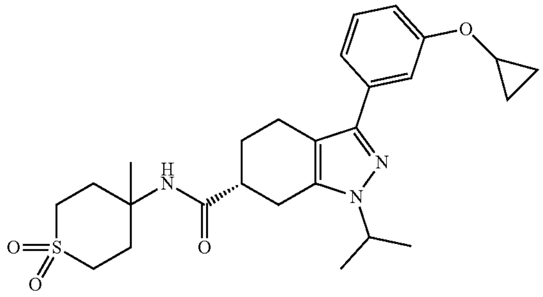 [SMILES: CC(C)n1nc(-c2cccc(OC3CC3)c2)c2c1C[C@H](C(=O)NC1(C)CCS(=O)(=O)CC1)CC2] | (R)-3-(3-cyclopropoxyphenyl)-1-isopropyl-N-(4-methyl-1,1-dioxidotetrahydro-2H-thiopyran-4-yl)-4,5,6,7-tetrahydro-1H-indazole-6-carboxamide | 486 | 29.1 |
| 33 | 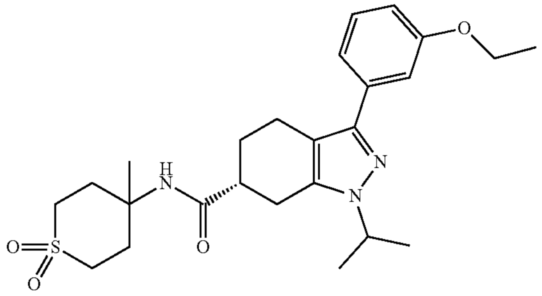 [SMILES: CCOc1cccc(-c2nn(C(C)C)c3c2CC[C@@H](C(=O)NC2(C)CCS(=O)(=O)CC2)C3)c1] | (R)-3-(3-ethoxyphenyl)-1-isopropyl-N-(4-methyl-1,1-dioxidotetrahydro-2H-thiopyran-4-yl)-4,5,6,7-tetrahydro-1H-indazole-6-carboxamide | 474 | 3.3 |
| 34 | 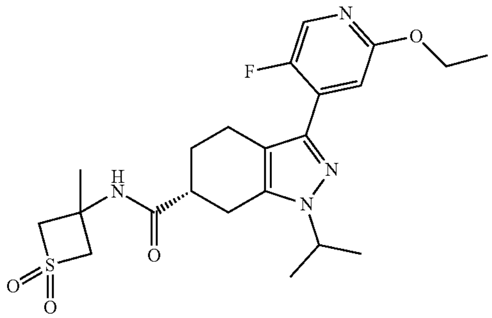 [SMILES: CCOc1cc(-c2nn(C(C)C)c3c2CC[C@@H](C(=O)NC2(C)CS(=O)(=O)C2)C3)c(F)cn1] | (R)-3-(2-ethoxy-5-fluoropyridin-4-yl)-1-isopropyl-N-(3-methyl-1,1-dioxidothietan-3-yl)-4,5,6,7-tetrahydro-1H-indazole-6-carboxamide | 465 | 117.3 |
| 35 | 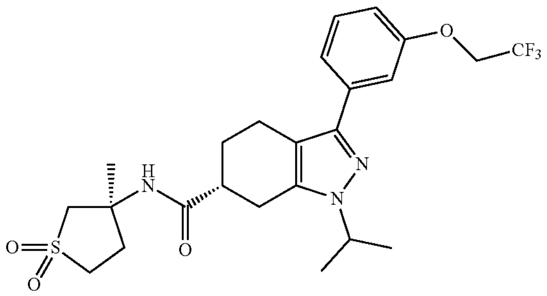 [SMILES: CC(C)n1nc(-c2cccc(OCC(F)(F)F)c2)c2c1C[C@H](C(=O)N[C@@]1(C)CCS(=O)(=O)C1)CC2] | (R)-1-isopropyl-N-((S)-3-methyl-1,1-dioxidotetrahydrothiophen-3-yl)-3-(3-(2,2,2-trifluoroethoxy)phenyl)-4,5,6,7-tetrahydro-1H-indazole-6-carboxamide | 514 | 35.2 |

-continued

| Example | Structure | Name | LCMS [M + 1] | DGAT2 $IC_{50}$ (nM) |
|---|---|---|---|---|
| 36 | 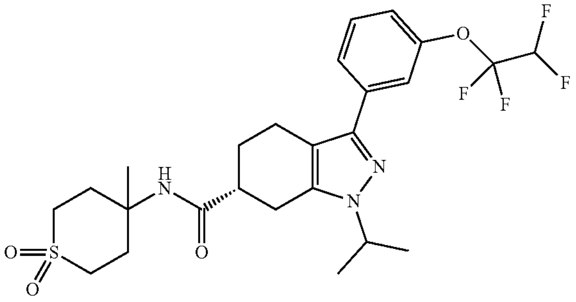 [SMILES: CC(C)n1nc(-c2cccc(OC(F)(F)C(F)F)c2)c2c1C[C@H](C(=O)NC1(C)CCS(=O)(=O)CC1)CC2] | (R)-1-isopropyl-N-(4-methyl-1,1-dioxidotetrahydro-2H-thiopyran-4-yl)-3-(3-(1,1,2,2-tetrafluoroethoxy)phenyl)-4,5,6,7-tetrahydro-1H-indazole-6-carboxamide | 546 | 353 |
| 37 | 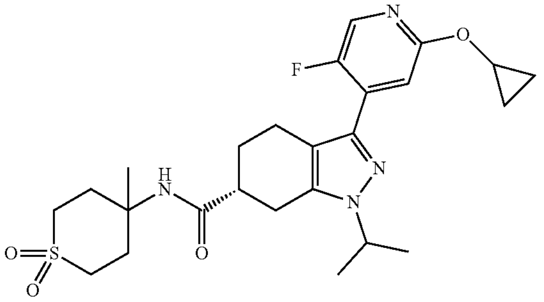 [SMILES: CC(C)n1nc(-c2cc(OC3CC3)ncc2F)c2c1C[C@H](C(=O)NC1(C)CCS(=O)(=O)CC1)CC2] | (R)-3-(2-cyclopropoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide | 505 | 93.2 |
| 38 | 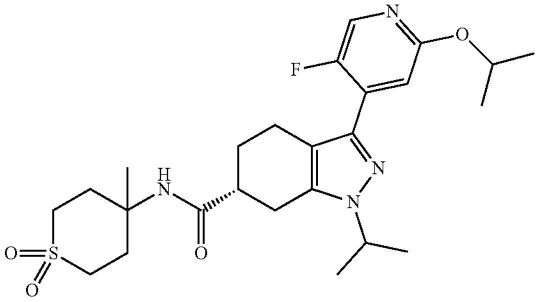 [SMILES: CC(C)Oc1cc(-c2nn(C(C)C)c3c2CC[C@@H](C(=O)NC2(C)CCS(=O)(=O)CC2)C3)c(F)cn1] | (R)-3-(5-fluoro-2-isopropoxypyridin-4-yl)-1-isopropyl-N-(4-methyl-1,1-dioxidotetrahydro-2H-thiopyran-4-yl)-4,5,6,7-tetrahydro-1H-indazole-6-carboxamide | 507 | 74.3 |
| 39 | 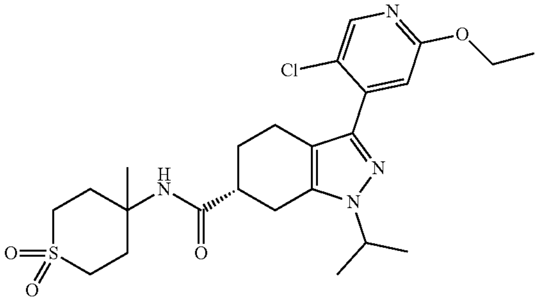 [SMILES: CCOc1cc(-c2nn(C(C)C)c3c2CC[C@@H](C(=O)NC2(C)CCS(=O)(=O)CC2)C3)c(Cl)cn1] | (R)-3-(5-chloro-2-ethoxypyridin-4-yl)-1-isopropyl-N-(4-methyl-1,1-dioxidotetrahydro-2H-thiopyran-4-yl)-4,5,6,7-tetrahydro-1H-indazole-6-carboxamide | 509 | 7.7 |
| 40 | 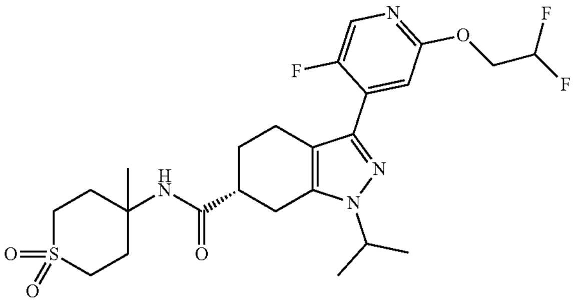 [SMILES: CC(C)n1nc(-c2cc(OCC(F)F)ncc2F)c2c1C[C@H](C(=O)NC1(C)CCS(=O)(=O)CC1)CC2] | (R)-3-(2-(2,2-difluoroethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide | 529 | 4.6 |

-continued

| Example | Structure | Name | LCMS [M + 1] | DGAT2 $IC_{50}$ (nM) |
|---|---|---|---|---|
| 41 | 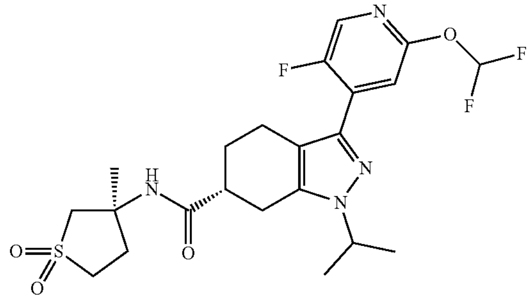 [SMILES: CC(C)n1nc(-c2cc(OC(F)F)ncc2F)c2c1C[C@H](C(=O)N[C@@]1(C)CCS(=O)(=O)C1)CC2] | (R)-3-(2-(difluoromethoxy)-5-fluoropyridin-4-yl)-1-isopropyl-N-((S)-3-methyl-1,1-dioxidotetrahydrothiophen-3-yl)-4,5,6,7-tetrahydro-1H-indazole-6-carboxamide | 501 | 138.6 |
| 42 | 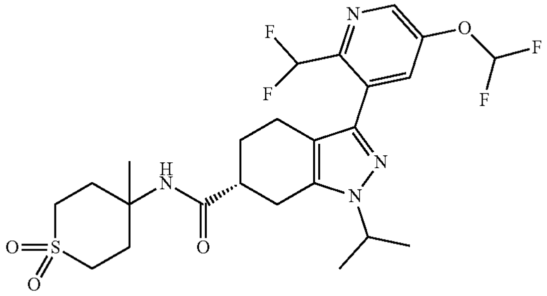 [SMILES: CC(C)n1nc(-c2cc(OC(F)F)cnc2C(F)F)c2c1C[C@H](C(=O)NC1(C)CCS(=O)(=O)CC1)CC2] | (R)-3-(5-(difluoromethoxy)-2-(difluoromethyl)pyridin-3-yl)-1-isopropyl-N-(4-methyl-1,1-dioxidotetrahydro-2H-thiopyran-4-yl)-4,5,6,7-tetrahydro-1H-indazole-6-carboxamide | 547 | 296.2 |
| 43 | 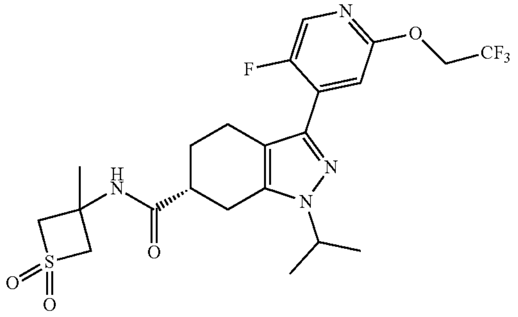 [SMILES: CC(C)n1nc(-c2cc(OCC(F)(F)F)ncc2F)c2c1C[C@H](C(=O)NC1(C)CS(=O)(=O)C1)CC2] | (R)-3-(5-fluoro-2-(2,2,2-trifluoroethoxy)pyridin-4-yl)-1-isopropyl-N-(3-methyl-1,1-dioxidothietan-3-yl)-4,5,6,7-tetrahydro-1H-indazole-6-carboxamide | 519 | 14.1 |
| 44 | 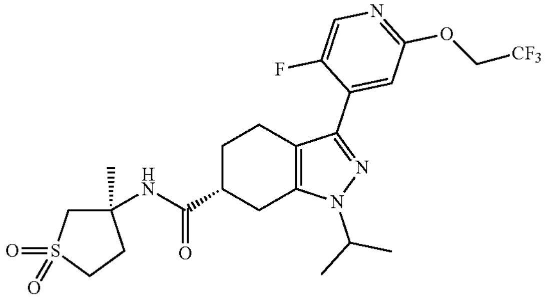 [SMILES: CC(C)n1nc(-c2cc(OCC(F)(F)F)ncc2F)c2c1C[C@H](C(=O)N[C@@]1(C)CCS(=O)(=O)C1)CC2] | (R)-3-(5-fluoro-2-(2,2,2-trifluoroethoxy)pyridin-4-yl)-1-isopropyl-N-((S)-3-methyl-1,1-dioxidotetrahydrothiophen-3-yl)-4,5,6,7-tetrahydro-1H-indazole-6-carboxamide | 533 | 5.3 |
| 45 | 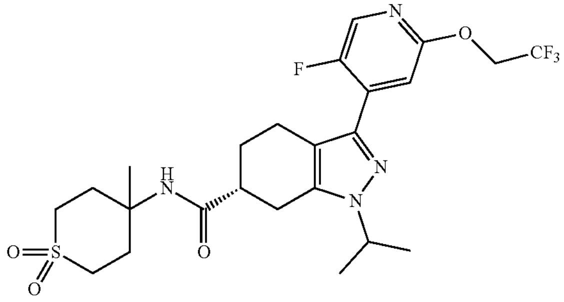 [SMILES: CC(C)n1nc(-c2cc(OCC(F)(F)F)ncc2F)c2c1C[C@H](C(=O)NC1(C)CCS(=O)(=O)CC1)CC2] | (R)-3-(5-fluoro-2-(2,2,2-trifluoroethoxy)pyridin-4-yl)-1-isopropyl-N-(4-methyl-1,1-dioxidotetrahydro-2H-thiopyran-4-yl)-4,5,6,7-tetrahydro-1H-indazole-6-carboxamide | 547 | 18.4 |

-continued

| Example | Structure | Name | LCMS [M + 1] | DGAT2 $IC_{50}$ (nM) |
|---|---|---|---|---|
| 46 | 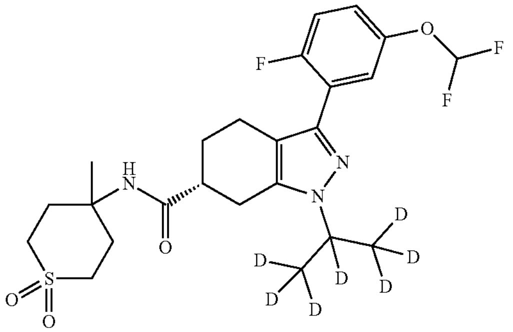 [SMILES: [2H]C([2H])([2H])C([2H])(n1nc(-c2cc(OC(F)F)ccc2F)c2c1C[C@H](C(=O)NC1(C)CCS(=O)(=O)CC1)CC2)C([2H])([2H])[2H]] | (R)-3-(5-(difluoromethoxy)-2-fluorophenyl)-N-(4-methyl-1,1-dioxidotetrahydro-2H-thiopyran-4-yl)-1-(propan-2-yl-d7)-4,5,6,7-tetrahydro-1H-indazole-6-carboxamide | 52 | 37.9 |
| 47 | 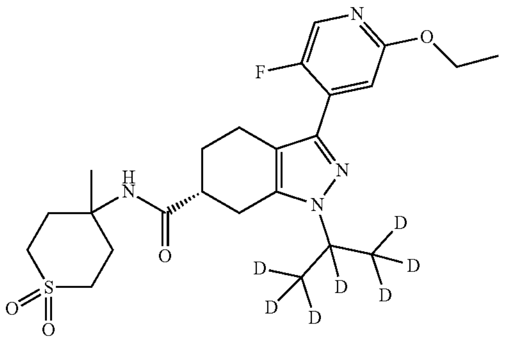 [SMILES: [2H]C([2H])([2H])C([2H])(n1nc(-c2cc(OCC)ncc2F)c2c1C[C@H](C(=O)NC1(C)CCS(=O)(=O)CC1)CC2)C([2H])([2H])[2H]] | (R)-3-(2-ethoxy-5-fluoropyridin-4-yl)-N-(4-methyl-1,1-dioxidotetrahydro-2H-thiopyran-4-yl)-1-(propan-2-yl-d7)-4,5,6,7-tetrahydro-1H-indazole-6-carboxamide | 500 | 65.9 |
| 48a | 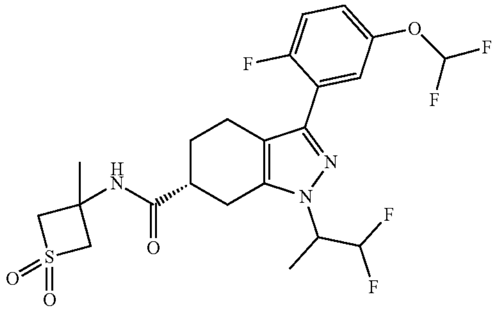 [SMILES: CC(C(F)F)n1nc(-c2cc(OC(F)F)ccc2F)c2c1C[C@H](C(=O)NC1(C)CS(=O)(=O)C1)CC2] | (6R)-3-(5-(difluoromethoxy)-2-fluorophenyl)-1-(1,1-difluoropropan-2-yl)-N-(3-methyl-1,1-dioxidothietan-3-yl)-4,5,6,7-tetrahydro-1H-indazole-6-carboxamide (faster eluting with OD-H column, 20% iPrOH/$CO_2$) | 522 | 90.3 |
| 48b | 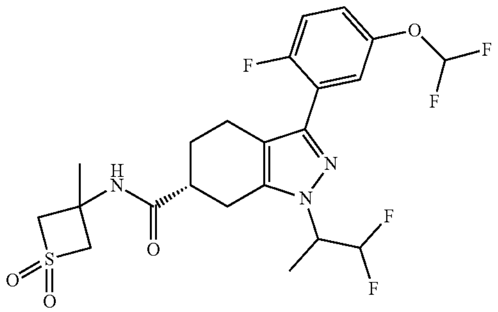 [SMILES: CC(C(F)F)n1nc(-c2cc(OC(F)F)ccc2F)c2c1C[C@H](C(=O)NC1(C)CS(=O)(=O)C1)CC2] | (6R)-3-(5-(difluoromethoxy)-2-fluorophenyl)-1-(1,1-difluoropropan-2-yl)-N-(3-methyl-1,1-dioxidothietan-3-yl)-4,5,6,7-tetrahydro-1H-indazole-6-carboxamide (slower eluting with OD-H column, 20% iPrOH/$CO_2$) | 522 | 19.8 |

-continued

| Example | Structure | Name | LCMS [M + 1] | DGAT2 $IC_{50}$ (nM) |
|---|---|---|---|---|
| 49a | 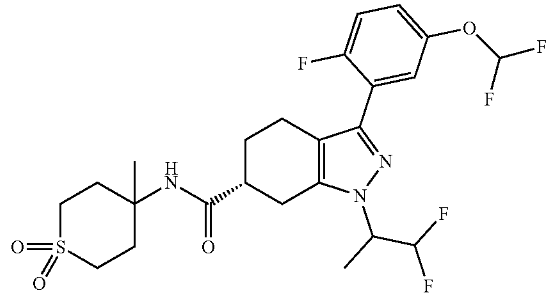 [SMILES: CC(C(F)F)n1nc(-c2cc(OC(F)F)ccc2F)c2c1C[C@H](C(=O)NC1(C)CCS(=O)(=O)CC1)CC2] | (6R)-3-(5-(difluoromethoxy)-2-fluorophenyl)-1-(1,1-difluoropropan-2-yl)-N-(4-methyl-1,1-dioxidotetrahydro-2/-thiopyran-4-yl)-4,5,6,7-tetrahydro-1H-indazole-6-carboxamide (faster eluting with OD-H column, 20% $EtOH/CO_2$) | 550 | 32.1 |
| 49b | 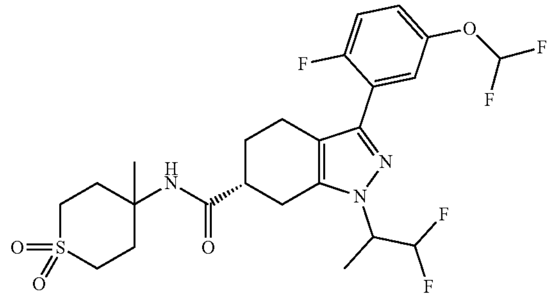 [SMILES: CC(C(F)F)n1nc(-c2cc(OC(F)F)ccc2F)c2c1C[C@H](C(=O)NC1(C)CCS(=O)(=O)CC1)CC2] | (6R)-3-(5-(difluoromethoxy)-2-fluorophenyl)-1-(1,1-difluoropropan-2-yl)-N-(4-methyl-1,1-dioxidotetrahydro-2H-thiopyran-4-yl)-4,5,6,7-tetrahydro-1H-indazole-6-carboxamide (slower eluting with OD-H column, 20% $EtOH/CO_2$) | 550 | 0.6 |
| 50 | 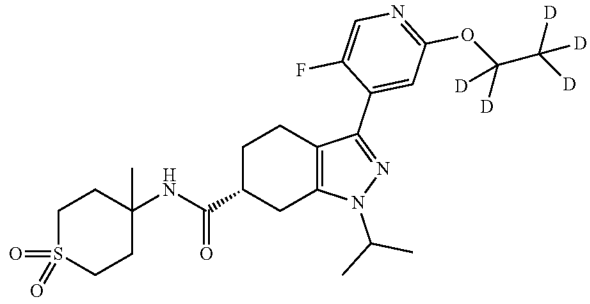 [SMILES: [2H]C([2H])([2H])C([2H])([2H])Oc1cc(-c2nn(C(C)C)c3c2CC[C@@H](C(=O)NC2(C)CCS(=O)(=O)CC2)C3)c(F)cn1] | (R)-3-(2-(ethoxy-d5)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide | 498 | 51.0 |
| 51 | 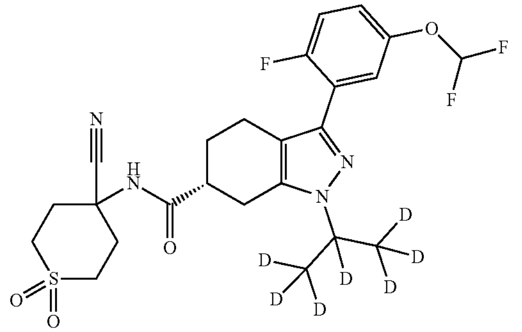 [SMILES: [2H]C([2H])([2H])C([2H])(n1nc(-c2cc(OC(F)F)ccc2F)c2c1C[C@H](C(=O)NC1(C#N)CCS(=O)(=O)CC1)CC2)C([2H])([2H])[2H]] | (R)-N-(4-cyano-1,1-dioxidotetrahydro-2H-thiopyran-4-yl)-3-(5-(difluoromethoxy)-2-fluorophenyl)-1-(propan-2-yl-d7)-4,5,6,7-tetrahydro-1H-indazole-6-carboxamide | 532 | 4.3 |

-continued

| Example | Structure | Name | LCMS [M + 1] | DGAT2 $IC_{50}$ (nM) |
| --- | --- | --- | --- | --- |
| 52 | 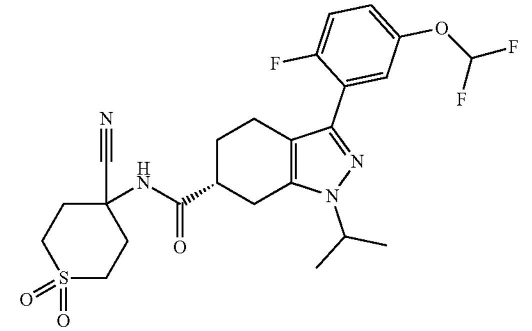 [SMILES: CC(C)n1nc(-c2cc(OC(F)F)ccc2F)c2c1C[C@H](C(=O)NC1(C#N)CCS(=O)(=O)CC1)CC2] | (R)-N-(4-cyano-1,1-dioxidotetrahydro-2H-thiopyran-4-yl)-3-(5-(difluoromethoxy)-2-fluorophenyl)-1-isopropyl-4,5,6,7-tetrahydro-1H-indazole-6-carboxamide | 525 | 4.7 |
| 53a | 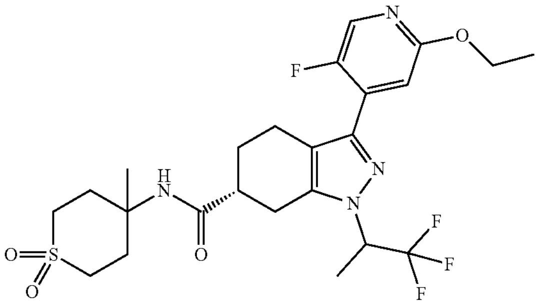 [SMILES: CCOc1cc(-c2nn(C(C)C(F)(F)F)c3c2CC[C@@H](C(=O)NC2(C)CCS(=O)(=O)CC2)C3)c(F)cn1] | (6R)-3-(2-ethoxy-5-fluoropyridin-4-yl)-N-(4-methyl-1,1-dioxidotetrahydro-2H-thiopyran-4-yl)-1-(1,1,1-trifluoropropan-2-yl)-4,5,6,7-tetrahydro-1H-indazole-6-carboxamide (faster eluting with: OD-H column, 20% MeOH/$CO_2$) | 547 | 162.1 |
| 53b | 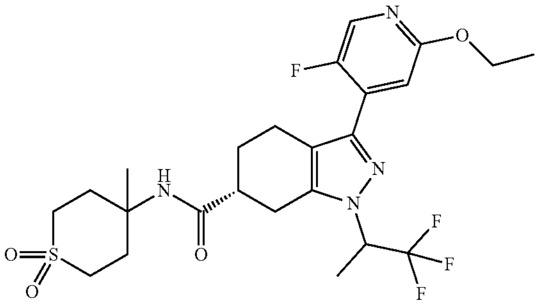 [SMILES: CCOc1cc(-c2nn(C(C)C(F)(F)F)c3c2CC[C@@H](C(=O)NC2(C)CCS(=O)(=O)CC2)C3)c(F)cn1] | (6R)-3-(2-ethoxy-5-fluoropyridin-4-yl)-N-(4-methyl-1,1-dioxidotetrahydro-2H-thiopyran-4-yl)-1-(1,1,1-trifluoropropan-2-yl)-4,5,6,7-tetrahydro-1H-indazole-6-carboxamide (slower eluting with OD-H column, 20% MeOH/$CO_2$) | 547 | 10.33 |
| 54 | 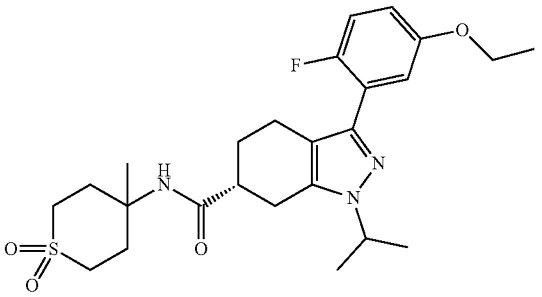 [SMILES: CCOc1ccc(F)c(-c2nn(C(C)C)c3c2CC[C@@H](C(=O)NC2(C)CCS(=O)(=O)CC2)C3)c1] | (R)-3-(5-ethoxy-2-fluorophenyl)-1-isopropyl-N-(4-methyl-1,1-dioxidotetrahydro-2H-thiopyran-4-yl)-4,5,6,7-tetrahydro-1H-indazole-6-carboxamide | 492 | 1.8 |
| 55 | 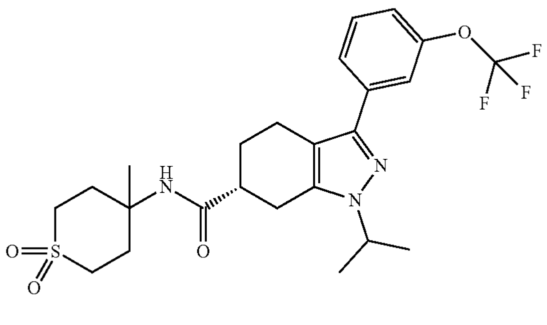 [SMILES: CC(C)n1nc(-c2cccc(OC(F)(F)F)c2)c2c1C[C@H](C(=O)NC1(C)CCS(=O)(=O)CC1)CC2] | (R)-1-isopropyl-N-(4-methyl-1,1-dioxidotetrahydro-2H-thiopyran-4-yl)-3-(3-(trifluoromethoxy)phenyl)-4,5,6,7-tetrahydro-1H-indazole-6-carboxamide | 514 | 86.6 |

-continued

| Example | Structure | Name | LCMS [M + 1] | DGAT2 $IC_{50}$ (nM) |
|---|---|---|---|---|
| 56 | 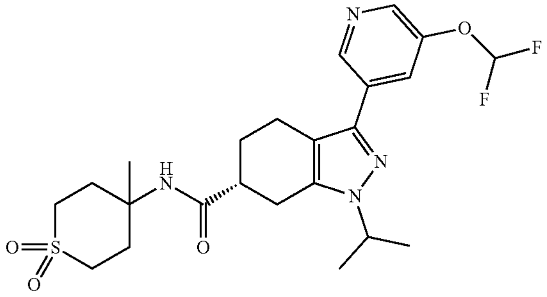 [SMILES: CC(C)n1nc(-c2cncc(OC(F)F)c2)c2c1C[C@H](C(=O)NC1(C)CCS(=O)(=O)CC1)CC2] | (R)-3-(5-(difluoromethoxy)pyridin-3-yl)-1-isopropyl-N-(4-methyl-1,1-dioxidotetrahydro-2H-thiopyran-4-yl)-4,5,6,7-tetrahydro-1H-indazole-6-carboxamide | 497 | 414 |
| 57 | 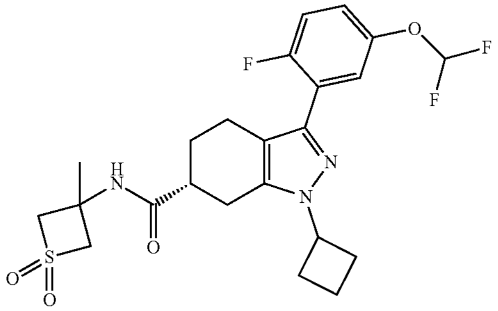 [SMILES: CC1(NC(=O)[C@@H]2CCc3c(-c4cc(OC(F)F)ccc4F)nn(C4CCC4)c3C2)CS(=O)(=O)C1] | (R)-1-cyclobutyl-3-(5-(difluoromethoxy)-2-fluorophenyl)-N-(3-methyl-1,1-dioxidothietan-3-yl)-4,5,6,7-tetrahydro-1H-indazole-6-carboxamide | 498 | 22.8 |
| 58a | 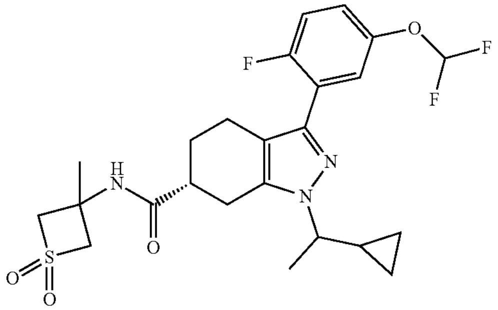 [SMILES: CC(C1CC1)n1nc(-c2cc(OC(F)F)ccc2F)c2c1C[C@H](C(=O)NC1(C)CS(=O)(=O)C1)CC2] | (6R)-1-(1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide (faster eluting with IC column, 35% $MeOH/CO_2$) | 512 | 23.4 |
| 58b | 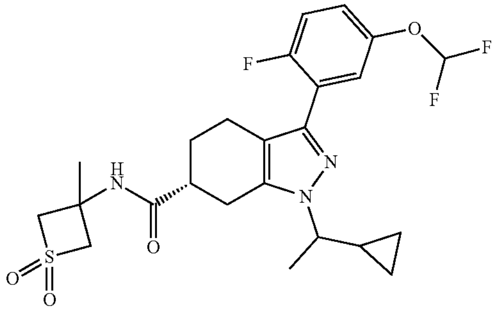 [SMILES: CC(C1CC1)n1nc(-c2cc(OC(F)F)ccc2F)c2c1C[C@H](C(=O)NC1(C)CS(=O)(=O)C1)CC2] | (6R)-1-(1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide (slower eluting with IC column, 35% $MeOH/CO_2$) | 512 | 2.5 |
| 59 | 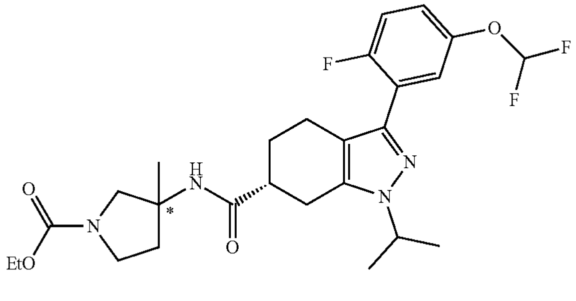 [SMILES: CCOC(=O)N1CCC(C)(NC(=O)[C@@H]2CCc3c(-c4cc(OC(F)F)ccc4F)nn(C(C)C)c3C2)C1] | ethyl 3-((R)-3-(5-(difluoromethoxy)-2-fluorophenyl)-1-isopropyl-4,5,6,7-tetrahydro-1H-indazole-6-carboxamido)-3-methylpyrrolidine-1-carboxylate (mixture of diastereomers) | 523 | 61.0 |

-continued

| Example | Structure | Name | LCMS [M + 1] | DGAT2 $IC_{50}$ (nM) |
|---|---|---|---|---|
| 60 | 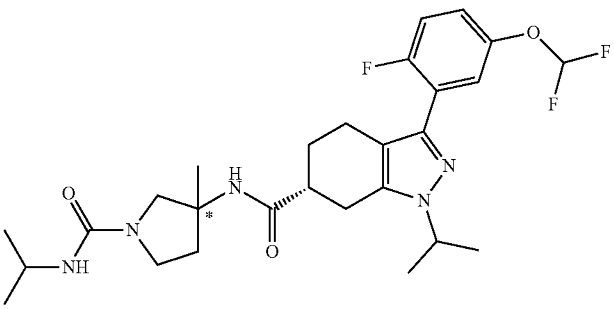 [SMILES: CC(C)NC(=O)N1CCC(C)(NC(=O)[C@@H]2CCc3c(-c4cc(OC(F)F)ccc4F)nn(C(C)C)c3C2)C1] | (6R)-3-(5-(difluoromethoxy)-2-fluorophenyl)-1-isopropyl-N-(1-(isopropylcarbamoyl)-3-methylpyrrolidin-3-yl)-4,5,6,7-tetrahydro-1H-indazole-6-carboxamide (mixture of diastereomers) | 536 | 29.2 |
| 61 | 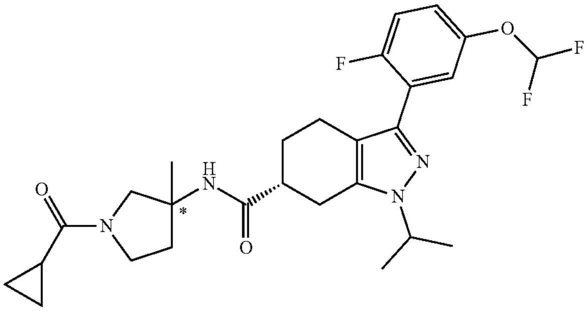 [SMILES: CC(C)n1nc(-c2cc(OC(F)F)ccc2F)c2c1C[C@H](C(=O)NC1(C)CCN(C(=O)C3CC3)C1)CC2] | (6R)-N-(1-(cyclopropanecarbonyl)-3-methylpyrrolidin-3-yl)-3-(5-(difluoromethoxy)-2-fluorophenyl)-1-isopropyl-4,5,6,7-tetrahydro-1H-indazole-6-carboxamide (mixture of diastereomers) | 519 | 26.2 |
| 62 | 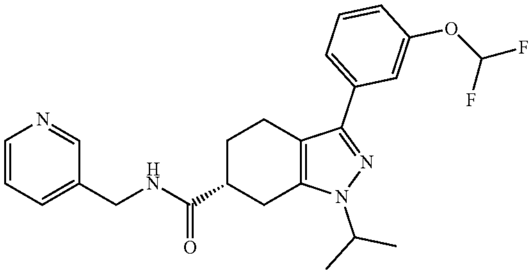 [SMILES: CC(C)n1nc(-c2cccc(OC(F)F)c2)c2c1C[C@H](C(=O)NCc1cccnc1)CC2] | (R)-3-(3-(difluoromethoxy)phenyl)-1-isopropyl-N-(pyridin-3-ylmethyl)-4,5,6,7-tetrahydro-1H-indazole-6-carboxamide | 441 | 8188 |
| 63 | 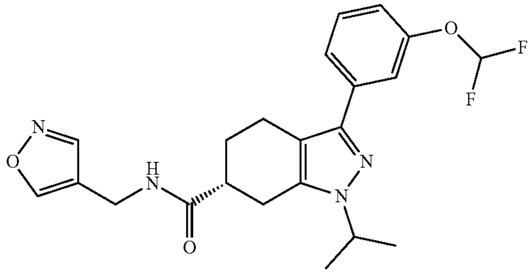 [SMILES: CC(C)n1nc(-c2cccc(OC(F)F)c2)c2c1C[C@H](C(=O)NCc1cnoc1)CC2] | (R)-3-(3-(difluoromethoxy)phenyl)-1-isopropyl-N-(isoxazol-4-ylmethyl)-4,5,6,7-tetrahydro-1H-indazole-6-carboxamide | 431 | 4561 |
| 64 | 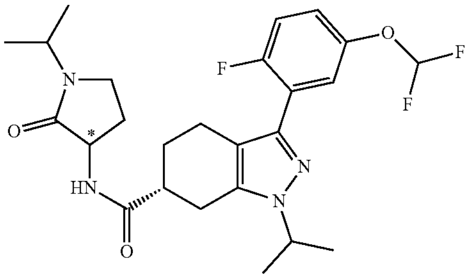 [SMILES: CC(C)N1CCC(NC(=O)[C@@H]2CCc3c(-c4cc(OC(F)F)ccc4F)nn(C(C)C)c3C2)C1=O] | (6R)-3-(5-(difluoromethoxy)-2-fluorophenyl)-1-isopropyl-N-(1-isopropyl-2-oxopyrrolidin-3-yl)-4,5,6,7-tetrahydro-1H-indazole-6-carboxamide | 493 | 622 |

-continued

| Example | Structure | Name | LCMS [M + 1] | DGAT2 $IC_{50}$ (nM) |
|---|---|---|---|---|
| 65 | 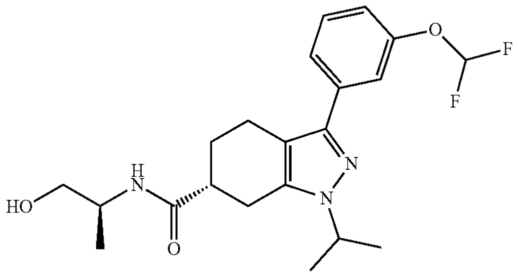 [SMILES: CC(C)n1nc(-c2cccc(OC(F)F)c2)c2c1C[C@H](C(=O)N[C@@H](C)CO)CC2] | (R)-3-(3-(difluoromethoxy)phenyl)-N-((S)-1-hydroxypropan-2-yl)-1-isopropyl-4,5,6,7-tetrahydro-1H-indazole-6-carboxamide | 408 | 7263 |
| 66 | 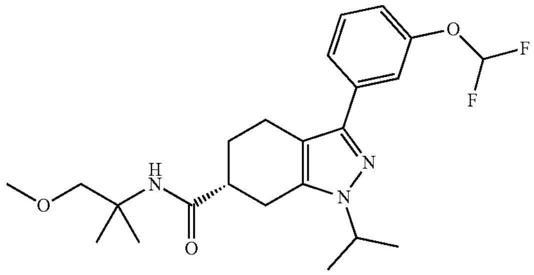 [SMILES: COCC(C)(C)NC(=O)[C@@H]1CCc2c(-c3cccc(OC(F)F)c3)nn(C(C)C)c2C1] | (R)-3-(3-(difluoromethoxy)phenyl)-1-isopropyl-N-(1-methoxy-2-methylpropan-2-yl)-4,5,6,7-tetrahydro-1H-indazole-6-carboxamide | 436 | 1329 |
| 67 | 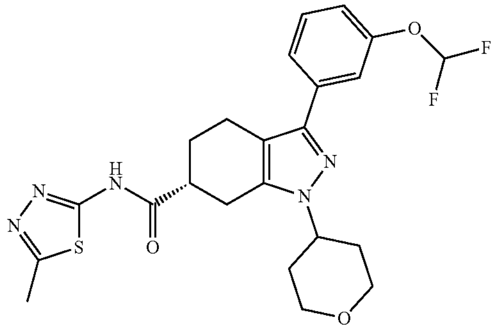 [SMILES: Cc1nnc(NC(=O)[C@@H]2CCc3c(-c4cccc(OC(F)F)c4)nn(C4CCOCC4)c3C2)s1] | (R)-3-(3-(difluoromethoxy)phenyl)-N-(5-methyl-1,3,4-thiadiazol-2-yl)-1-(tetrahydro-2H-pyran-4-yl)-4,5,6,7-tetrahydro-1H-indazole-6-carboxamide | 490 | >10000 |
| 68 | 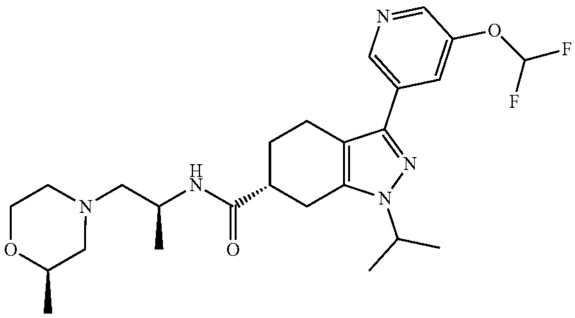 [SMILES: CC(C)n1nc(-c2cncc(OC(F)F)c2)c2c1C[C@H](C(=O)N[C@@H](C)CN1CCO[C@H](C)C1)CC2] | (R)-3-(5-(difluoromethoxy)pyridin-3-yl)-1-isopropyl-N-((S)-1-((R)-2-methylmorpholino)propan-2-yl)-4,5,6,7-tetrahydro-1H-indazole-6-carboxamide | 492 | >10000 |
| 69 | 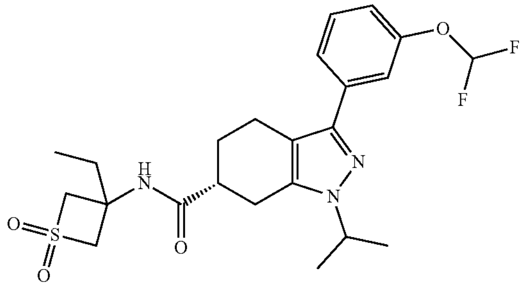 [SMILES: CCC1(NC(=O)[C@@H]2CCc3c(-c4cccc(OC(F)F)c4)nn(C(C)C)c3C2)CS(=O)(=O)C1] | (R)-3-(3-(difluoromethoxy)phenyl)-N-(3-ethyl-1,1-dioxidothietan-3-yl)-1-isopropyl-4,5,6,7-tetrahydro-1H-indazole-6-carboxamide | 482 | 90 |

-continued

| Example | Structure | Name | LCMS [M + 1] | DGAT2 $IC_{50}$ (nM) |
|---|---|---|---|---|
| 70 | 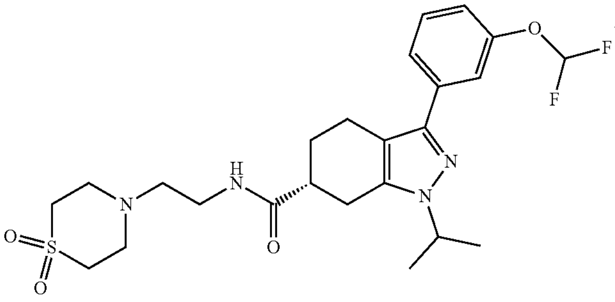 [SMILES: CC(C)n1nc(-c2cccc(OC(F)F)c2)c2c1C[C@H](C(=O)NCCN1CCS(=O)(=O)CC1)CC2] | (R)-3-(3-(difluoromethoxy)phenyl)-N-(2-(1,1-dioxidothiomorpholino)ethyl)-1-isopropyl-4,5,6,7-tetrahydro-1H-indazole-6-carboxamide | 511 | 18010 |
| 71 | 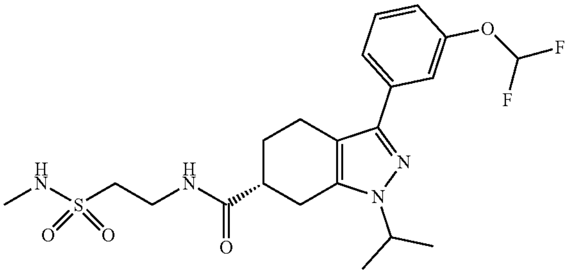 [SMILES: CNS(=O)(=O)CCNC(=O)[C@@H]1CCc2c(-c3cccc(OC(F)F)c3)nn(C(C)C)c2C1] | (R)-3-(3-(difluoromethoxy)phenyl)-1-isopropyl-N-(2-(N-methylsulfamoyl)ethyl)-4,5,6,7-tetrahydro-1H-indazole-6-carboxamide | 471 | >10000 |
| 72 | 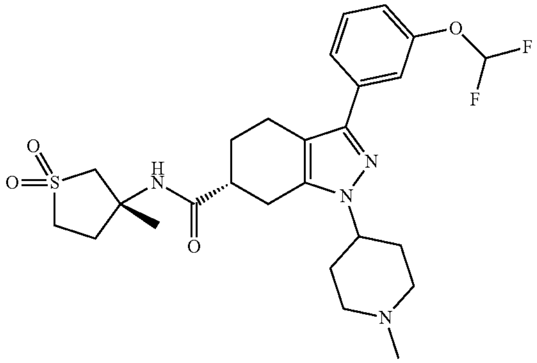 [SMILES: CN1CCC(n2nc(-c3cccc(OC(F)F)c3)c3c2C[C@H](C(=O)N[C@]2(C)CCS(=O)(=O)C2)CC3)CC1] | (R)-3-(3-(difluoromethoxy)phenyl)-N-((R)-3-methyl-1,1-dioxidotetrahydrothiophen-3-yl)-1-(1-methylpiperidin-4-yl)-4,5,6,7-tetrahydro-1H-indazole-6-carboxamide | 537 | >10000 |
| 73 | 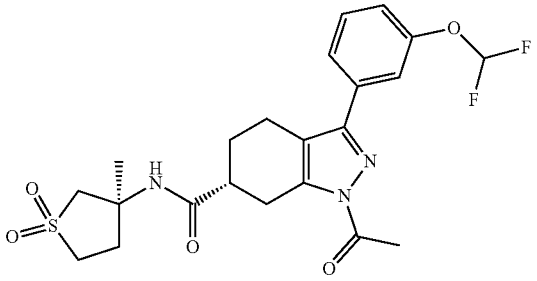 [SMILES: CC(=O)n1nc(-c2cccc(OC(F)F)c2)c2c1C[C@H](C(=O)N[C@@]1(C)CCS(=O)(=O)C1)CC2] | (R)-1-acetyl-3-(3-(difluoromethoxy)phenyl)-N-((S)-3-methyl-1,1-dioxidotetrahydrothiophen-3-yl)-4,5,6,7-tetrahydro-1H-indazole-6-carboxamide | 482 | >10000 |
| 74 | 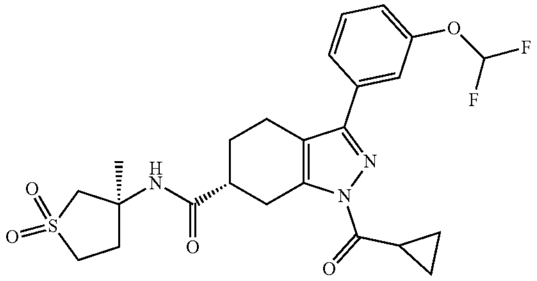 [SMILES: C[C@]1(NC(=O)[C@@H]2CCc3c(-c4cccc(OC(F)F)c4)nn(C(=O)C4CC4)c3C2)CCS(=O)(=O)C1] | (R)-1-(cyclopropanecarbonyl)-3-(3-(difluoromethoxy)phenyl)-N-((S)-3-methyl-1,1-dioxidotetrahydrothiophen-3-yl)-4,5,6,7-tetrahydro-1H-indazole-6-carboxamide | 508 | 2914 |

-continued

| Example | Structure | Name | LCMS [M + 1] | DGAT2 $IC_{50}$ (nM) |
|---|---|---|---|---|
| 75 | 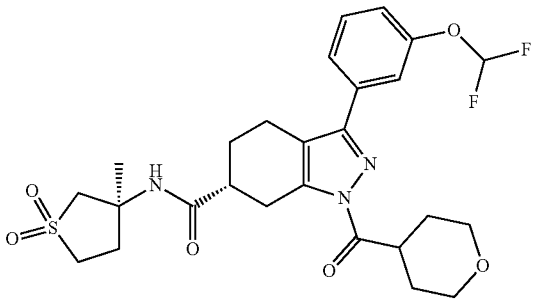 [SMILES: C[C@]1(NC(=O)[C@@H]2CCc3c(-c4cccc(OC(F)F)c4)nn(C(=O)C4CCOCC4)c3C2)CCS(=O)(=O)C1] | (R)-3-(3-(difluoromethoxy)phenyl)-N-((S)-3-methyl-1,1-dioxidotetrahydrothiophen-3-yl)-1-(tetrahydro-2H-pyran-4-carbonyl)-4,5,6,7-tetrahydro-1H-indazole-6-carboxamide | 552 | >10000 |
| 76 | 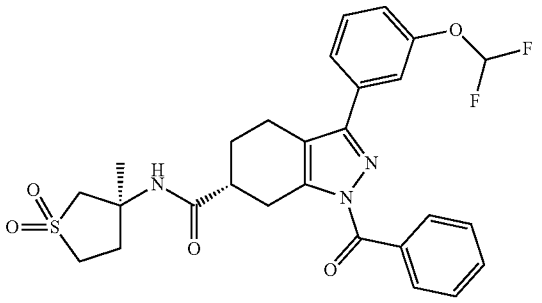 [SMILES: C[C@]1(NC(=O)[C@@H]2CCc3c(-c4cccc(OC(F)F)c4)nn(C(=O)c4ccccc4)c3C2)CCS(=O)(=O)C1] | (R)-1-benzoyl-3-(3-(difluoromethoxy)phenyl)-N-((S)-3-methyl-1,1-dioxidotetrahydrothiophen-3-yl)-4,5,6,7-tetrahydro-1H-indazole-6-carboxamide | 544 | 2739 |
| 77 | 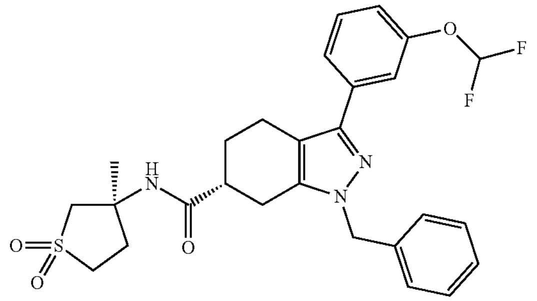 [SMILES: C[C@]1(NC(=O)[C@@H]2CCc3c(-c4cccc(OC(F)F)c4)nn(Cc4ccccc4)c3C2)CCS(=O)(=O)C1] | (R)-1-benzyl-3-(3-(difluoromethoxy)phenyl)-N-((S)-3-methyl-1,1-dioxidotetrahydrothiophen-3-yl)-4,5,6,7-tetrahydro-1H-indazole-6-carboxamide | 530 | 577 |
| 78 | 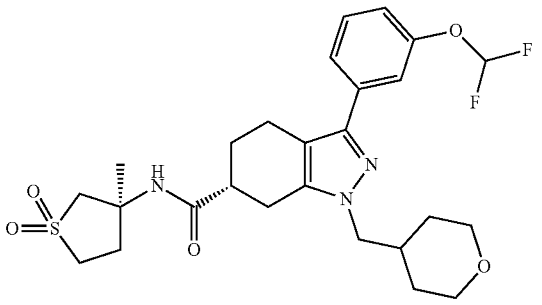 [SMILES: C[C@]1(NC(=O)[C@@H]2CCc3c(-c4cccc(OC(F)F)c4)nn(CC4CCOCC4)c3C2)CCS(=O)(=O)C1] | (R)-3-(3-(difluoromethoxy)phenyl)-N-((S)-3-methyl-1,1-dioxidotetrahydrothiophen-3-yl)-1-((tetrahydro-2H-pyran-4-yl)methyl)-4,5,6,7-tetrahydro-1H-indazole-6-carboxamide | 538 | >10000 |
| 79 | 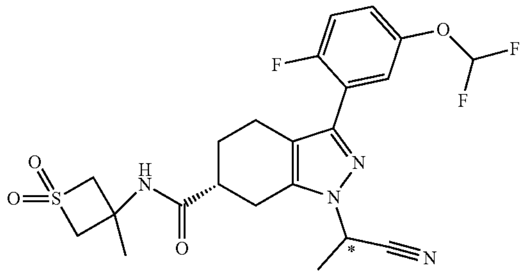 [SMILES: CC(C#N)n1nc(-c2cc(OC(F)F)ccc2F)c2c1C[C@H](C(=O)NC1(C)CS(=O)(=O)C1)CC2] | (6R)-1-(1-cyanoethyl)-3-(5-(difluoromethoxy)-2-fluorophenyl)-N-(3-methyl-1,1-dioxidothietan-3-yl)-4,5,6,7-tetrahydro-1H-indazole-6-carboxamide (mixture of diastereomers) | 497 | 59.1 |

-continued

| Example | Structure | Name | LCMS [M + 1] | DGAT2 $IC_{50}$ (nM) |
|---|---|---|---|---|
| 80 | 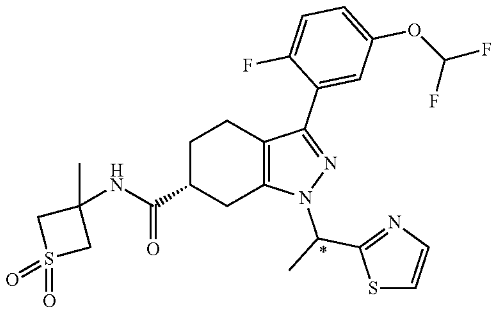 [SMILES: CC(c1nccs1)n1nc(-c2cc(OC(F)F)ccc2F)c2c1C[C@H](C(=O)NC1(C)CS(=O)(=O)C1)CC2] | (6R)-3-(5-(difluoromethoxy)-2-fluorophenyl)-N-(3-methyl-1,1-dioxidothietan-3-yl)-1-(1-(thiazol-2-yl)ethyl)-4,5,6,7-tetrahydro-1H-indazole-6-carboxamide (mixture of diastereomers) | 555 | 174 |

Example 81

(R)-3-(2-fluoro-5-isopropoxyphenyl)-1-isopropyl-N-(3-methyl-1,1-dioxidothietan-3-yl)-4,5,6,7-tetrahydro-1H-indazole-6-carboxamide

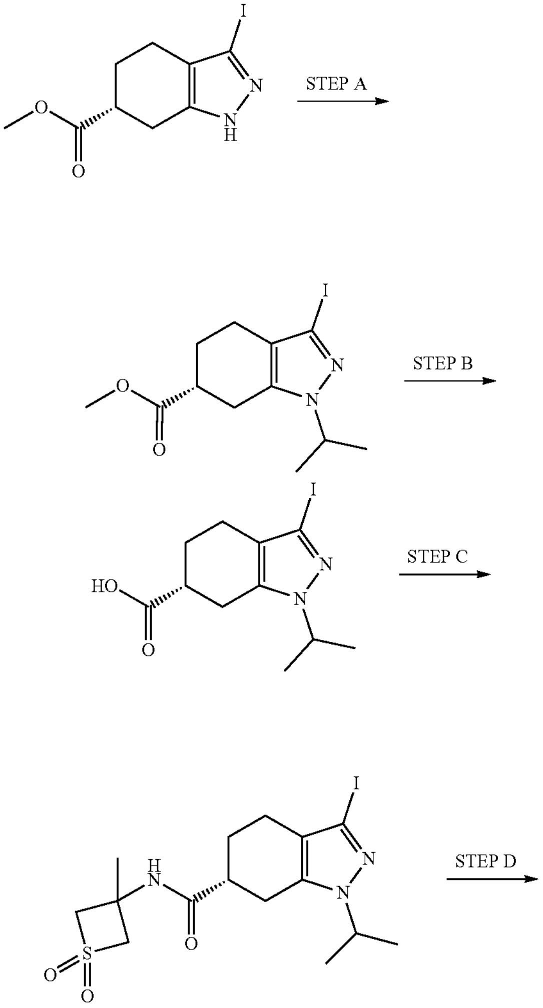

-continued

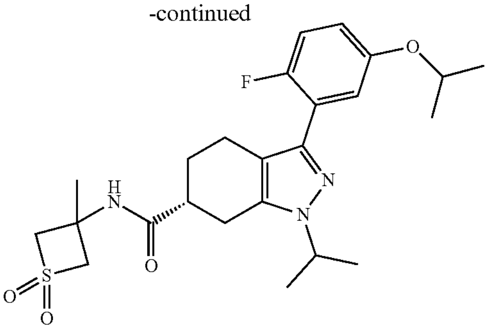

Ex-81

Step A: Methyl (R)-3-iodo-1-isopropyl-4,5,6,7-tetrahydro-1H-indazole-6-carboxylate To a mixture of methyl (R)-3-iodo-4,5,6,7-tetrahydro-1H-indazole-6-carboxylate (3.0 g, 9.8 mmol), 2-iodopropane (3.3 g, 6.5 mmol), $Cs_2CO_3$ (12.8 g, 39.2 mmol) was added DMF (20 ml). The mixture was stirred at 100° C. for 30 minutes. The reaction mixture was cooled to rt and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (20% EtOAc in hexanes) to afford the title compound. LC/MS=349 [M+1].

Step B: (R)-3-iodo-1-isopropyl-4,5,6,7-tetrahydro-1H-indazole-6-carboxylic acid

To a mixture of methyl (R)-3-iodo-1-isopropyl-4,5,6,7-tetrahydro-1H-indazole-6-carboxylate (3.4 g, 9.8 mmol), LiOH (0.94 g, 39.3 mmol), THF (10.5 mL), MeOH (10.5 mL), and water (10.5 mL) were added. The mixture was stirred at rt for 25 minutes, then acidified with 1N HCl (aq.) to pH 1. The mixture was then extracted with EtOAc, washed with water and brine, dried over $MgSO_4$ (s), filtered, and the volatiles evaporated to afford the title compound. The crude product was used without purification. LC/MS=335 [M+1].

Step C: (R)-3-iodo-1-isopropyl-N-(3-methyl-1,1-dioxidothietan-3-yl)-4,5,6,7-tetrahydro-1H-indazole-6-carboxamide To a mixture of (R)-3-iodo-1-isopropyl-4,5,6,7-tetrahydro-1H-indazole-6-carboxylic acid (3.1 g, 9.3 mmol) in DMF (13 mL) was added HATU (4.2 g, 11.2 mmol), DIPEA (6.5 mL, 37.2 mmol), and then 3-amino-3-methylthietane 1,1-dioxide hydrochloride (1.76 g, 10.2 mmol). The mixture was stirred at rt for 15 minutes. Then, water was added and the aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (70% EtOAc in hexanes) to afford the title compound. LC/MS=452 [M+1].

Step D: (R)-3-(2-fluoro-5-isopropoxyphenyl)-1-isopropyl-N-(3-methyl-1,1-dioxidothietan-3-yl)-4,5,6,7-tetrahydro-1H-indazole-6-carboxamide To a stirred solution of (R)-3-iodo-1-isopropyl-N-(3-methyl-1,1-dioxidothietan-3-yl)-4,5,6,7-tetrahydro-1H-indazole-6-carboxamide (100 mg, 0.22 mmol), (5-ethoxy-2-fluorophenyl)boronic acid (61 mg, 0.33 mmol), $Pd(dppf)Cl_2$ (36 mg, 0.04 mmol), $Na_2CO_3$ (70.5 mg, 0.67 mmol), and dioxane (1.1 mL) was added water (1.1 mL). The reaction mixture was sparged with $N_2$ for 5 min at rt then heated to 100° C. for 15 min. After cooling to rt, the mixture was filtered and purified by mass triggered reverse phase HPLC (ACN/water with 0.1% FA modifier) to afford the title compound (Ex-81). LC/MS=478 [M+1]. $^1H$ NMR (500 MHz, Chloroform-d) δ 7.09 (dd, J=5.9, 3.1 Hz, 1H), 7.03-6.98 (m, 1H), 6.82 (dt, J=8.9, 3.6 Hz, 1H), 6.49 (s, 1H), 4.54-4.48 (m, 1H), 4.48-4.42 (m, 1H), 4.37 (td, J=12.8, 12.3, 6.1 Hz, 2H), 3.97 (ddd, J=26.4, 13.9, 2.4 Hz, 2H), 2.82-2.60 (m, 2H), 2.57 (d, J=5.7 Hz, 2H), 1.98 (q, J=13.1, 9.9 Hz, 2H), 1.57 (s, 2H), 1.51 (dd, J=33.0, 6.6 Hz, 6H), 1.35-1.29 (m, 6H). DGAT2 $IC_{50}$ (nM)=24.5.

By using procedures similar to those described in Example 81 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 82 | 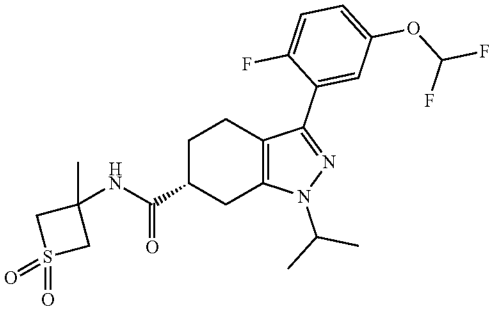 | (R)-3-(5-(difluoromethoxy)-2-fluorophenyl)-1-isopropyl-N-(3-methyl-1,1-dioxidothietan-3-yl)-4,5,6,7-tetrahydro-1H-indazole-6-carboxamide | 486 | 30.8 |
| 83 | 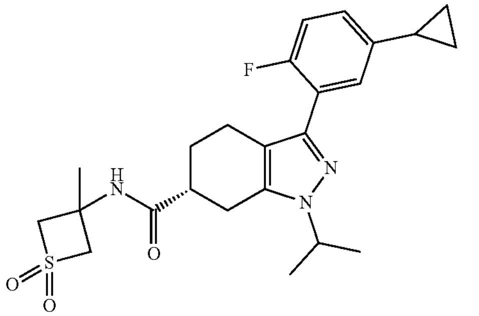 | (R)-3-(5-cyclopropyl-2-fluorophenyl)-1-isopropyl-N-(3-methyl-1,1-dioxidothietan-3-yl)-4,5,6,7-tetrahydro-1H-indazole-6-carboxamide | 460 | 46.0 |
| 84 | 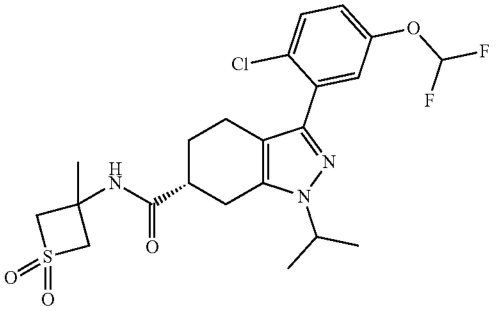 [SMILES: CC(C)n1nc(-c2cc(OC(F)F)ccc2Cl)c2c1C[C@H](C(=O)NC1(C)CS(=O)(=O)C1)CC2] | (R)-3-(2-chloro-5-(difluoromethoxy)phenyl)-1-isopropyl-N-(3-methyl-1,1-dioxidothietan-3-yl)-4,5,6,7-tetrahydro-1H-indazole-6-carboxamide | 502 | 7.92 |

-continued

| Example | Structure | Name | LCMS [M + 1] | DGAT2 $IC_{50}$ (nM) |
|---|---|---|---|---|
| 85 | 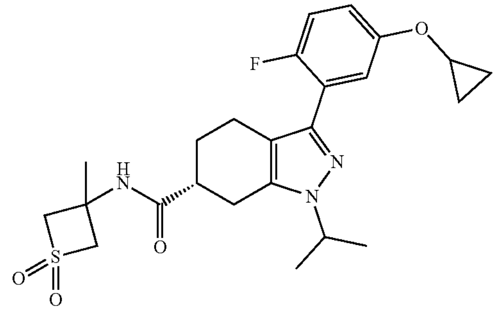 [SMILES: CC(C)n1nc(-c2cc(OC3CC3)ccc2F)c2c1C[C@H](C(=O)NC1(C)CS(=O)(=O)C1)CC2] | (R)-3-(5-cyclopropoxy-2-fluorophenyl)-1-isopropyl-N-(3-methyl-1,1-dioxidothietan-3-yl)-4,5,6,7-tetrahydro-1H-indazole-6-carboxamide | 476 | 15.6 |
| 86 | 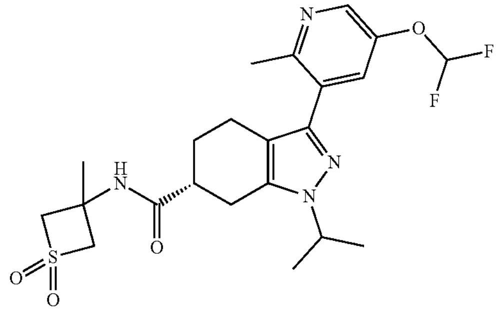 [SMILES: Cc1ncc(OC(F)F)cc1-c1nn(C(C)C)c2c1CC[C@@H](C(=O)NC1(C)CS(=O)(=O)C1)C2] | (R)-3-(5-(difluoromethoxy)-2-methylpyridin-3-yl)-1-isopropyl-N-(3-methyl-1,1-dioxidothietan-3-yl)-4,5,6,7-tetrahydro-1H-indazole-6-carboxamide | 483 | 169.9 |
| 87 | 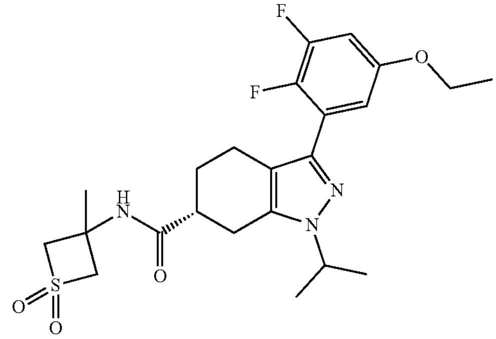 [SMILES: CCOc1cc(F)c(F)c(-c2nn(C(C)C)c3c2CC[C@@H](C(=O)NC2(C)CS(=O)(=O)C2)C3)c1] | (R)-3-(5-ethoxy-2,3-difluorophenyl)-1-isopropyl-N-(3-methyl-1,1-dioxidothietan-3-yl)-4,5,6,7-tetrahydro-1H-indazole-6-carboxamide | 482 | 3.6 |
| 88 | 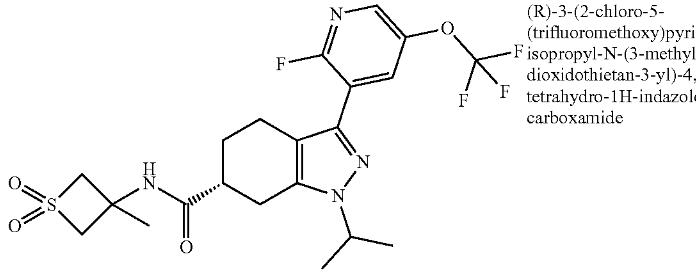 | (R)-3-(2-chloro-5-(trifluoromethoxy)pyridin-3-yl)-1-isopropyl-N-(3-methyl-1,1-dioxidothietan-3-yl)-4,5,6,7-tetrahydro-1H-indazole-6-carboxamide | 521 | 274.7 |
| 89 | 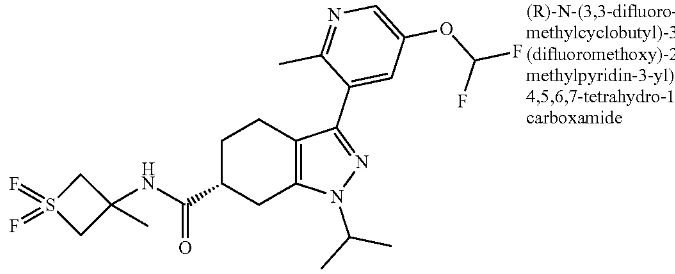 | (R)-N-(3,3-difluoro-1-methylcyclobutyl)-3-(5-(difluoromethoxy)-2-methylpyridin-3-yl)-1-isopropyl-4,5,6,7-tetrahydro-1H-indazole-6-carboxamide | 469 | 318.0 |

-continued

| Example | Structure | Name | LCMS [M + 1] | DGAT2 $IC_{50}$ (nM) |
|---|---|---|---|---|
| 90 | 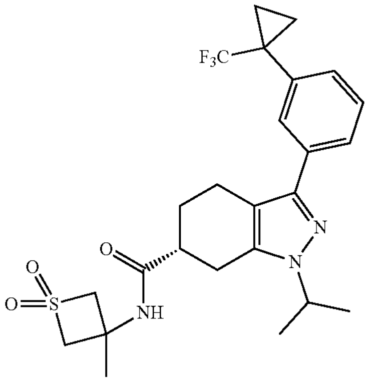 [SMILES: CC(C)n1nc(-c2cccc(C3(C(F)(F)F)CC3)c2)c2c1C[C@H](C(=O)NC1(C)CS(=O)(=O)C1)CC2] | (R)-1-isopropyl-N-(3-methyl-1,1-dioxidothietan-3-yl)-3-(3-(1-(trifluoromethyl)cyclopropyl)phenyl)-4,5,6,7-tetrahydro-1H-indazole-6-carboxamide | 510 | >10000 |
| 91 | 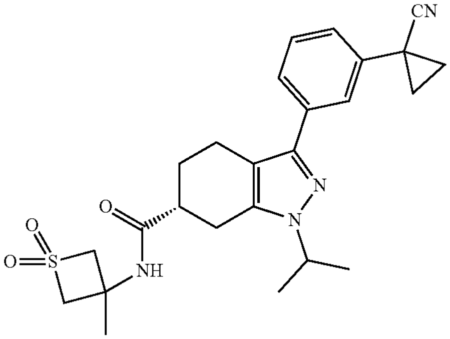 [SMILES: CC(C)n1nc(-c2cccc(C3(C#N)CC3)c2)c2c1C[C@H](C(=O)NC1(C)CS(=O)(=O)C1)CC2] | (R)-3-(3-(1-cyanocyclopropyl)phenyl)-1-isopropyl-N-(3-methyl-1,1-dioxidothietan-3-yl)-4,5,6,7-tetrahydro-1H-indazole-6-carboxamide | 467 | >10000 |
| 92 | 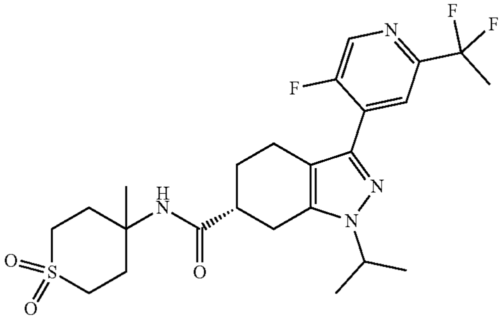 [SMILES: CC(C)n1nc(-c2cc(C(C)(F)F)ncc2F)c2c1C[C@H](C(=O)NC1(C)CCS(=O)(=O)CC1)CC2] | (R)-3-(2-(1,1-difluoroethyl)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide | 513 | 1214 |
| 93 | 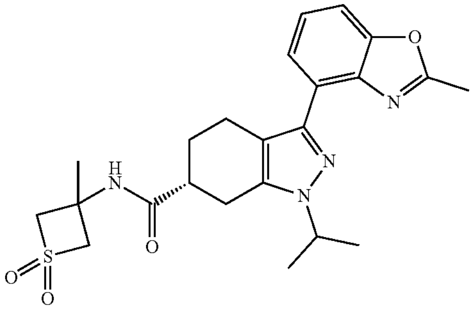 [SMILES: Cc1nc2c(-c3nn(C(C)C)c4c3CC[C@@H](C(=O)NC3(C)CS(=O)(=O)C3)C4)cccc2o1] | (R)-1-isopropyl-N-(3-methyl-1,1-dioxidothietan-3-yl)-3-(2-methylbenzo[d]oxazol-4-yl)-4,5,6,7-tetrahydro-1H-indazole-6-carboxamide | 457 | >10000 |

-continued

| Example | Structure | Name | LCMS [M + 1] | DGAT2 $IC_{50}$ (nM) |
|---|---|---|---|---|
| 94 | 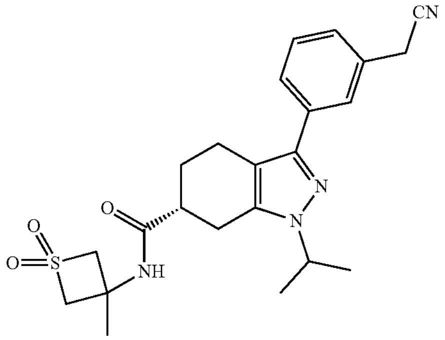 [SMILES: CC(C)n1nc(-c2cccc(CC#N)c2)c2c1C[C@H](C(=O)NC1(C)CS(=O)(=O)C1)CC2] | (R)-3-(3-(cyanomethyl)phenyl)-1-isopropyl-N-(3-methyl-1,1-dioxidothietan-3-yl)-4,5,6,7-tetrahydro-1H-indazole-6-carboxamide | 441 | >10000 |
| 95 | 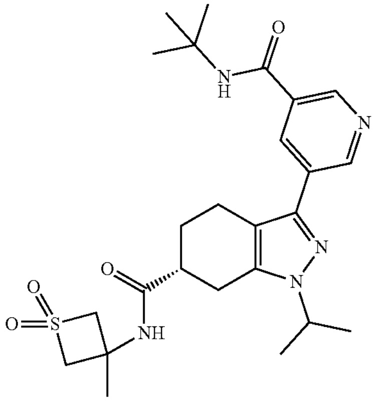 [SMILES: CC(C)n1nc(-c2cncc(C(=O)NC(C)(C)C)c2)c2c1C[C@H](C(=O)NC1(C)CS(=O)(=O)C1)CC2] | (R)-3-(5-(tert-butylcarbamoyl)pyridin-3-yl)-1-isopropyl-N-(3-methyl-1,1-dioxidothietan-3-yl)-4,5,6,7-tetrahydro-1H-indazole-6-carboxamide | 502 | >10000 |
| 96 | 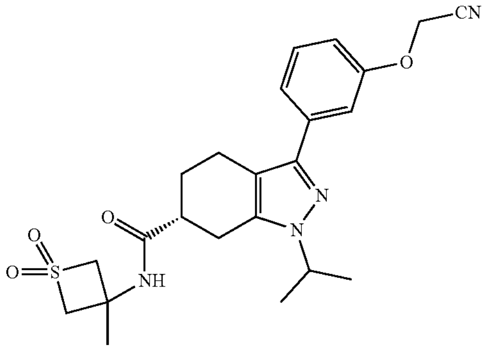 [SMILES: CC(C)n1nc(-c2cccc(OCC#N)c2)c2c1C[C@H](C(=O)NC1(C)CS(=O)(=O)C1)CC2] | (R)-3-(3-(cyanomethoxy)phenyl)-1-isopropyl-N-(3-methyl-1,1-dioxidothietan-3-yl)-4,5,6,7-tetrahydro-1H-indazole-6-carboxamide | 457 | >10000 |
| 97 | 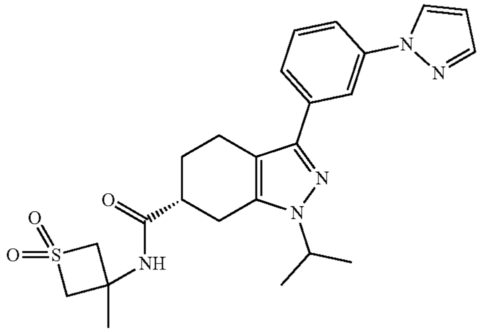 [SMILES: CC(C)n1nc(-c2cccc(-n3cccn3)c2)c2c1C[C@H](C(=O)NC1(C)CS(=O)(=O)C1)CC2] | (R)-3-(3-(1H-pyrazol-1-yl)phenyl)-1-isopropyl-N-(3-methyl-1,1-dioxidothietan-3-yl)-4,5,6,7-tetrahydro-1H-indazole-6-carboxamide | 468 | >10000 |

-continued

| Example | Structure | Name | LCMS [M + 1] | DGAT2 $IC_{50}$ (nM) |
|---|---|---|---|---|
| 98 | 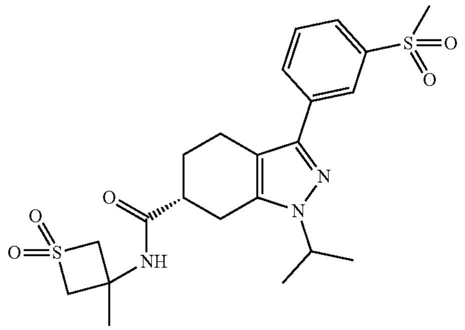 [SMILES: CC(C)n1nc(-c2cccc(S(C)(=O)=O)c2)c2c1C[C@H](C(=O)NC1(C)CS(=O)(=O)C1)CC2] | (R)-1-isopropyl-N-(3-methyl-1,1-dioxidothietan-3-yl)-3-(3-(methylsulfonyl)phenyl)-4,5,6,7-tetrahydro-1H-indazole-6-carboxamide | 480 | >10000 |
| 99 | 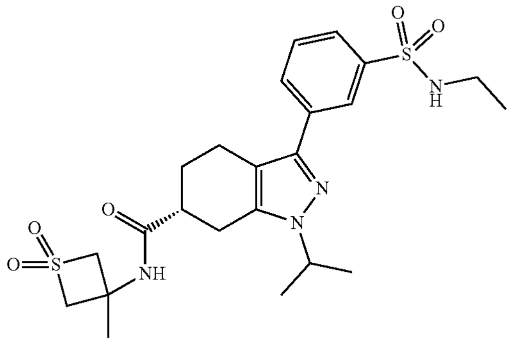 [SMILES: CCNS(=O)(=O)c1cccc(-c2nn(C(C)C)c3c2CC[C@@H](C(=O)NC2(C)CS(=O)(=O)C2)C3)c1] | (R)-3-(3-(N-ethylsulfamoyl)phenyl)-1-isopropyl-N-(3-methyl-1,1-dioxidothietan-3-yl)-4,5,6,7-tetrahydro-1H-indazole-6-carboxamide | 509 | >10000 |
| 100 | 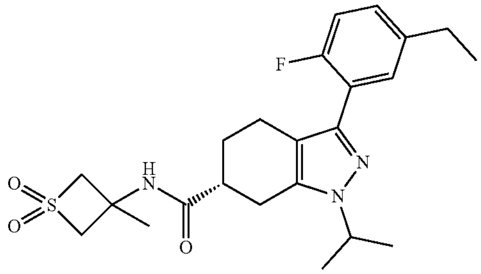 [SMILES: CCc1ccc(F)c(-c2nn(C(C)C)c3c2CC[C@@H](C(=O)NC2(C)CS(=O)(=O)C2)C3)c1] | (R)-3-(5-ethyl-2-fluorophenyl)-1-isopropyl-N-(3-methyl-1,1-dioxidothietan-3-yl)-4,5,6,7-tetrahydro-1H-indazole-6-carboxamide | 448 | 158 |
| 101 | 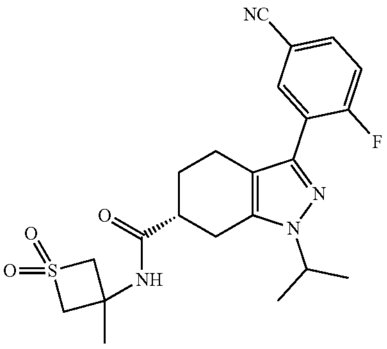 [SMILES: CC(C)n1nc(-c2cc(C#N)ccc2F)c2c1C[C@H](C(=O)NC1(C)CS(=O)(=O)C1)CC2] | (R)-3-(5-cyano-2-fluorophenyl)-1-isopropyl-N-(3-methyl-1,1-dioxidothietan-3-yl)-4,5,6,7-tetrahydro-1H-indazole-6-carboxamide | 445 | >10000 |

-continued

| Example | Structure | Name | LCMS [M + 1] | DGAT2 $IC_{50}$ (nM) |
|---|---|---|---|---|
| 102 | 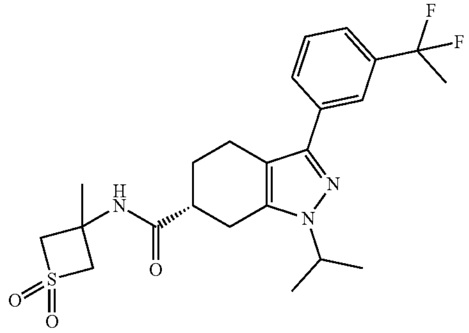 [SMILES: CC(C)n1nc(-c2cccc(C(C)(F)F)c2)c2c1C[C@H](C(=O)NC1(C)CS(=O)(=O)C1)CC2] | (R)-3-(3-(1,1-difluoroethyl)phenyl)-1-isopropyl-N-(3-methyl-1,1-dioxidothietan-3-yl)-4,5,6,7-tetrahydro-1H-indazole-6-carboxamide | 466 | 8840 |
| 103 | 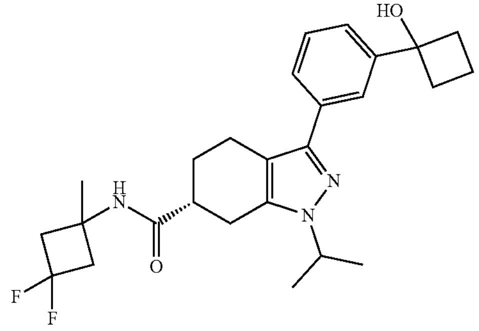 [SMILES: CC(C)n1nc(-c2cccc(C3(O)CCC3)c2)c2c1C[C@H](C(=O)NC1(C)CC(F)(F)C1)CC2] | (R)-N-(3,3-difluoro-1-methylcyclobutyl)-3-(3-(1-hydroxycyclobutyl)phenyl)-1-isopropyl-4,5,6,7-tetrahydro-1H-indazole-6-carboxamide | 458 | >10000 |

Example 104

(R)-1-isopropyl-N-(3-methyl-1,1-dioxidothietan-3-yl)-3-(5-(1,1,2,2-tetrafluoroethoxy)pyridin-3-yl)-4,5,6,7-tetrahydro-1H-indazole-6-carboxamide

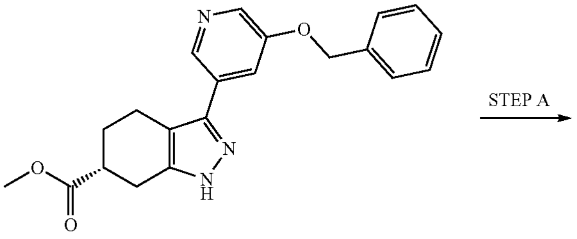

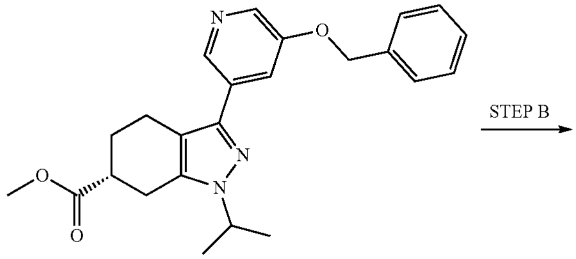

-continued

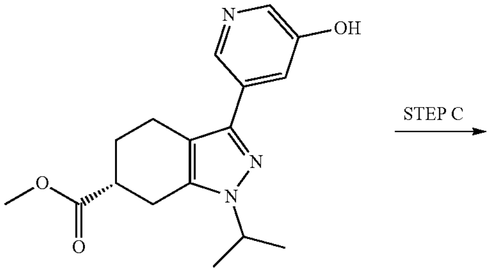

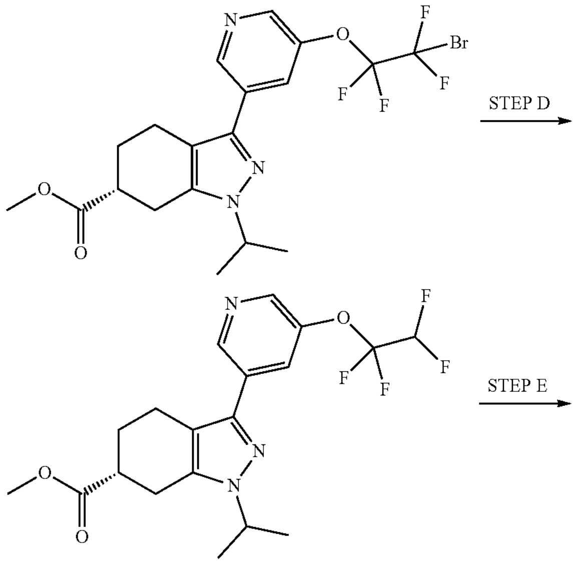

-continued

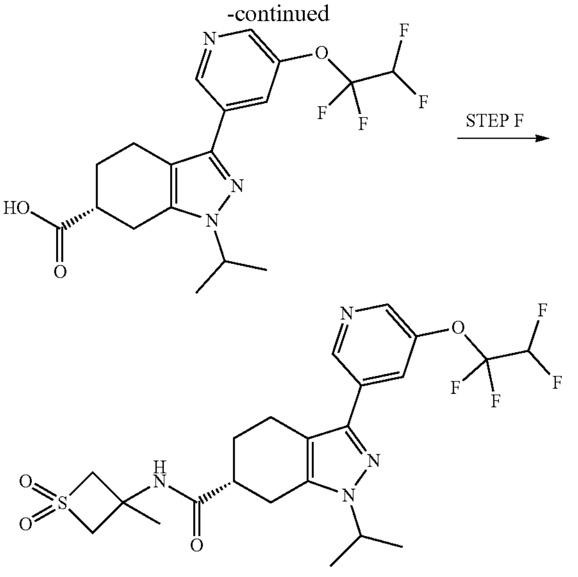

EX-104

Step A: methyl (R)-3-(5-(benzyloxy)pyridin-3-yl)-1-isopropyl-4,5,6,7-tetrahydro-1H-indazole-6-carboxylate To a solution of (R)-methyl 3-(5-(benzyloxy)pyridin-3-yl)-4,5,6,7-tetrahydro-1H-indazole-6-carboxylate (200 mg, 0.550 mmol) in DMF (5 mL) was added 2-iodopropane (187 mg, 1.1 mmol) and $Cs_2CO_3$ (538 mg, 1.651 mmol). The mixture was stirred at 50° C. for 16 hrs. LCMS showed that desired product was formed. The mixture was poured into $H_2O$, and then the mixture was extracted with EtOAc (×3). The combined organic layers were washed with brine, dried over $Na_2SO_4$, and then filtered and concentrated under reduced pressure. The residue was purified by column chromatography on silica (0-100% EtOAc/hexanes) to afford the title compound. LC/MS=406 [M+1].

Step B: methyl (R)-3-(5-hydroxypyridin-3-yl)-1-isopropyl-4,5,6,7-tetrahydro-1H-indazole-6-carboxylate A mixture of (R)-methyl 3-(5-(benzyloxy)pyridin-3-yl)-1-isopropyl-4,5,6,7-tetrahydro-1H-indazole-6-carboxylate (170 mg, 0.419 mmol) and Pd/C (44.6 mg, 0.042 mmol) in MeOH (10 mL) was stirred at 20° C. for 30 mins. LCMS showed that desired compound was formed. The mixture was poured into ethyl acetate, through filter, then the filter cake was dissolved in ethyl acetate, dried over $Na_2SO_4$, and then filtered and concentrated under reduced pressure to afford the title compound. LC/MS=316 [M+1].

Step C: methyl (R)-3-(5-(2-bromo-1,1,2,2-tetrafluoroethoxy)pyridin-3-yl)-1-isopropyl-4,5,6,7-tetrahydro-1H-indazole-6-carboxylate A 10 mL tube was charged with $Cs_2CO_3$ (62 mg, 0.19 mmol), (R)-methyl 3-(5-hydroxypyridin-3-yl)-1-isopropyl-4,5,6,7-tetrahydro-1H-indazole-6-carboxylate (40 mg, 0.127 mmol) and 1,2-dibromo-1,1,2,2-tetrafluoroethane (0.033 mL, 0.254 mmol) in DMSO (2 mL). Then the mixture was stirred at 50° C. for 2 hrs. LCMS showed that desired product was formed. The mixture was poured into $H_2O$, and the mixture was extracted with ethyl acetate (×3). The combined organic layers were washed with brine, dried over $Na_2SO_4$, and then filtered and concentrated under reduced pressure to afford the title compound. LC/MS=494/496 [M+1].

Step D: methyl (R)-1-isopropyl-3-(5-(1,1,2,2-tetrafluoroethoxy)pyridin-3-yl)-4,5,6,7-tetrahydro-1H-indazole-6-carboxylate A mixture of (R)-methyl 3-(5-(2-bromo-1,1,2,2-tetrafluoroethoxy)pyridin-3-yl)-1-isopropyl-4,5,6,7-tetrahydro-1H-indazole-6-carboxylate (60 mg, 0.121 mmol) and zinc (24 mg, 0.364 mmol) in HOAc (5 mL) was stirred at 60° C. for 3 hrs. LCMS showed that desired compound was formed. The mixture was dissolved in $H_2O$. $NaHCO_3$ was added to the mixture until pH=7. Then the mixture was extracted with ethyl acetate (×3). The combined organic layers were washed with brine, dried over $Na_2SO_4$, and then filtered and concentrated under reduced pressure to afford the title compound. LC/MS=416 [M+1].

Step E: (R)-1-isopropyl-3-(5-(1,1,2,2-tetrafluoroethoxy)pyridin-3-yl)-4,5,6,7-tetrahydro-1H-indazole-6-carboxylic acid A mixture of LiOH $H_2O$ (15 mg, 0.36 mmol) and (R)-methyl 1-isopropyl-3-(5-(1,1,2,2-tetrafluoroethoxy)pyridin-3-yl)-4,5,6,7-tetrahydro-1H-indazole-6-carboxylate (50 mg, 0.12 mmol) in MeOH (1 mL)/Water (1 mL)/THF (1 mL) was stirred at 40° C. for 1 hr. LCMS showed that desired target was formed. The mixture was concentrated under reduced pressure and was dissolved in $H_2O$. HCl (1N in water) was added to the mixture until pH=5. Then the mixture was extracted with ethyl acetate (×3). The combined organic layers were washed with brine, dried over $Na_2SO_4$, and then filtered and concentrated under reduced pressure to afford the title compound. LC/MS=402 [M+1]

Step F: (R)-1-isopropyl-N-(3-methyl-1,1-dioxidothietan-3-yl)-3-(5-(1,1,2,2-tetrafluoroethoxy)pyridin-3-yl)-4,5,6,7-tetrahydro-1H-indazole-6-carboxamide A mixture of 2-(3H-[1,2,3]triazolo[4,5-b]pyridin-3-yl)-1,1,3,3-tetramethylisouronium hexafluorophosphate(V) (91 mg, 0.239 mmol), N-ethyl-N-isopropylpropan-2-amine (0.1 mL, 0.598 mmol), 3-amino-3-methylthietane 1,1-dioxide (24.25 mg, 0.179 mmol) and (R)-1-isopropyl-3-(5-(1,1,2,2-tetrafluoroethoxy)pyridin-3-yl)-4,5,6,7-tetrahydro-1H-indazole-6-carboxylic acid (48 mg, 0.120 mmol) in DMF (1 mL) was stirred at 25° C. for 30 mins. LCMS showed that desired product was formed. The residue was purified by mass triggered reverse phase HPLC (ACN/water with 0.1% TFA modifier) to afford EX-61. LC/MS=519 [M+1]. 1H NMR (400 MHz, METHANOL-$d_4$) δ 8.70-8.89 (m, 2H), 8.45 (br s, 1H), 8.05 (s, 1H), 6.41-6.57 (m, 1H), 4.48-4.55 (m, 1H), 4.38-4.47 (m, 2H), 4.11-4.18 (m, 2H), 2.76-2.94 (m, 4H), 2.67-2.74 (m, 1H), 2.10-2.18 (m, 1H), 1.77-1.87 (m, 1H), 1.73 (s, 3H), 1.48 (d, J=6.60 Hz, 6H). Human DGAT2 IC50=1000 nM By using procedures similar to those described in Example 104 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 105 | 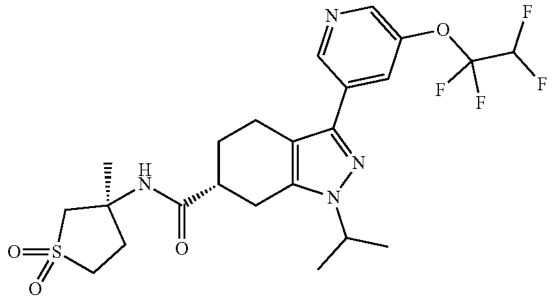 [SMILES: CC(C)n1nc(-c2cncc(OC(F)(F)C(F)F)c2)c2c1C[C@H](C(=O)N[C@@]1(C)CCS(=O)(=O)C1)CC2] | (R)-1-isopropyl-N-((S)-3-methyl-1,1-dioxidotetrahydrothiophen-3-yl)-3-(5-(1,1,2,2-tetrafluoroethoxy)pyridin-3-yl)-4,5,6,7-tetrahydro-1H-indazole-6-carboxamide | 533 | 117.8 |
| 106 | 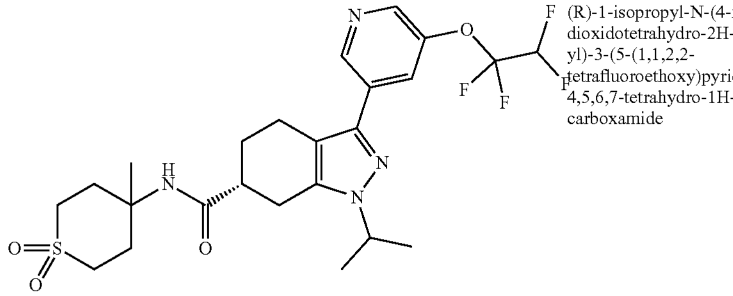 | (R)-1-isopropyl-N-(4-methyl-1,1-dioxidotetrahydro-2H-thiopyran-4-yl)-3-(5-(1,1,2,2-tetrafluoroethoxy)pyridin-3-yl)-4,5,6,7-tetrahydro-1H-indazole-6-carboxamide | 547 | 203.7 |

Example 107

(6R)-3-(5-fluoro-2-(2,2,2-trifluoroethoxy)pyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide

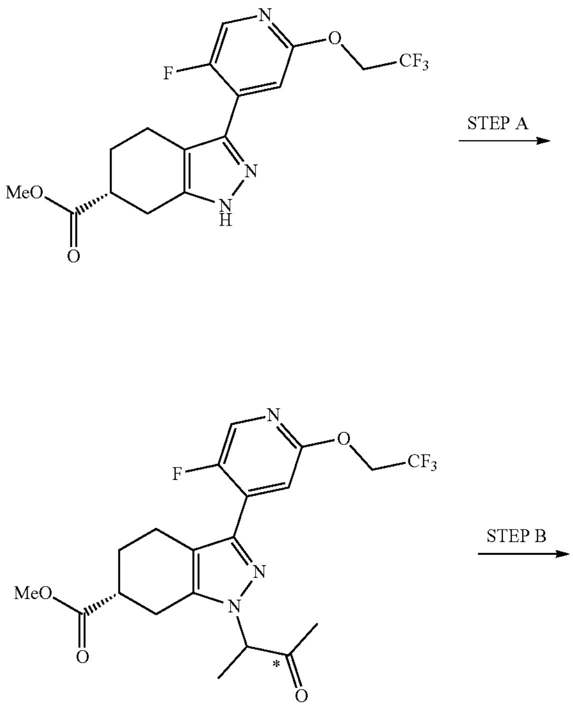

-continued

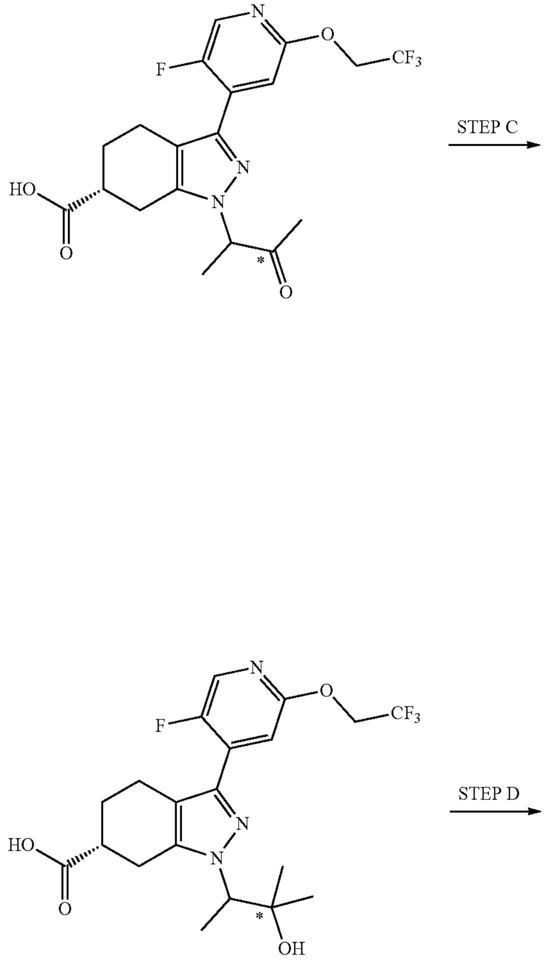

-continued

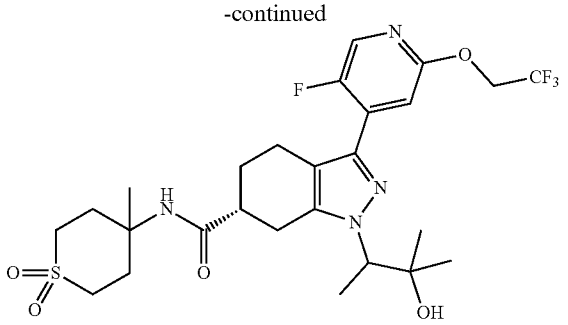

EX-107

Step A: Methyl (6R)-3-(5-fluoro-2-(2,2,2-trifluoro-ethoxy)pyridin-4-yl)-1-(3-oxobutan-2-yl)-4,5,6,7-tetrahydro-1H-indazole-6-carboxylate To a stirred solution of methyl (R)-3-(5-fluoro-2-(2,2,2-trifluoroethoxy)pyridin-4-yl)-4,5,6,7-tetrahydro-1H-indazole-6-carboxylate (360 mg, 0.96 mmol), 3-bromobutan-2-one (218 mg, 1.45 mmol), and DMF (2.8 mL) was added $Cs_2CO_3$ (0.94 g, 2.89 mmol). The mixture was stirred at 80° C. for 30 minutes. The reaction mixture was cooled to rt and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (0-70% EtOAc in hexanes) to afford the title compound. LC/MS=444 [M+1].

Step B: (6R)-3-(5-fluoro-2-(2,2,2-trifluoroethoxy) pyridin-4-yl)-1-(3-oxobutan-2-yl)-4,5,6,7-tetra-hydro-1H-indazole-6-carboxylic acid To a mixture of methyl (6R)-3-(5-fluoro-2-(2,2,2-trifluoroethoxy)pyridin-4-yl)-1-(3-oxobutan-2-yl)-4,5,6,7-tetrahydro-1H-indazole-6-carboxylate (329 mg, 0.74 mmol), and LiOH (71 mg, 2.97 mmol), was added THF (1.6 mL), MeOH (0.5 mL), and water (1.6 mL). The mixture was stirred at rt for 10 minutes, then acidified with concentrated HCl to pH 1. The mixture was extracted with EtOAc. The combined organic layers were washed with water and brine, dried over $MgSO_4$ (s), filtered, and the volatiles were evaporated to afford the title compound. The crude product was used without purification. LC/MS=430 [M+1].

Step C: (6R)-3-(5-fluoro-2-(2,2,2-trifluoroethoxy) pyridin-4-yl)-1-(3-hydroxy-3-methylbutan-2-yl)-4,5,6,7-tetrahydro-1H-indazole-6-carboxylic acid At 0° C., to a mixture of (6R)-3-(5-fluoro-2-(2,2,2-trifluoroethoxy)pyridin-4-yl)-1-(3-oxobutan-2-yl)-4,5,6,7-tetrahydro-1H-indazole-6-carboxylic acid (319 mg, 0.74 mmol) and THF (4.9 mL) was added methylmagnesium bromide (1.5 mL, 4.5 mmol, 3.0 M in $Et_{20}$). The mixture was stirred at 0° C. for 10 minutes. Water was added, and the mixture was acidified with concentrated HCl to pH 1. The aqueous layer was extracted three times with EtOAc. The combined organic layers were washed with water and brine. The organic layer was then dried over $MgSO_4$ (s), filtered, and concentrated in vacuo. The crude product was used without purification. LC/MS=446 [M+1].

Step D: (6R)-3-(5-fluoro-2-(2,2,2-trifluoroethoxy) pyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide To a mixture of (6R)-3-(5-fluoro-2-(2,2,2-trifluoroethoxy)pyridin-4-yl)-1-(3-hydroxy-3-methylbutan-2-yl)-4,5,6,7-tetrahydro-1H-indazole-6-carboxylic acid (100 mg, 0.23 mmol) in DCM (0.6 mL) was added HATU (102 mg, 0.27 mmol), DIPEA (137 μL, 0.79 mmol), and then (4-amino-4-methyltetrahydro-2H-thiopyran 1,1-dioxide hydrochloride (54 mg, 0.27 mmol). The mixture was stirred at rt for 1 h. The mixture was purified by flash silica gel column chromatography (0-80% EtOAc in hexanes) to afford the title compound. LC/MS=591 [M+1]. The mixture of two stereoisomers was purified by chiral preparative SFC (OD-H column, 25% $EtOH/CO_2$) to afford Ex-107a (faster eluting) and Ex-107b (slower eluting). Ex-107a (faster eluting): $^1$H NMR (500 MHz, Methanol-$d_4$) δ 8.09 (d, J=2.0 Hz, 1H), 7.07 (d, J=4.9 Hz, 1H), 4.85 (q, 2H), 4.25 (q, J=6.9 Hz, 1H), 3.24-3.12 (m, 2H), 3.03-2.94 (m, 3H), 2.88-2.62 (m, 6H), 2.17-2.03 (m, 3H), 1.84-1.74 (m, 1H), 1.53 (d, J=6.9 Hz, 3H), 1.44 (s, 3H), 1.24 (s, 3H), 1.14 (s, 3H).

By using procedures similar to those described in Example 107 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 107a | 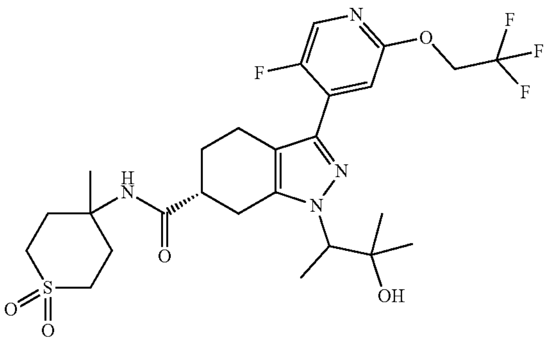 [SMILES: CC(n1nc(-c2cc(OCC(F)(F)F)ncc2F)c2c1C[C@H](C(=O)NC1(C)CCS(=O)(=O)CC1)CC2)C(C)(C)O] | (6R)-3-(5-fluoro-2-(2,2,2-trifluoroethoxy)pyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (faster eluting with OD-H column, 25% $EtOH/CO_2$) | 591 | 3.9 |

-continued

| Example | Structure | Name | LCMS [M + 1] | DGAT2 $IC_{50}$ (nM) |
|---|---|---|---|---|
| 107b | 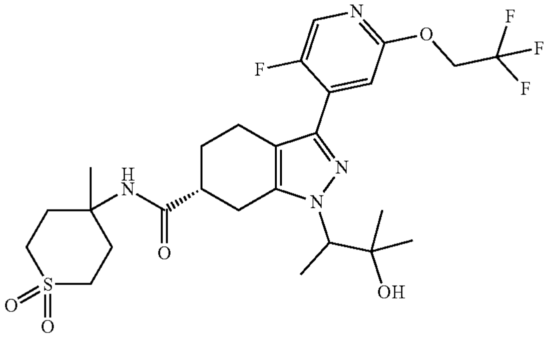 [SMILES: CC(n1nc(-c2cc(OCC(F)(F)F)ncc2F)c2c1C[C@H](C(=O)NC1(C)CCS(=O)(=O)CC1)CC2)C(C)(C)O] | (6R)-3-(5-fluoro-2-(2,2,2-trifluoroethoxy)pyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (slower eluting with OD-H column, 25% $EtOH/CO_2$) | 591 | 5.4 |
| 108a | 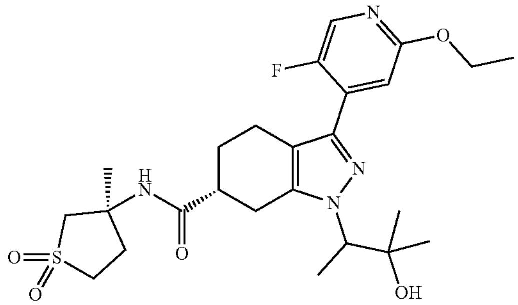 [SMILES: CCOc1cc(-c2nn(C(C)C(C)(C)O)c3c2CC[C@@H](C(=O)N[C@@]2(C)CCS(=O)(=O)C2)C3)c(F)cn1] | (6R)-3-(2-ethoxy-5-fluoropyridin-4-yl)-1-(3-hydroxy-3-methylbutan-2-yl)-N-((S)-3-methyl-1,1-dioxidotetrahydrothiophen-3-yl)-4,5,6,7-tetrahydro-1H-indazole-6-carboxamide (faster eluting with OD-H column, 15% $MeOH/CO_2$) | 523 | 44.1 |
| 108b | 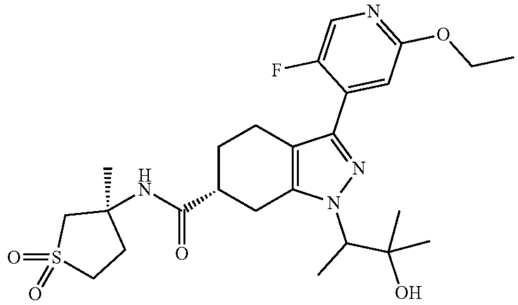 [SMILES: CCOc1cc(-c2nn(C(C)C(C)(C)O)c3c2CC[C@@H](C(=O)N[C@@]2(C)CCS(=O)(=O)C2)C3)c(F)cn1] | (6R)-3-(2-ethoxy-5-fluoropyridin-4-yl)-1-(3-hydroxy-3-methylbutan-2-yl)-N-((S)-3-methyl-1,1-dioxidotetrahydrothiophen-3-yl)-4,5,6,7-tetrahydro-1H-indazole-6-carboxamide (slower eluting with OD-H column, 15% $MeOH/CO_2$) | 523 | 172.5 |
| 109a | 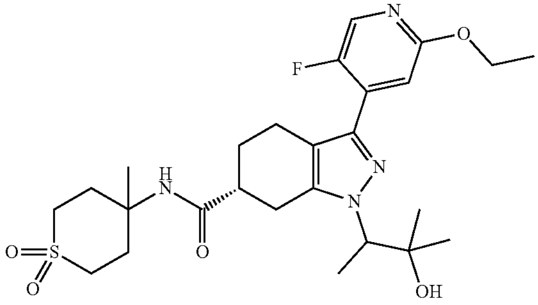 [SMILES: CCOc1cc(-c2nn(C(C)C(C)(C)O)c3c2CC[C@@H](C(=O)NC2(C)CCS(=O)(=O)CC2)C3)c(F)cn1] | (6R)-3-(2-ethoxy-5-fluoropyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (slower eluting with OJ-H column, 10% $MeOH/CO_2$) | 537 | 49.5 |

-continued

| Example | Structure | Name | LCMS [M + 1] | DGAT2 $IC_{50}$ (nM) |
|---|---|---|---|---|
| 109b | 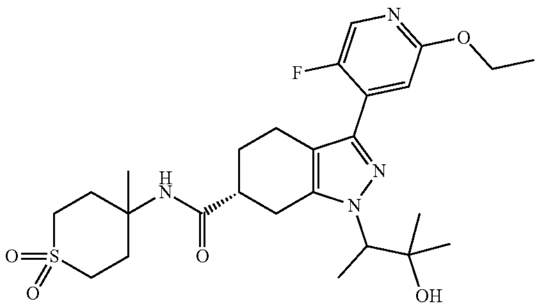 [SMILES: CCOc1cc(-c2nn(C(C)C(C)(C)O)c3c2CC[C@@H](C(=O)NC2(C)CCS(=O)(=O)CC2)C3)c(F)cn1] | (6R)-3-(2-ethoxy-5-fluoropyridin-4-yl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (faster eluting with OJ-H column, 10% MeOH/$CO_2$) | 537 | 30.7 |
| 110a | 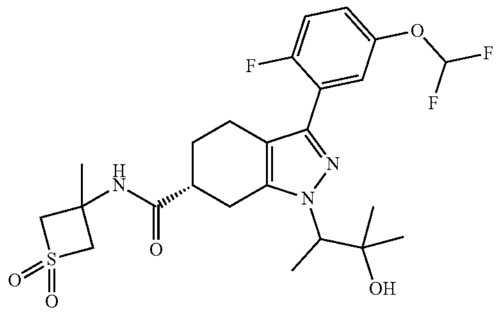 [SMILES: CC(n1nc(-c2cc(OC(F)F)ccc2F)c2c1C[C@H](C(=O)NC1(C)CS(=O)(=O)C1)CC2)C(C)(C)O] | (6R)-3-(5-(difluoromethoxy)-2-fluorophenyl)-1-(3-hydroxy-3-methylbutan-2-yl)-N-(3-methyl-1,1-dioxidothietan-3-yl)-4,5,6,7-tetrahydro-1H-indazole-6-carboxamide (faster eluting with OD-H column, 15% MeOH/$CO_2$) | 530 | 30.8 |
| 110b | 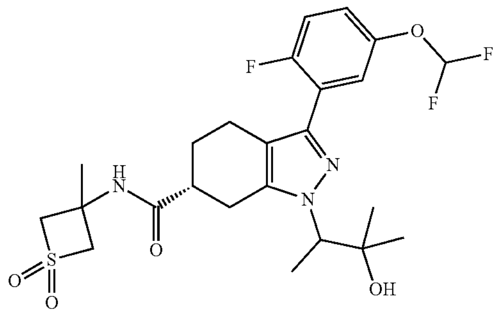 [SMILES: CC(n1nc(-c2cc(OC(F)F)ccc2F)c2c1C[C@H](C(=O)NC1(C)CS(=O)(=O)C1)CC2)C(C)(C)O] | (6R)-3-(5-(difluoromethoxy)-2-fluorophenyl)-1-(3-hydroxy-3-methylbutan-2-yl)-N-(3-methyl-1,1-dioxidothietan-3-yl)-4,5,6,7-tetrahydro-1H-indazole-6-carboxamide (slower eluting with OD-H column, 15% MeOH/$CO_2$) | 530 | 243.4 |
| 111a | 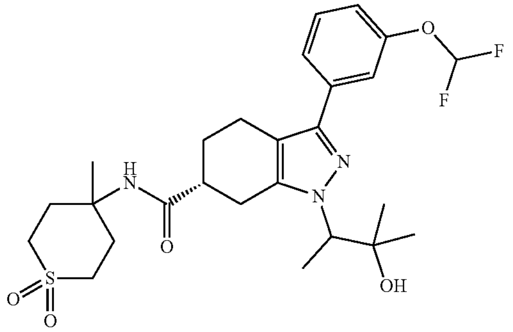 [SMILES: CC(n1nc(-c2cccc(OC(F)F)c2)c2c1C[C@H](C(=O)NC1(C)CCS(=O)(=O)CC1)CC2)C(C)(C)O] | (6R)-3-(3-(difluoromethoxy)phenyl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (faster eluting with IC column, 30% iPrOH/$CO_2$) | 540 | 2066 |

-continued

| Example | Structure | Name | LCMS [M + 1] | DGAT2 $IC_{50}$ (nM) |
|---|---|---|---|---|
| 111b | 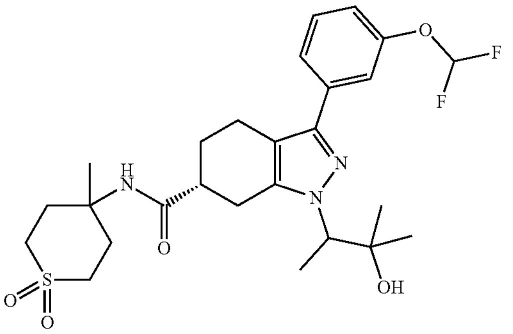 [SMILES: CC(n1nc(-c2cccc(OC(F)F)c2)c2c1C[C@H](C(=O)NC1(C)CCS(=O)(=O)CC1)CC2)C(C)(C)O] | (6R)-3-(3-(difluoromethoxy)phenyl)-1-(3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide (slower eluting with IC column, 30% iPrOH/$CO_2$) | 540 | 229.6 |
| 112a | 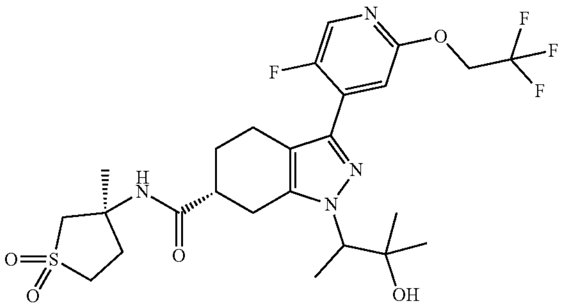 [SMILES: CC(n1nc(-c2cc(OCC(F)(F)F)ncc2F)c2c1C[C@H](C(=O)N[C@@]1(C)CCS(=O)(=O)C1)CC2)C(C)(C)O] | (6R)-3-(5-fluoro-2-(2,2,2-trifluoroethoxy)pyridin-4-yl)-1-(3-hydroxy-3-methylbutan-2-yl)-N-((S)-3-methyl-1,1-dioxidotetrahydrothiophen-3-yl)-4,5,6,7-tetrahydro-1H-indazole-6-carboxamide (faster eluting with OD-H column, 15% EtOH/$CO_2$) | 577 | 11.3 |
| 112b | 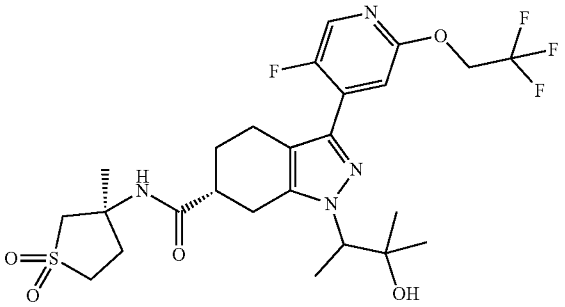 [SMILES: CC(n1nc(-c2cc(OCC(F)(F)F)ncc2F)c2c1C[C@H](C(=O)N[C@@]1(C)CCS(=O)(=O)C1)CC2)C(C)(C)O] | (6R)-3-(5-fluoro-2-(2,2,2-trifluoroethoxy)pyridin-4-yl)-1-(3-hydroxy-3-methylbutan-2-yl)-N-((S)-3-methyl-1,1-dioxidotetrahydrothiophen-3-yl)-4,5,6,7-tetrahydro-1H-indazole-6-carboxamide (slower eluting with OD-H column, 15% EtOH/$CO_2$) | 577 | 31.6 |
| 113a | 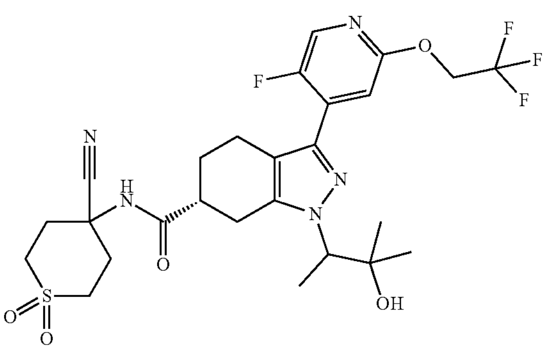 [SMILES: CC(n1nc(-c2cc(OCC(F)(F)F)ncc2F)c2c1C[C@H](C(=O)NC1(C#N)CCS(=O)(=O)CC1)CC2)C(C)(C)O] | (6R)-N-(4-cyano-1,1-dioxidotetrahydro-2H-thiopyran-4-yl)-3-(5-fluoro-2-(2,2,2-trifluoroethoxy)pyridin-4-yl)-1-(3-hydroxy-3-methylbutan-2-yl)-4,5,6,7-tetrahydro-1H-indazole-6-carboxamide (faster eluting with OD-H column, 12% EtOH/$CO_2$) | 602 | 27.8 |

-continued

| Example | Structure | Name | LCMS [M + 1] | DGAT2 $IC_{50}$ (nM) |
|---|---|---|---|---|
| 113b | 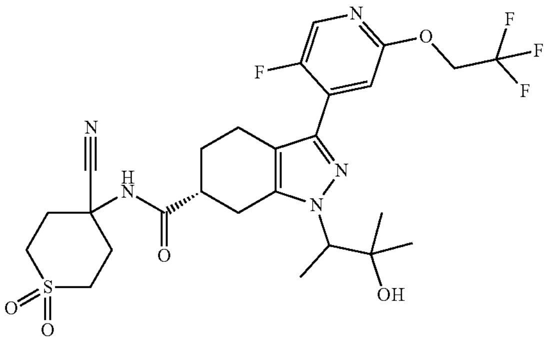 [SMILES: CC(n1nc(-c2cc(OCC(F)(F)F)ncc2F)c2c1C[C@H](C(=O)NC1(C#N)CCS(=O)(=O)CC1)CC2)C(C)(C)O] | (6R)-N-(4-cyano-1,1-dioxidotetrahydro-2H-thiopyran-4-yl)-3-(5-fluoro-2-(2,2,2-trifluoroethoxy)pyridin-4-yl)-1-(3-hydroxy-3-methylbutan-2-yl)-4,5,6,7-tetrahydro-1H-indazole-6-carboxamide (slower eluting with OD-H column, 12% $EtOH/CO_2$) | 602 | 70.3 |

Example 114

(6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide

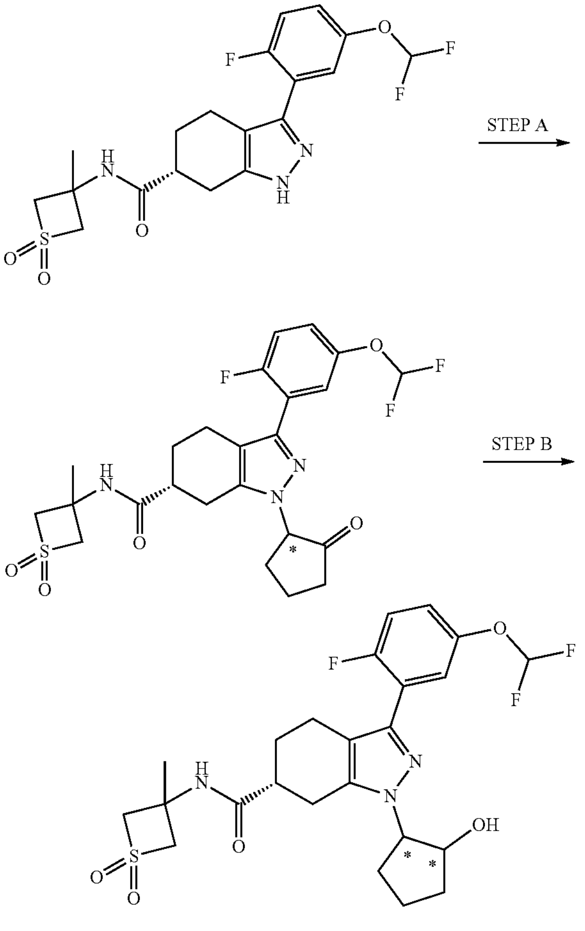

EX-114

Step A: (6R)-3-(5-(difluoromethoxy)-2-fluorophenyl)-N-(3-methyl-1,1-dioxidothietan-3-yl)-1-(2-oxocyclopentyl)-4,5,6,7-tetrahydro-1H-indazole-6-carboxamide To a stirred solution of (R)-3-(5-(difluoromethoxy)-2-fluorophenyl)-N-(3-methyl-1,1-dioxidothietan-3-yl)-4,5,6,7-tetrahydro-1H-indazole-6-carboxamide (110 mg, 0.25 mmol), 2-bromocyclopentan-1-one (81 mg, 0.50 mmol), and DMF (0.7 mL) was added $K_2CO_3$ (103 mg, 0.74 mmol). The mixture was stirred at 60° C. for 24 hours. The reaction mixture was cooled to rt and directly purified by flash silica gel column chromatography (0-70% EtOAc/hexanes) to afford the title compound. LC/MS=526 [M+1].

Step B: (6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide At 0° C., to a mixture of (6R)-3-(5-(difluoromethoxy)-2-fluorophenyl)-N-(3-methyl-1,1-dioxidothietan-3-yl)-1-(2-oxocyclopentyl)-4,5,6,7-tetrahydro-1H-indazole-6-carboxamide (66 mg, 0.13 mmol) in MeOH (1.2 mL) was added sodium borohydride (14 mg, 0.38 mmol). The mixture was stirred at 0° C. for 1.5 hours. Sat. aq. $NH_4Cl$ was added, and the mixture was extracted three times with EtOAc. The combined organic layers were washed with water and brine. The organic layer was then dried over $MgSO_4$ (s), filtered, and concentrated in vacuo. The mixture of four stereoisomers was purified by chiral preparative SFC (Step 1: Lux-Cellulose-4 column, 25% $MeOH/CO_2$, Step 2: AD-H, 35% $EtOH/CO_2$) to afford Ex-114a ($1^{st}$ eluting), Ex-114b ($2^{nd}$ eluting), Ex-114c ($3^{rd}$ eluting), Ex-114d ($4^{th}$ eluting). Ex-114a: $^1H$ NMR (500 MHz, Methanol-$d_4$) δ 7.31 (dd, J=5.8, 2.9 Hz, 1H), 7.23-7.14 (m, 2H), 6.80 (t, J=74.0 Hz, 1H), 4.48-4.41 (m, 3H), 4.41-4.34 (m, 1H), 4.20-4.12 (m, 2H), 3.02 (dd, J=15.8, 5.4 Hz, 1H), 2.83 (dd, J=15.8, 10.4 Hz, 1H), 2.72 (tdd, J=11.4, 5.4, 2.5 Hz, 1H), 2.61-2.53 (m, 2H), 2.23-2.16 (m, 2H), 2.16-2.04 (m, 2H), 1.97-1.82 (m, 2H), 1.79-1.72 (m, 4H), 1.72-1.62 (m, 1H).

By using procedures similar to those described in Example 114 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 114a | 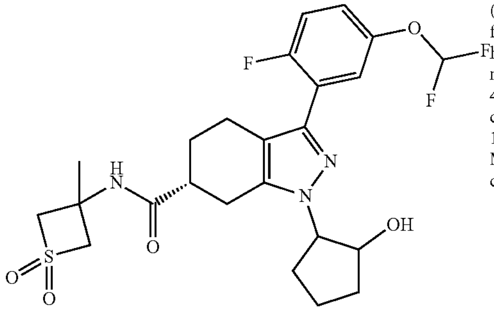 [SMILES: CC1(NC(=O)[C@@H]2CCc3c(-c4cc(OC(F)F)ccc4F)nn(C4CCCC4O)c3C2)CS(=O)(=O)C1] | (6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide (1st eluting with Step 1: Lux Cellulose-4 column, 25% $MeOH/CO_2$; Step 2: AD-H column, 35% $EtOH/CO_2$) | 528 | 44.5 |
| 114b | 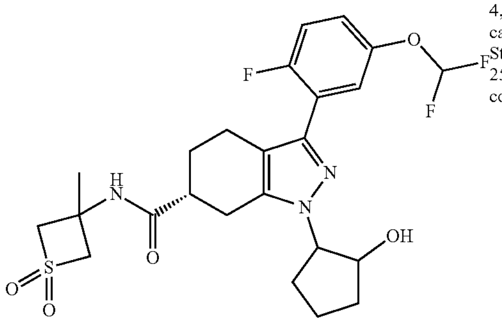 | (6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide (2nd eluting with Step 1: Lux Cellulose-4 column, 25% $MeOH/CO_2$; Step 2: AD-H column, 35% $EtOH/CO_2$) | 528 | 129.0 |
| 114c | 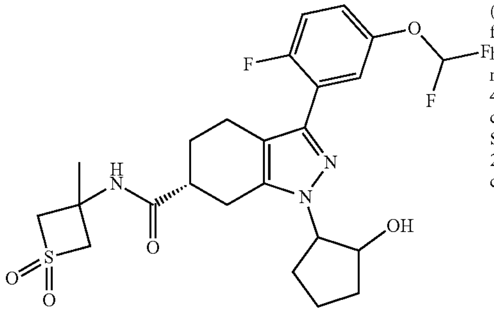 [SMILES: CC1(NC(=O)[C@@H]2CCc3c(-c4cc(OC(F)F)ccc4F)nn(C4CCCC4O)c3C2)CS(=O)(=O)C1] | (6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide (3rd eluting with Step 1: Lux Cellulose-4 column, 25% $MeOH/CO_2$; Step 2: AD-H column, 35% $EtOH/CO_2$) | 528 | 99.9 |
| 114d | 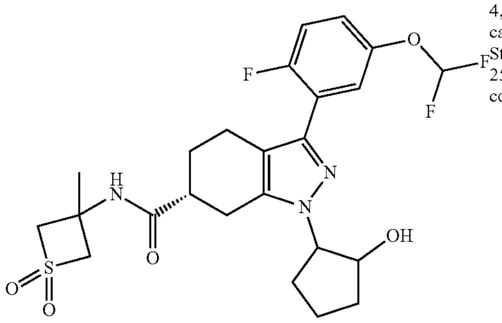 | (6R)-3-(5-(difluoromethoxy)-2-fluorophenyl)-1-(2-hydroxycyclopentyl)-N-(3-methyl-1,1-dioxidothietan-3-yl)-4,5,6,7-tetrahydro-1H-indazole-6-carboxamide (4th eluting with Step 1: Lux Cellulose-4 column, 25% $MeOH/CO_2$; Step 2: AD-H column, 35% $EtOH/CO_2$) | 528 | 105 |

Example 115

(R)-3-(5-(difluoromethoxy)-2-fluorophenyl)-N-(3-methyl-1,1-dioxidothietan-3-yl)-1-(methylsulfonyl)-4,5,6,7-tetrahydro-1H-indazole-6-carboxamide

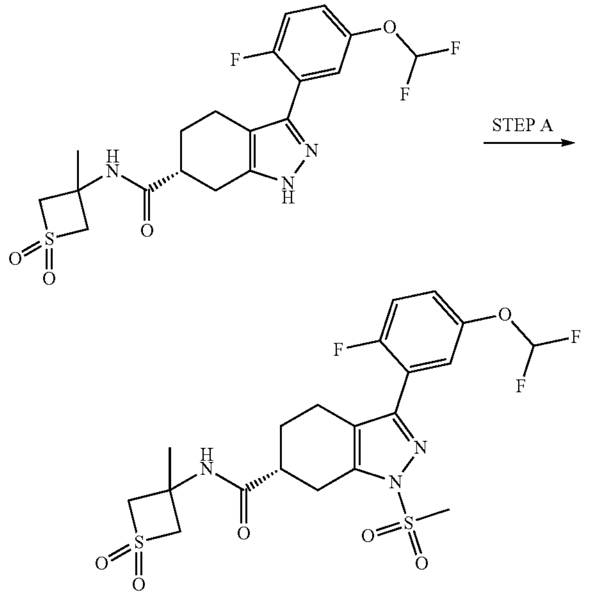

EX-115

Step A: (R)-3-(5-(difluoromethoxy)-2-fluorophenyl)-N-(3-methyl-1,1-dioxidothietan-3-yl)-1-(methylsulfonyl)-4,5,6,7-tetrahydro-1H-indazole-6-carboxamide At 0° C., NaH (21.7 mg, 0.54 mmol) was added to a stirred solution of (R)-3-(5-(difluoromethoxy)-2-fluorophenyl)-N-(3-methyl-1,1-dioxidothietan-3-yl)-4,5,6,7-tetrahydro-1H-indazole-6-carboxamide (60.0 mg, 0.14 mmol) and DMF (0.5 mL). The reaction mixture was stirred for 5 min at 0° C. Methanesulfonyl chloride (62.0 mg, 0.54 mmol) was added and the reaction mixture was stirred at rt for 30 minutes. Water was added and the aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (0-70% EtOAc/hexanes) to afford the title compound. LC/MS=522 [M+1]. $^1$H NMR (500 MHz, Chloroform-d) δ 7.39 (dd, J=5.7, 2.9 Hz, 1H), 7.22-7.12 (m, 2H), 6.51 (t, J=73.4 Hz, 1H), 5.93 (s, 1H), 4.50-4.37 (m, 2H), 4.16-4.08 (m, 2H), 3.38 (s, 3H), 3.29 (dd, J=18.3, 5.8 Hz, 1H), 3.16 (dd, J=17.8, 9.4 Hz, 1H), 2.67-2.55 (m, 3H), 2.13-2.03 (m, 1H), 1.89-1.84 (m, 1H), 1.82 (s, 3H). DGAT2 $IC_{50}$ (nm)=107.5.

By using procedures similar to those described in Example 115 with appropriate reagents, the following compound was synthesized. This compound was characterized by LC/MS.

| Example | Structure | Name | LCMS [M + 1] | DGAT2 $IC_{50}$ (nM) |
|---|---|---|---|---|
| 116 | 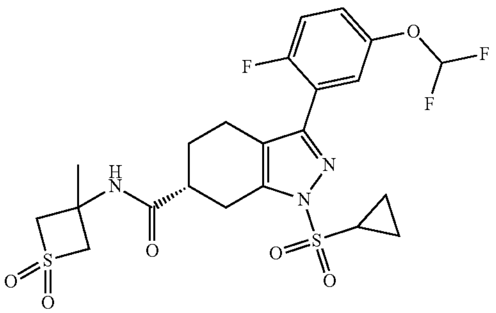 [SMILES: CC1(NC(=O)[C@@H]2CCc3c(-c4cc(OC(F)F)ccc4F)nn(S(=O)(=O)C4CC4)c3C2)CS(=O)(=O)C1] | (R)-1-(cyclopropylsulfonyl)-3-(5-(difluoromethoxy)-2-fluorophenyl)-N-(3-methyl-1,1-dioxidothietan-3-yl)-4,5,6,7-tetrahydro-1H-indazole-6-carboxamide | 548 | 68.1 |

Example 117

3-(3-(difluoromethoxy)phenyl)-4,4-difluoro-N-(3-methyl-1,1-dioxidotetrahydrothiophen-3-yl)-1-(tetrahydro-2H-pyran-4-yl)-4,5,6,7-tetrahydro-1H-indazole-6-carboxamide

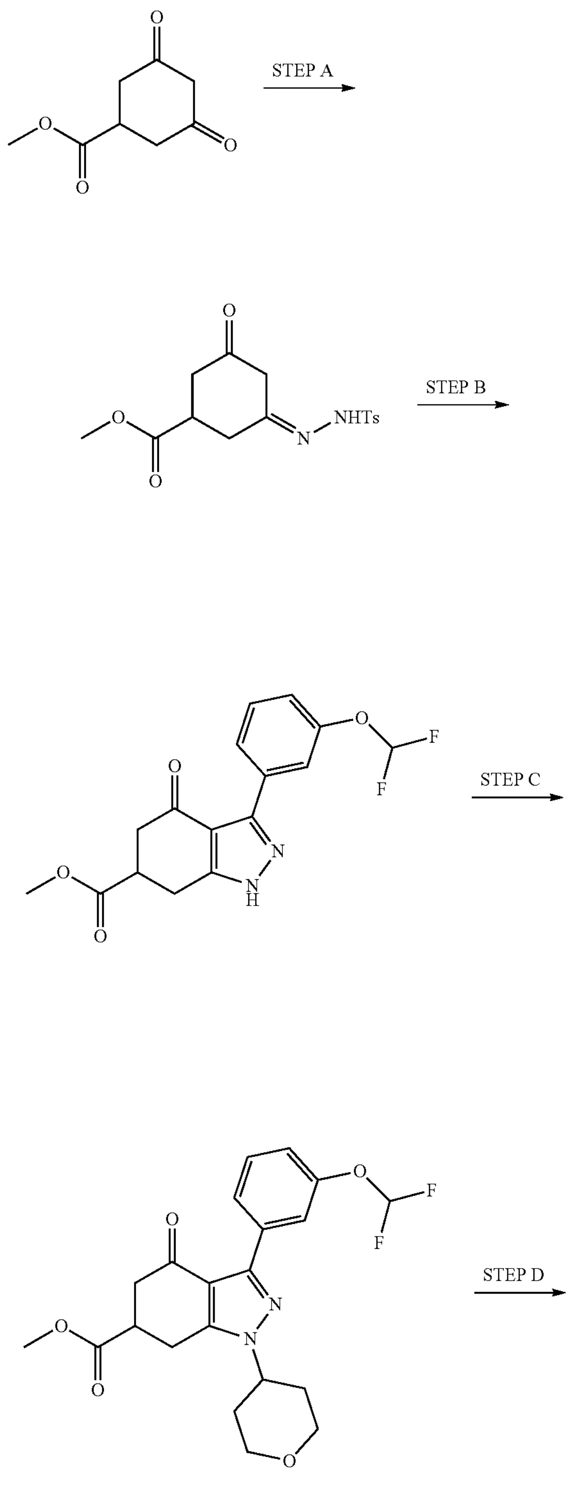

-continued

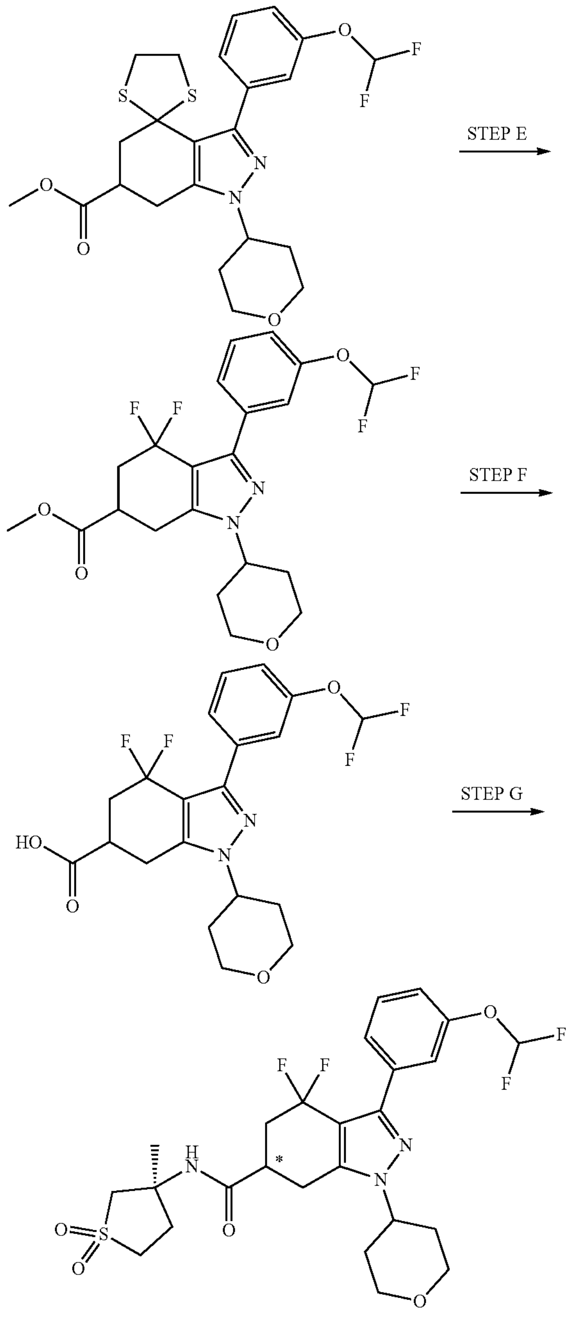

EX-117

Step A: Methyl-3-oxo-5-(2-tosylhydrazono)cyclohexane-1-carboxylate

To a stirred solution of methyl 3,5-dioxocyclohexane-1-carboxylate (3.3 g, 19.2 mmol), 4-methylbenzenesulfonohydrazide (3.6 g, 19.2 mmol), and MeOH (38 mL) was added 5 drops of sulfuric acid. The reaction mixture was stirred at rt for 16 h. The reaction mixture was filtered and precipitate collected. The crude product was used without purification. LC/MS=339 [M+1].

Step B: Methyl 3-(3-(difluoromethoxy)phenyl)-4-oxo-4,5,6,7-tetrahydro-1H-indazole-6-carboxylate To a stirred solution of methyl-3-oxo-5-(2-tosylhydrazono)cyclohexane-1-carboxylate (1.5 g, 4.3 mmol), 3-(difluoromethoxy)benzaldehyde (0.8 g, 4.8 mmol), piperidine (0.47 mL, 4.78 mmol), and DMSO (11 mL) was added acetic acid (0.03 mL, 0.43 mmol). The reaction mixture was stirred at 100° C. for 10 min. The reaction mixture was cooled to rt and water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (50% EtOAc in hexanes) to afford the title compound. LC/MS=337 [M+1].

Step C: Methyl 3-(3-(difluoromethoxy)phenyl)-4-oxo-1-(tetrahydro-2H-pyran-4-yl)-4,5,6,7-tetrahydro-1H-indazole-6-carboxylate To a stirred solution of methyl 3-(3-(difluoromethoxy)phenyl)-4-oxo-4,5,6,7-tetrahydro-1H-indazole-6-carboxylate (600 mg, 1.78 mmol), tetrahydro-2H-pyran-4-yl 4-methylbenzenesulfonate (915 mg, 3.57 mmol), and DMF (8.9 mL) was added $Cs_2CO_3$ (2.32 g, 7.14 mmol). The reaction mixture was stirred at 100° C. for 1 h. After cooling to rt, water was added. The aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (50% EtOAc in hexanes) to afford the title compound. LC/MS=421 [M+1].

Step D: Methyl 3-(3-(difluoromethoxy)phenyl)-1-(tetrahydro-2H-pyran-4-yl)-1,5,6,7-tetrahydrospiro[indazole-4,2'-[1,3]dithiolane]-6-carboxylate To a stirred solution of methyl 3-(3-(difluoromethoxy)phenyl)-4-oxo-1-(tetrahydro-2H-pyran-4-yl)-4,5,6,7-tetrahydro-1H-indazole-6-carboxylate (350 mg, 0.83 mmol), ethane-1,2-dithiol (0.21 mL, 2.49 mmol), and DCM (4.2 mL) was added boron trifluoride acetic acid complex (0.35 mL, 2.49 mmol). The reaction mixture was stirred at rt for 1 h and sat. aq. $NaHCO_3$ was added. The aqueous layer was extracted three times with DCM. The combined organic layers were washed with water and brine. The organic layer was then dried over $MgSO_4$ (s), filtered, and concentrated in vacuo. The crude product was purified by flash silica gel column chromatography (40% EtOAc in hexanes) to afford the title compound. LC/MS=497 [M+1].

Step E: Methyl 3-(3-(difluoromethoxy)phenyl)-4,4-difluoro-1-(tetrahydro-2H-pyran-4-yl)-4,5,6,7-tetrahydro-1H-indazole-6-carboxylate To a stirred solution of methyl 3-(3-(difluoromethoxy)phenyl)-1-(tetrahydro-2H-pyran-4-yl)-1,5,6,7-tetrahydrospiro[indazole-4,2'-[1,3]dithiolane]-6-carboxylate (180 mg, 0.36 mmol), NIS (245 mg, 1.08 mmol), and DCM (3.6 mL) at −78° C. was slowly added pyridine-HF (108 mg, 1.08 mmol). The reaction mixture was stirred at −78° C. for 1 h then warmed to 0° C. and sat. aq. $NaHCO_3$ was added. The aqueous layer was extracted three times with DCM. The combined organic layers were washed with 1 M aq. NaOH and brine. The organic layer was then dried over $MgSO_4$ (s), filtered, and concentrated in vacuo. The crude product was purified by flash silica gel column chromatography (50% EtOAc in hexanes) to the title compound. LC/MS=443 [M+1].

Step F: 3-(3-(difluoromethoxy)phenyl)-4,4-difluoro-1-(tetrahydro-2H-pyran-4-yl)-4,5,6,7-tetrahydro-1H-indazole-6-carboxylic acid To a stirred solution of methyl 3-(3-(difluoromethoxy)phenyl)-4,4-difluoro-1-(tetrahydro-2H-pyran-4-yl)-4,5,6,7-tetrahydro-1H-indazole-6-carboxylate (67 mg, 0.15 mmol), LiOH (14.5 mg, 0.60 mmol), THF (0.3 mL), and MeOH (0.1 mL) was added water (0.3 mL). The reaction mixture was stirred at rt for 5 min and then acidified with concentrated HCl to pH 1. The reaction mixture was then extracted with EtOAc three times. The combined organic layers with washed with brine, dried with $MgSO_4$ (s), filtered, and concentrated in vacuo. The crude product was used without purification. LC/MS=429 [M+1].

Step G: 3-(3-(difluoromethoxy)phenyl)-4,4-difluoro-N-(3-methyl-1,1-dioxidotetrahydrothiophen-3-yl)-1-(tetrahydro-2H-pyran-4-yl)-4,5,6,7-tetrahydro-1H-indazole-6-carboxamide To a stirred solution of 3-(3-(difluoromethoxy)phenyl)-4,4-difluoro-1-(tetrahydro-2H-pyran-4-yl)-4,5,6,7-tetrahydro-TH-indazole-6-carboxylic acid (55.6 mg, 0.13 mmol) in DMF (0.6 mL) was added DIPEA (0.11 mL, 0.65 mmol), HATU (59.2 mg, 0.16 mmol), and 3-amino-3-methyltetrahydrothiophene 1,1-dioxide (23.2 mg, 0.16 mmol). The reaction mixture was stirred at rt for 5 min. The mixture was filtered and purified by mass triggered reverse phase HPLC (ACN/water with 0.1% FA modifier) to afford the title compound (Ex-117). LC/MS=560 [M+1]. DGAT2 $IC_{50}$ (nm)=498.9. The mixture of two stereoisomers was purified by chiral preparative SFC (IC column, 40% EtOH (0.1% DEA)/$CO_2$) to afford Ex-117a (faster eluting) and Ex-117b (slower eluting). Ex-117b $^1$H NMR (600 MHz, Chloroform-d) δ 7.85 (d, J=9.5 Hz, 1H), 7.37 (t, J=7.9 Hz, 1H), 7.12 (d, J=7.9 Hz, 1H), 6.99 (d, J=12.0 Hz, 1H), 6.58 (t, J=73.9 Hz, 1H), 4.38-4.23 (m, 1H), 4.10 (d, J=10.2 Hz, 2H), 3.84 (dd, J=58.6, 13.8 Hz, 1H), 3.50 (p, J=12.7, 12.0 Hz, 2H), 3.34 (dq, J=59.8, 11.5, 11.1 Hz, 1H), 3.21 (td, J=15.5, 10.3 Hz, 2H), 3.15-3.02 (m, 2H), 3.02-2.97 (m, 1H), 2.71 (dq, J=34.5, 15.5, 15.0 Hz, 3H), 2.47-2.24 (m, 2H), 2.14 (p, J=12.2 Hz, 1H), 1.87 (t, J=14.0 Hz, 2H), 1.58 (d, J=4.9 Hz, 3H). LC/MS=560 [M+1].

By using procedures similar to those described in Example 117 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 117a | 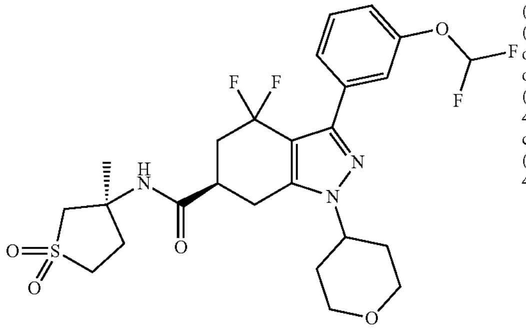 | (R)-3-(3-(difluoromethoxy)phenyl)-4,4-difluoro-N-((S)-3-methyl-1,1-dioxidotetrahydrothiophen-3-yl)-1-(tetrahydro-2H-pyran-4-yl)-4,5,6,7-tetrahydro-1H-indazole-6-carboxamide (faster eluting with IC column, 40% EtOH (0.1% DEA)/$CO_2$) | 560 | >10000 |
| 117b | 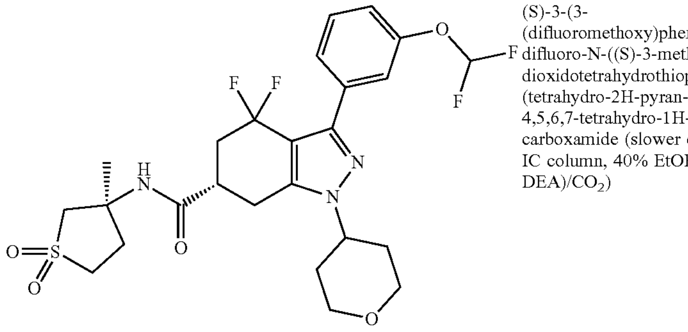 | (S)-3-(3-(difluoromethoxy)phenyl)-4,4-difluoro-N-((S)-3-methyl-1,1-dioxidotetrahydrothiophen-3-yl)-1-(tetrahydro-2H-pyran-4-yl)-4,5,6,7-tetrahydro-1H-indazole-6-carboxamide (slower eluting with IC column, 40% EtOH (0.1% DEA)/$CO_2$) | 560 | 177.6 |

Example 118

3-(3-(difluoromethoxy)phenyl)-1-(5-fluoropyridin-2-yl)-N-(3-methyl-1,1-dioxidotetrahydrothiophen-3-yl)-1,5,6,7-tetrahydropyrano[3,2-c]pyrazole-6-carboxamide

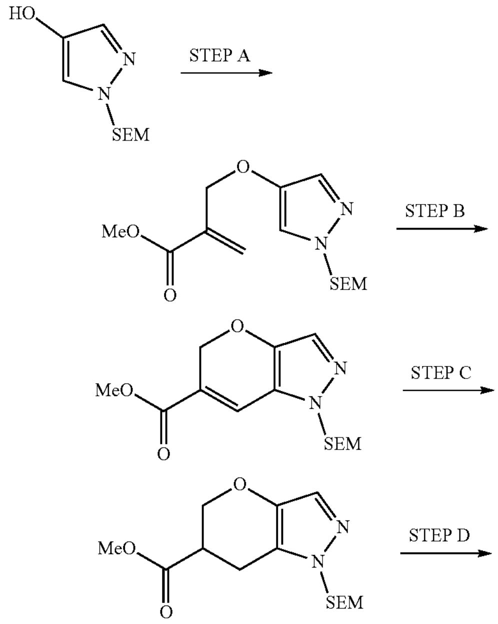

-continued

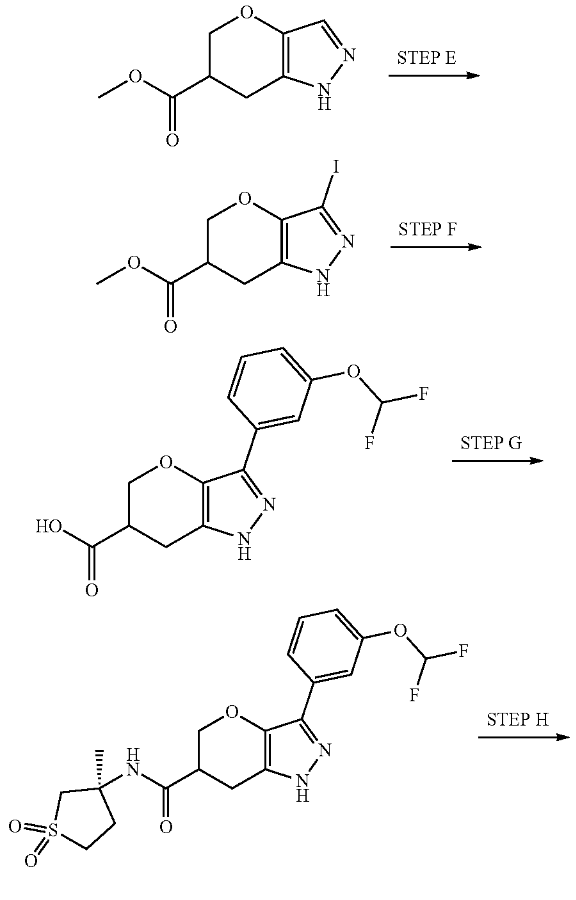

-continued

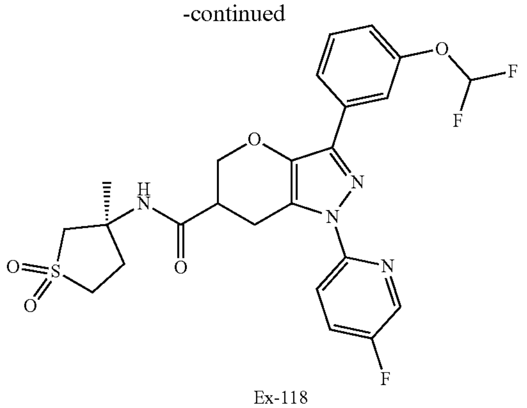

Ex-118

Step A: methyl 2-(((1-((2-(trimethylsilyl)ethoxy)methyl)-1H-pyrazol-4-yl)oxy)methyl)acrylate To a mixture of 1-((2-(trimethylsilyl)ethoxy)methyl)-1H-pyrazol-4-ol (3.0 g, 14.0 mmol) and $K_2CO_3$ (5.8 g, 42.0 mmol) in DMF (17.5 ml) was added methyl 2-(bromomethyl)acrylate (2.5 ml, 21.0 mmol). The reaction was stirred at rt for 1 h. Water was added to quench the reaction, followed by EtOAc. The layers were separated, and the aqueous layer was extracted three times with EtOAc. The combined organic layers were dried with $MgSO_4$ (s), filtered, and concentrated in vacuo. The residue was purified by flash silica gel column chromatography (10% EtOAc in hexanes) to afford the title compound. LC/MS=313 [M+1].

Step B: 1-((2-(trimethylsilyl)ethoxy)methyl)-1,5-dihydropyrano[3,2-c]pyrazole-6-carboxylate At rt, $Pd(OAc)_2$ (0.29 g, 1.3 mmol), KOAc (1.89 g, 19.2 mmol), and acetylvaline (0.41 g, 2.6 mmol) were added to a round bottom flask. Dioxane (14 ml) was added, followed by a solution of methyl 2-(((1-((2-(trimethylsilyl)ethoxy)methyl)-1H-pyrazol-4-yl)oxy)methyl)acrylate (2.0 g, 6.4 mmol) in DMA (28 ml). A reflux condenser was placed over the flask open to air. The reaction was heated to 100° C. and the reaction was stirred for 24 h. The reaction was cooled to rt and concentrated in vacuo. Brine and EtOAc were added, the layers were separated, and the aqueous layer was extracted three times with EtOAc. The organic layers were dried with $Na_2SO_4$ (s), filtered, and concentrated. The residue was purified by flash silica gel column chromatography (0-50% EtOAc in Hexanes) to afford the title compound. LC/MS=311 [M+1].

Step C: methyl 1-((2-(trimethylsilyl)ethoxy)methyl)-1,5,6,7-tetrahydropyrano[3,2-c]pyrazole-6-carboxylate To a stirred solution of methyl 1-((2-(trimethylsilyl)ethoxy)methyl)-1,5-dihydropyrano[3,2-c]pyrazole-6-carboxylate (100 mg, 0.32 mmol) and MeOH (1.6 mL) was added 10% Pd/C (34.3 mg, 0.32 mmol Pd). The mixture was sparged with $N_2$ for 10 min, then a balloon of $H_2$ was placed over the reaction mixture, the reaction mixture was sparged with $H_2$, and the reaction mixture was heated to 30° C. and stirred for 2 days. The mixture was then filtered over Celite®, which was washed with methanol, and the filtrate was concentrated under in vacuo. The crude residue was purified by flash silica gel column chromatography (0-50% EtOAc in hexanes) to afford the title compound. LC/MS=313 [M+1].

Step D: methyl 1,5,6,7-tetrahydropyrano[3,2-c]pyrazole-6-carboxylate

To a stirred solution of methyl 1-((2-(trimethylsilyl)ethoxy)methyl)-1,5,6,7-tetrahydropyrano[3,2-c]pyrazole-6-carboxylate (58 mg, 0.19 mmol) in DCM (743 μl) at 0° C. was added TFA (143 μl, 1.86 mmol). The mixture was allowed to warm to rt and was stirred for 2 h. After that time, TFA (143 μl, 1.86 mmol) was added at rt, and the reaction was continued. After an additional 3 h, TFA (71.5 μl, 0.93 mmol) was added at rt, and the reaction was continued. After an additional 2 h, the reaction was concentrated in vacuo. The crude residue was purified by flash silica gel column chromatography (0-10% MeOH in DCM) to afford the title compound. LC/MS=183 [M+1].

Step E: methyl 3-iodo-1,5,6,7-tetrahydropyrano[3,2-c]pyrazole-6-carboxylate

To a stirred solution of methyl 1,5,6,7-tetrahydropyrano[3,2-c]pyrazole-6-carboxylate (28 mg, 0.15 mmol) in DMF (615 μl) was added NIS (51.9 mg, 0.23 mmol), and the reaction was heated to 80° C. for 1 h. The reaction was then cooled to rt and quenched with sat. aq. $NaHCO_3$. EtOAc was added, the layers were separated, and the aqueous layer was extracted three times with EtOAc. The combined organic layers were dried with $MgSO_{4\ (s)}$, filtered, and concentrated in vacuo. The crude residue was purified via flash silica gel column chromatography (0-10% MeOH in DCM) to afford the title compound. LC/MS=309 [M+1].

Step F: 3-(3-(difluoromethoxy)phenyl)-1,5,6,7-tetrahydropyrano[3,2-c]pyrazole-6-carboxylic acid A mixture of methyl 3-iodo-1,5,6,7-tetrahydropyrano[3,2-c]pyrazole-6-carboxylate (24 mg, 0.08 mmol), (3-(difluoromethoxy)phenyl)boronic acid (17.6 mg, 0.09 mmol), $Pd(dppf)Cl_2$ (5.7 mg, 7.8 μmol), and $Na_2CO_3$ (16.5 mg, 0.16 mmol) was put under $N_2$, and dioxane (195 μl) and water (195 μl) were added. The mixture was heated to 100° C. for 1 h. The reaction was cooled to rt, water was added, and the pH was adjusted to 2 with 1 N HCl. The aqueous layer was extracted with EtOAc three times, and the combined organic layers were dried with $MgSO_4$ (s), filtered, and concentrated in vacuo. The crude product was used without purification. LC/MS=311 [M+1].

Step G: 3-(3-(difluoromethoxy)phenyl)-N-(3-methyl-1,1-dioxidotetrahydrothiophen-3-yl)-1,5,6,7-tetrahydropyrano[3,2-c]pyrazole-6-carboxamide To a stirred solution of 3-(3-(difluoromethoxy)phenyl)-1,5,6,7-tetrahydropyrano[3,2-c]pyrazole-6-carboxylic acid (24 mg, 0.08 mmol), HATU (32.4 mg, 0.09 mmol), and 3-amino-3-methyltetrahydrothiophene 1,1-dioxide (12.7 mg, 0.09 mmol) in DMF (387 μl) was added DIPEA (40.5 μl, 0.23 mmol). The reaction was stirred for 1 h at rt, then concentrated in vacuo. The crude residue was first purified by flash silica gel column chromatography (0-100% EtOAc in Hexanes), then again by flash silica gel column chromatography (0-10% MeOH in DCM) to afford the title compound. LC/MS=442 [M+1].

Step H: 3-(3-(difluoromethoxy)phenyl)-1-(5-fluoropyridin-2-yl)-N-(3-methyl-1,1-dioxidotetra-hydrothiophen-3-yl)-1,5,6,7-tetrahydropyrano[3,2-c]pyrazole-6-carboxamide To a stirred solution of 3-(3-(difluoromethoxy)phenyl)-N-(3-methyl-1,1-dioxidotetrahydro-thiophen-3-yl)-1,5,6,7-tetrahydropyrano[3,2-c]pyrazole-6-carboxamide (6 mg, 0.01 mmol), 2-bromo-5-fluoropyridine (3.6 mg, 0.02 mmol), (1S,2S)—N1,N2-dimethylcyclohexane-1,2-diamine (9.7 mg, 0.07 mmol), CuI (1.3 mg, 6.8 μmol), and dioxane (400 μl) was added $K_3PO_4$ (8.7 mg, 0.04 mmol). The reaction was heated to 100° C. for 1.5 h. The mixture was then was cooled to rt, diluted with acetone, and purified directly by flash silica gel column chromatography (0-100% EtOAc in hexanes) to afford the title compound Ex-118. LC/MS=537 [M+1]. DGAT2 $IC_{50}$ (nm)=0.44.

By using procedures similar to those described in Example 118 with appropriate reagents, the following compound was synthesized. These compounds were characterized by LC/MS.

| Example | Structure | Name | LCMS [M + 1] | DGAT2 $IC_{50}$ (nM) |
|---|---|---|---|---|
| 119 | 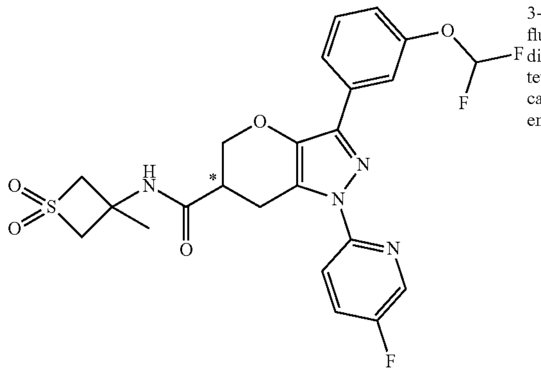 | 3-(3-(difluoromethoxy)phenyl)-1-(5-fluoropyridin-2-yl)-N-(3-methyl-1,1-dioxidothietan-3-yl)-1,5,6,7-tetrahydropyrano[3,2-c]pyrazole-6-carboxamide (mixture of enantiomers) | 523 | 0.33 |

Example 120

3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide

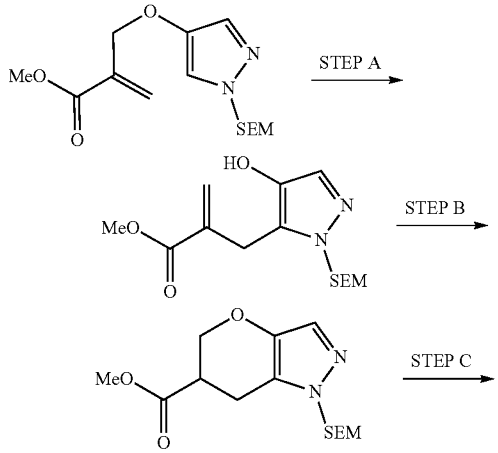

-continued

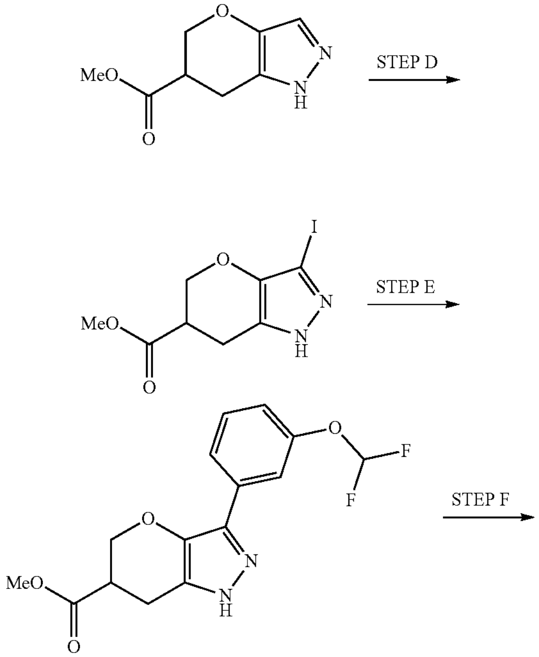

-continued

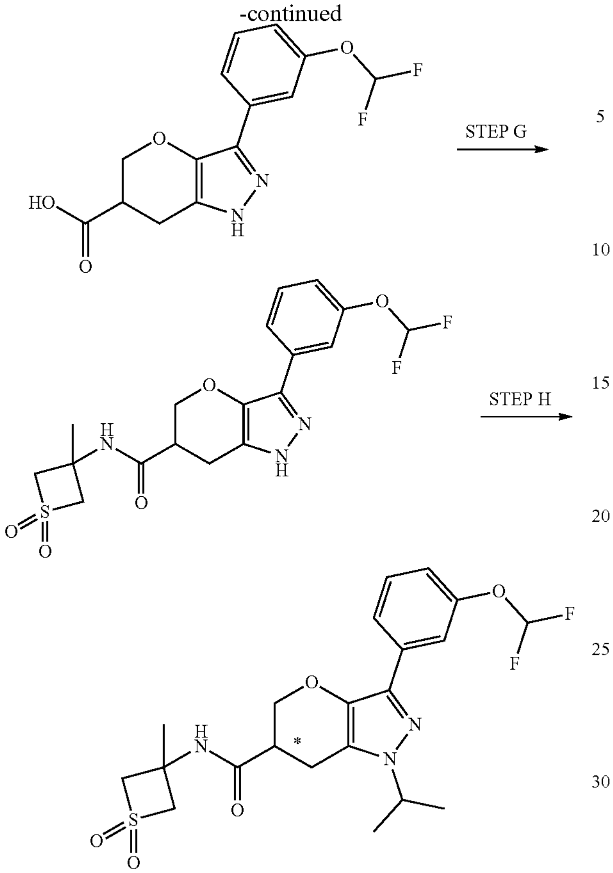

EX-120

Step A: Methyl 2-((4-hydroxy-1-((2-(trimethylsilyl) ethoxy)methyl)-1H-pyrazol-5-yl)methyl)acrylate A solution of methyl 2-(((1-((2-(trimethylsilyl)ethoxy) methyl)-1H-pyrazol-4-yl)oxy)methyl)acrylate (9.6 g, 30.7 mmol) and DMA (288 mL) was stirred at 120° C. for 16 h. After cooling to rt, water was added and the aqueous layer was extracted three times with EtOAc. The combined organic layers were washed with water and brine. The organic layer was then dried over $Na_2SO_4$ (s), filtered, and concentrated in vacuo. The crude product was used without purification. LC/MS=313 [M+1].

Step B: Methyl 1-((2-(trimethylsilyl)ethoxy) methyl)-1,5,6,7-tetrahydropyrano[3,2-c]pyrazole-6-carboxylate To a stirring solution of methyl 2-((4-hydroxy-1-((2-(trimethylsilyl)ethoxy)methyl)-1H-pyrazol-5-yl)methyl) acrylate (5 g, 16 mmol) and toluene (100 mL) was added $Cs_2CO_3$ (5.21 g, 16 mmol). The reaction mixture was stirred at 55° C. for 16 h. After cooling to rt, the reaction mixture was filtered and concentrated. The crude product was purified by flash silica gel column chromatography (15% EtOAc in hexanes) to afford the title compound. LC/MS=313 [M+1].

Step C: Methyl 1,5,6,7-tetrahydropyrano[3,2-c] pyrazole-6-carboxylate

To a stirring solution of methyl 1-((2-(trimethylsilyl) ethoxy)methyl)-1,5,6,7-tetrahydropyrano[3,2-c]pyrazole-6-carboxylate (2.2 g, 7.04 mmol) and DCM (14 mL) was added TFA (10.9 mL, 141 mmol). The reaction mixture was stirred at rt for 16 h. The reaction mixture was washed with sat. aq. $NaHCO_3$ and brine. The organic layer was then dried over $MgSO_4$ (s), filtered, and concentrated in vacuo. The crude product was used without purification. LC/MS=183 [M+1].

Step D: Methyl 3-iodo-1,5,6,7-tetrahydropyrano[3, 2-c]pyrazole-6-carboxylate

To a stirring solution of methyl 1,5,6,7-tetrahydropyrano [3,2-c]pyrazole-6-carboxylate (0.97 g, 5.3 mmol) and DMF (13 mL) was added NIS (1.44 g, 6.4 mmol). The reaction mixture was stirred at 80° C. for 1.5 h. After cooling to rt, sat. aq. $NaHCO_3$ was added and the aqueous layer was extracted three times with EtOAc. The combined organic layers were washed with water and brine, dried over $MgSO_4$ (s), filtered, and concentrated in vacuo. The crude product was purified by flash silica gel column chromatography (100% EtOAc) to afford the title compound. LC/MS=309 [M+1].

Step E: Methyl 3-(3-(difluoromethoxy)phenyl)-1,5, 6,7-tetrahydropyrano[3,2-c]pyrazole-6-carboxylate To a stirred solution of methyl 3-iodo-1,5,6,7-tetrahydro-pyrano[3,2-c]pyrazole-6-carboxylate (500 mg, 1.62 mmol), (3-(difluoromethoxy)phenyl)boronic acid (336 mg, 1.78 mmol), $Pd(dppf)Cl_2$ (238 mg, 0.33 mmol), $Na_2CO_3$ (344 mg, 3.25 mmol), and dioxane (8.1 mL) was added water (8.1 mL). The reaction mixture was sparged with $N_2$ for 5 min at rt then heated to 100° C. for 5 min. After cooling to rt, water was added and the mixture was extracted three times with EtOAc. The combined organic layers were washed with water and brine, dried over $MgSO_4$ (s), filtered, and concentrated in vacuo. The crude product was purified by flash silica gel column chromatography (50% EtOAc) to afford the title compound. LC/MS=325 [M+1].

Step F: 3-(3-(difluoromethoxy)phenyl)-1,5,6,7-tetra-hydropyrano[3,2-c]pyrazole-6-carboxylic acid To a mixture of methyl 3-(3-(difluoromethoxy)phenyl)-1,5,6,7-tetrahydropyrano[3,2-c]pyrazole-6-carboxylate (197 mg, 0.6 mmol), LiOH (58 mg, 2.4 mmol), THF (1.0 mL), MeOH (1.0 mL), and water (1.0 mL). The mixture was stirred at rt for 10 minutes, then acidified with concentrated HCl to pH 1. The mixture was then extracted three times with EtOAc. The combined organic layers were washed with water and brine, dried over $MgSO_4$ (s), filtered, and the volatiles evaporated to afford the title compound. The crude product was used without purification. LC/MS=311 [M+1].

Step G: 3-(3-(difluoromethoxy)phenyl)-N-(3-methyl-1,1-dioxidothietan-3-yl)-1,5,6,7-tetrahydro-pyrano[3,2-c]pyrazole-6-carboxamide To a mixture of 3-(3-(difluoromethoxy)phenyl)-1,5,6,7-tetrahydropyrano[3,2-c]pyrazole-6-carboxylic acid (193 mg, 0.62 mmol) in DMF (2.1 mL) was added HATU (284 g, 0.75 mmol), DIPEA (543 μL, 3.1 mmol), and then 3-amino-3-methylthietane 1,1-dioxide hydrochloride (128 mg, 0.75 mmol). The mixture was stirred at rt for 5 minutes. Then water was added and the aqueous layer was extracted three times with EtOAc. The combined organic layers were washed with water and brine. The organic layer was then dried over $MgSO_4$ (s), filtered, and concentrated in vacuo. The crude product was purified by flash silica gel column chromatography (100% EtOAc) to afford the title compound. LC/MS=428 [M+1].

Step H: 3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide To a mixture of 3-(3-(difluoromethoxy)phenyl)-N-(3-methyl-1,1-dioxidothietan-3-yl)-1,5,6,7-tetrahydropyrano[3,2-c]pyrazole-6-carboxamide (157 mg, 0.37 mmol), 2-iodopropane (125 mg, 0.74 mmol), $Cs_2CO_3$ (479 mg, 1.47 mmol) was added DMF (1.2 ml). The mixture was stirred at 100° C. for 15 minutes. The reaction mixture was cooled to rt, filtered, and purified by mass triggered reverse phase HPLC (ACN/water with 0.1% FA modifier) to afford the title compound (Ex-120). LC/MS=470 [M+1]. DGAT2 $IC_{50}$ (nm)=18.8. The mixture of two stereoisomers was purified by chiral preparative SFC (AD-H column, 35% MeOH/$CO_2$) to afford Ex-120a (faster eluting) and Ex-120b (slower eluting). $^1H$ NMR (500 MHz, MeOD) δ 7.54 (t, J=8.0 Hz, 1H), 7.28 (d, J=7.8 Hz, 1H), 7.16-7.23 (m, 2H), 6.72-7.09 (m, 1H), 4.55 (td, $J_1$=13.2 Hz, $J_2$=6.6 Hz, 1H), 4.46 (d, J=14.8 Hz, 2H), 4.36 (br d, J=11.1 Hz, 1H), 4.13-4.20 (m, 2H), 3.98-4.05 (m, 1H), 3.95-3.05 (m, 3H), 1.76 (s, 3H), 1.43 (dd, $J_1$=15.8 Hz, $J_2$=6.6 Hz, 6H).

By using procedures similar to those described in Example 120 with appropriate reagents, the following compounds were synthesized. These compounds were characterized by LC/MS.

| Example | Structure | Name | LCMS [M + 1] | DGAT2 $IC_{50}$ (nM) |
|---|---|---|---|---|
| 120a | 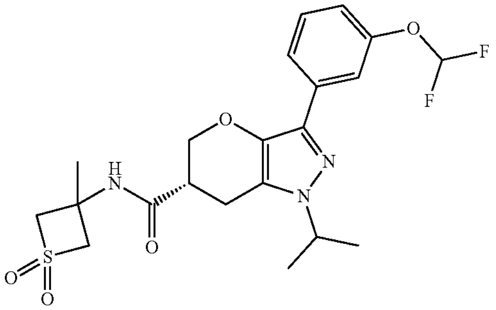 [SMILES: CC(C)n1nc(-c2cccc(OC(F)F)c2)c2c1C[C@H](C(=O)NC1(C)CS(=O)(=O)C1)CO2] | (S)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide (faster eluting with AD-H column, 40% MeOH/$CO_2$) | 470 | 7.6 |
| 120b | 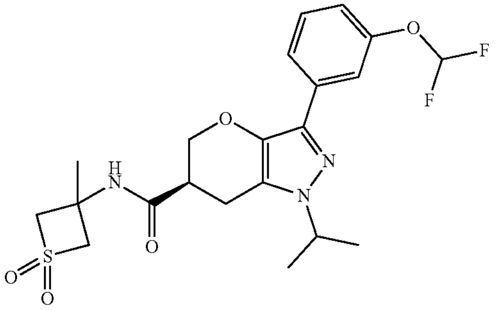 [SMILES: CC(C)n1nc(-c2cccc(OC(F)F)c2)c2c1C[C@@H](C(=O)NC1(C)CS(=O)(=O)C1)CO2] | (R)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide (slower eluting with AD-H column, 40% MeOH/$CO_2$) | 470 | >10000 |
| 121 | 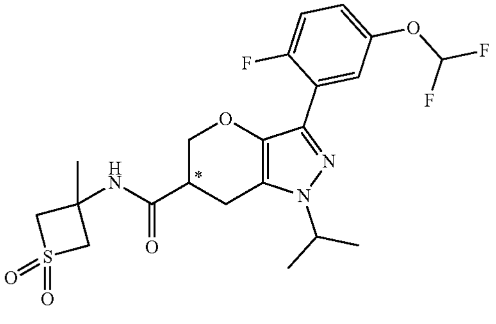 [SMILES: CC(C)n1nc(-c2cc(OC(F)F)ccc2F)c2c1CC(C(=O)NC1(C)CS(=O)(=O)C1)CO2] | 3-(5-(difluoromethoxy)-2-fluorophenyl)-1-isopropyl-N-(3-methyl-1,1-dioxidothietan-3-yl)-1,5,6,7-tetrahydropyrano[3,2-c]pyrazole-6-carboxamide (mixture of enantiomers) | 488 | 21.5 |

-continued

| Example | Structure | Name | LCMS [M + 1] | DGAT2 $IC_{50}$ (nM) |
|---|---|---|---|---|
| 122 | 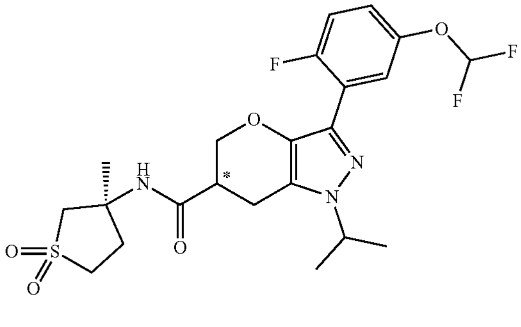 [SMILES: CC(C)n1nc(-c2cc(OC(F)F)ccc2F)c2c1CC(C(=O)N[C@@]1(C)CCS(=O)(=O)C1)CO2] | 3-(5-(difluoromethoxy)-2-fluorophenyl)-1-isopropyl-N-((S)-3-methyl-1,1-dioxidotetrahydrothiophen-3-yl)-1,5,6,7-tetrahydropyrano[3,2-c]pyrazole-6-carboxamide (mixture of diastereomers) | 502 | 5.8 |
| 123 | 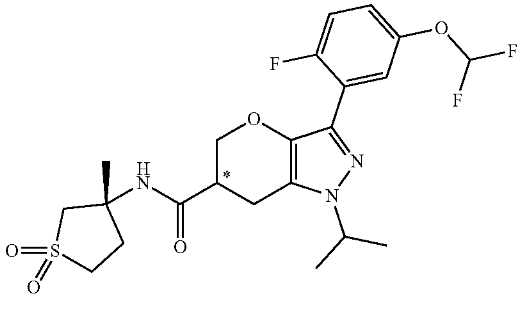 [SMILES: CC(C)n1nc(-c2cc(OC(F)F)ccc2F)c2c1CC(C(=O)N[C@]1(C)CCS(=O)(=O)C1)CO2] | 3-(5-(difluoromethoxy)-2-fluorophenyl)-1-isopropyl-N-((R)-3-methyl-1,1-dioxidotetrahydrothiophen-3-yl)-1,5,6,7-tetrahydropyrano[3,2-c]pyrazole-6-carboxamide (mixture of diastereomers) | 502 | 24.3 |
| 124 | 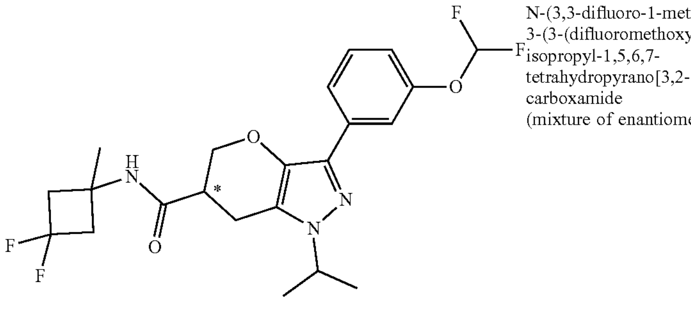 | N-(3,3-difluoro-1-methylcyclobutyl)-3-(3-(difluoromethoxy )phenyl)-1-isopropyl-1,5,6,7-tetrahydropyrano[3,2-c]pyrazole-6-carboxamide (mixture of enantiomers) | 456 | 56.4 |
| 125 | 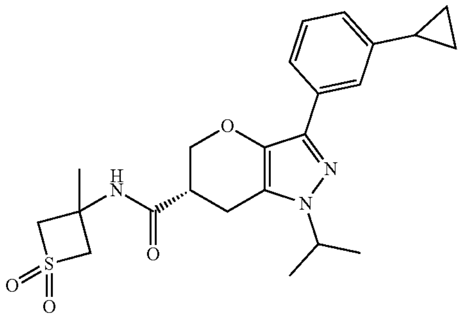 [SMILES: CC(C)n1nc(-c2cccc(C3CC3)c2)c2c1C[C@H](C(=O)NC1(C)CS(=O)(=O)C1)CO2] | (S)-3-(3-cyclopropylphenyl)-1-isopropyl-N-(3-methyl-1,1-dioxidothietan-3-yl)-1,5,6,7-tetrahydropyrano[3,2-c]pyrazole-6-carboxamide | 444 | 22.2 |

Example 126
3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide
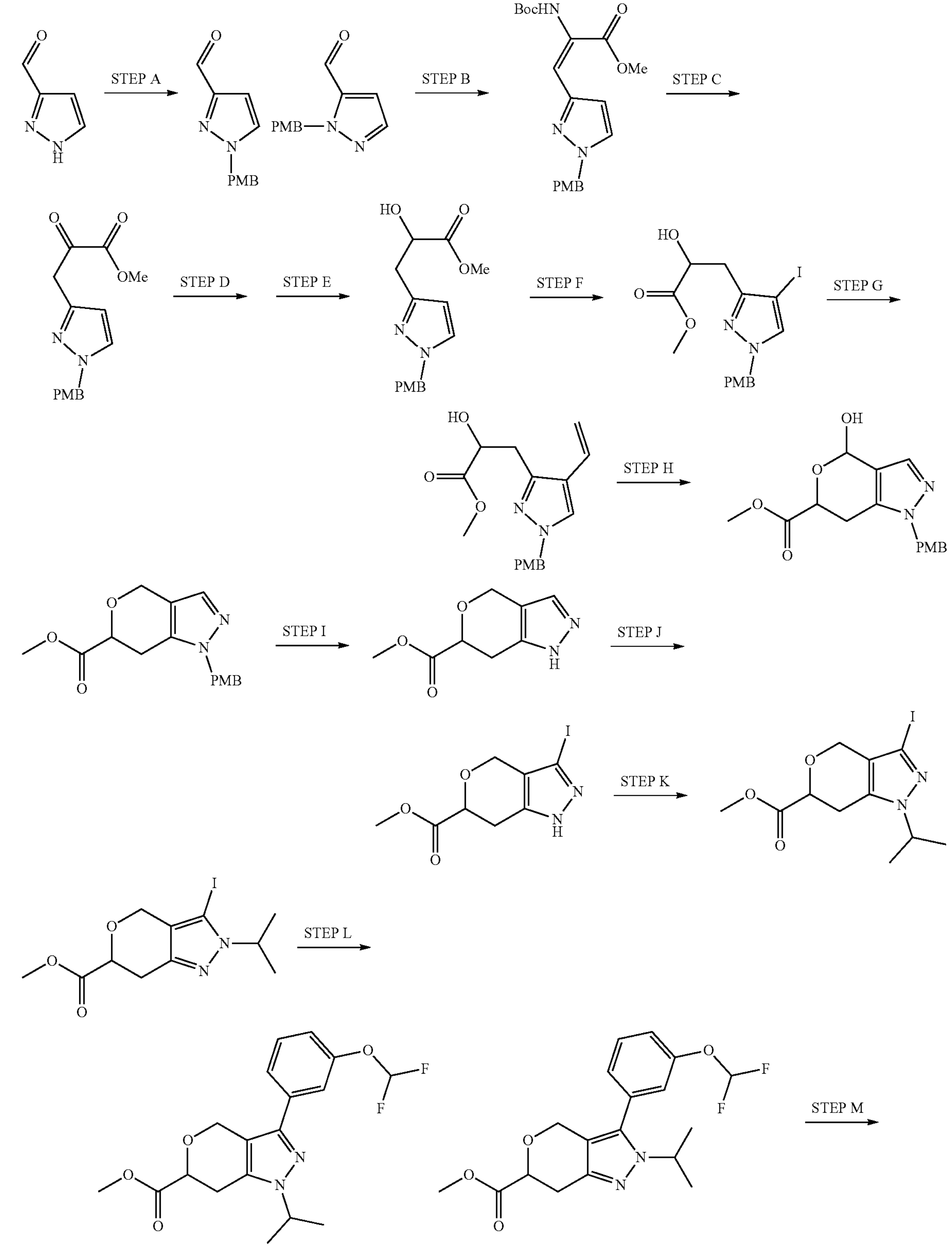

-continued

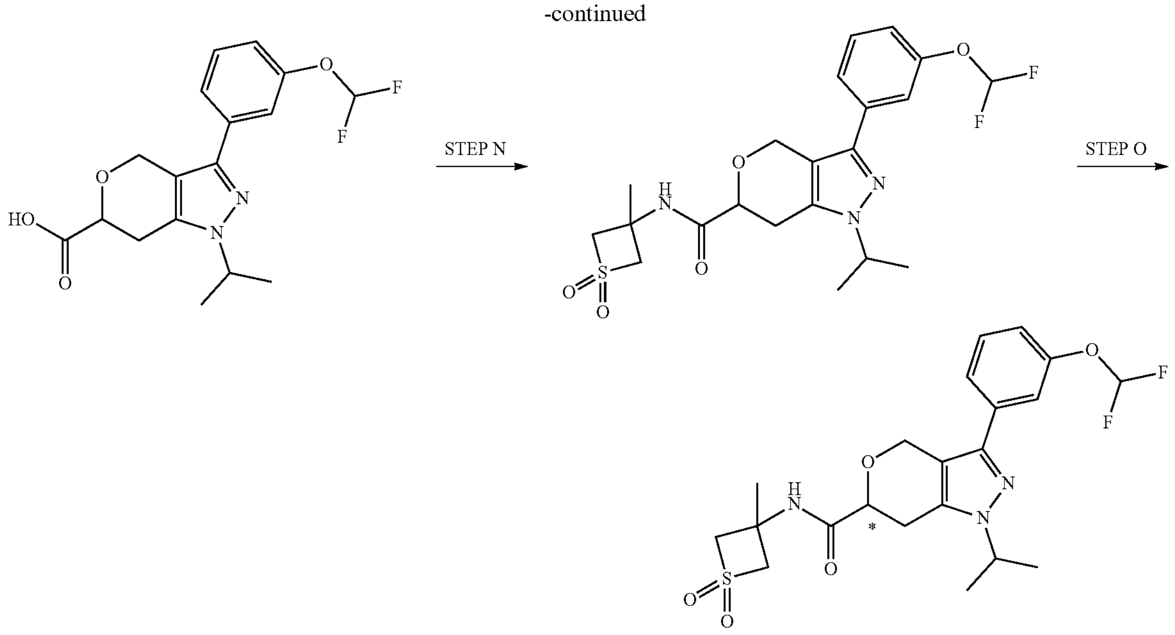

EX-126

Step A: 1-(4-methoxybenzyl)-1H-pyrazole-5-carbaldehyde

To a solution of 1H-pyrazole-5-carbaldehyde (8.9 g, 93 mmol) in acetonitrile (180 mL) was added $K_2CO_3$ (38.4 g, 278 mmol) and 1-(chloromethyl)-4-methoxybenzene (21.76 g, 139 mmol) at 25° C. The mixture was stirred at 25° C. for 16 h, then poured into sat. $NH_4Cl$, and extracted with DCM (×3). The combined organic layers were washed with brine, dried over $Na_2SO_4$, filtered, and concentrated under reduced pressure. The residue was purified by column chromatography on silica (0-100% EtOAc/hexanes) to afford the title compound. LC/MS=217 [M+1].

Step B: (E)-methyl 2-((tert-butoxycarbonyl)amino)-3-(1-(4-methoxybenzyl)-1H-pyrazol-3-yl)acrylate To a solution of methyl 2-((tert-butoxycarbonyl)amino)-2-(dimethoxyphosphoryl)acetate (9.62 g, 32.4 mmol) at −78° C. was added 1,1,3,3-tetramethylguanidine (4.85 g, 42.1 mmol). The mixture was stirred for 15 min, then 1-(4-methoxybenzyl)-1H-pyrazole-3-carbaldehyde (7 g, 32.4 mmol) was added. The reaction was stirred for 1 h at −78° C. and 1.5 h at 25° C. The mixture was poured into sat. $NH_4Cl$, then extracted with DCM (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=388 [M+1].

Step C: methyl 3-(1-(4-methoxybenzyl)-1H-pyrazol-3-yl)-2-oxopropanoate

To a solution of (E)-methyl 2-((tert-butoxycarbonyl)amino)-3-(1-(4-methoxybenzyl)-1H-pyrazol-3-yl)acrylate (11.9 g, 30.7 mmol) in $CH_2Cl_2$ (100 mL) was added TFA (60 mL, 779 mmol) at 0° C. The mixture was stirred at 25° C. for 16 h. LCMS showed the reaction was complete. The mixture was cooled, and the solvent was evaporated under reduced pressure. A saturated solution of $NaHCO_3$ was added until the pH reached to 8, the aqueous phase was extracted with DCM (×3), filtered and the solvent was evaporated under reduced pressure to afford the crude title compound, which was used into next step directly. LC/MS=389 [M+1].

Step D: methyl 2-hydroxy-3-(1-(4-methoxybenzyl)-1H-pyrazol-3-yl)propanoate

To a solution of methyl 3-(1-(4-methoxybenzyl)-1H-pyrazol-3-yl)-2-oxopropanoate (9.8 g, 34.0 mmol) in THF (100 mL) was added $NaBH_4$ (1.929 g, 51.0 mmol) at 0° C. under $N_2$ atmosphere. The mixture was stirred at 25° C. for 15 min, then poured into sat. $NH_4Cl$ and extracted with DCM (×3) The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=291 [M+1].

Step E: methyl 2-hydroxy-3-(4-iodo-1-(4-methoxybenzyl)-1H-pyrazol-3-yl)propanoate To a solution of methyl 2-hydroxy-3-(1-(4-methoxybenzyl)-1H-pyrazol-3-yl)propanoate (1 g, 3.44 mmol) in DMF (10 mL) was added NIS (1.162 g, 5.17 mmol) at 25° C. under $N_2$ atmosphere. The mixture was stirred at 25° C. for 6 h, then poured into sat. $NH_4Cl$, and extracted with DCM (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=417 [M+1].

Step F: methyl 2-hydroxy-3-(1-(4-methoxybenzyl)-4-vinyl-1H-pyrazol-3-yl)propanoate To a solution of methyl 2-hydroxy-3-(4-iodo-1-(4-methoxybenzyl)-1H-pyrazol-3-yl)propanoate (1.4 g, 3.36 mmol) in dioxane (6 mL)/water (2 mL) was added potassium vinyltrifluoroborate (0.901 g, 6.73 mmol), $K_2CO_3$ (1.395 g, 10.09 mmol) and $PdCl_2$(dppf) (0.492 g, 0.673 mmol) under $N_2$ atmosphere. The mixture was stirred at 90° C. for 4 h. The mixture was poured into sat. $NH_4Cl$, then extracted with DCM (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=317 [M+1].

Step G: methyl 4-hydroxy-2-(4-methoxybenzyl)-2,4,6,7-tetrahydropyrano[4,3-c]pyrazole-6-carboxylate or methyl 4-hydroxy-1-(4-methoxybenzyl)-1,4,6,7-tetrahydropyrano[4,3-c]pyrazole-6-carboxylate To a solution of methyl 2-hydroxy-3-(1-(4-methoxybenzyl)-4-vinyl-1H-pyrazol-3-yl)propanoate (750 mg, 2.371 mmol) in dioxane (5 mL)/water (1 mL) was added 2,6-lutidine (0.552 mL, 4.74 mmol), sodium periodate (1014 mg, 4.74 mmol) and osmium tetroxide (0.372 mL, 1.185 mmol) under $N_2$ atmosphere. The mixture was stirred at 50° C. for 1 h. The mixture was poured into sat. $NH_4Cl$, then extracted with DCM (×3). The combined organic layers were washed with brine, dried over $Na_2SO_4$, then filtered and concentrated under reduced pressure. The residue was purified by column chromatography on silica (0-100% EtOAc/hexanes) to afford the title compound. LC/MS=319 [M+1].

Step H: methyl 2-(4-methoxybenzyl)-2,4,6,7-tetrahydropyrano[4,3-c]pyrazole-6-carboxylate To a solution of methyl 4-hydroxy-2-(4-methoxybenzyl)-2,4,6,7-tetrahydropyrano[4,3-c]pyrazole-6-carboxylate (400 mg, 1.257 mmol) in TFA (2 mL, 26.0 mmol) was added triethylsilane (1.606 mL, 10.05 mmol) under $N_2$ atmosphere. The mixture was stirred at 25° C. for 1 h. The mixture was evaporated under reduced pressure to give the crude product. The crude product was purified by column chromatography on silica (0-100% EtOAc/hexanes) to afford the title compound. LC/MS=303 [M+1].

Step I: methyl 2,4,6,7-tetrahydropyrano[4,3-c]pyrazole-6-carboxylate

A solution of methyl 2-(4-methoxybenzyl)-2,4,6,7-tetrahydropyrano[4,3-c]pyrazole-6-carboxylate (200 mg, 0.662 mmol) in TFA (0.051 mL, 0.662 mmol) was stirred at 120° C. for 1 h. The mixture was filtered and the solvent was evaporated under reduced pressure to give the crude product, which was purified by mass triggered reverse phase HPLC (ACN/water with 0.1% TFA modifier) to afford the title compound. LC/MS=183 [M+1].

Step J: methyl 3-iodo-2,4,6,7-tetrahydropyrano[4,3-c]pyrazole-6-carboxylate

To a solution of methyl 2,4,6,7-tetrahydropyrano[4,3-c]pyrazole-6-carboxylate (95 mg, 0.521 mmol) in DMF (1 mL) was added NIS (176 mg, 0.782 mmol) under $N_2$ atmosphere. The mixture was stirred at 60° C. for 1 h, then evaporated under reduced pressure to give the crude product. The crude product was purified by mass triggered reverse phase HPLC (ACN/water with 0.10% TFA modifier) to afford the title compound. LC/MS=309 [M+1].

Step K: methyl 3-iodo-1-isopropyl-1,4,6,7-tetrahydropyrano[4,3-c]pyrazole-6-carboxylate and methyl 3-iodo-2-isopropyl-2,4,6,7-tetrahydropyrano[4,3-c]pyrazole-6-carboxylate To a solution of methyl 3-iodo-2,4,6,7-tetrahydropyrano[4,3-c]pyrazole-6-carboxylate (65 mg, 0.211 mmol) in acetonitrile (4 mL) was added $Cs_2CO_3$ (206 mg, 0.633 mmol) and 2-iodopropane (179 mg, 1.055 mmol) The mixture was stirred at 50° C. for 3 h, then filtered. The solvent was evaporated under reduced pressure to give the crude product, and the crude product was purified by mass triggered reverse phase HPLC (ACN/water with 0.1% TFA modifier) to afford the title compound. LC/MS=351 [M+1].

Step L: methyl 3-(3-(difluoromethoxy)phenyl)-1-isopropyl-1,4,6,7-tetrahydropyrano[4,3-c]pyrazole-6-carboxylate and methyl 3-(3-(difluoromethoxy)phenyl)-2-isopropyl-2,4,6,7-tetrahydropyrano[4,3-c]pyrazole-6-carboxylate To a solution of methyl 3-iodo-1-isopropyl-1,4,6,7-tetrahydropyrano[4,3-c]pyrazole-6-carboxylate (30 mg, 0.086 mmol) and methyl 3-iodo-2-isopropyl-2,4,6,7-tetrahydropyrano[4,3-c]pyrazole-6-carboxylate (30.0 mg, 0.086 mmol) in dioxane (3 mL)/water (0.5 mL) was added $Na_2CO_3$ (27.2 mg, 0.257 mmol), 2-(3-(difluoromethoxy)phenyl)-4,4,5,5-tetramethyl-1,3,2-dioxaborolane (50.9 mg, 0.188 mmol) and $PdCl_2$(dppf) (12.54 mg, 0.017 mmol) under $N_2$ atmosphere The mixture was stirred at 80° C. for 3 h, then filtered, and the solvent was evaporated under reduced pressure to give the crude product, which was purified by mass triggered reverse phase HPLC (ACN/water with 0.1% TFA modifier) to afford the title compound. LC/MS=367 [M+1].

Step M: 3-(3-(difluoromethoxy)phenyl)-1-isopropyl-1,4,6,7-tetrahydropyrano[4,3-c]pyrazole-6-carboxylic acid To a solution of methyl 3-(3-(difluoromethoxy)phenyl)-1-isopropyl-1,4,6,7-tetrahydropyrano[4,3-c]pyrazole-6-carboxylate (23 mg, 0.063 mmol) in MeOH (1 mL)/water (0.2 mL) was added LiOH $H_2O$ (3.01 mg, 0.126 mmol) at room temperature. The solution was stirred at 25° C. for 3 h. LCMS showed the reaction was complete. The mixture was concentrated under reduced pressure. The residue was dissolved in $H_2O$. HCl (1N in water) was added to the mixture until pH=4. Then the mixture was extracted with DCM (×3). The combined organic layers were washed with brine, dried over $Na_2SO_4$, then filtered and concentrated under reduced pressure to afford the title compound. LC/MS=353 [M+1].

Step N: 3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide To a mixture of 3-(3-(difluoromethoxy)phenyl)-1-isopropyl-1,4,6,7-tetrahydropyrano[4,3-c]pyrazole-6-carboxylic acid (18 mg, 0.051 mmol) in DCM (3 mL) was added DIEA (0.027 mL, 0.153 mmol), HATU (38.9 mg, 0.102 mmol) and 3-amino-3-methylthietane 1,1-dioxide (8.29 mg, 0.061 mmol) at 25° C. The mixture was stirred at 25° C. for 2 h, then filtered, and the solvent was evaporated under reduced pressure to give the crude product, which was purified by mass triggered reverse phase HPLC (ACN/water with 0.1% TFA modifier) to afford the title compound. LC/MS=470 [M+1]. The mixture of the two stereoisomers was purified by chiral SFC (Phenomenex-Cellulose-2 column, 40%/60% ethanol/$CO_2$) to afford isomer EX-134a (faster eluting). LC/MS=470 [M+1]. $^1$H NMR (500 MHz, MeOD) δ 7.24-7.36 (m, 3H), 6.99 (dd, $J_1$=7.3 Hz, $J_2$=1.8 Hz, 1H), 6.56-6.88 (m, 1H), 4.85-4.96 (m, 2H), 4.41-4.48 (m, 3H), 4.06-4.16 (m, 3H), 3.03-3.07 (m, 1H), 2.72 (dd, $J_1$=15.8 Hz, $J_2$=10.8 Hz, 1H), 1.65-1.70 (m, 3H), 1.42 (dd, $J_1$=10.1 Hz, $J_2$=6.7 Hz, 6H). DGAT2 $IC_{50}$ (nM)>10000 nM, Isomer EX-134b (slower eluting). LC/MS=470 [M+1]. $^1$H NMR (500 MHz, MeOD) δ 7.24-7.35 (m, 3H), 6.95-7.02 (m, 1H), 6.53-6.86 (m, 1H), 4.85-4.98 (m, 2H), 4.40-4.49 (m, 3H), 4.06-4.16 (m, 3H), 3.04-3.08 (m, 1H), 2.72 (dd, $J_1$=15.8 Hz, $J_2$=10.8 Hz, 1H), 1.68 (s, 3H), 1.43 (dd, $J_1$=10.4 Hz, $J_2$=6.7 Hz, 6H). DGAT2 $IC_{50}$ (nM)=7607 nM. The structure of final compounds was confirmed by 2D NMR.

By using procedures similar to those described in Example 126 with appropriate reagents, the following compounds were synthesized. These compounds were characterized by LC/MS.

buffer, and frozen (−80° C.) for later use. The protein concentration was determined with the Pierce™ BCA Protein Assay Kit (Thermo Fisher Scientific). Expression of protein levels was analyzed by immunoblotting with rabbit anti-DGAT2 antibody (Abcam, ab102831) and donkey anti-rabbit IgG H&L Alexa Fluor® 647 (Abcam, ab150075) followed by detection using Typhoon FLA9000 (GE Healthcare).

LC/MS/MS Analysis Method

LC/MS/MS analyses were performed using Thermal Fisher's LX4-TSQ Vantage system. This system consists of an Agilent binary high-performance liquid chromatography (HPLC) pump and a TSQ Vantage triple quadrupole MS/MS instrument. For each sample, 2 μL samples from the top organic layer of in-plate liquid-liquid extraction were injected onto a Thermo Betabasic C4 column (2.1 mm×20 mm, 5 μm particle size). The samples were then eluted using the following conditions; mobile phase: Isopropanol: acetonitrile/10 mM ammonium formate=50/35/15 (v/v/v), flow rate: 0.8 mL/min, temperature: 25° C. Data was acquired in positive mode using a heated electrospray ionization (HESI) interface. The operational parameters for the

| Example | Structure | Name | LCMS [M + 1] | DGAT2 $IC_{50}$ (nM) |
|---|---|---|---|---|
| 127 | 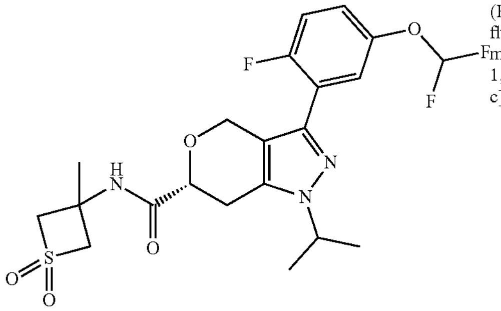 | (R)-3-(5-(difluoromethoxy)-2-fluorophenyl)-1-isopropyl-N-(3-methyl-1,1-dioxidothietan-3-yl)-1,4,6,7-tetrahydropyrano[4,3-c]pyrazole-6-carboxamide | 488 | 343 |
| 128 | 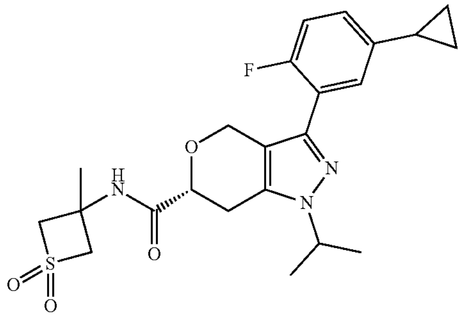 | (R)-3-(5-cyclopropyl-2-fluorophenyl)-1-isopropyl-N-(3-methyl-1,1-dioxidothietan-3-yl)-1,4,6,7-tetrahydropyrano[4,3-c]pyrazole-6-carboxamide | 462 | 320 |

Assays

Insect Cell Expression and Membrane Preparation

Sf-9 insect cells were maintained in Grace's insect cell culture medium with 10% heated-inactivated fetal bovine serum, 1% Pluronic F-68 and 0.14 μg/ml Kanamycine sulfate at 27° C. in a shaker incubator. After infection with untagged baculovirus expressing human DGAT2 (hDGAT2) at multiplicity of infection (MOI) 3 for 48 hours, cells were harvested. Cell pellets were suspended in buffer containing 10 mM Tris-HCl pH 7.5, 1 mM EDTA, 250 mM sucrose and Complete Protease Inhibitor Cocktail (Sigma Aldrich), and sonicated on ice. Cell debris were removed by centrifugation at 2000×g for 15 minutes. Membrane fractions were isolated by ultracentrifugation (100,000×g), resuspended in the same TSQ Vantage MS/MS instrument were a spray voltage of 3000 V, capillary temperature of 280° C., vaporizer temperature 400° C., sheath gas 45 arbitrary unit, Aux gas 10 arbitrary units, S-lens 165 and collision gas 1.0 mTorr. Standard reference material (SRM) chromatograms of $^{13}C_{18}$-triolein (Q1:920.8>Q3:621.3) and internal standard $^{13}C_{21}$-triolein (Q1:923.8>Q3:617.3) were collected for 33 sec. The peak area was integrated by Xcalibur Quan software. The ratio between the $^{13}C_{18}$triolein generated in the reaction and spiked in internal standard $^{13}C_{21}$-triolein was used to generate percentage inhibition and $IC_{50}$ values. Compound percentage inhibition was calculated by the following formula: Inhibition %=1−[(compound response−low control)/(high control−low control)]×100%. Potent compounds were titrated and $IC_{50}$ were calculated by 4 parameter sigmoidal curve fitting formula.

DGAT2 Enzymatic Activity Assay

DGAT2 activity was determined by measuring the amount of enzymatic product $^{13}C_{18}$-triolein ($^{13}$C-1,2,3-Tri(cis-9-octadecenoyl)glycerol) using the membrane prep mentioned above. The assay was carried out in ABgene 384-well assay plates in a final volume of 25 μL at rt. The assay mixture contained the following: assay buffer (100 mM Tris·Cl, pH 7.0, 20 mM $MgCl_2$, 5% ethanol), 25 μM of diolein, 5 μM of $^{13}$C oleoyl-CoA and 8 ng/μL of DGAT2 membrane.

What is claimed is:

1. A compound of Formula I:

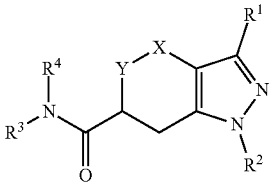

or pharmaceutically acceptable salts thereof wherein:

X and Y are independently selected from O or $C(R^5)_2$; wherein X and Y are both not O; and $R^1$ is (1) phenyl unsubstituted or substituted with 1, 2, or 3 $R^6$, (2) 5- or 6-membered heteroaryl containing 1, 2, 3 or 4 heteroatoms independently selected from N, O, and S, wherein the heteroaryl is unsubstituted or substituted with 1, 2, or 3 $R^6$, or (3) 8- to 10-membered fused heteroaryl containing 1, 2, 3 heteroatoms independently selected from N, O, and S, wherein the heteroaryl is unsubstituted or substituted with 1, 2, or 3 $R^6$;

$R^2$ is (1) aryl unsubstituted or substituted with 1, 2, or 3 $R^7$, (2) 5- or 6-membered heteroaryl containing 1, 2 or 3 heteroatoms independently selected from N, O, and S, wherein the heteroaryl is unsubstituted or substituted with 1, 2, or 3 $R^7$, (3) $C_{1-6}$alkyl unsubstituted or optionally mono-substituted, disubstituted or trisubstituted with halogen, OH, $CF_3$, —CN, or $(C_{3-6})$cycloalkyl, (4) $(C_{3-6})$cycloalkyl unsubstituted or optionally mono-substituted, disubstituted or trisubstituted with $C_{1-6}$alkyl, halogen, OH, $CF_3$, or —CN, (5) —$(C_{3-6})$alkylC(O)$NH_2$, (6) 4- to 6-membered heterocyclyl containing 1 or 2 heteroatoms independently selected from N, O and S wherein the heterocyclyl is unsubstituted or substituted by 1, 2, or 3 $R^7$, (7) —$CH_2$-aryl unsubstituted or substituted by 1, 2, or 3 $R^7$, (8) —$CH_2$-heterocyclyl unsubstituted or substituted by 1, 2, or 3 $R^7$, (9) —C(═O) $(C_{1-6})$alkyl unsubstituted or substituted with 1, 2, or 3 $R^7$,

(10) —C(═O) $(C_{3-6})$cycloalkyl unsubstituted or substituted with 1, 2, or 3 $R^7$,

(11) —C(═O) $(C_{1-6})$heterocyclyl unsubstituted or substituted with 1, 2, or 3 $R^7$,

(12) —C(═O) aryl unsubstituted or substituted with 1, 2, or 3 $R^7$,

(13) —$SO_2(C_{1-6})$alkyl unsubstituted or substituted with 1, 2, or 3 $R^7$, or

(14) —$SO_2$-aryl unsubstituted or substituted with 1, 2, or 3 $R^7$;

$R^3$ is (1) 4- to 7-membered heterocyclyl containing 1 or 2 heteroatoms independently selected from N, O and S, (2) 5- or 6-membered heteroaryl containing 1, 2 or 3 heteroatoms independently selected from N, O, and S, (3) —$(C_{1-6})$alkyl-heteroaryl, wherein the heteroaryl is a 5- or 6-membered heteroaryl containing 1, 2 or 3 heteroatoms independently selected from N, O and S, (4) —$(C_{1-6})$alkyl-aryl, (5) —$(C_{1-6})$alkyl-heterocyclyl, wherein the heterocyclyl is a 3- to 6-membered ring containing 1 or 2 heteroatoms independently selected from N, O and S, (6) —$(C_{1-6})$alkyl, (7) —$(C_{3-6})$cycloalkyl, (8) —$(C_{3-6})$cycloalkyl-heterocyclyl wherein the heterocyclyl is a 3- to 6-membered ring containing 1 or 2 heteroatoms independently selected from N, O and S, (9) —$(C_{1-6})$hydroxyalkyl,

(10) —$(C_{1-6})$alkyl-$S(O)_2$—$NR^{8a}R^{8b}$,

(11) —$(C_{1-6})$alkyl-$S(O)_2$—$(C_{1-3})$alkyl,

(12) —$(C_{1-3})$alkyl-heteroaryl, wherein the heteroaryl is an 8- to 10-membered fused ring, and wherein the heteroaryl contains 1, 2, 3, or 4 heteroatoms independently selected from N, O, and S,

(13) —$(C_{1-6})$alkyl-SONH—$(C_{1-3})$alkyl,

(14) —$(C_{1-6})$alkyl-$(C_{3-6})$cycloalkyl,

(15) fused aryl,

(16) —$C(_{1-6})$alkyl-$N(R^{11})_2$,

(17) —$C(_{1-6})$alkyl-O—$C_{1-3}$alkyl, or

(18) —$C(_{1-6})$alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$;

$R^4$ is (1) hydrogen, (2) $(C_{1-3})$alkyl, or $R^3$ and $R^4$, together with the nitrogen atom to which they are attached, combine to form a mono- or bicyclic heterocyclyl ring containing 1 N and optionally containing 1 additional heteroatoms independently selected from N, O and S, wherein the heterocyclyl ring is unsubstituted or substituted by 1, 2, or 3 $R^{11}$;

when present, each $R^5$ is selected from (1) hydrogen, (2) halogen, or (3) cyano;

when present, each $R^6$ is independently selected from (1) cyano, (2) halogen, (3) $(C_{1-6})$alkyl or $OC_{1-6}$alkyl wherein the alkyl moiety is optionally substituted with cyano, (4) $(C_{3-6})$cycloalkyl, optionally substituted with halogen, $C_{1-6}$alkyl, $C_{1-6}$haloalkyl, cyano, OH or $OC_{1-6}$ alkyl, (5) —$C(O)N(R^{11})_2$, (6) $(C_{3-6})$cycloalkyloxy wherein the cycloalkyl is optionally substituted with halogen, $C_{1-6}$alkyl, $C_{1-6}$haloalkyl, cyano, OH, or $OC_{1-6}$alkyl,
(7) hydroxy,
(8) —$NR^{11}R^{11}$,
(9) $(C_{1-6})$haloalkyl-,
(10) $(C_{1-6})$haloalkoxy-,
(11) —$SO_2(C_{1-6})$alkyl,
(12) —$SONH(C_{1-6})$alkyl,
(13) $C_{1-6}$alkyl-$NR^{11}R^{11}$, or
(14) 5 membered heteroaryl comprising 2 nitrogen atoms;

when present, each $R^7$ is independently selected from
(1) $(C_{1-6})$alkyl,
(2) halo,
(3) $(C_{1-6})$alkoxy-,
(4) $(C_{1-6})$haloalkyl-,
(5) $(C_{3-6})$cycloalkyl,
(6) C(O)H or —C(O)—OH,
(7) $C(O)(C_{1-6})$alkyl or —C(O)O—$(C_{1-6})$alkyl,
(8) hydroxy,
(9) CN,
(10) deuterium,
(11) $OC_{1-3}$haloalkyl, or
(12) oxo;

when present, $R^{8a}$ and $R^{8b}$ are independently selected from
(1) hydrogen,
(2) $(C_{1-3})$alkyl,
(3) —$(C_{1-3})$alkyl-phenyl,
(4) 5- or 6-membered heteroaryl containing 1, 2, or 3 heteroatoms independently selected from N, O, and S, or
(5) phenyl;

when present, each $R^9$ is independently selected from
(1) $(C_{1-3})$alkyl,
(2) $(C_{1-3})$ haloalkyl-,
(3) oxo,
(4) $(C_{3-6})$cycloalkyl,
(5) —C(O)O—$(C_{1-4})$alkyl,
(6) —$NR^{11}R^{11}$,
(7) hydroxy,
(8) phenyl, unsubstituted or substituted with halo,
(9) hydroxy$(C_{1-3})$alkyl-,
(10) cyano,
(11) halo,
(12) $C(O)C_{1-6}$alkyl or $C(O)C_{3-6}$cycloalkyl,
(13) $C(O)NHC_{1-3}$alkyl, or
(14) 6 membered heterocycle containing one Oxygen and one Nitrogen;

when present, $R^{10}$ is
(1) $(C_{1-3})$alkyl,
(2) $(C_{1-3})$hydroxy alkyl-,
(3) $(C_{1-3})$alkoxy-,
(4) hydroxy,
(5) halogen,
(6) $(C_{1-3})$haloalkyl-,
(7) $N(R^{11})_2$,
(8) $(C_{1-3})$alkyl-S—, or
(9) phenyl;

when present, $R^{11}$ is independently
(1) hydrogen, or
(2) $(C_{1-6})$alkyl;

when present, $R^{12}$, $R^{12a}$ and $R^{12b}$ are independently
(1) hydrogen,
(2) $(C_{1-6})$alkyl,
(3) $(C_{3-6})$cycloalkyl, or
(4) $(C_{1-6})$haloalkyl.

2. The compound of claim 1, or a pharmaceutically acceptable salt thereof, wherein $R^1$ is
(a) phenyl substituted with one to three substituents independently selected from hydroxy, halogen, hydroxy, CN, $C_{1-3}$alkyl, $C_{1-3}$alkyl-CN, $OC_{1-3}$alkyl-CN, $C_{1-3}$haloalkyl, $C_{3-6}$cycloalkyl, —$OC_{1-3}$alkyl, —$OC_{1-3}$ haloalkyl, —$OC_{3-6}$cycloalkyl, 5 membered heteroaryl containing 2 nitrogen atoms, $S(O)_2C_{1-6}$alkyl, $S(O)_2$ $NHC_{1-3}$alkyl, or $C_{1-3}$alkyl$NH_2$, and optionally further substituted with 1 or 2 substituents independently selected from halogen, $C_{1-3}$alkyl, $C_{1-3}$haloalkyl, CN, or OH;
(b) a 6 membered heteroaryl containing one or two nitrogen atoms substituted with one to two substituent selected from: halogen, hydroxy, $C_{1-3}$alkyl, $C_{1-3}$haloalkyl, $C_{3-6}$cycloalkyl, —$OC_{1-3}$alkyl, —$OC_{1-3}$haloalkyl, —O—$C_{3-6}$cycloalkyl, $C(O)NC_{1-6}$alkyl, or CN, and optionally further substituted with 1 or 2 fluoro atoms or $C_{1-3}$alkyl;
(c) a 5 membered heteroaryl containing one to four nitrogen atoms or heteroatoms independently selected from N, O, and S optionally substituted with one to two substituents independently selected from with halogen, $(C_{1-3})$alkyl, $(C_{3-6})$cycloalkyl, $(C_{1-3})$haloalkyl-, OH or $OC_{1-3}$alkyl; or
(d) 8- to 10-membered fused heteroaryl containing at least one nitrogen and optionally containing one oxygen optionally substituted with 1 or 2 substituents independently selected from halogen, $C_{1-3}$alkyl, $C_{1-3}$haloalkyl, $OC_{1-3}$alkyl, or $OC_{1-3}$haloalkyl.

3. The compound of claim 1, or a pharmaceutically acceptable salt thereof, wherein $R^1$ is
(a) phenyl substituted with a substituent selected from: hydroxy, halogen, CN, $C_{1-3}$alkyl, $C_{1-3}$alkyl-CN, $OC_{1-3}$ alkyl-CN, $C_{1-3}$haloalkyl, $C_{3-6}$cycloalkyl, —$OC_{1-3}$alkyl, —$OC_{1-3}$haloalkyl, —O-cyclopropyl, 5 membered heteroaryl containing 2 nitrogen atoms, $S(O)_2C_{1-3}$alkyl, $S(O)_2NHC_{1-3}$alkyl, or $C_{1-3}$alkyl$NH_2$, and optionally further substituted with 1 or 2 substituents independently selected from F, $CH_3$, $CF_3$, CN, or OH;
(b) a 6 membered heteroaryl containing one or two nitrogen atoms substituted with one or two substituents selected from: halogen, hydroxy, $C_{1-3}$alkyl, $C_{1-3}$haloalkyl, —$OC_{1-3}$alkyl, —$OC_{1-3}$haloalkyl, —O-cyclopropyl, or $C(O)NHC_{1-6}$alkyl, and optionally further substituted with 1 or 2 fluorine atoms or $CH_3$;
(c) 5 membered heteroaryl containing one to four nitrogen atoms or heteroatoms independently selected from N, O, and S optionally substituted with one to two substituents independently selected from with halogen, $(C_{1-3})$alkyl; or
(d) 9 or 10-membered fused heteroaryl containing one or two heteroatoms independently selected from nitrogen or oxygen optionally substituted with 1 or 2 methyl substituents.

4. The compound of claim 1, or a pharmaceutically acceptable salt thereof, wherein $R^1$ is

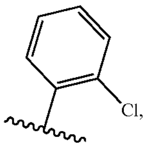
,
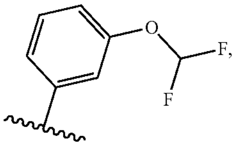
,

-continued
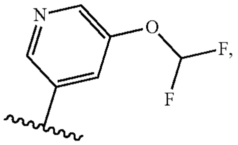,
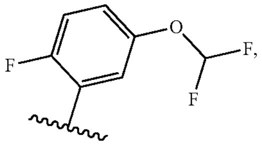,
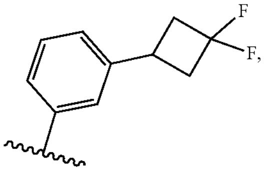,
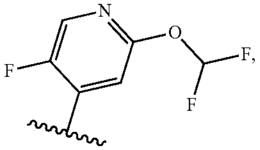,
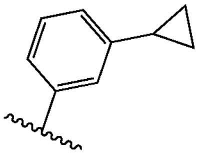,
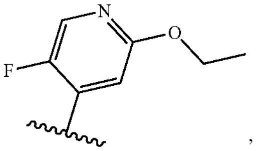,
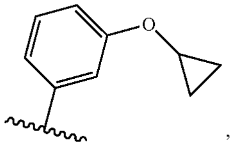,
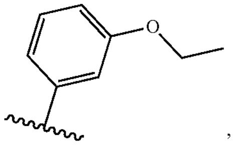,
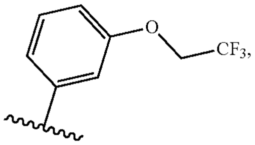,
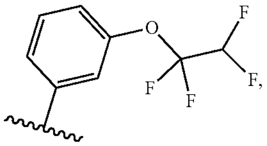,
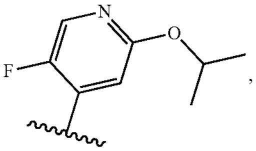,
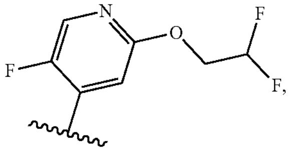,
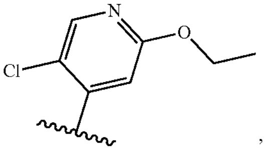,
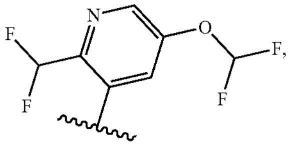,
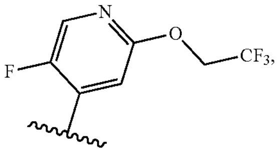,
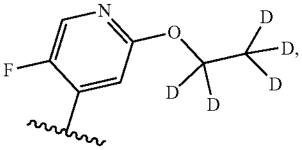,
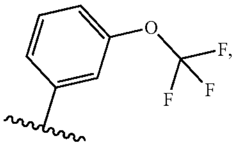,
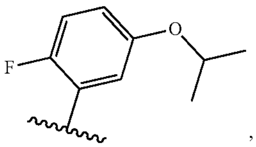,
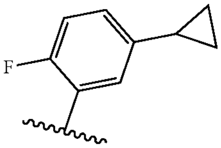,
-continued
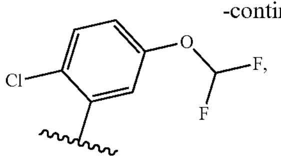,
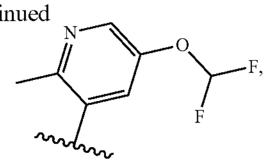,
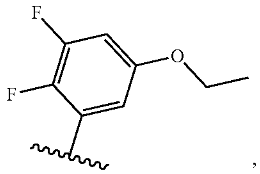,
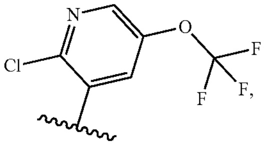,
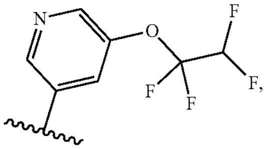,
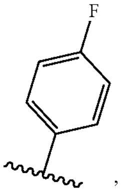,
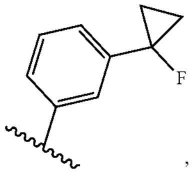,
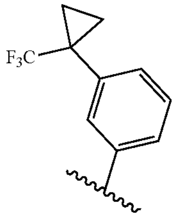,
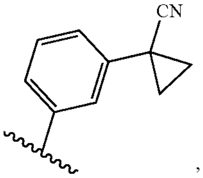,
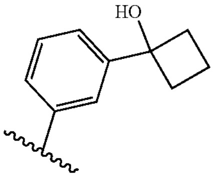,
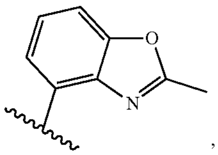,
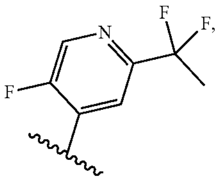
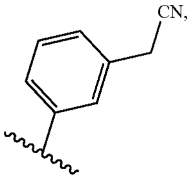,
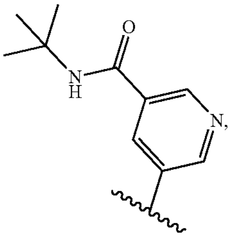, -continued

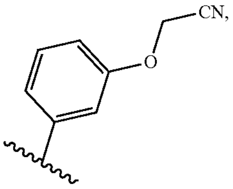

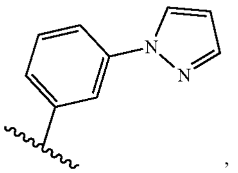

,

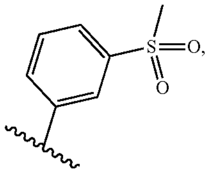

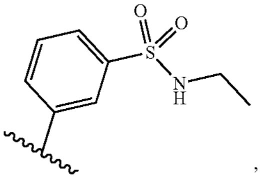

,

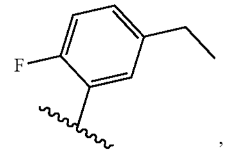

,

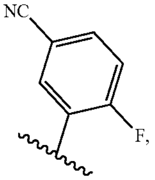

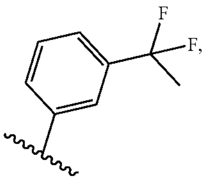

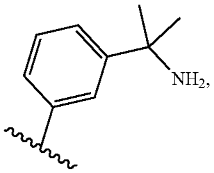

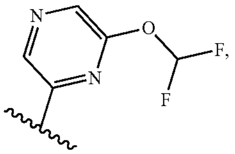

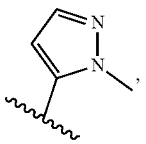

,

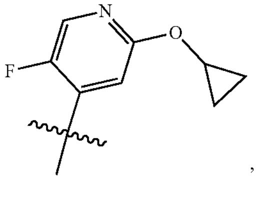

,

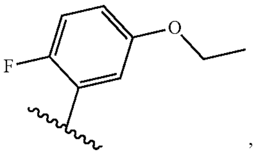

,

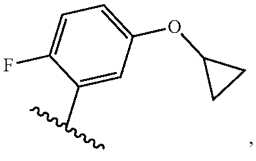

, or

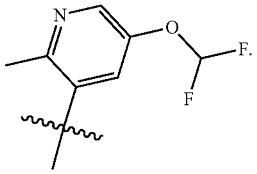

5. The compound of claim 1, or a pharmaceutically acceptable salt thereof, wherein $R^1$ is

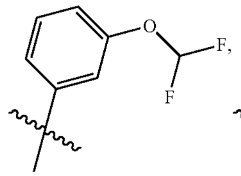

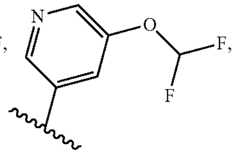

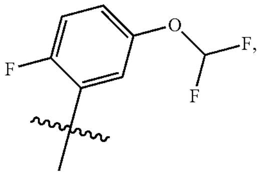

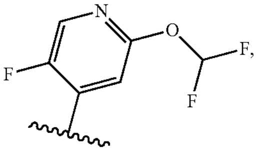

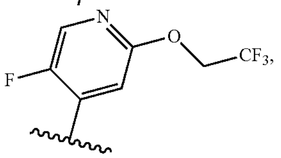

or

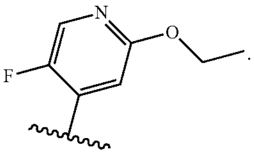

6. The compound of claim 1, or a pharmaceutically acceptable salt thereof, wherein $R^2$ is (a) phenyl unsubstituted or substituted with 1, 2, or 3 $R^7$, (b) 5- or 6-membered heteroaryl containing 1, 2 or 3 heteroatoms independently selected from N, O, and S, wherein the heteroaryl is unsubstituted or substituted with 1, 2, or 3 $R^7$, (c) $C_{1-6}$alkyl unsubstituted or mono-substituted, disubstituted, or trisubstituted with halogen, OH, $CF_3$, —CN, deuterium, or $(C_{3-6})$cycloalkyl, (d) $(C_{3-6})$cycloalkyl unsubstituted or optionally mono-substituted, disubstituted or trisubstituted with $C_{1-6}$alkyl, halogen, OH, $CF_3$, or —CN, (e) —$(C_{3-6})$alkylC(O)$NH_2$, (f) 4- to 6-membered heterocyclyl containing 1 or 2 heteroatoms independently selected from N, O and S wherein the heterocyclyl is unsubstituted or substituted by 1, 2, or 3 $R^7$, (g) —$CH_2$-heteroaryl unsubstituted or substituted by 1, 2, or 3 $R^7$, (h) —$CH_2$-aryl unsubstituted or substituted by 1, 2, or 3 $R^7$, (i) —$CH_2$-heterocyclyl unsubstituted or substituted by 1, 2, or 3 $R^7$, (j) —C(═O) $(C_{1-6})$alkyl unsubstituted or substituted with 1, 2, or 3 $R^7$, (k) —C(═O) $(C_{3-6})$cycloalkyl unsubstituted or substituted with 1, 2, or 3 $R^7$, (l) —C(═O) $(C_{1-6})$heterocyclyl unsubstituted or substituted with 1, 2, or 3 $R^7$, (m) —C(═O) aryl unsubstituted or substituted with 1, 2, or 3 $R^7$, (n) —$SO_2(C_{1-6})$alkyl unsubstituted or substituted with 1, 2, or 3 $R^7$, (o) ¯$SO_2(C_{3-6})$cycloalkyl unsubstituted or substituted with 1, 2, or 3 $R^7$, or (p) —$SO_2$-aryl unsubstituted or substituted with 1, 2, or 3 $R^7$.

7. The compound of claim 1, or a pharmaceutically acceptable salt thereof, wherein $R^2$ is (a) phenyl unsubstituted or substituted with 1, 2, or 3 $R^7$, (b) 5- or 6-membered heteroaryl containing 1, 2 or 3 heteroatoms independently selected from N and S, wherein the heteroaryl is unsubstituted or substituted with 1 or 2 halogen, $C_{1-3}$alkyl, or cyclopropyl, (c) $C_{1-6}$alkyl unsubstituted or mono-substituted, disubstituted, or trisubstituted with halogen, OH, $CF_3$, —CN, deuterium, or $(C_{3-6})$cycloalkyl, (d) $(C_{3-6})$cycloalkyl unsubstituted or optionally mono-substituted, disubstituted or trisubstituted with halogen, $C_{1-6}$alkyl, $OC_{1-3}$haloalkyl, OH, $CF_3$, or —CN, (e) —$(C_{3-6})$alkylC(O)$NH_2$, (f) 4- to 6-membered heterocyclyl containing 1 or 2 heteroatoms independently selected from N, O and S wherein the heterocyclyl is unsubstituted or substituted with 1 or 2 substituents selected from $CH_3$ or oxo, (g) —$CH_2$-heteroaryl unsubstituted or substituted with 1 or 2 methyl substituents, (h) —$CH_2$-aryl, (i) $CH_2$-heterocyclyl, (j) —C(═O) $(C_{1-6})$alkyl, (k) —C(═O) $(C_{3-6})$cycloalkyl, (l) —C(═O) $(C_{1-6})$ heterocyclyl, (m) —C(═O) aryl, (n) —$SO_2(C_{1-6})$alkyl, (o) —$SO_2$ $(C_{3-6})$cycloalkyl.

8. The compound of claim 1, or a pharmaceutically acceptable salt thereof, wherein $R^2$ is (a) phenyl unsubstituted or substituted with halogen or $OCHF_2$, (b) 5- or 6-membered heteroaryl containing 1, 2 or 3 heteroatoms independently selected from N and S, wherein the heteroaryl is unsubstituted or substituted with 1 or 2 halogen, $C_{1-3}$alkyl, or cyclopropyl, (c) $C_{1-6}$alkyl unsubstituted or mono-substituted, disubstituted, or trisubstituted with halogen, OH, $CF_3$, —CN, deuterium, or $(C_{3-6})$cycloalkyl, (d) $(C_{3-6})$cycloalkyl unsubstituted or optionally mono-substituted, disubstituted or trisubstituted with halogen, $C_{1-6}$alkyl, $OC_{1-3}$haloalkyl, OH, $CF_3$, or —CN, (e) —$(C_{3-6})$alkylC(O)$NH_2$, (f) 4- to 6-membered heterocyclyl containing 1 or 2 heteroatoms independently selected from N, O and S wherein the heterocyclyl is unsubstituted or substituted with 1 or 2 substituents selected from $CH_3$ or oxo, (g) —$CH_2$-heteroaryl unsubstituted or substituted with 1 or 2 methyl substituents, (h) —$CH_2$-aryl, (i) —$CH_2$-heterocyclyl, (j) —C(═O) $(C_{1-6})$alkyl, (k) —C(═O) $(C_{3-6})$cycloalkyl, (l) —C(═O) $(C_{1-6})$ heterocyclyl, (m) —C(═O) aryl, (n) —$SO_2(C_{1-6})$alkyl, or (o) —$SO_2(C_{3-6})$cycloalkyl.

9. The compound of claim 1, or a pharmaceutically acceptable salt thereof, wherein $R^2$ is

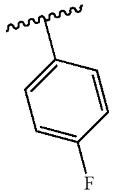, 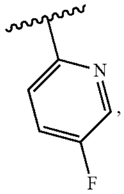, 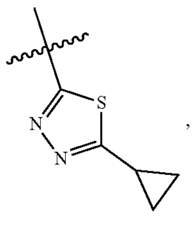,

-continued

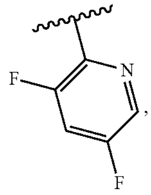, 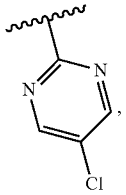, 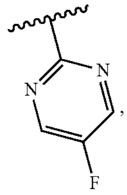,

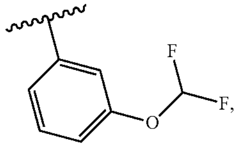 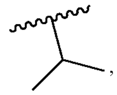, 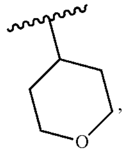,

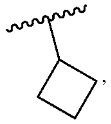, 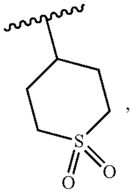, 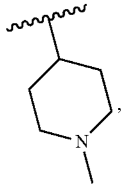,

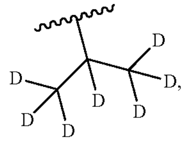 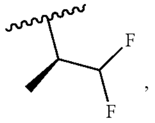, 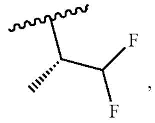,

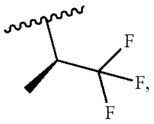 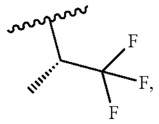 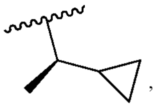,

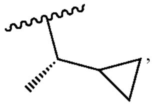, 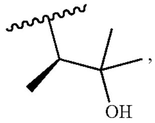, 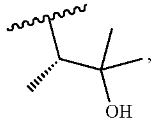,

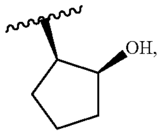 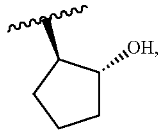

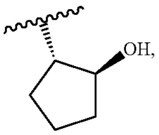 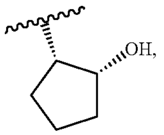 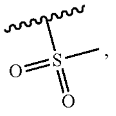,

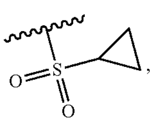, 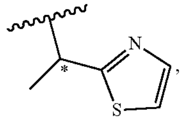, 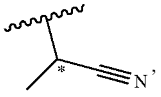

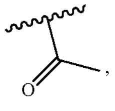, 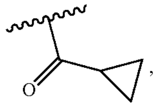, 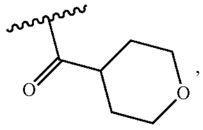,

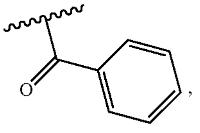, 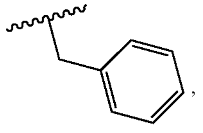, or

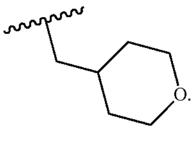

10. The compound of claim 1, or a pharmaceutically acceptable salt thereof, wherein $R^3$ is (a) 4- to 7-membered heterocyclyl containing 1 or 2 heteroatoms independently selected from N, O and S, (b) 5- or 6-membered heteroaryl containing 1, 2 or 3 heteroatoms independently selected from N, O, and S, (c) —$(C_{1-6})$alkyl-heteroaryl, wherein the heteroaryl is a 5- or 6-membered heteroaryl containing 1, 2, or 3 heteroatoms independently selected from N, O and S, (d) —$(C_{1-6})$alkyl-aryl, (e) —$(C_{1-6})$alkyl-heterocyclyl, wherein the heterocyclyl is a 3- to 6-membered ring containing 1 or 2 heteroatoms independently selected from N, O and S, (f) —$(C_{1-6})$alkyl, (g) —$(C_{3-6})$cycloalkyl, (h) —$(C_{3-6})$cycloalkyl-heterocyclyl wherein the heterocyclyl is a 3- to 6-membered ring containing 1 or 2 heteroatoms independently selected from N, O and S, (i) —$(C_{1-6})$hydroxyalkyl, (j) —$(C_{1-6})$alkyl-$S(O)_2$—$NR^{8a}R^{8b}$, (k) —$(C_{1-6})$alkyl-$S(O)_2$—$(C_{1-3})$alkyl, (l) —$(C_{1-3})$alkyl-heteroaryl, wherein the heteroaryl is an 8- to 10-membered fused ring, and wherein the heteroaryl contains 1, 2, 3, or 4 heteroatoms independently selected from N, O, and S, (m) —$(C_{1-6})$alkyl-SONH—$(C_{1-3})$alkyl, (n) —$(C_{1-6})$alkyl-$(C_{3-6})$cycloalkyl, (o) fused aryl, (p) —$C(_{1-6})$alkyl-$N(R^{11})_2$, (q) —$C(_{1-6})$alkyl-O—$C_{1-3}$alkyl, or (r) —$C(_{1-6})$alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

11. The compound of claim 1, or a pharmaceutically acceptable salt thereof, wherein $R^3$ is (a) 4- to 7-membered heterocyclyl containing 1 or 2 heteroatoms independently selected from N, O and S, (b) 5- or 6-membered heteroaryl containing 1, 2 or 3 heteroatoms independently selected from N, O, and S, (c) —$(C_{1-6})$alkyl-heteroaryl, wherein the heteroaryl is a 5- or 6-membered heteroaryl containing 1, 2, or 3 heteroatoms independently selected from N, O and S, (d) —$(C_{1-6})$alkyl-aryl, (e) —$(C_{1-6})$alkyl-heterocyclyl, wherein the heterocyclyl is a 3- to 6-membered ring containing 1 or 2 heteroatoms independently selected from N, O and S, (f) —$(C_{1-6})$alkyl, (g) —$(C_{3-6})$cycloalkyl, (h) —$(C_{3-6})$cycloalkyl-heterocyclyl wherein the heterocyclyl is a 3- to 6-membered ring containing 1 or 2 heteroatoms independently selected from N, O and S, or (i) —$(C_{1-6})$alkyl-$S(O)_2$—$NR^{8a}R^{8b}$, (j) —$C(_{1-6})$alkyl-O—$C_{1-3}$alkyl, or (k) —$C(_{1-6})$alkyl-O—$C_{3-6}$cycloalkyl, wherein each aryl, fused aryl, heteroaryl, cycloalkyl, or heterocyclyl is unsubstituted or substituted with 1, 2, or 3 $R^9$, and wherein each alkyl is unsubstituted or substituted with 1, 2, or 3 $R^{10}$.

12. The compound of claim 1, or a pharmaceutically acceptable salt thereof, wherein $R^3$ is

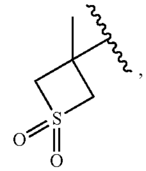, 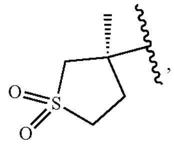, 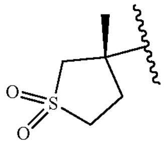,

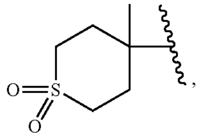, 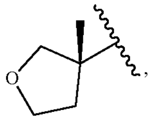, 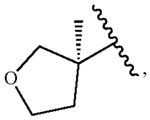,

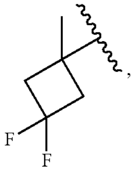, 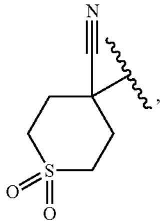, 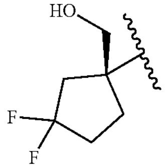,

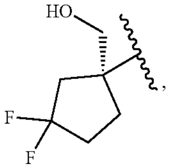, 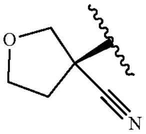, 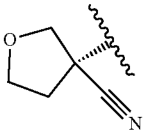,

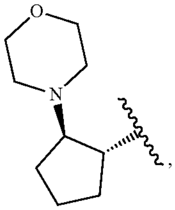, 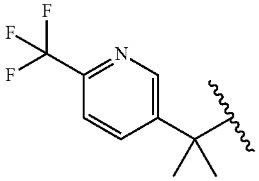,

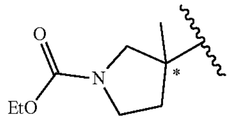, 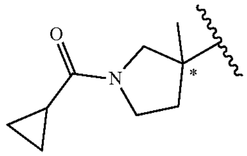,

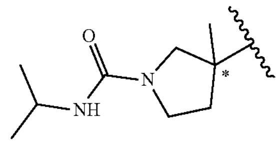, 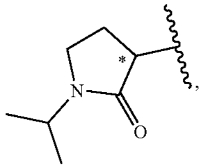,

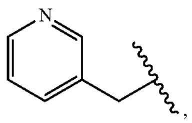, 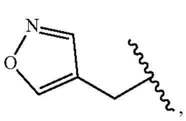, 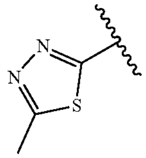,

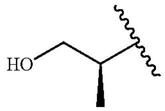, 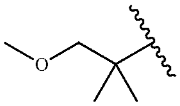,

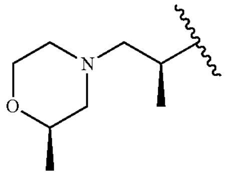, 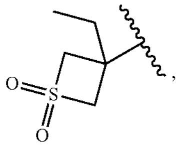,

-continued

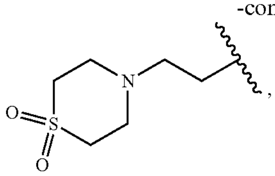

, or

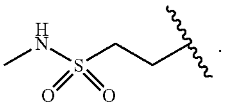

13. The compound of claim 1, or a pharmaceutically acceptable salt thereof, wherein $R^4$ is H.

14. The compound of claim 1, or a pharmaceutically acceptable salt thereof, wherein $R^5$ is H, halogen, or CN.

15. The compound of claim 1, or a pharmaceutically acceptable salt thereof, wherein $R^5$ is H, F, Cl, or CN.

16. The compound of claim 1, or a pharmaceutically acceptable salt thereof, wherein $R^6$ is halogen, hydroxy, CN, $C_{1-3}$alkyl, $C_{1-3}$haloalkyl, $C_{3-6}$cycloalkyl, $OC_{1-3}$alkyl, $OC_{1-3}$ haloalkyl, $OC_{3-6}$cycloalkyl, $S(O)_2C_{1-3}$alkyl, $S(O)_2NHC_{1-3}$ alkyl, $C(O)NHC_{1-3}$alkyl, $C_{1-6}$alkyl$NR^{11}R^{11}$, or 5 membered heteroaryl with 2 N atoms, and wherein the cycloalkyl is optionally substituted with halogen.

17. The compound of claim 1, or a pharmaceutically acceptable salt thereof, wherein $R^6$ is $C_{1-3}$alkyl, O—$C_{3-6}$ cycloalkyl, $OC_{1-3}$alkyl, $S(O)_2C_{1-3}$alkyl, $S(O)_2NHC_{1-3}$alkyl, $C(O)NHC_{1-3}$alkyl, $C_{1-6}$alkyl$NR^{11}R^{11}$, or 5 membered heteroaryl with 2 N atoms, and wherein the cycloalkyl is additionally optionally substituted with 1-3 F.

18. The compound of claim 1, or a pharmaceutically acceptable salt thereof, wherein $R^6$ is $CH_3$, $OCH_2CH_3$, $C(O)NHC(CH_3)_3$, $C(CH_3)_2NH_2$, $S(O_2)CH_3$, $S(O_2)NHCH_2CH_3$, $OCD_2CD_3$, pyrazolidine, or O-cyclopropyl, and wherein the cyclopropyl is additionally optionally substituted with one to three halogen atoms: CN, $CF_3$, or OH.

19. The compound of claim 1, or a pharmaceutically acceptable salt thereof, wherein $R^7$ is halogen, oxo, $C_{1-6}$alkyl, $OC_{1-6}$haloalkyl, CN, deuterium, or $C_{3-6}$cycloalkyl.

20. The compound of claim 1, or a pharmaceutically acceptable salt thereof, wherein $R^7$ is F, Cl, oxo, $OCHF_2$, $CH_3$, CN, deuterium, or cyclopropyl.

21. The compound of claim 1, or a pharmaceutically acceptable salt thereof, wherein $R^{8a}$ and $R^{8b}$ are independently selected from hydrogen or $(C_{1-3})$alkyl.

22. The compound of claim 1, or a pharmaceutically acceptable salt thereof, wherein $R^9$ is =O, halogen, OH, $C_{1-6}$alkyl, $C_{1-6}$haloalky, $C_{1-3}$alkyl-CN, $C(O)C_{3-6}$cycloalkyl, $C(O)C_{1-3}$alkylOH, $C(O)NHC_{1-3}$alkyl, or $C_{1-6}$alkylOH, or a 6 membered heterocycle containing one Oxygen and one Nitrogen atom.

23. The compound of claim 1, or a pharmaceutically acceptable salt thereof, wherein $R^9$ is =O, $CH_3$, $CH_2CH_3$, F, $CF_3$, $CH_3CN$, C(O)cyclopropyl, C(O)EtO, $CH(CH_3)_2$, or $C(O)NHCH(CH_3)_2$, or a 6 membered heterocycle containing one Oxygen and one Nitrogen atom.

24. The compound of claim 1, or a pharmaceutically acceptable salt thereof, wherein $R^{10}$ is =O, halogen, OH, $C_{1-6}$alkyl, $C_{1-6}$haloalky, or $C_{1-6}$alkylOH.

25. The compound of claim 1, or a pharmaceutically acceptable salt thereof, wherein $R^{10}$ is OH, $CH_3$, or $OCH_3$.

26. The compound of claim 1, or a pharmaceutically acceptable salt thereof, wherein X and Y are $C(R^5)$.

27. The compound of claim 1, or a pharmaceutically acceptable salt thereof, wherein X is O, and Y is $C(R^5)$.

28. The compound of claim 1, or a pharmaceutically acceptable salt thereof, wherein X is $C(R^5)$, and Y is O.

29. The compound of claim 1, or a pharmaceutically acceptable salt thereof, which is 3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (S)-3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(2-chlorophenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N-(3-methyl-1,1-dioxidothietan-3-yl)-4,5,6,7-tetrahydro-1H-indazole-6-carboxamide, 1-(5-cyclopropyl-1,3,4-thiadiazol-2-yl)-3-(5-(difluoromethoxy)pyridin-3-yl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-1-(5-fluoropyridin-2-yl)-N—((R)-3-methyltetrahydrofuran-3-yl)-4,5,6,7-tetrahydro-1H-indazole-6-carboxamide, (R)-3-(3-(difluoromethoxy)phenyl)-1-(5-fluoropyridin-2-yl)-N—((S)-3-methyltetrahydrofuran-3-yl)-4,5,6,7-tetrahydro-1H-indazole-6-carboxamide, (R)—N-(3,3-difluoro-1-methylcyclobutyl)-3-(3-(difluoromethoxy)phenyl)-1-(5-fluoropyridin-2-yl)-4,5,6,7-tetrahydro-1H-indazole-6-carboxamide, (R)—N—((R)-3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide, (R)—N—((S)-3,3-difluoro-1-(hydroxymethyl)cyclopentyl)-3-(3-(difluoromethoxy)phenyl)-1-(5-fluoropyridin-2-yl)-4,5,6,7-tetrahydro-1H-indazole-6-carboxamide, (R)-3-(3-(difluoromethoxy)phenyl)-1-(3,5-difluoropyridin-2-yl)-N-(3-methyl-1,1-dioxidothietan-3-yl)-4,5,6,7-tetrahydro-1H-indazole-6-carboxamide, 1-(5-chloropyrimidin-2-yl)-3-(3-(difluoromethoxy)phenyl)-N—((S)-3-methyl-1,1-dioxidotetrahydrothiophen-3-yl)-4,5,6,7-tetrahydro-1H-indazole-6-carboxamide, ((R)-3-(5-(difluoromethoxy)-2-fluorophenyl)-1-(3,5-difluoropyridin-2-yl)-N-(3-methyl-1,1-dioxidothietan-3-yl)-4,5,6,7-tetrahydro-1H-indazole-6-carboxamide, (R)-3-(5-(difluoromethoxy)pyridin-3-yl)-1-(5-fluoropyridin-2-yl)-N-(3-methyl-1,1-dioxidothietan-3-yl)-4,5,6,7-tetrahydro-1H-indazole-6-carboxamide, (R)-3-(3-(3,3-difluorocyclobutyl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(5-(difluoromethoxy)pyridin-3-yl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)—N—((S)-3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide, (R)—N—((R)-3-cyanotetrahydrofuran-3-yl)-3-(5-(difluoromethoxy)pyridin-3-yl)-1-(5-fluoropyridin-2-yl)-4,5,6,7-tetrahydro-1H-indazole-6-carboxamide, 3-(3-(difluoromethoxy)phenyl)-1-(5-fluoropyridin-2-yl)-N-((1R,2R)-2-morpholinocyclopentyl)-4,5,6,7-tetrahydro-1H-indazole-6-carboxamide,
(R)-3-(2-(difluoromethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(2-ethoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(3-(difluoromethoxy)phenyl)-N-(3-methyl-1,1-dioxidothietan-3-yl)-1-(tetrahydro-2H-pyran-4-yl)-4,5,6,7-tetrahydro-1H-indazole-6-carboxamide,
(R)-3-(3-(difluoromethoxy)phenyl)-1-(1,1-dioxidotetrahydro-2H-thiopyran-4-yl)-N—((S)-3-methyl-1,1-dioxidotetrahydrothiophen-3-yl)-4,5,6,7-tetrahydro-1H-indazole-6-carboxamide,
(R)-3-(3-(difluoromethoxy)phenyl)-1-isopropyl-N—((S)-3-methyl-1,1-dioxidotetrahydrothiophen-3-yl)-4,5,6,7-tetrahydro-1H-indazole-6-carboxamide,
(R)-3-(3-(difluoromethoxy)phenyl)-1-isopropyl-N-(3-methyl-1,1-dioxidothietan-3-yl)-4,5,6,7-tetrahydro-1H-indazole-6-carboxamide,
(R)-3-(3-(difluoromethoxy)phenyl)-1-(tetrahydro-2H-pyran-4-yl)-N-(2-(6-(trifluoromethyl) pyridin-3-yl) propan-2-yl)-4,5,6,7-tetrahydro-1H-indazole-6-carboxamide,
(R)-3-(5-(difluoromethoxy)-2-fluorophenyl)-1-isopropyl-N—((S)-3-methyl-1,1-dioxidotetrahydrothiophen-3-yl)-4,5,6,7-tetrahydro-1H-indazole-6-carboxamide,
(R)-3-(5-(difluoromethoxy)-2-fluorophenyl)-1-isopropyl-N—((R)-3-methyl-1,1-dioxidotetrahydrothiophen-3-yl)-4,5,6,7-tetrahydro-1H-indazole-6-carboxamide,
(R)-3-(5-(difluoromethoxy)-2-fluorophenyl)-1-isopropyl-N-(4-methyl-1,1-dioxidotetrahydro-2H-thiopyran-4-yl)-4,5,6,7-tetrahydro-1H-indazole-6-carboxamide,
(R)-3-(3-(difluoromethoxy)phenyl)-1-isopropyl-N-(4-methyl-1,1-dioxidotetrahydro-2H-thiopyran-4-yl)-4,5,6,7-tetrahydro-1H-indazole-6-carboxamide,
(R)-3-(3-cyclopropoxyphenyl)-1-isopropyl-N-(4-methyl-1,1-dioxidotetrahydro-2H-thiopyran-4-yl)-4,5,6,7-tetrahydro-1H-indazole-6-carboxamide,
(R)-3-(3-ethoxyphenyl)-1-isopropyl-N-(4-methyl-1,1-dioxidotetrahydro-2H-thiopyran-4-yl)-4,5,6,7-tetrahydro-1H-indazole-6-carboxamide,
(R)-3-(2-ethoxy-5-fluoropyridin-4-yl)-1-isopropyl-N-(3-methyl-1,1-dioxidothietan-3-yl)-4,5,6,7-tetrahydro-1H-indazole-6-carboxamide,
(R)-1-isopropyl-N—((S)-3-methyl-1,1-dioxidotetrahydrothiophen-3-yl)-3-(3-(2,2,2-trifluoroethoxy)phenyl)-4,5,6,7-tetrahydro-1H-indazole-6-carboxamide,
(R)-1-isopropyl-N-(4-methyl-1,1-dioxidotetrahydro-2H-thiopyran-4-yl)-3-(3-(1,1,2,2-tetrafluoroethoxy)phenyl)-4,5,6,7-tetrahydro-1H-indazole-6-carboxamide,
(R)-3-(2-cyclopropoxy-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(5-fluoro-2-isopropoxypyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(5-chloro-2-ethoxypyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(2-(2,2-difluoroethoxy)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(2-(difluoromethoxy)-5-fluoropyridin-4-yl)-1-isopropyl-N—((S)-3-methyl-1,1-dioxidotetrahydrothiophen-3-yl)-4,5,6,7-tetrahydro-1H-indazole-6-carboxamide,
(R)-3-(5-(difluoromethoxy)-2-(difluoromethyl) pyridin-3-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(5-fluoro-2-(2,2,2-trifluoroethoxy)pyridin-4-yl)-1-isopropyl-N-(3-methyl-1,1-dioxidothietan-3-yl)-4,5,6,7-tetrahydro-1H-indazole-6-carboxamide,
(R)-3-(5-fluoro-2-(2,2,2-trifluoroethoxy)pyridin-4-yl)-1-isopropyl-N—((S)-3-methyl-1,1-dioxidotetrahydrothiophen-3-yl)-4,5,6,7-tetrahydro-1H-indazole-6-carboxamide,
(R)-3-(5-fluoro-2-(2,2,2-trifluoroethoxy)pyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-3-(5-(difluoromethoxy)-2-fluorophenyl)-N-(4-methyl-1,1-dioxidotetrahydro-2H-thiopyran-4-yl)-1-(propan-2-yl-$d_7$)-4,5,6,7-tetrahydro-1H-indazole-6-carboxamide,
(R)-3-(2-ethoxy-5-fluoropyridin-4-yl)-N-(4-methyl-1,1-dioxidotetrahydro-2H-thiopyran-4-yl)-1-(propan-2-yl-$d_7$)-4,5,6,7-tetrahydro-1H-indazole-6-carboxamide,
(R)-3-(5-(difluoromethoxy)-2-fluorophenyl)-1-((R)-1,1-difluoropropan-2-yl)-N-(3-methyl-1,1-dioxidothietan-3-yl)-4,5,6,7-tetrahydro-1H-indazole-6-carboxamide,
(R)-3-(5-(difluoromethoxy)-2-fluorophenyl)-1-((S)-1,1-difluoropropan-2-yl)-N-(3-methyl-1,1-dioxidothietan-3-yl)-4,5,6,7-tetrahydro-1H-indazole-6-carboxamide,
(R)-3-(5-(difluoromethoxy)-2-fluorophenyl)-1-((R)-1,1-difluoropropan-2-yl)-N-(4-methyl-1,1-dioxidotetrahydro-2H-thiopyran-4-yl)-4,5,6,7-tetrahydro-1H-indazole-6-carboxamide,
(R)-3-(5-(difluoromethoxy)-2-fluorophenyl)-1-((S)-1,1-difluoropropan-2-yl)-N-(4-methyl-1,1-dioxidotetrahydro-2H-thiopyran-4-yl)-4,5,6,7-tetrahydro-1H-indazole-6-carboxamide,
(R)-3-(2-(ethoxy-$d_5$)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)—N-(4-cyano-1,1-dioxidotetrahydro-2H-thiopyran-4-yl)-3-(5-(difluoromethoxy)-2-fluorophenyl)-1-(propan-2-yl-d7)-4,5,6,7-tetrahydro-1H-indazole-6-carboxamide,
(R)—N-(4-cyano-1,1-dioxidotetrahydro-2H-thiopyran-4-yl)-3-(5-(difluoromethoxy)-2-fluorophenyl)-1-isopropyl-4,5,6,7-tetrahydro-1H-indazole-6-carboxamide,
(R)-3-(2-ethoxy-5-fluoropyridin-4-yl)-N-(4-methyl-1,1-dioxidotetrahydro-2H-thiopyran-4-yl)-1-((R)-1,1,1-trifluoropropan-2-yl)-4,5,6,7-tetrahydro-1H-indazole-6-carboxamide,
(R)-3-(2-ethoxy-5-fluoropyridin-4-yl)-N-(4-methyl-1,1-dioxidotetrahydro-2H-thiopyran-4-yl)-1-((S)-1,1,1-trifluoropropan-2-yl)-4,5,6,7-tetrahydro-1H-indazole-6-carboxamide,
(R)-3-(5-ethoxy-2-fluorophenyl)-1-isopropyl-N-(4-methyl-1,1-dioxidotetrahydro-2H-thiopyran-4-yl)-4,5,6,7-tetrahydro-1H-indazole-6-carboxamide,
(R)-1-isopropyl-N-(4-methyl-1,1-dioxidotetrahydro-2H-thiopyran-4-yl)-3-(3-(trifluoromethoxy)phenyl)-4,5,6,7-tetrahydro-1H-indazole-6-carboxamide,
(R)-3-(5-(difluoromethoxy)pyridin-3-yl)-1-isopropyl-N-(4-methyl-1,1-dioxidotetrahydro-2H-thiopyran-4-yl)-4,5,6,7-tetrahydro-1H-indazole-6-carboxamide, (R)-1-cyclobutyl-3-(5-(difluoromethoxy)-2-fluorophenyl)-N-(3-methyl-1,1-dioxidothietan-3-yl)-4,5,6,7-tetrahydro-1H-indazole-6-carboxamide, (R)-1-((R)-1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide, (R)-1-((S)-1-cyclopropylethyl)-3-(5-(difluoromethoxy)-2-fluorophenyl)-N-(3-methyl-1,1-dioxidothietan-3-yl)-4,5,6,7-tetrahydro-1H-indazole-6-carboxamide, ethyl 3-((R)-3-(5-(difluoromethoxy)-2-fluorophenyl)-1-isopropyl-4,5,6,7-tetrahydro-1H-indazole-6-carboxamido)-3-methylpyrrolidine-1-carboxylate, (6R)-3-(5-(difluoromethoxy)-2-fluorophenyl)-1-isopropyl-N-(1-(isopropylcarbamoyl)-3-methylpyrrolidin-3-yl)-4,5,6,7-tetrahydro-1H-indazole-6-carboxamide, (6R)—N-(1-(cyclopropanecarbonyl)-3-methylpyrrolidin-3-yl)-3-(5-(difluoromethoxy)-2-fluorophenyl)-1-isopropyl-4,5,6,7-tetrahydro-1H-indazole-6-carboxamide, (R)-3-(2-fluoro-5-isopropoxyphenyl)-1-isopropyl-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-isopropyl-N-(3-methyl-1,1-dioxidothietan-3-yl)-4,5,6,7-tetrahydro-1H-indazole-6-carboxamide, (R)-3-(5-cyclopropyl-2-fluorophenyl)-1-isopropyl-N-(3-methyl-1,1-dioxidothietan-3-yl)-4,5,6,7-tetrahydro-1H-indazole-6-carboxamide, (R)-3-(2-chloro-5-(difluoromethoxy)phenyl)-1-isopropyl-N-(3-methyl-1,1-dioxidothietan-3-yl)-4,5,6,7-tetrahydro-1H-indazole-6-carboxamide, (R)-3-(5-cyclopropoxy-2-fluorophenyl)-1-isopropyl-N-(3-methyl-1,1-dioxidothietan-3-yl)-4,5,6,7-tetrahydro-1H-indazole-6-carboxamide, (R)-3-(5-(difluoromethoxy)-2-methylpyridin-3-yl)-1-isopropyl-N-(3-methyl-1,1-dioxidothietan-3-yl)-4,5,6,7-tetrahydro-1H-indazole-6-carboxamide, (R)-3-(5-ethoxy-2,3-difluorophenyl)-1-isopropyl-N-(3-methyl-1,1-dioxidothietan-3-yl)-4,5,6,7-tetrahydro-1H-indazole-6-carboxamide, (R)-3-(2-chloro-5-(trifluoromethoxy)pyridin-3-yl)-1-isopropyl-N-(3-methyl-1,1-dioxidothietan-3-yl)-4,5,6,7-tetrahydro-1H-indazole-6-carboxamide, (R)—N-(3,3-difluoro-1-methylcyclobutyl)-3-(5-(difluoromethoxy)-2-methylpyridin-3-yl)-1-isopropyl-4,5,6,7-tetrahydro-1H-indazole-6-carboxamide, (R)-1-isopropyl-N-(3-methyl-1,1-dioxidothietan-3-yl)-3-(5-(1,1,2,2-tetrafluoroethoxy)pyridin-3-yl)-4,5,6,7-tetrahydro-1H-indazole-6-carboxamide, (R)-1-isopropyl-N—((S)-3-methyl-1,1-dioxidotetrahydrothiophen-3-yl)-3-(5-(1,1,2,2-tetrafluoroethoxy) pyridin-3-yl)-4,5,6,7-tetrahydro-1H-indazole-6-carboxamide, (R)-1-isopropyl-N-(4-methyl-1,1-dioxidotetrahydro-2H-thiopyran-4-yl)-3-(5-(1,1,2,2-tetrafluoroethoxy)pyridin-3-yl)-4,5,6,7-tetrahydro-1H-indazole-6-carboxamide, (R)-3-(5-fluoro-2-(2,2,2-trifluoroethoxy)pyridin-4-yl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-fluoro-2-(2,2,2-trifluoroethoxy)pyridin-4-yl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-((R)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(2-ethoxy-5-fluoropyridin-4-yl)-1-((S)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(2-ethoxy-5-fluoropyridin-4-yl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(2-ethoxy-5-fluoropyridin-4-yl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-(difluoromethoxy)-2-fluorophenyl)-1-((R)-3-hydroxy-3-methylbutan-2-yl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((S)-3-hydroxy-3-methylbutan-2-yl)-N-(3-methyl-1,1-dioxidothietan-3-yl)-4,5,6,7-tetrahydro-1H-indazole-6-carboxamide, (R)-3-(3-(difluoromethoxy)phenyl)-1-((R)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(3-(difluoromethoxy)phenyl)-1-((S)-3-hydroxy-3-methylbutan-2-yl)-N-(4-methyl-1,1-dioxidotetrahydro-2H-thiopyran-4-yl)-4,5,6,7-tetrahydro-1H-indazole-6-carboxamide, (R)-3-(5-fluoro-2-(2,2,2-trifluoroethoxy)pyridin-4-yl)-1-((R)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)-3-(5-fluoro-2-(2,2,2-trifluoroethoxy)pyridin-4-yl)-1-((S)-3-hydroxy-3-methylbutan-2-yl)-N—((S)-3-methyl-1,1-dioxidotetrahydrothiophen-3-yl)-4,5,6,7-tetrahydro-1H-indazole-6-carboxamide, (R)—N-(4-cyano-1,1-dioxidotetrahydro-2H-thiopyran-4-yl)-3-(5-fluoro-2-(2,2,2-trifluoroethoxy)pyridin-4-yl)-1-((R)-3-hydroxy-3-methylbutan-2-yl)-4,5,6,7-tetrahydro-1H-indazole-6-carboxamide, (R)—N-(4-cyano-1,1-dioxidotetrahydro-2/I-thiopyran-4-yl)-3-(5-fluoro-2-(2,2,2-trifluoroethoxy)pyridin-4-yl)-1-((S)-3-hydroxy-3-methylbutan-2-yl)-4,5,6,7-tetrahydro-1H-indazole-6-carboxamide, (R)-3-(5-(difluoromethoxy)-2-fluorophenyl)-1-((1R,2S)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1R,2R)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1S,2S)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-1-((1S,2R)-2-hydroxycyclopentyl)-N-(3-methyl-1,1-dioxidothietan-3-yl)-4,5,6,7-tetrahydro-1H-indazole-6-carboxamide, (R)-3-(5-(difluoromethoxy)-2-fluorophenyl)-N-(3-methyl-1,1-dioxidothietan-3-yl)-1-(methylsulfonyl)-4,5,6,7-tetrahydro-1H-indazole-6-carboxamide, (R)-1-(cyclopropylsulfonyl)-3-(5-(difluoromethoxy)-2-fluorophenyl)-N-(3-methyl-1,1-dioxidothietan-3-yl)-4,5,6,7-tetrahydro-1H-indazole-6-carboxamide, 3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, (R)-3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, (S)-3-(3-(difluoromethoxy)phenyl)-4,4-difluoro-N—((S)-3-methyl-1,1-dioxidotetrahydrothiophen-3-yl)-1-(tetrahydro-2H-pyran-4-yl)-4,5,6,7-tetrahydro-1H-indazole-6-carboxamide, 3-(3-(difluoromethoxy)phenyl)-1-(5-fluoropyridin-2-yl)-N—((S)-3-methyl-1,1-dioxidotetrahydrothiophen-3-yl)-1,5,6,7-tetrahydropyrano[3,2-c]pyrazole-6-carboxamide, 3-(3-(difluoromethoxy)phenyl)-1-(5-fluoropyridin-2-yl)-N-(3-methyl-1,1-dioxidothietan-3-yl)-1,5,6,7-tetrahydropyrano[3,2-c]pyrazole-6-carboxamide, 3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, (S)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, (R)-3-(3-(difluoromethoxy)phenyl)-1-isopropyl-N-(3-methyl-1,1-dioxidothietan-3-yl)-1,5,6,7-tetrahydropyrano[3,2-c]pyrazole-6-carboxamide, 3-(5-(difluoromethoxy)-2-fluorophenyl)-1-isopropyl-N-(3-methyl-1,1-dioxidothietan-3-yl)-1,5,6,7-tetrahydropyrano[3,2-c]pyrazole-6-carboxamide, 3-(5-(difluoromethoxy)-2-fluorophenyl)-1-isopropyl-N—((S)-3-methyl-1,1-dioxidotetrahydrothiophen-3-yl)-1,5,6,7-tetrahydropyrano[3,2-c]pyrazole-6-carboxamide, 3-(5-(difluoromethoxy)-2-fluorophenyl)-1-isopropyl-N—((R)-3-methyl-1,1-dioxidotetrahydrothiophen-3-yl)-1,5,6,7-tetrahydropyrano[3,2-c]pyrazole-6-carboxamide, N-(3,3-difluoro-1-methylcyclobutyl)-3-(3-(difluoromethoxy)phenyl)-1-isopropyl-1,5,6,7-tetrahydropyrano[3,2-c]pyrazole-6-carboxamide, (S)-3-(3-cyclopropylphenyl)-1-isopropyl-N-(3-methyl-1,1-dioxidothietan-3-yl)-1,5,6,7-tetrahydropyrano[3,2-c]pyrazole-6-carboxamide, (R)-3-(3-(1-fluorocyclopropyl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(3-(2-aminopropan-2-yl)phenyl)-1-(4-fluorophenyl)-N—((S)-3-methyl-1,1-dioxidotetrahydrothiophen-3-yl)-4,5,6,7-tetrahydro-1H-indazole-6-carboxamide, (R)-3-(6-(difluoromethoxy) pyrazin-2-yl)-1-(5-fluoropyridin-2-yl)-N—((S)-3-methyl-1,1-dioxidotetrahydrothiophen-3-yl)-4,5,6,7-tetrahydro-1H-indazole-6-carboxamide, (R)-1-(5-fluoropyridin-2-yl)-N—((S)-3-methyl-1,1-dioxidotetrahydrothiophen-3-yl)-3-(1-methyl-1H-pyrazol-5-yl)-4,5,6,7-tetrahydro-1H-indazole-6-carboxamide, (R)-3-(3-(difluoromethoxy)phenyl)-1-isopropyl-N-(pyridin-3-ylmethyl)-4,5,6,7-tetrahydro-1H-indazole-6-carboxamide, (R)-3-(3-(difluoromethoxy)phenyl)-1-isopropyl-N-(isoxazol-4-ylmethyl)-4,5,6,7-tetrahydro-1H-indazole-6-carboxamide, (6R)-3-(5-(difluoromethoxy)-2-fluorophenyl)-1-isopropyl-N-(1-isopropyl-2-oxopyrrolidin-3-yl)-4,5,6,7-tetrahydro-1H-indazole-6-carboxamide, (R)-3-(3-(difluoromethoxy)phenyl)-N—((S)-1-hydroxypropan-2-yl)-1-isopropyl-4,5,6,7-tetrahydro-1H-indazole-6-carboxamide, (R)-3-(3-(difluoromethoxy)phenyl)-1-isopropyl-N-(1-methoxy-2-methylpropan-2-yl)-4,5,6,7-tetrahydro-1H-indazole-6-carboxamide, (R)-3-(3-(difluoromethoxy)phenyl)-N-(5-methyl-1,3,4-thiadiazol-2-yl)-1-(tetrahydro-2H-pyran-4-yl)-4,5,6,7-tetrahydro-1H-indazole-6-carboxamide, (R)-3-(5-(difluoromethoxy)pyridin-3-yl)-1-isopropyl-N—((S)-1-((R)-2-methylmorpholino) propan-2-yl)-4,5,6,7-tetrahydro-1H-indazole-6-carboxamide, (R)-3-(3-(difluoromethoxy)phenyl)-N-(3-ethyl-1,1-dioxidothietan-3-yl)-1-isopropyl-4,5,6,7-tetrahydro-1H-indazole-6-carboxamide, (R)-3-(3-(difluoromethoxy)phenyl)-N-(2-(1,1-dioxidothiomorpholino)ethyl)-1-isopropyl-4,5,6,7-tetrahydro-1H-indazole-6-carboxamide, (R)-3-(3-(difluoromethoxy)phenyl)-1-isopropyl-N-(2-(N-methylsulfamoyl)ethyl)-4,5,6,7-tetrahydro-1H-indazole-6-carboxamide, (R)-3-(3-(difluoromethoxy)phenyl)-N—((R)-3-methyl-1,1-dioxidotetrahydrothiophen-3-yl)-1-(1-methylpiperidin-4-yl)-4,5,6,7-tetrahydro-1H-indazole-6-carboxamide, (R)-1-acetyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-1-(cyclopropanecarbonyl)-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-N—((S)-3-methyl-1,1-dioxidotetrahydrothiophen-3-yl)-1-(tetrahydro-2H-pyran-4-carbonyl)-4,5,6,7-tetrahydro-1H-indazole-6-carboxamide, (R)-1-benzoyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-1-benzyl-3-(3-(difluoromethoxy)phenyl)-N—((S)-3-methyl-1,1-dioxidotetrahydrothiophen-3-yl)-4,5,6,7-tetrahydro-1H-indazole-6-carboxamide, (R)-3-(3-(difluoromethoxy)phenyl)-N—((S)-3-methyl-1,1-dioxidotetrahydrothiophen-3-yl)-1-((tetrahydro-2H-pyran-4-yl)methyl)-4,5,6,7-tetrahydro-1H-indazole-6-carboxamide, (6R)-1-(1-cyanoethyl)-3-(5-(difluoromethoxy)-2-fluorophenyl)-N-(3-methyl-1,1-dioxidothietan-3-yl)-4,5,6,7-tetrahydro-1H-indazole-6-carboxamide, (6R)-3-(5-(difluoromethoxy)-2-fluorophenyl)-N-(3-methyl-1,1-dioxidothietan-3-yl)-1-(1-(thiazol-2-yl)ethyl)-4,5,6,7-tetrahydro-1H-indazole-6-carboxamide, (R)-1-isopropyl-N-(3-methyl-1,1-dioxidothietan-3-yl)-3-(3-(1-(trifluoromethyl)cyclopropyl)phenyl)-4,5,6,7-tetrahydro-1H-indazole-6-carboxamide, (R)-3-(3-(1-cyanocyclopropyl)phenyl)-1-isopropyl-N-(3-methyl-1,1-dioxidothietan-3-yl)-4,5,6,7-tetrahydro-1H-indazole-6-carboxamide, (R)-3-(2-(1,1-difluoroethyl)-5-fluoropyridin-4-yl)-1-isopropyl-N-(4-methyl-1,1-dioxidotetrahydro-2H-thiopyran-4-yl)-4,5,6,7-tetrahydro-1H-indazole-6-carboxamide,
(R)-1-isopropyl-N-(3-methyl-1,1-dioxidothietan-3-yl)-3-(2-methylbenzo[d]oxazol-4-yl)-4,5,6,7-tetrahydro-1H-indazole-6-carboxamide,
(R)-3-(3-(cyanomethyl)phenyl)-1-isopropyl-N-(3-methyl-1,1-dioxidothietan-3-yl)-4,5,6,7-tetrahydro-1H-indazole-6-carboxamide,
(R)-3-(5-(tert-butylcarbamoyl)pyridin-3-yl)-1-isopropyl-N-(3-methyl-1,1-dioxidothietan-3-yl)-4,5,6,7-tetrahydro-1H-indazole-6-carboxamide,
(R)-3-(3-(cyanomethoxy)phenyl)-1-isopropyl-N-(3-methyl-1,1-dioxidothietan-3-yl)-4,5,6,7-tetrahydro-1H-indazole-6-carboxamide,
(R)-3-(3-(1H-pyrazol-1-yl)phenyl)-1-isopropyl-N-(3-methyl-1,1-dioxidothietan-3-yl)-4,5,6,7-tetrahydro-1H-indazole-6-carboxamide,
(R)-1-isopropyl-N-(3-methyl-1,1-dioxidothietan-3-yl)-3-(3-(methylsulfonyl)phenyl)-4,5,6,7-tetrahydro-1H-indazole-6-carboxamide,
(R)-3-(3-(N-ethylsulfamoyl)phenyl)-1-isopropyl-N-(3-methyl-1,1-dioxidothietan-3-yl)-4,5,6,7-tetrahydro-1H-indazole-6-carboxamide,
(R)-3-(5-ethyl-2-fluorophenyl)-1-isopropyl-N-(3-methyl-1,1-dioxidothietan-3-yl)-4,5,6,7-tetrahydro-1H-indazole-6-carboxamide,
(R)-3-(5-cyano-2-fluorophenyl)-1-isopropyl-N-(3-methyl-1,1-dioxidothietan-3-yl)-4,5,6,7-tetrahydro-1H-indazole-6-carboxamide,
(R)-3-(3-(1,1-difluoroethyl)phenyl)-1-isopropyl-N-(3-methyl-1,1-dioxidothietan-3-yl)-4,5,6,7-tetrahydro-1H-indazole-6-carboxamide,
(R)—N-(3,3-difluoro-1-methylcyclobutyl)-3-(3-(1-hydroxycyclobutyl)phenyl)-1-isopropyl-4,5,6,7-tetrahydro-1H-indazole-6-carboxamide,
(R)-3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide,
(S)-3-(3-(difluoromethoxy)phenyl)-1-isopropyl-N-(3-methyl-1,1-dioxidothietan-3-yl)-1,4,6,7-tetrahydropyrano[4,3-c]pyrazole-6-carboxamide,
(R)-3-(5-(difluoromethoxy)-2-fluorophenyl)-1-isopropyl-N-(3-methyl-1,1-dioxidothietan-3-yl)-1,4,6,7-tetrahydropyrano[4,3-c]pyrazole-6-carboxamide, or
(R)-3-(5-cyclopropyl-2-fluorophenyl)-1-isopropyl-N-(3-methyl-1,1-dioxidothietan-3-yl)-1,4,6,7-tetrahydropyrano[4,3-c]pyrazole-6-carboxamide.

30. The compound of claim 1, or a pharmaceutically acceptable salt thereof, which is

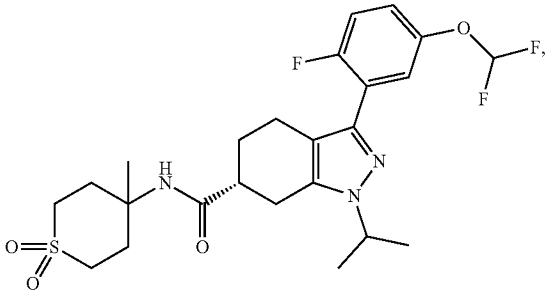

-continued

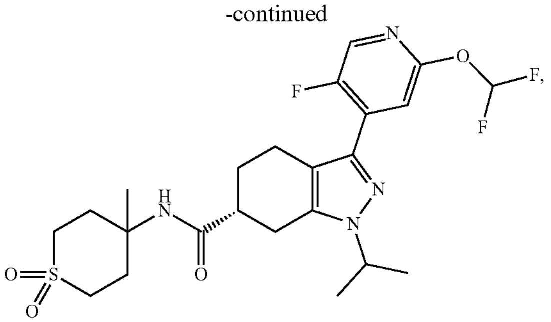

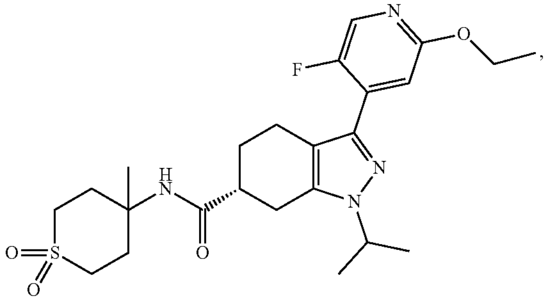

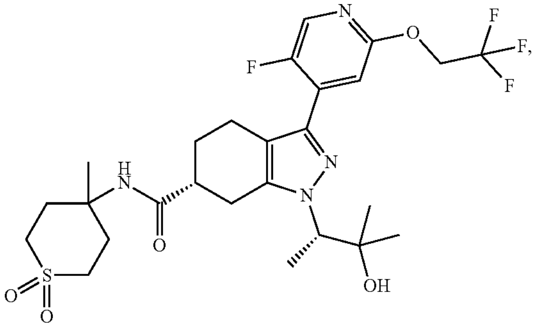

or

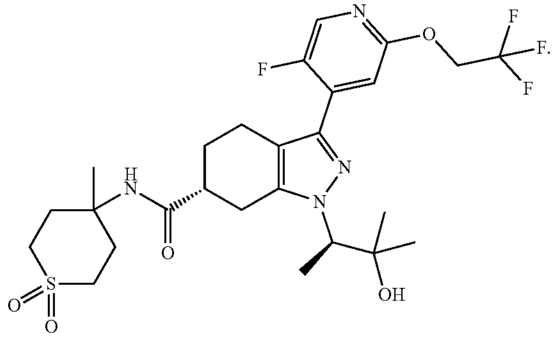

31. A composition for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising a compound of claim 1, or a pharmaceutically acceptable salt thereof, and a pharmaceutically carrier.

32. A composition comprising a pharmaceutically acceptable carrier and a compound according to claim 1, or a pharmaceutically acceptable salt thereof.

33. A method for treating a condition selected from hepatic steatosis, nonalcoholic steatohepatitis (NASH), fibrosis, type-2 diabetes mellitus, obesity, hyperlipidemia, hypercholesterolemia, atherosclerosis, cognitive decline, dementia, cardiorenal diseases and heart failure comprising administering to a patient in need thereof a therapeutically effective amount of a compound of claim 1, or a pharmaceutically acceptable salt thereof.

* * * * *